United States Patent
Funahashi

(10) Patent No.: US 7,425,653 B2
(45) Date of Patent: Sep. 16, 2008

(54) AROMATIC AMINE DERIVATIVE AND ORGANIC ELECTROLUMINESCENCE DEVICE EMPLOYING THE SAME

(75) Inventor: Masakazu Funahashi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 51 days.

(21) Appl. No.: 11/282,697

(22) Filed: Nov. 21, 2005

(65) Prior Publication Data
US 2006/0152146 A1 Jul. 13, 2006

Related U.S. Application Data

(63) Continuation of application No. PCT/JP05/15523, filed on Aug. 26, 2005.

(30) Foreign Application Priority Data

Aug. 31, 2004 (JP) ............................. 2004-251691
May 19, 2005 (JP) ............................. 2005-147208

(51) Int. Cl.
C07C 211/54 (2006.01)
(52) U.S. Cl. ..................................... 564/434
(58) Field of Classification Search ................. None
See application file for complete search history.

(56) References Cited

U.S. PATENT DOCUMENTS

| 6,747,287 | B1 | 6/2004 | Toguchi et al. | |
| 2003/0072966 | A1* | 4/2003 | Hosokawa et al. | 428/690 |
| 2003/0082404 | A1 | 5/2003 | Sotoyama et al. | |
| 2005/0038296 | A1 | 2/2005 | Hosokawa et al. | |
| 2005/0064233 | A1 | 3/2005 | Matsuura et al. | |
| 2005/0107430 | A1* | 5/2005 | Banik et al. | 514/319 |
| 2006/0152146 | A1 | 7/2006 | Funahashi | |
| 2006/0194074 | A1 | 8/2006 | Funahashi | |

FOREIGN PATENT DOCUMENTS

| EP | 1 561 794 A1 | 8/2005 |
| JP | 2003-124472 | 4/2003 |
| JP | 2003-151775 | 5/2003 |
| WO | WO 2004/018588 A1 | 3/2004 |
| WO | WO 2004/044088 A1 | 5/2004 |

OTHER PUBLICATIONS

U.S. Appl. No. 11/550,519, filed Oct. 18, 2006, Funahashi et al.
U.S. Appl. No. 11/596,299, filed Nov. 13, 2006, Funahashi.
U.S. Appl. No. 11/282,697, filed Nov. 21, 2005, Funahashi.
U.S. Appl. No. 11/336;855, filed Jan. 23, 2006, Funahashi et al.
U.S. Appl. No. 11/336;857, filed Jan. 23, 2006, Funahashi.
U.S. Appl. No. 11282;697, filed Nov. 21, 2005, Funahashi.
U.S. Appl. No. 11/575,441, filed Mar. 16, 2007, Funahashi.

* cited by examiner

*Primary Examiner*—Samuel A. Barts
(74) *Attorney, Agent, or Firm*—Oblon, Spivak, McClelland, Maier & Neustadt, P.C.

(57) ABSTRACT

A specified aromatic amine derivative having a chrysene structure. An organic electroluminescence device which comprises at least one organic thin film layer comprising a light emitting layer sandwiched between a pair of electrode consisting of an anode and a cathode, wherein at least one of the organic thin film layer comprises the aromatic amine derivative singly or as its mixture component. Organic electroluminescence devices having a long lifetime and a high efficiency of light emission, and aromatic amine derivatives capable of realizing such organic electroluminescence devices are provided.

17 Claims, 12 Drawing Sheets

AROMATIC AMINE DERIVATIVE AND ORGANIC ELECTROLUMINESCENCE DEVICE EMPLOYING THE SAME

TECHNICAL FIELD

The present invention relates to an aromatic amine derivative and an organic electroluminescence device using the derivative and, more particularly, to an organic electroluminescence device having long lifetime, an enhanced efficiency of light emission and emitting highly pure blue light; and to an aromatic amine derivative realizing the organic electroluminescence device.

BACKGROUND ART

Organic electroluminescence ("electroluminescence" will be occasionally referred to as "EL", hereinafter) devices which utilize organic substances are expected to be useful for application as an inexpensive full color display device of the solid light emission type having a great size and various developments on the organic EL devices are being conducted. In general, an organic EL device has a construction comprising a light emitting layer and a pair of electrodes sandwiching the light emitting layer. The light emission of the organic EL device is a phenomenon in which, when an electric field is applied between the two electrodes, electrons are injected from the cathode side and holes are injected from the anode side, the electrons are recombined with the holes in the light emitting layer to form an excited state, and energy generated when the excited state returns to the ground state is emitted as light.

As compared with an inorganic light emitting diode, conventional organic EL devices requires high driving voltage and only exhibited low luminance or low efficiency of light emission. Moreover, characteristic degradation of the conventional organic EL devices was also extravagant and as a result, they were not practically used. Although recent organic EL devices are improved step by steps, it has been still demanded to develop organic EL devices with favorable efficiency of light emission and having long lifetime.

For example, there is disclosed such a technique using a single monoanthracene compound as an organic light-emitting material (refer to Patent Literature 1 below). However, in this technique, a luminance obtained by using the material is as low as 1650 cd/m$^2$, for example, at a current density of 165 mA/cm$^2$, and an efficiency of light emission thereof is very low, i.e., only 1 cd/A, which is practically unusable. Also, there is disclosed a technique using a single bisanthracene compound as an organic light emitting material (refer to Patent Literature 2 below). However, in this technique, an efficiency of light emission obtained by using the material is also as low as about 1 to 3 cd/A. Therefore, further improvement of the technique has bee demanded for rendering it practically usable. Further, there is disclosed a technique using a distyryl compound and adding styrylamine or so as organic light emitting material (refer to Patent Literature 3 below). However, the device described therein fails to show a sufficiently long lifetime and, therefore, further improvement has been demanded.

Furthermore, a technique of employing mono- or bis-anthracene compound and a distyryl compound as an organic light emitting medium layer is disclosed (refer to Patent Literature 4 below). However in these technologies, a conjugated structure of the styryl compound lengthened wave length of a light emission spectrum and deteriorated the purity of color.

Still further, Patent Literature 5 below discloses a blue luminescence device with the use of diaminochrysene derivatives. However, despite the superiority in light emission efficiency, because the device is not sufficient in its lifetime, further improvement was required.

Patent Literature 1: Japanese Unexamined Patent Application Laid-Open No. Hei 11-3782A
Patent Literature 2: Japanese Unexamined Patent Application Laid-Open No. Hei 8(1996)-012600
Patent Literature 3: International Patent Application Published under PCT No. WO 00/06402
Patent Literature 4: Japanese Unexamined Patent Application Laid-Open No. 2001-284050
Patent Literature 5: International Application Published under PCT No. WO 04/04088

DISCLOSURE OF THE INVENTION

The present invention has been made to overcome the above problems. An object of the present invention is to provide organic EL devices having a long lifetime and a high efficiency of light emission, and aromatic amine derivatives capable of realizing such organic EL devices.

As a result of extensive researches for developing aromatic amine derivatives having the above suitable properties and organic EL devices using the aromatic amine derivatives, the inventors have found that the object of the present invention can be achieved by using aromatic amine derivatives represented by a following general formula (1) or (2) in which an amino group is bonded to a substituted chrysene structure. The present invention has been accomplished on the basis of the above finding.

Namely, the present invention provides an aromatic amine derivative represented by the following general formula (1) or general formula (2):

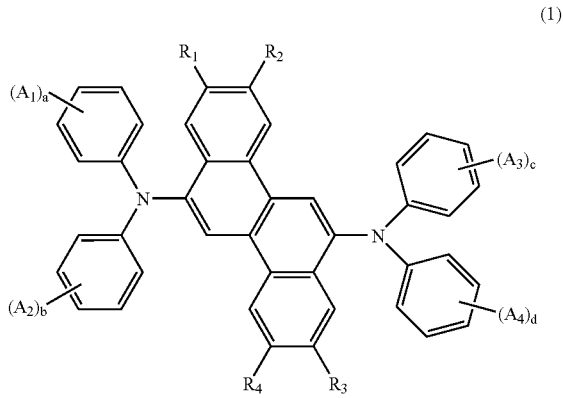

In the general formula (1), $A_1$ to $A_4$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 1 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 3 to 50 ring carbon atoms, a substituted or unsubstituted silyl group having 3 to 50 carbon atoms or a halogen atom;

a, b, c and d each independently represents an integer of 0 to 5, when a, b, c or d each is 2 or greater, $A_1$ to $A_4$ may be the same with or different from each other, and may bond each other to form a saturated or unsaturated ring; and further, a couple of $A_1$ and $A_2$, and a couple of $A_3$ and $A_4$ may bond each other to form a saturated or unsaturated ring;

$R_1$ to $R_4$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted arylamino group having 5 to 20 ring carbon atoms, a substituted or unsubstituted alkylamino group having 1 to 20 carbon atoms, a substituted or unsubstituted heterocyclic group having 3 to 50 ring carbon atoms or a substituted or unsubstituted silyl group having 3 to 50 carbon atoms; a couple of $R_1$ and $R_2$, and a couple of $R_3$ and $R_4$ may bond each other to form a saturated or unsaturated ring.

However, a case where all of $R_1$ to $R_4$ in the general formula (1) are hydrogen atoms is excluded.

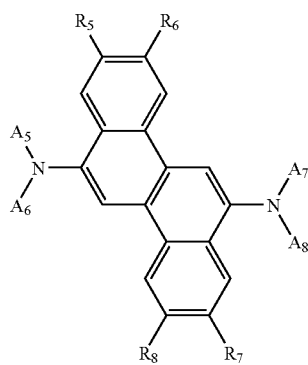

(2)

In the general formula (2), $A_5$ to $A_8$ each independently represents a substituted or unsubstituted alkyl group having 1 to 50 carbon atoms, a substituted or unsubstituted aryl group having 5 to 50 ring carbon atoms, a substituted or unsubstituted cycloalkyl group having 3 to 50 ring carbon atoms or a substituted or unsubstituted heterocyclic group having 3 to 50 ring carbon atoms;

$R_5$ to $R_8$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted arylamino group having 5 to 20 ring carbon atoms, a substituted or unsubstituted alkylamino group having 1 to 20 carbon atoms or a substituted or unsubstituted heterocyclic group having 3 to 50 ring carbon atoms; and a couple of $R_5$ and $R_6$, and a couple of $R_7$ and $R_8$ may bond each other to form a saturated or unsaturated ring.

Further, the present invention provides an organic EL device which comprises at least one organic thin film layer comprising a light emitting layer sandwiched between a pair of electrode consisting of an anode and a cathode, wherein at least one of the organic thin film layers comprises the aromatic amine derivative singly or as its mixture component.

The organic EL device employing the aromatic amine derivative of the present invention reveals practically sufficient luminance even under low applied voltage, exhibits an enhanced efficiency of light emission, and is resistant to degrade even after a long time usage demonstrating a prolonged lifetime.

THE PREFERRED EMBODIMENT TO CARRY OUT THE INVENTION

Figure 1:
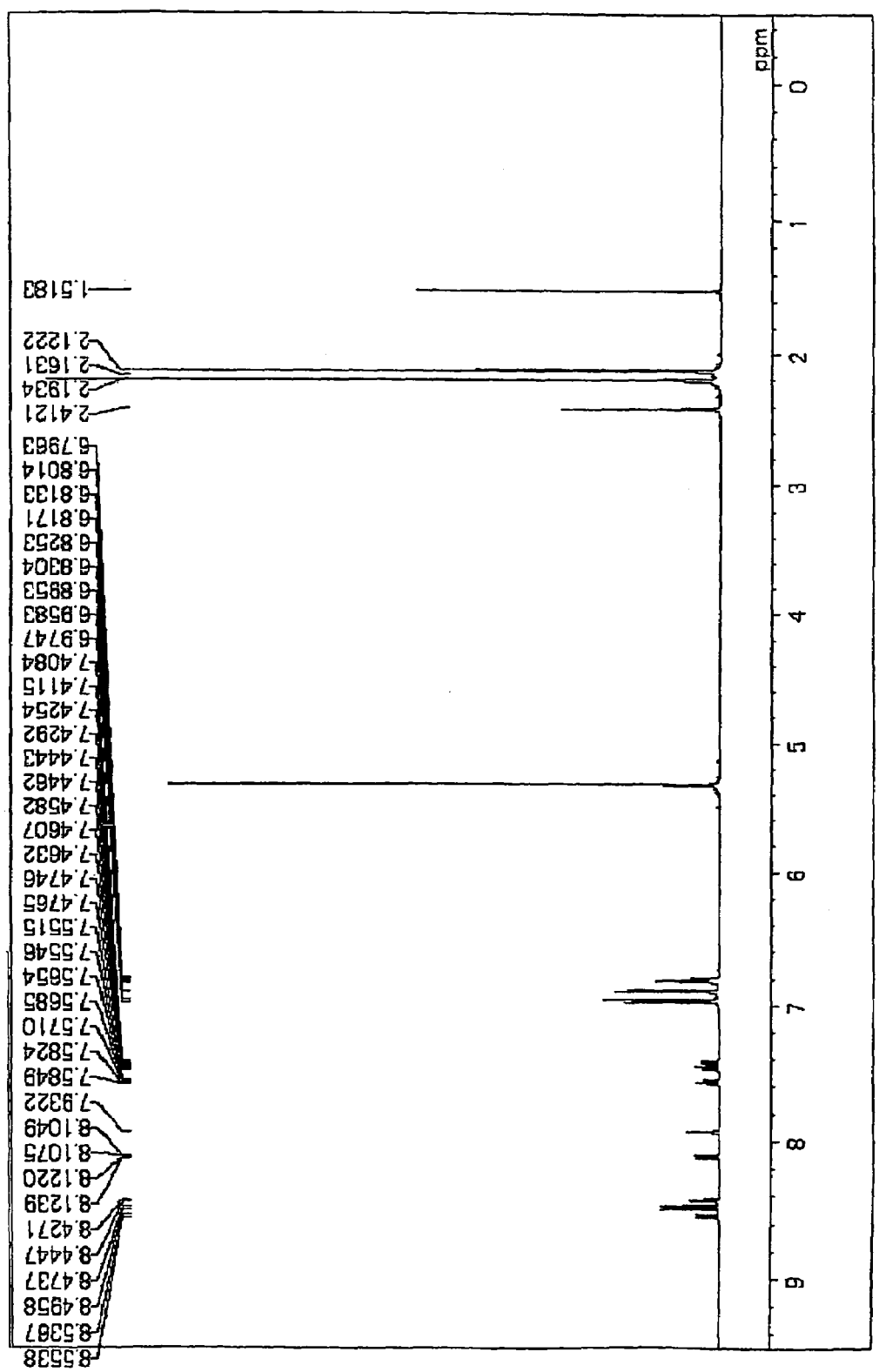
FIG. 1 is a chart showing a result of $^1$H-NMR measurement about Compound (4) obtained in Synthesis Example 1.

The present invention provides an aromatic amine derivative represented by a following general formula (1) or a general formula (2):

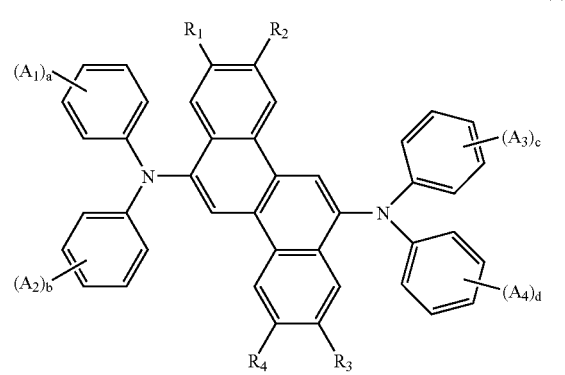

(1)

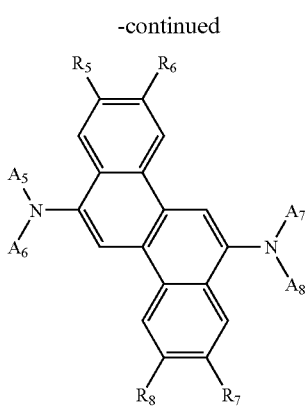

(2)

First, the aromatic amine derivative represented by the general formula (1) will be explained below.

In the general formula (1), $A_1$ to $A_4$ each independently represents a hydrogen atom, a substituted or unsubstituted alkyl group having 1 to 50 (preferably 1 to 20) carbon atoms, a substituted or unsubstituted aryl group having 5 to 50 (preferably 5 to 20) ring carbon atoms, a substituted or unsubstituted aralkyl group having 1 to 50 (preferably 6 to 20) ring carbon atoms, a substituted or unsubstituted cycloalkyl group having 3 to 50 (preferably 5 to 12) ring carbon atoms, a substituted or unsubstituted alkoxyl group having 1 to 50 (preferably 1 to 6) carbon atoms, a substituted or unsubstituted aryloxy group having 5 to 50 (preferably 5 to 18) ring carbon atoms, a substituted or unsubstituted arylamino group having 5 to 50 (preferably 5 to 18) ring carbon atoms, a substituted or unsubstituted alkylamino group having 1 to 20 (preferably 1 to 6) carbon atoms, a substituted or unsubstituted heterocyclic group having 3 to 50 (preferably 3 to 20) ring carbon atoms, a substituted or unsubstituted silyl group having 3 to 50 (preferably 3 to 20) carbon atoms or a halogen atom.

Examples of the substituted or unsubstituted alkyl group represented by $A_1$ to $A_4$ include methyl group, ethyl group, propyl group, isopropyl group, butyl group, sec-butyl group, tert-butyl group, pentyl group, hexyl group, heptyl group, octyl group, stearyl group, trichloromethyl group, trifluoromethyl group, etc.

Examples of the substituted or unsubstituted aryl group represented by $A_1$ to $A_4$ include phenyl group, 2-methylphenyl group, 3-methylphenyl group, 4-methylphenyl group, 4-ethylphenyl group, biphenyl group, 4-methylbiphenyl group, 4-ethylbiphenyl group, 4-cyclohexylbiphenyl group, terphenyl group, 3,5-dichlorophenyl group, naphthyl group, 5-methylnaphthyl group, anthryl group, pyrenyl group, etc.

Examples of the substituted or unsubstituted aralkyl group represented by $A_1$ to $A_4$ include benzyl group, α,α-methylphenylbenzyl group, triphenylmethyl group, 1-phenylethyl group, 2-phenylethyl group, 1-phenylisopropyl group, 2-phenylisopropyl group, phenyl-t-butyl group, -naphthylmethyl group, 1-α-naphthylethyl group, 2-α-naphthylethy group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, α-phenoxybenzyl group, α-benzyloxy benzyl group, α,α-ditrifluoromethylbenzyl group, 1-pyrrolylmethyl group, 2-(1-pyrrolyl)ethyl, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group, etc.

Examples of the cycloalkyl group represented by $A_1$ to $A_4$ include cyclopropyl group, cyclobutyl group, cyclopentyl group, cyclohexyl group, etc.

Examples of the alkoxy group represented by $A_1$ to $A_4$ include methoxy group, ethoxy group, propoxy group, isopropoxy group, butoxy group, isobutoxy group, s-butoxy group, t-butoxy group, various pentyloxy groups, various hexyloxy groups, etc.

Examples of the aryloxy group represented by $A_1$ to $A_4$ include phenoxy group, tolyloxy group, naphthyloxy group, etc.

Examples of the arylamino group represented by $A_1$ to $A_4$ include diphenylamino group, ditolylamino group, isopropyldiphenylamino group, t-butyldiphenylamino group, diisopropyldiphenylamino group, di-t-butyldiphenylamino group, dinaphthylamino group, naphthylphenylamino group, etc.

Examples of the alkylamino group represented by $A_1$ to $A_4$ include dimethylamino group, diethylamino group, dihexylamino group, etc.

Examples of the heterocyclic group represented by $A_1$ to $A_4$ include moieties of imidazole, benzimidazole, pyrrole, furan, thiophene, benzothiophene, oxadi azoline, indoline, carbazole, pyridine, quinoline, isoquinoline, benzoquinone, pyrazoline, imidazolidine, piperidine, etc.

Examples of the substituted or unsubstituted silyl group represented by $A_1$ to $A_4$ include trimethylsilyl group, triethylsilyl group, t-butyldimethylsilyl group, vinyldimethylsilyl group, propyldimethylsilyl group, methyldiphenylsilyl group, dimethylphenylsilyl group, triphenylsilyl group), etc.

Examples of the halogen atom represented by $A_1$ to $A_4$ include fluorine atom, chlorine atom, bromine atom, etc.

In the general formula (1), a, b, c and d each independently represents an integer of 0 to 5, preferably an integer of 0 to 3, and more preferably an integer of 0 to 2.

When a, b, c or d each is 2 or greater, $A_1$ to $A_4$ may be the same with or different from each other, and may bond each other to form a saturated or unsaturated ring; and further, a couple of $A_1$ and $A_2$, and a couple of $A_3$ and $A_4$ may bond each other to form a saturated or unsaturated ring;

Examples of the ring include cycloalkane having 4 to 12 carbon atoms such as cyclobutane, cyclopentane, cyclohexane, adamantane, norbornane, etc.; cycloalkene having 4 to 12 carbon atoms such as cyclobutene, cyclopentene, cyclohexene, cyclo heptene, cyclo octene, etc.; cycloalkadiene having 6 to 12 carbon atoms such as cyclohexa diene, cyclohepta diene, cyclo octadiene, etc.; aromatic ring having 6 to 50 carbon atoms such as benzene, naphthalene, phenanthrene, anthracene, pyrene, chrysene, acenaphthylene, etc.; and the like.

In the general formula (1), $R_1$ to $R_4$ each independently represents a hydrogen atom, a substituted or unsubstituted alkyl group (preferably a primary or a secondary alkyl group) having 1 to 50 (preferably 1 to 20) carbon atoms, a substituted or unsubstituted aryl group having 5 to 50 (preferably 5 to 20) ring carbon atoms, a substituted or unsubstituted aralkyl group having 6 to 50 (preferably 6 to 20) ring carbon atoms, a substituted or unsubstituted cycloalkyl group having 3 to 50 (preferably 5 to 12) ring carbon atoms, a substituted or unsubstituted arylamino group having 5 to 20 (preferably 5 to 18)

ring carbon atoms, a substituted or unsubstituted alkylamino group having 1 to 20 (preferably 1 to 10) carbon atoms, a substituted or unsubstituted heterocyclic group having 3 to 50 (preferably 3 to 20) ring carbon atoms, a substituted or unsubstituted silyl group having 3 to 50 (preferably 3 to 20) carbon atoms; a couple of $R_1$ and $R_2$, and a couple of $R_3$ and $R_4$ may bond each other to form a saturated or unsaturated ring.

Specific examples of the substituted or unsubstituted alkyl group, aryl group, aralkyl group, cycloalkyl group, arylamino group, alkylamino group, heterocyclic group, silyl group and the saturated or unsaturated ring represented by $R_1$ to $R_4$ are the same as those exemplified as $A_1$ to $A_4$ above.

It is particularly preferable that the alkyl group represented by $R_2$ and $R_4$ are primary or secondary.

Further, examples of the substituent for $A_1$ to $A_4$ and $R_1$ to $R_4$ include a substituted or unsubstituted aryl group having 5 to 50 (preferably 5 to 20) ring carbon atoms, a substituted or unsubstituted alkyl group having 1 to 50 (preferably 1 to 20) carbon atoms, a substituted or unsubstituted alkoxy group having 1 to 50 (preferably 1 to 20) carbon atoms, a substituted or unsubstituted aralkyl group having 6 to 50 (preferably 6 to 20) ring carbon atoms, a substituted or unsubstituted aryloxy group having 5 to 50 (preferably 5 to 20) ring carbon atoms, a substituted or unsubstituted arylthio group having 5 to 50 (preferably 5 to 20) ring carbon atoms, a substituted or unsubstituted alkoxycarbonyl group having 1 to 50 (preferably 1 to 20) carbon atoms, amino group, halogen atom, cyano group, nitro group, hydroxyl group, carboxyl group, etc.

However, a case where all of $R_1$ to $R_4$ in the general formula (1) are hydrogen atoms is excluded.

Further in the general formula (1), it is preferable that $R_1$ and/or $R_3$ independently represents a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms or a substituted or unsubstituted cycloalkyl group having 3 to 50 ring carbon atoms. It is preferable that $R_1$ and $R_3$ each independently represents a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms or a substituted or unsubstituted cycloalkyl group having 3 to 50 ring carbon atoms.

Still further in the general formula (1), it is preferable that $R_1$ to $R_4$ each independently represents a hydrogen atom, a substituted or unsubstituted arylamino group having 5 to 20 ring carbon atoms, a substituted or unsubstituted alkylamino group having 1 to 20 carbon atoms, a substituted or unsubstituted heterocyclic group having 5 to 50 ring carbon atoms or a substituted or unsubstituted silyl group having 3 to 50 carbon atoms.

Further, it is preferable that $R_1$ and/or $R_3$ represents a methyl group, an ethyl group, a propyl group, an isopropyl group, a butyl group, a s-butyl group, a t-butyl group or a cyclohexyl group.

Furthermore, it is preferable that $R_2$ and/or $R_4$ represents a methyl group, an ethyl group, a propyl group, an isopropyl group, a butyl group, a s-butyl group, a t-butyl group or a cyclohexyl group.

Next, the aromatic amine derivative represented by the general formula (2) will be explained below.

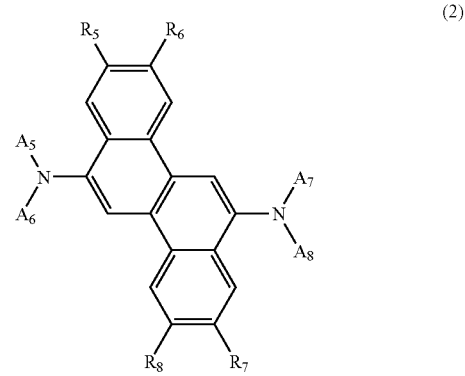

In the general formula (2), $A_5$ to $A_8$ each independently represents a hydrogen atom, a substituted or unsubstituted alkyl group having 1 to 50 (preferably 1 to 20) carbon atoms, a substituted or unsubstituted aryl group having 5 to 50 (preferably 5 to 20) ring carbon atoms, a substituted or unsubstituted cycloalkyl group having 3 to 50 (preferably 5 to 12) ring carbon atoms or a substituted or unsubstituted heterocyclic group having 3 to 50 (preferably 3 to 20) ring carbon atoms;

In the general formula (2), $R_5$ to $R_8$ each independently represents a hydrogen atom, a substituted or unsubstituted alkyl group having 1 to 50 (preferably 1 to 20) carbon atoms, a substituted or unsubstituted aryl group having 5 to 50 (preferably 5 to 20) ring carbon atoms, a substituted or unsubstituted aralkyl group having 6 to 50 (preferably 6 to 20) ring carbon atoms, a substituted or unsubstituted cycloalkyl group having 3 to 50 (preferably 5 to 12) ring carbon atoms, a substituted or unsubstituted arylamino group having 5 to 20 (preferably 5 to 12) ring carbon atoms, a substituted or unsubstituted alkylamino group having 1 to 20 (preferably 1 to 10) carbon atoms or a substituted or unsubstituted heterocyclic group having 3 to 50 (preferably 3 to 20) ring carbon atoms; a couple of $R_5$ and $R_6$, and a couple of $R_7$ and $R_8$ may bond each other to form a saturated or unsaturated ring.

Specific examples of the groups represented by $A_5$ to $A_8$ and $R_5$ to $R_8$ in the general formula (2), specific examples of those substituent and specific examples of those saturated or unsaturated ring are the same as those exemplified as $A_1$ to $A_4$ and $R_1$ to $R_4$ in the foregoing general formula (1).

Specific examples of the aromatic amine derivatives represented by the general formula (1) or the general formula (2) will be illustrated below, though not particularly limited thereto. Meanwhile, in the following compounds, Me represents a methyl group.

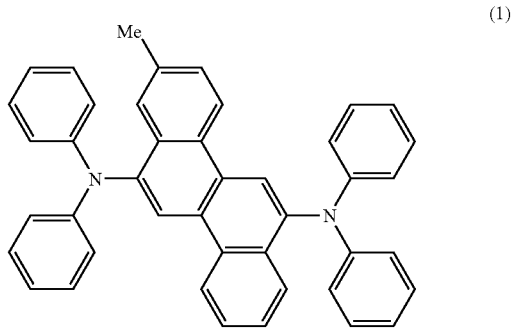

-continued
(2)
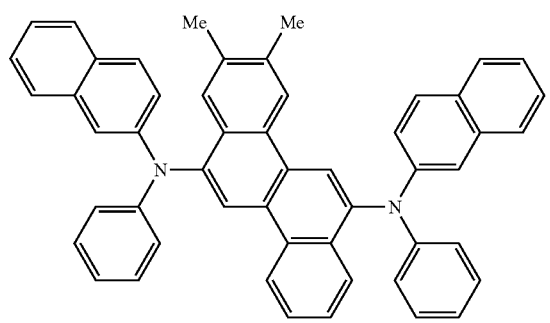
(3)
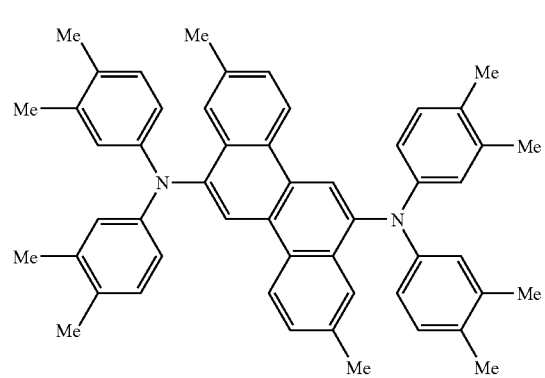
(4)
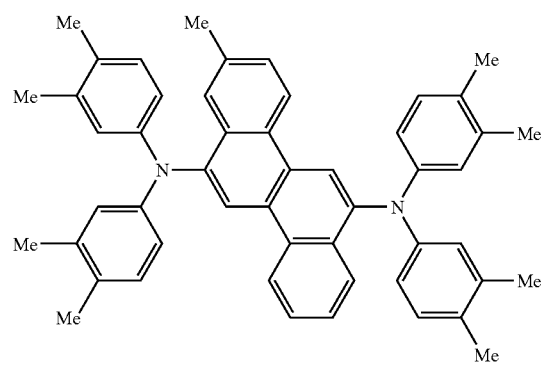
(5)
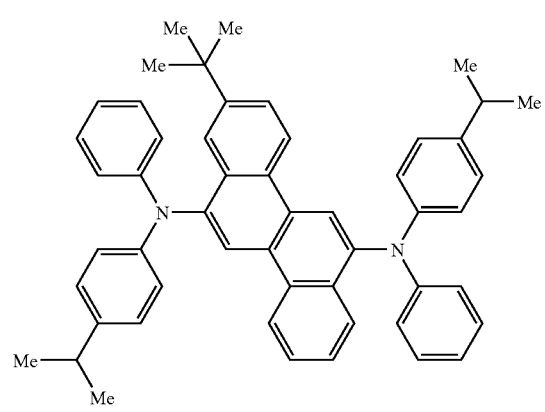
-continued
(6)
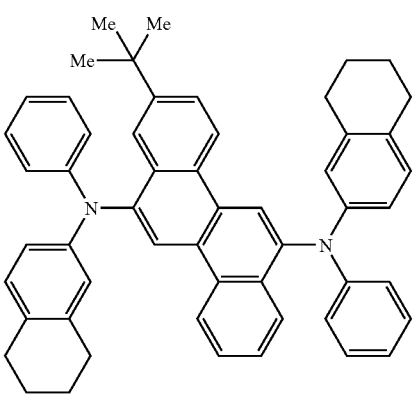
(7)
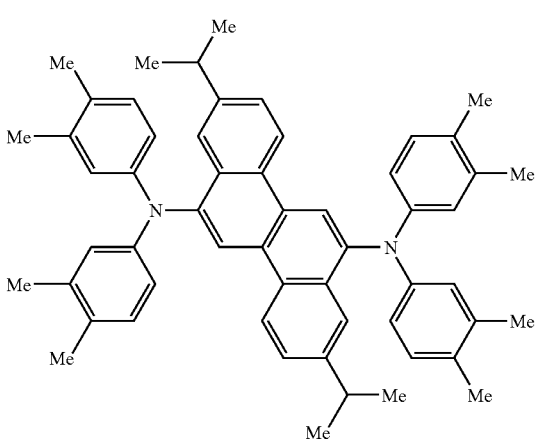
(8)
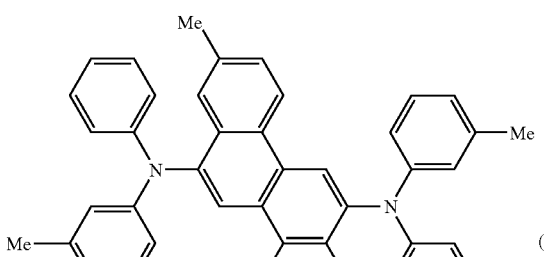
(9)
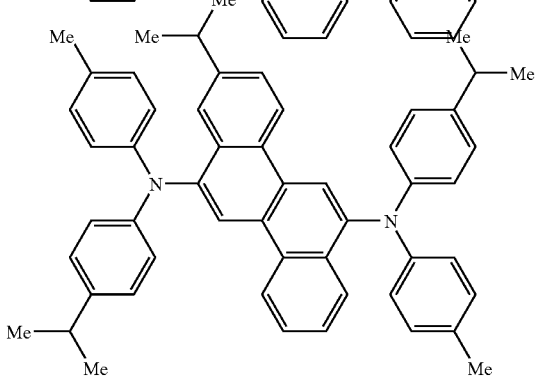

(10)
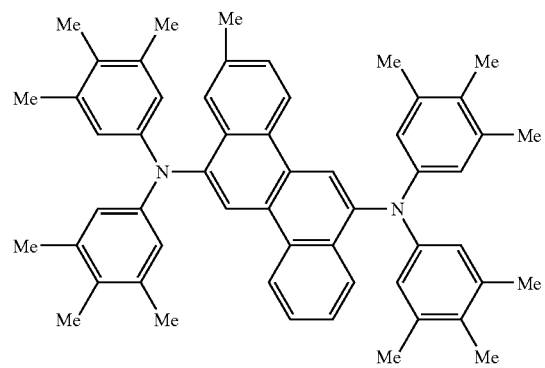
(11)
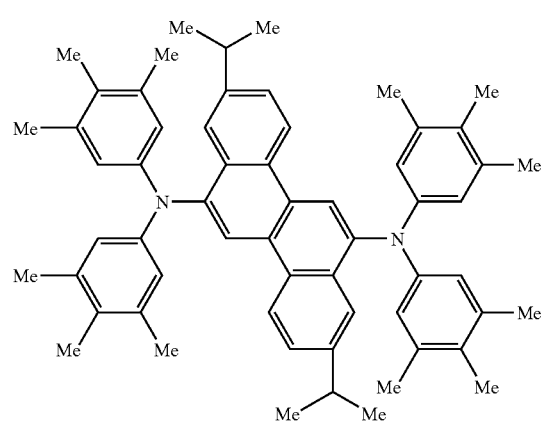
(12)
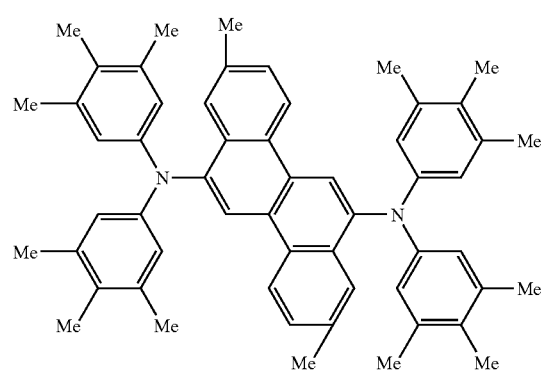
(13)
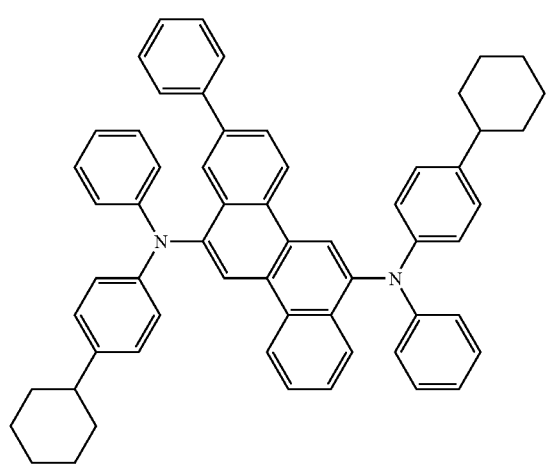
(14)
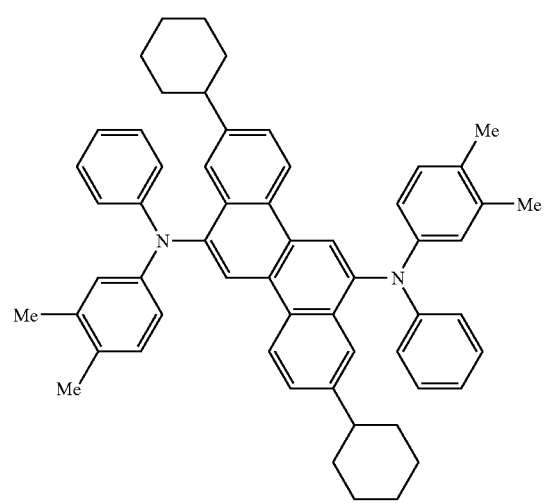
(15)
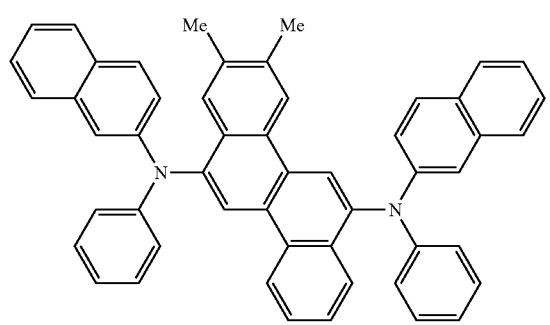

(16)
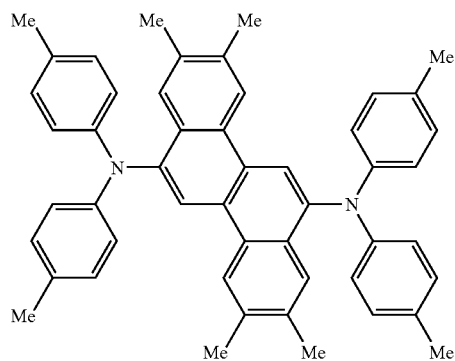
(17)
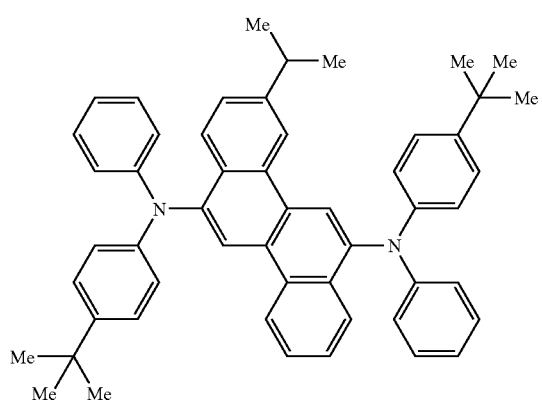
(18)
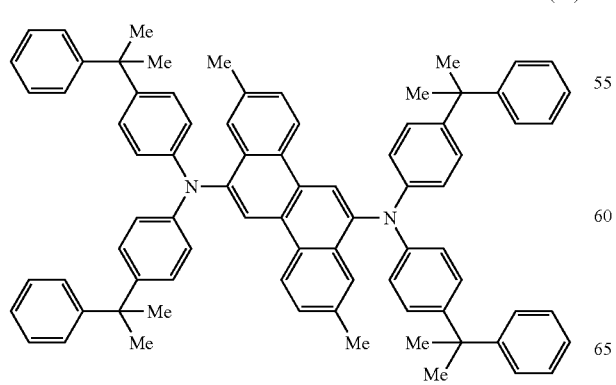
(19)
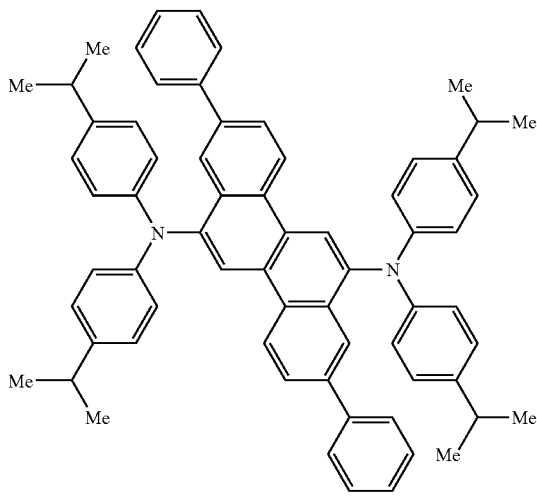
(20)
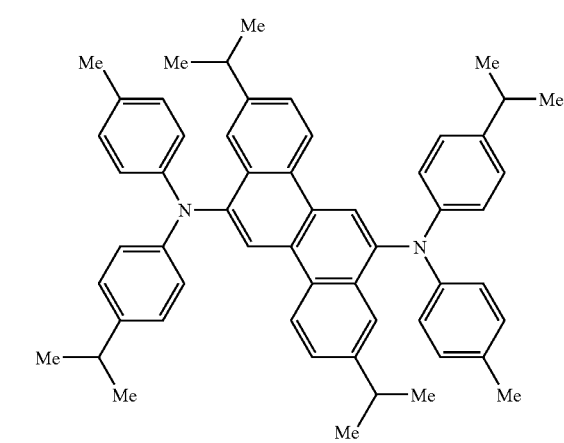
(21)
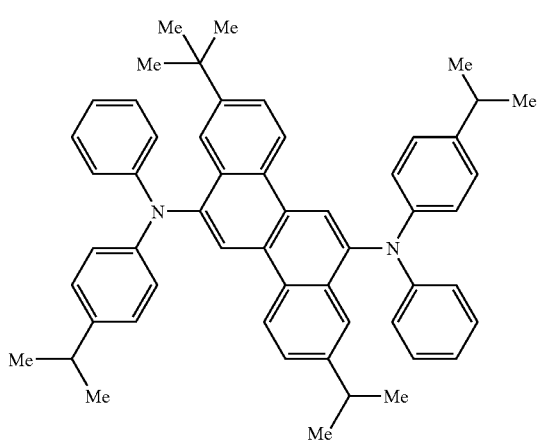

(22)
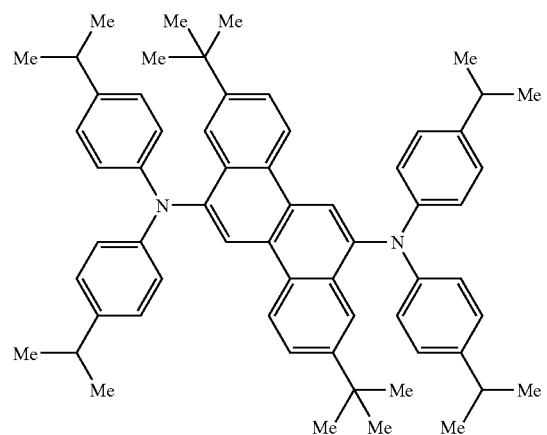
(23)
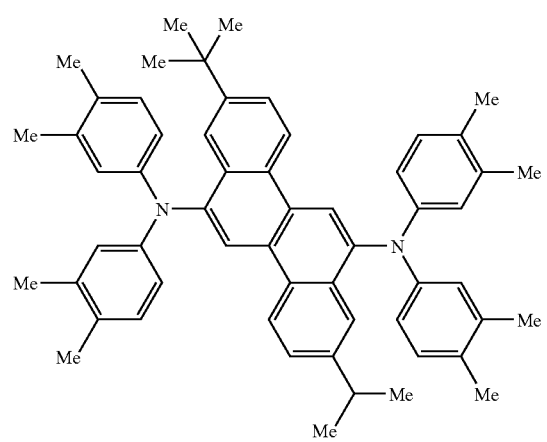
(24)
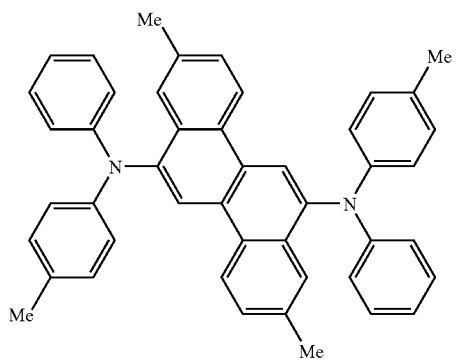
(25)
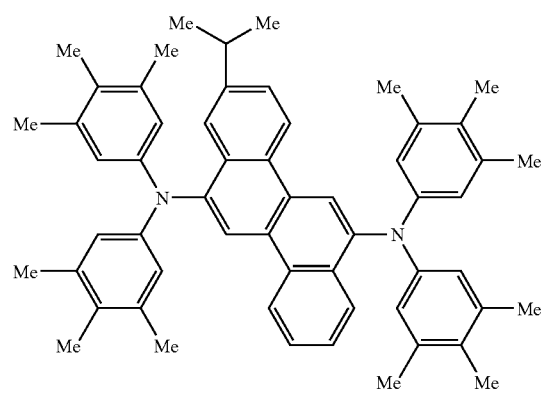
(26)
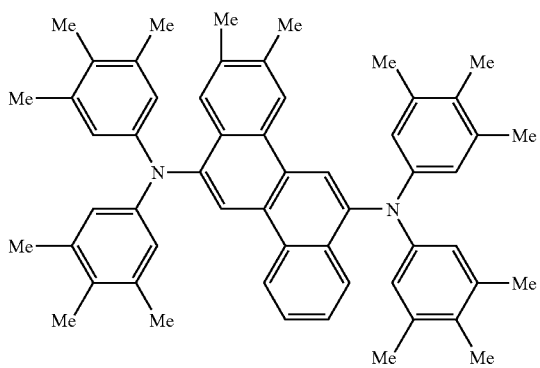
(27)
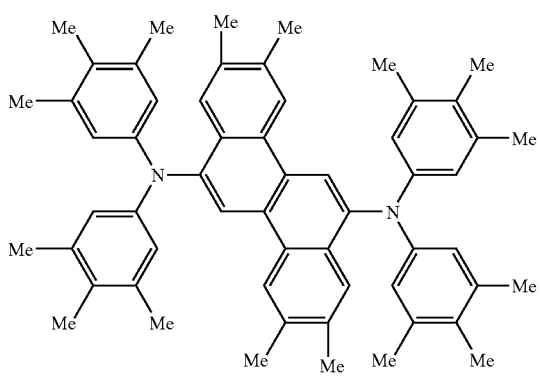
(28)
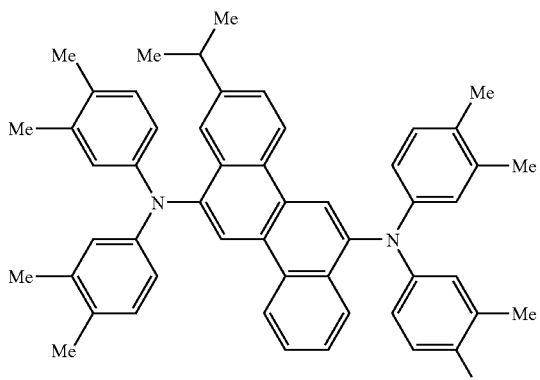
(29)
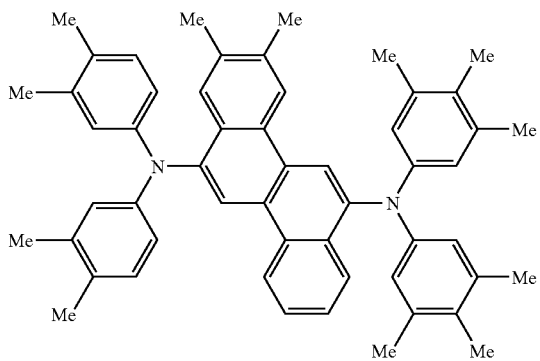

-continued
(30)
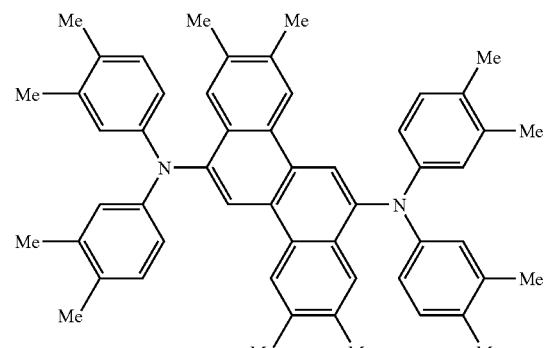
(31)
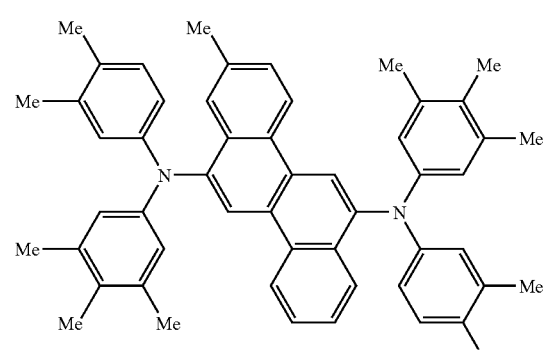
(32)
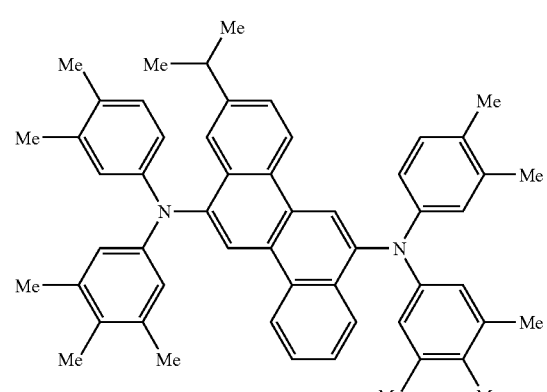
(33)
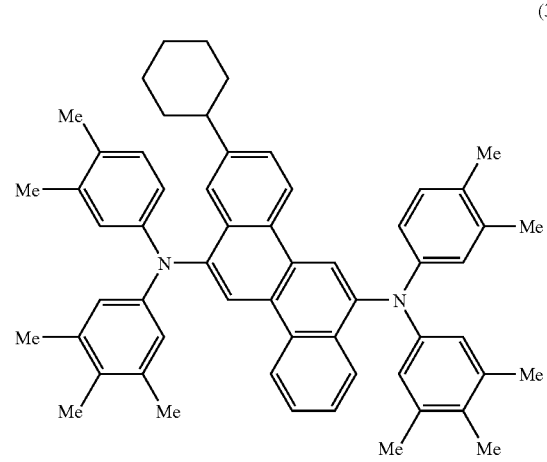
(34)
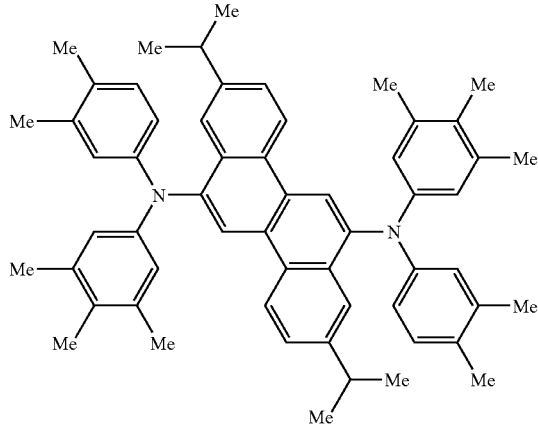
(35)
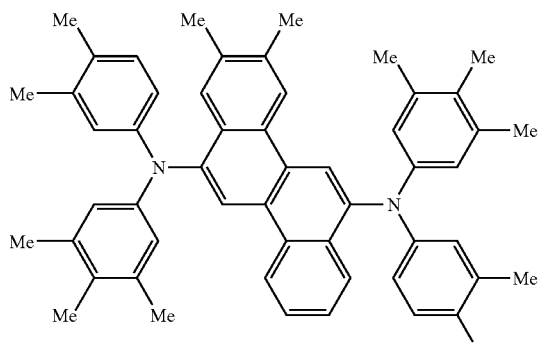
(36)
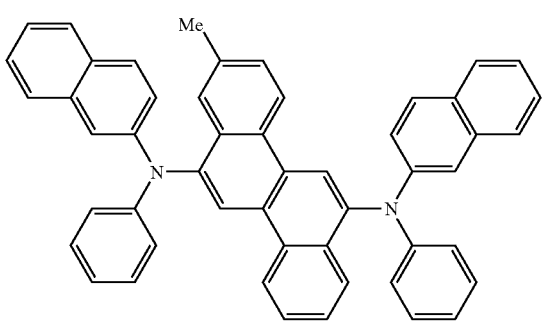
(37)
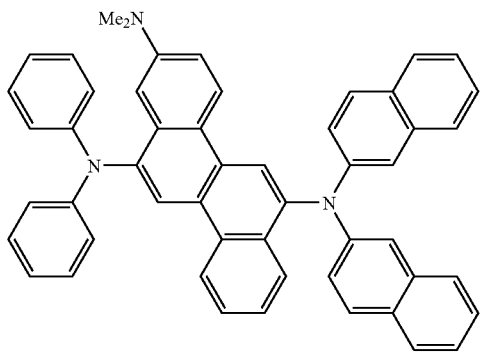

-continued
(38)
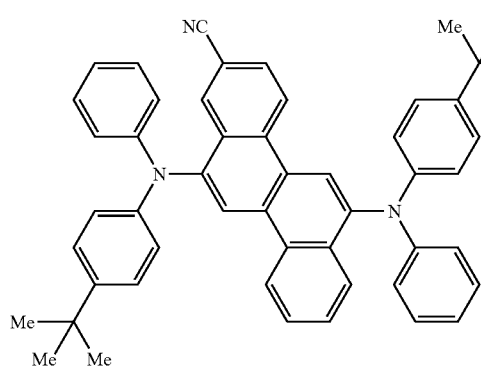
(39)
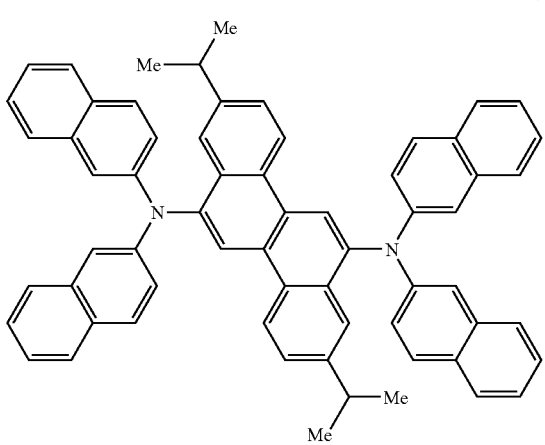
(40)
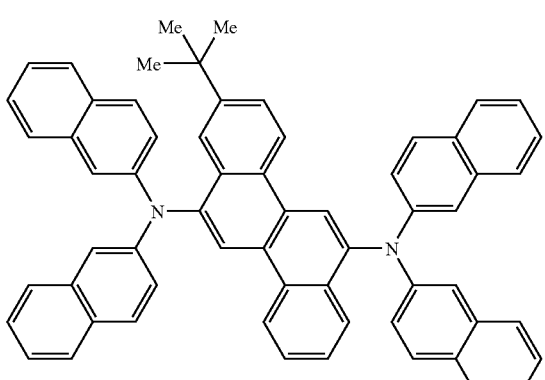
(41)
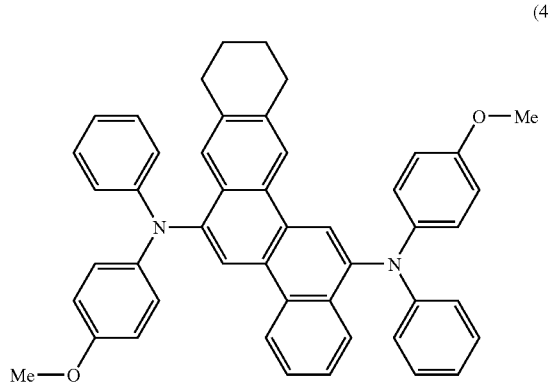
-continued
(42)
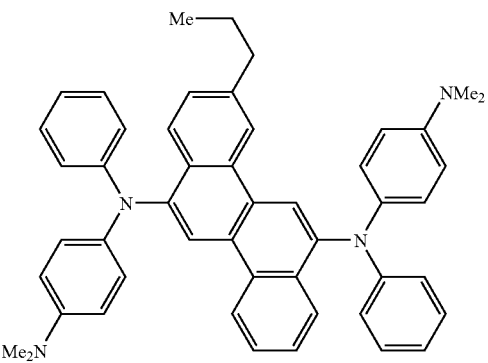
(43)
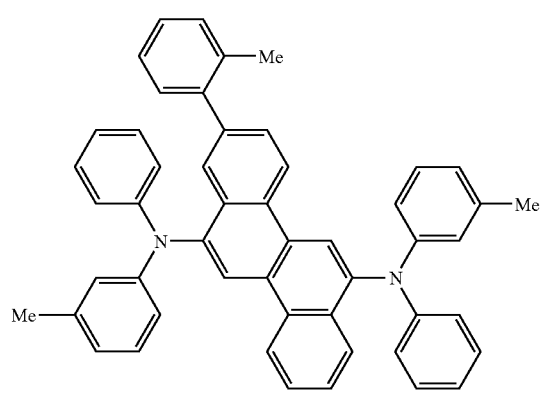
(44)
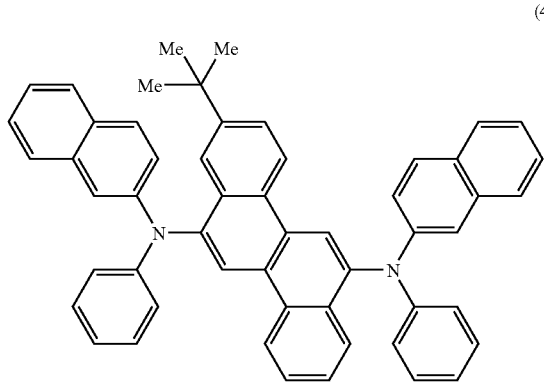

(45)
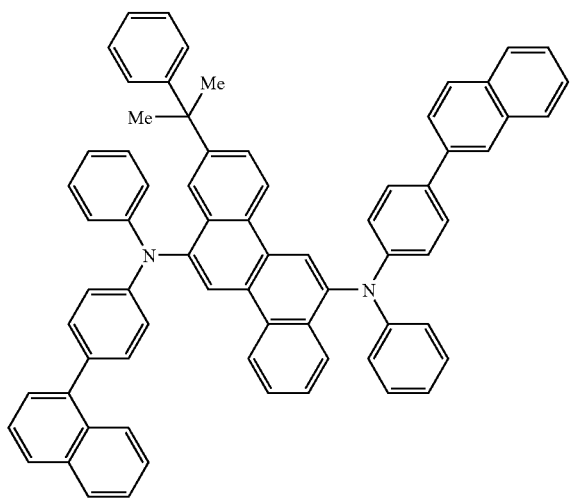
(46)
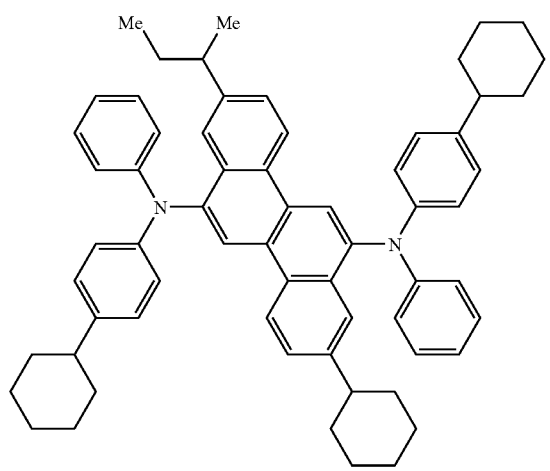
(47)
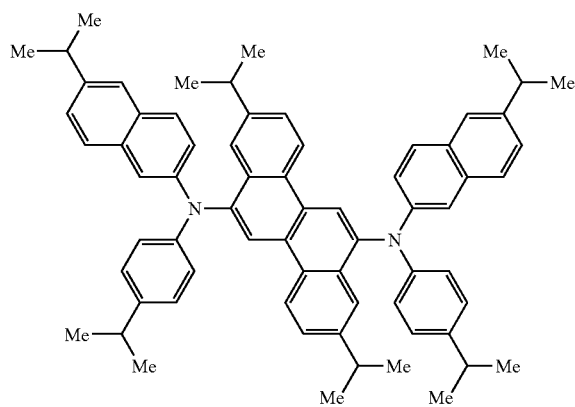
(48)
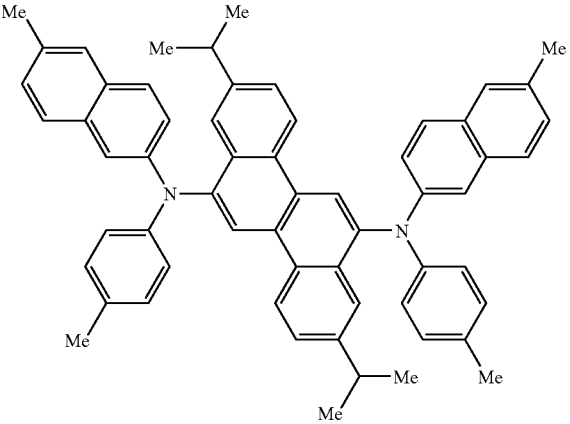
(49)
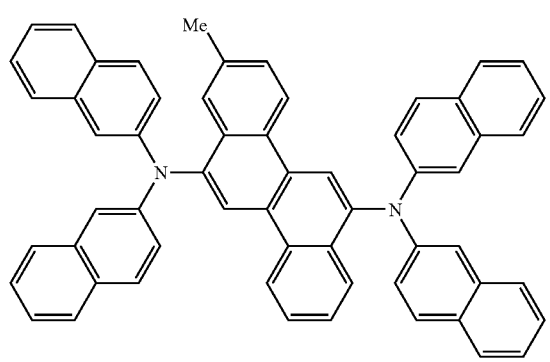
(50)
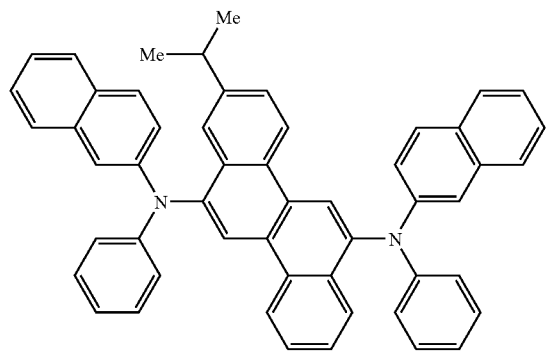

-continued
(51)
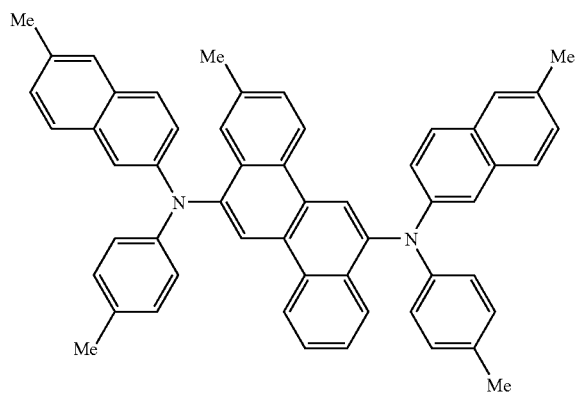
(52)
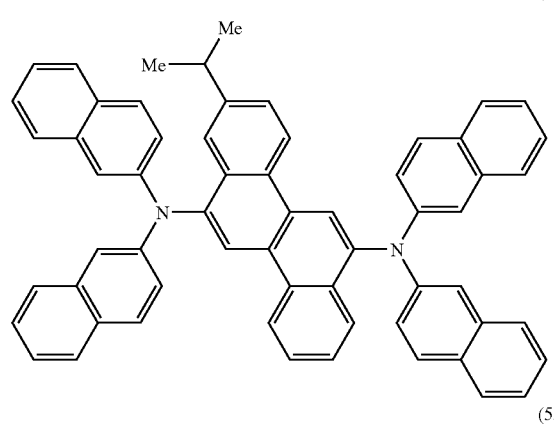
(53)
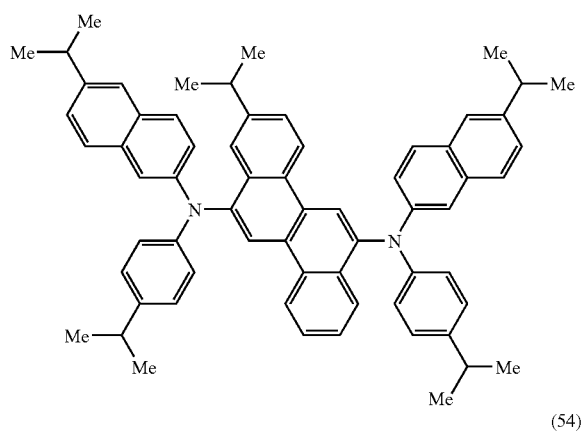
(54)
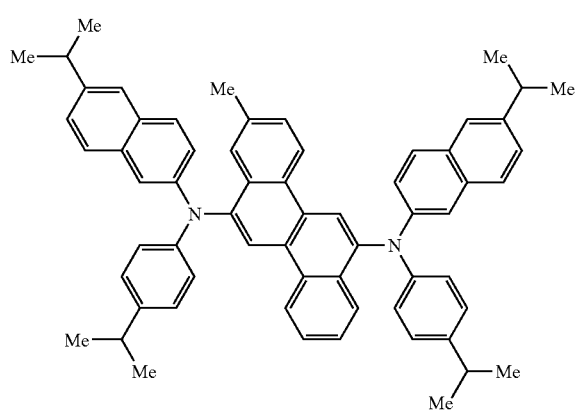
-continued
(55)
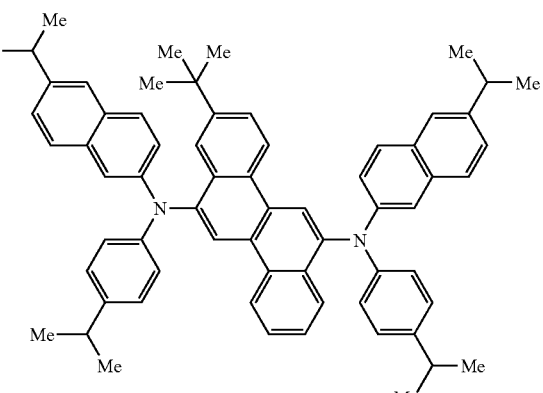
(56)
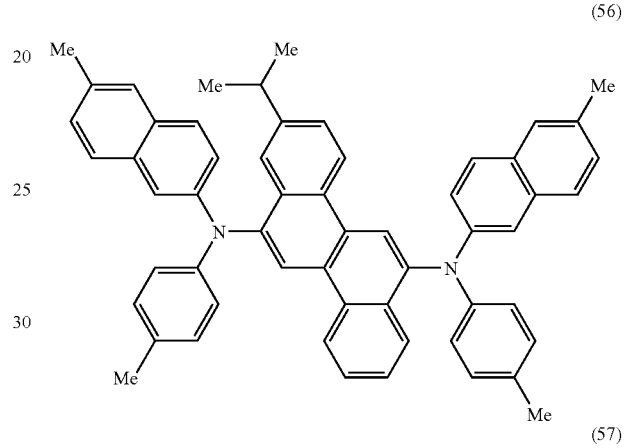
(57)
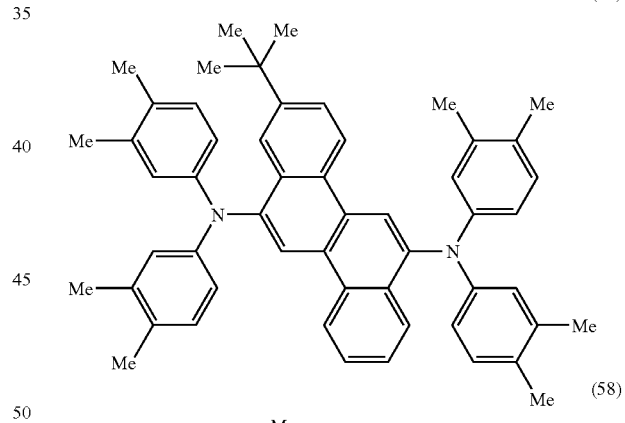
(58)
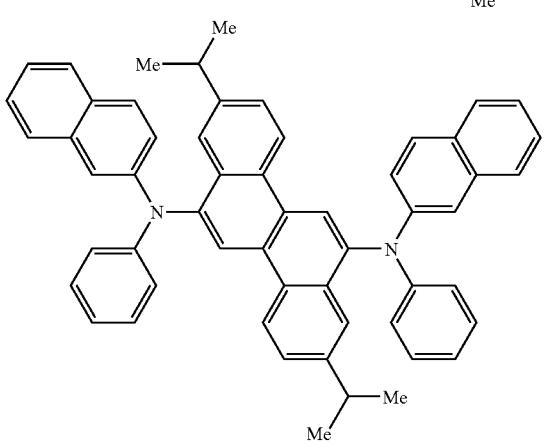

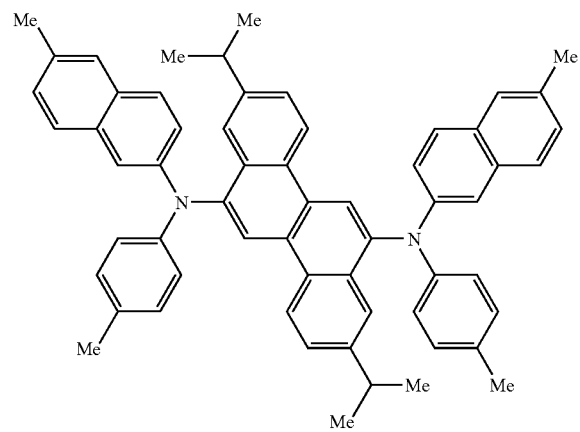
(59)
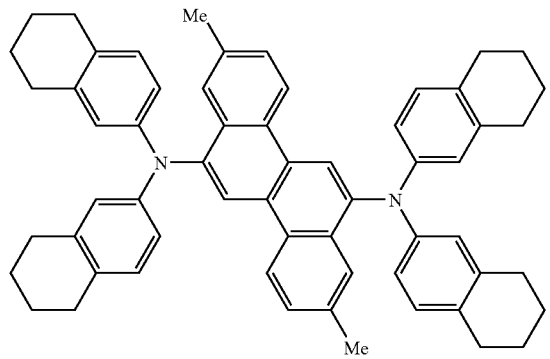
(62)
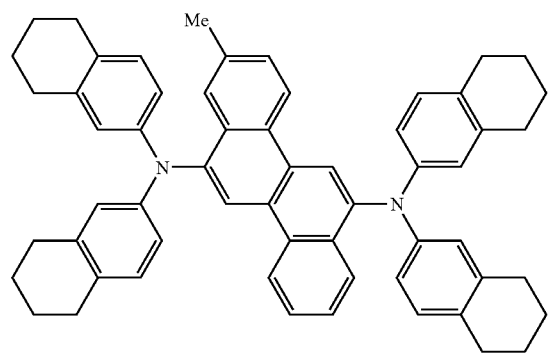
(60)
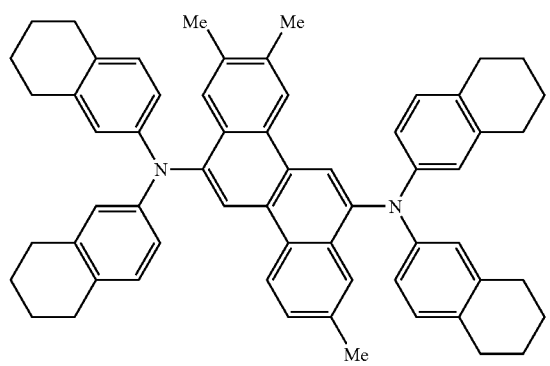
(63)
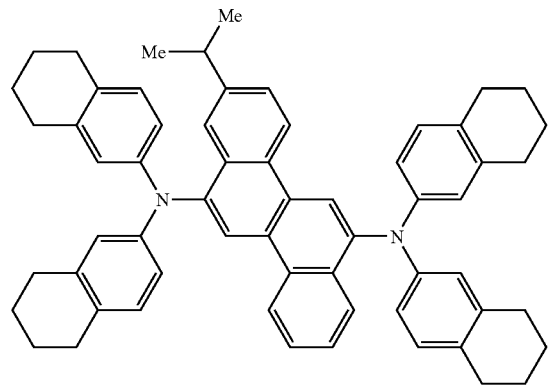
(61)
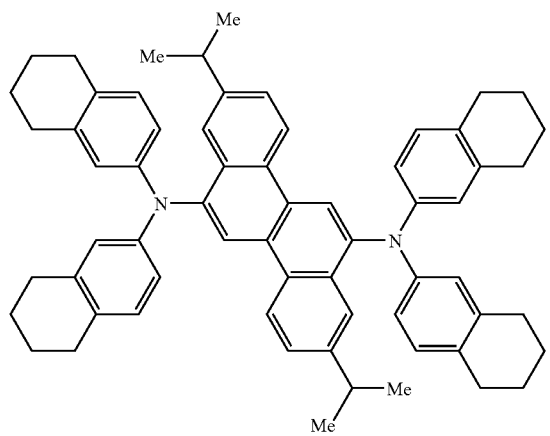
(64)

-continued
(65)
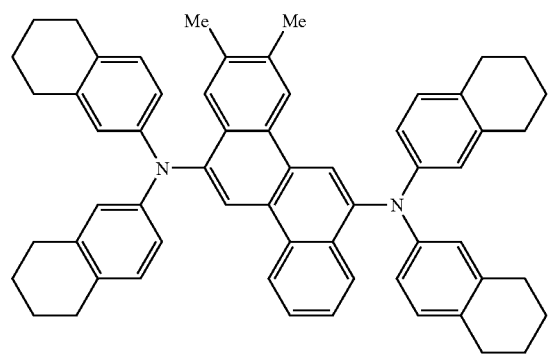
(66)
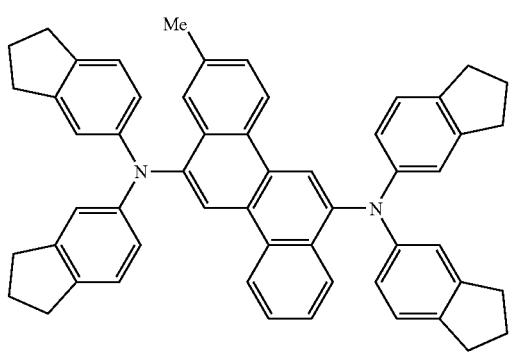
(67)
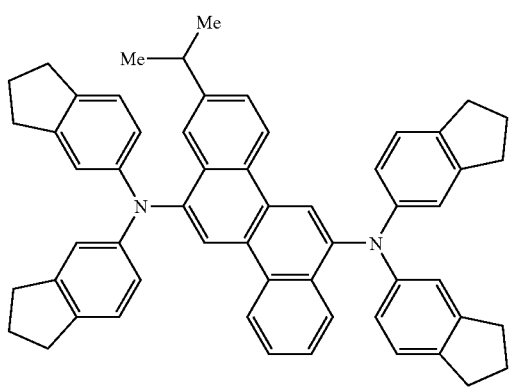
-continued
(68)
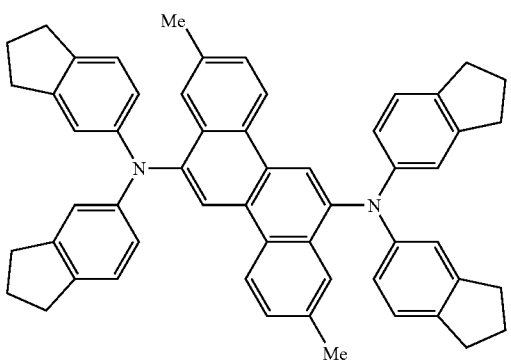
(69)
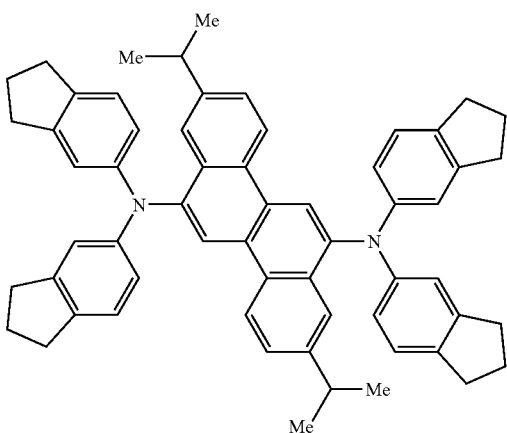
(70)
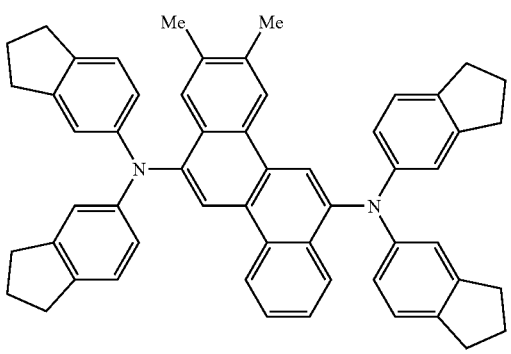

-continued
(71)
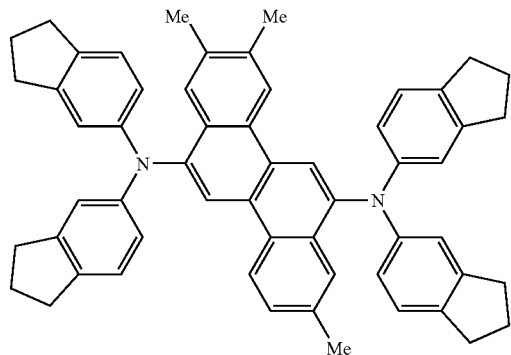
(72)
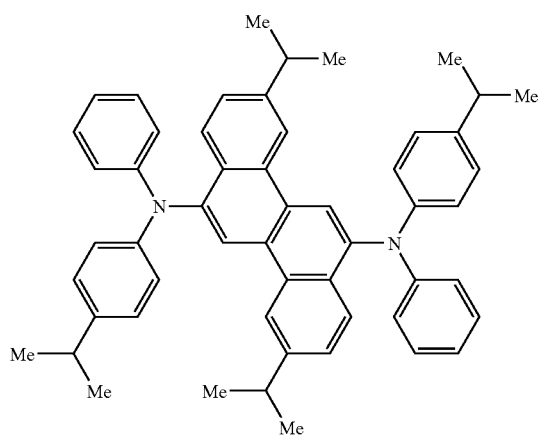
(73)
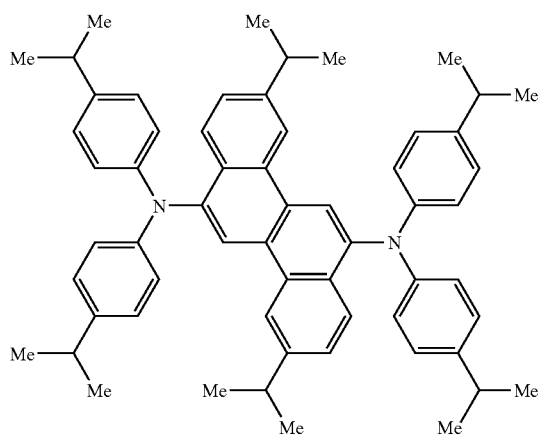
-continued
(74)
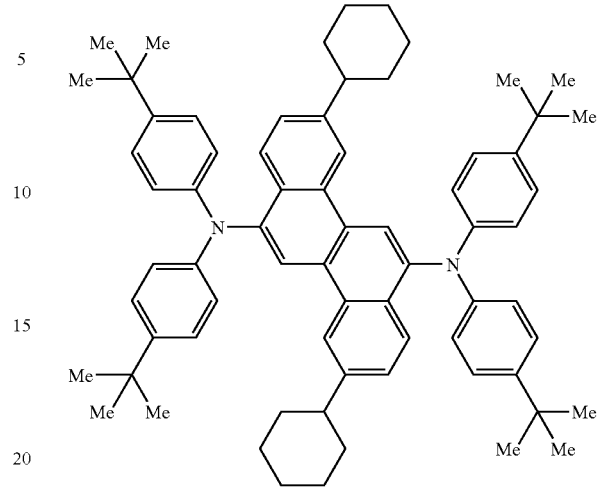
(75)
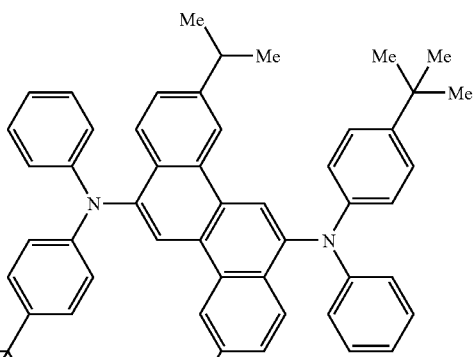
(76)
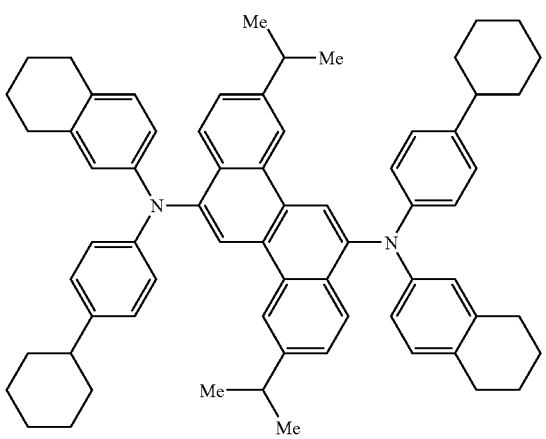

(77) 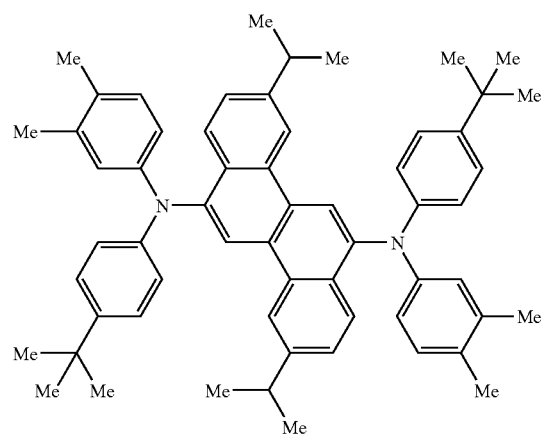
(78) 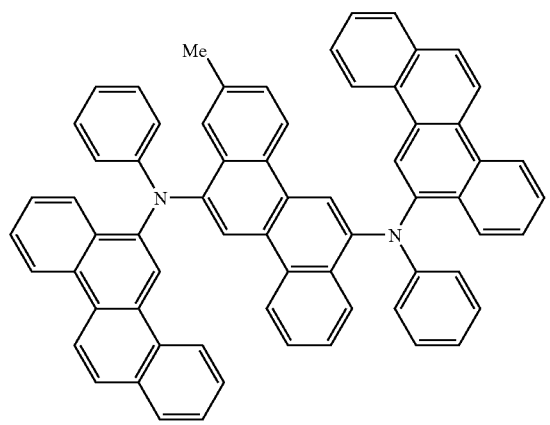
(79) 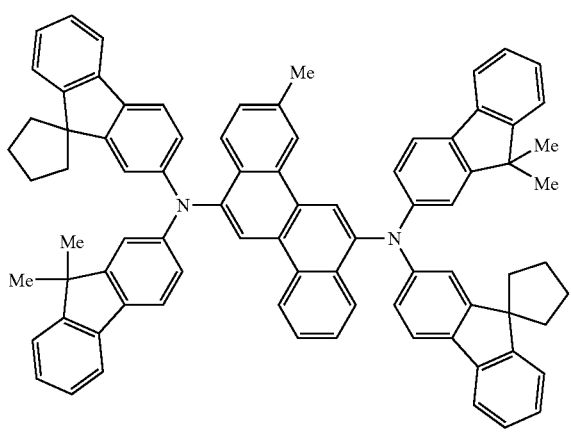
(80) 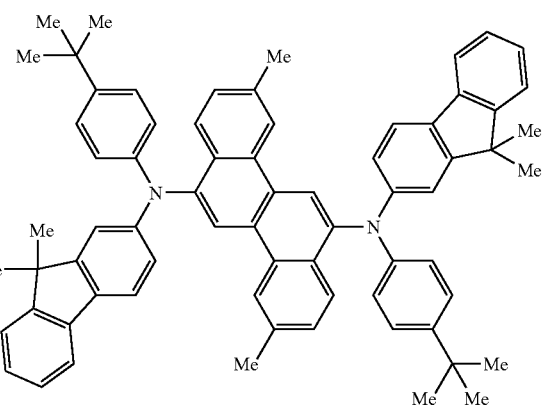
(81) 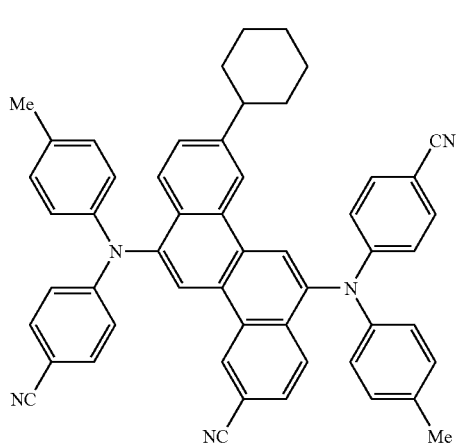
(82) 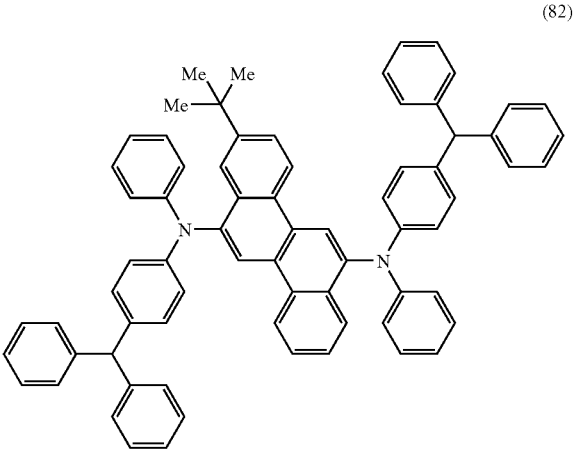

-continued
(83)
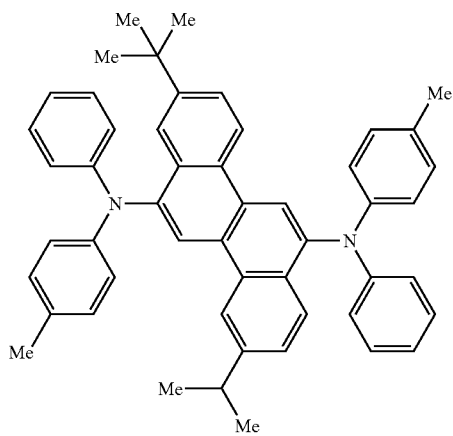
(84)
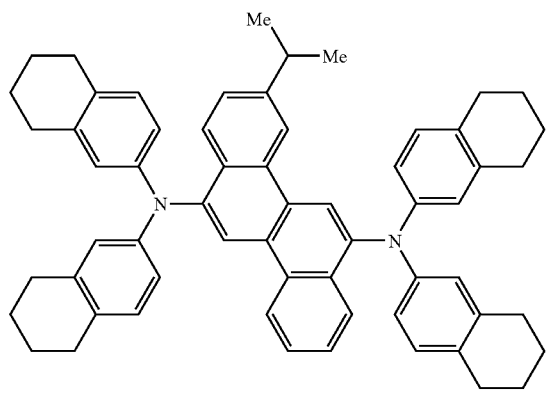
(85)
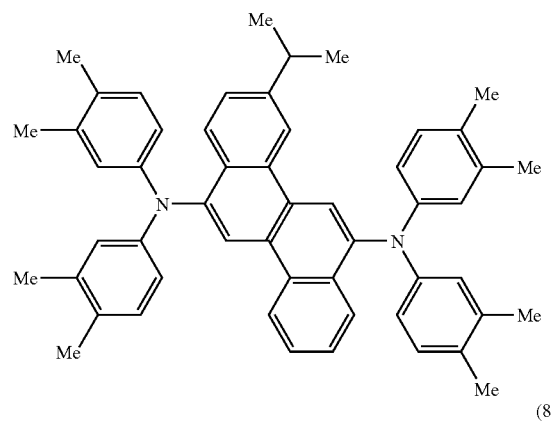
(86)
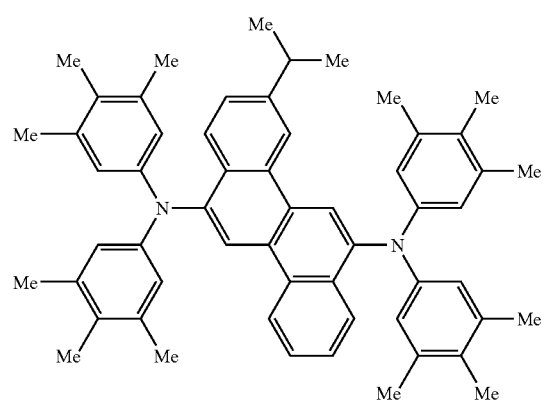
-continued
(87)
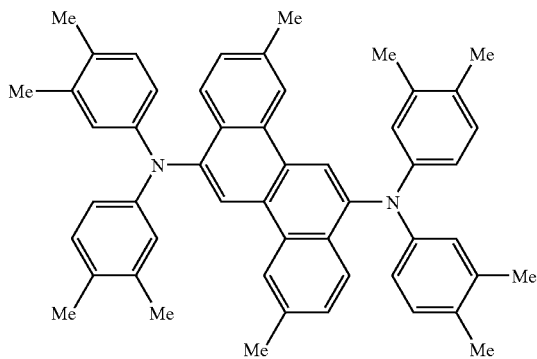
(88)
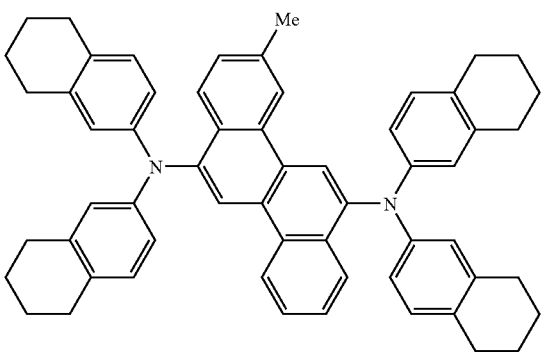
(89)
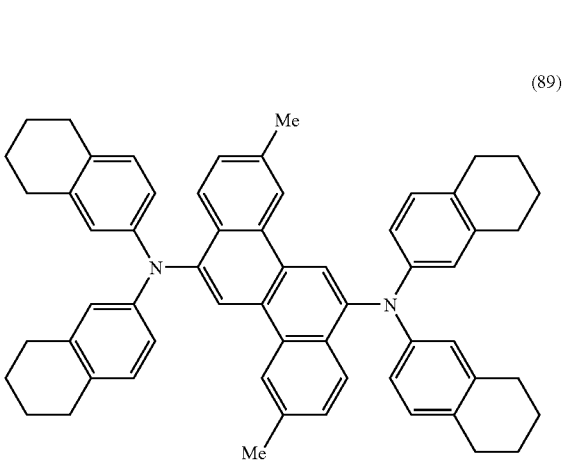
(90)
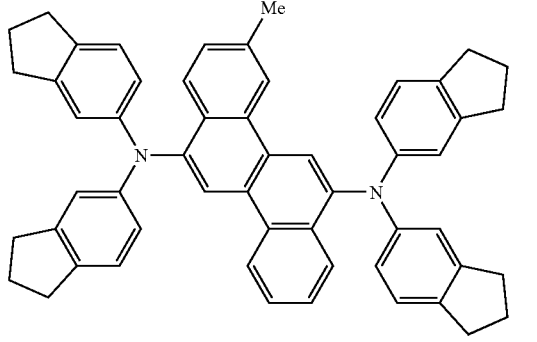

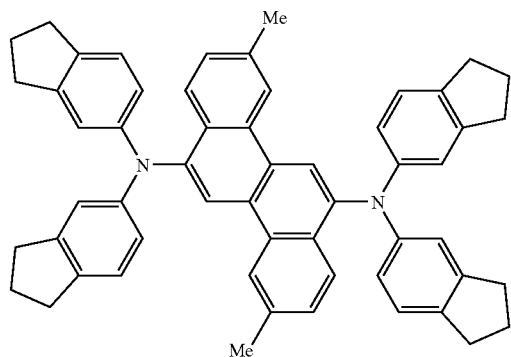
(91)
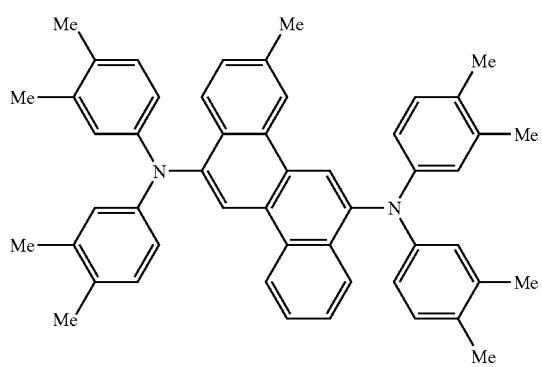
(92)
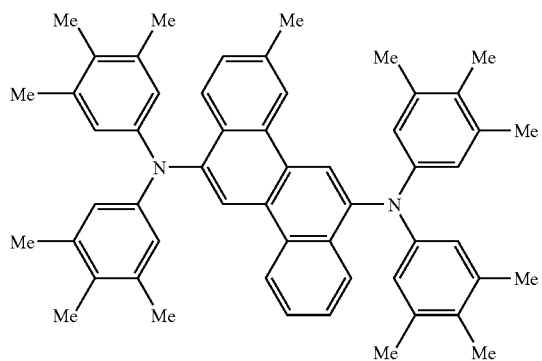
(93)
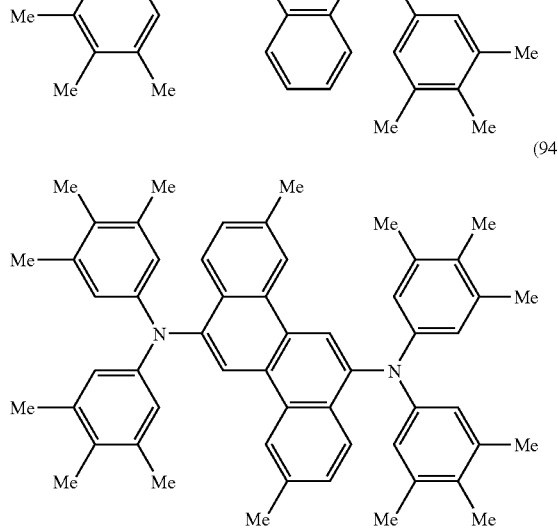
(94)
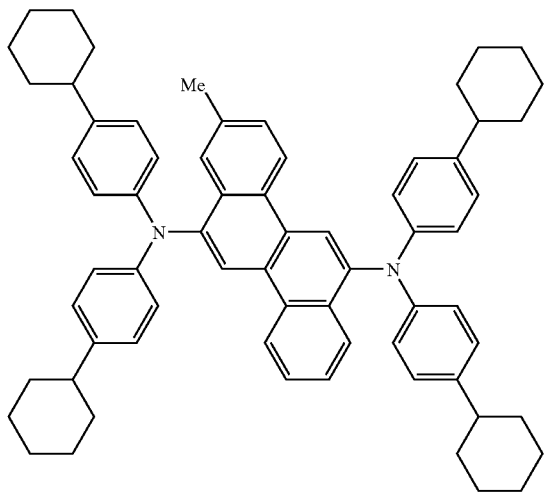
(95)
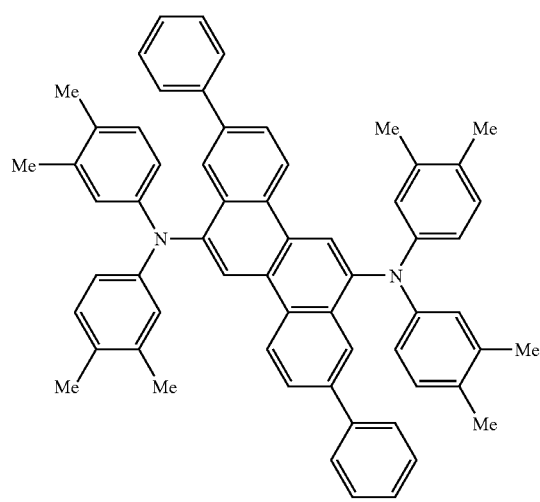
(96)
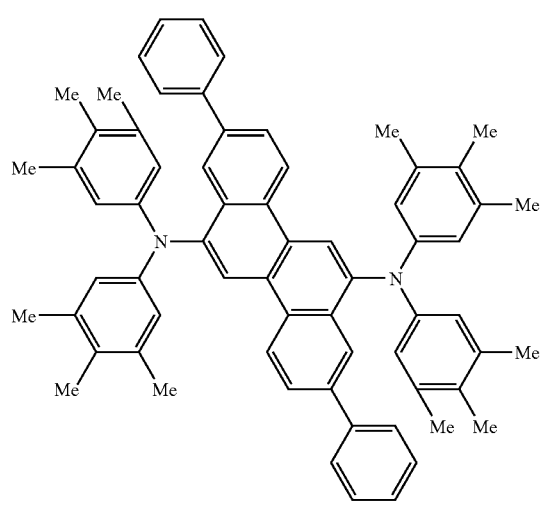
(97)

(98)
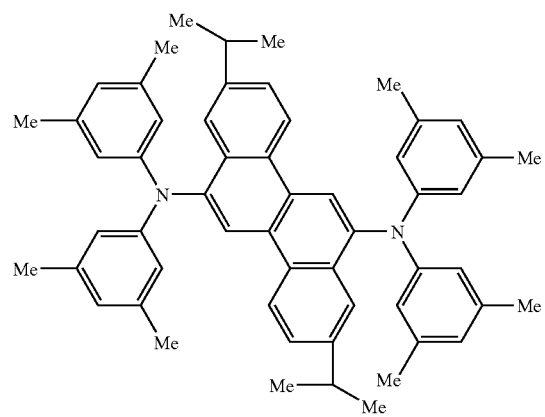
(102)
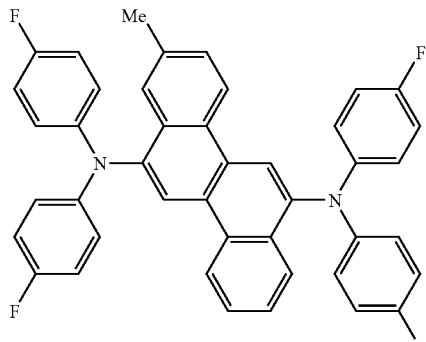
(99)
(103)
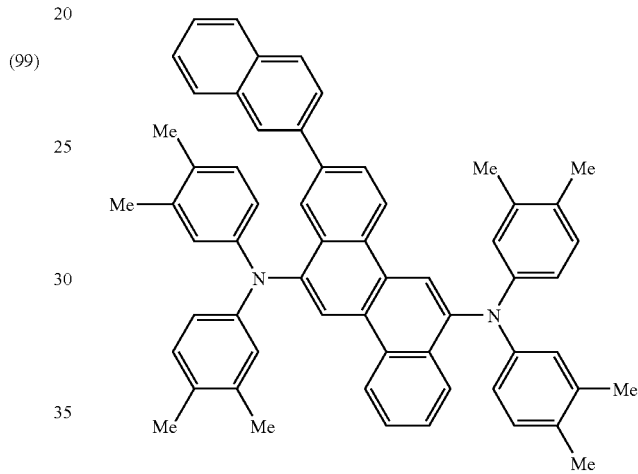
(100)
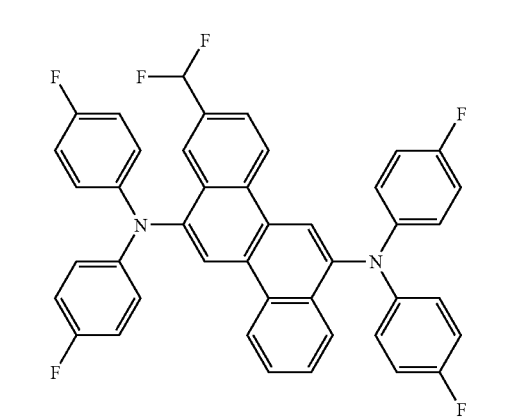
(104)
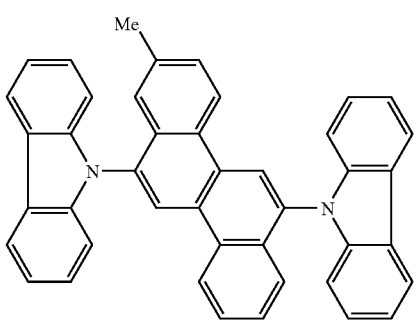
(101)
(105)
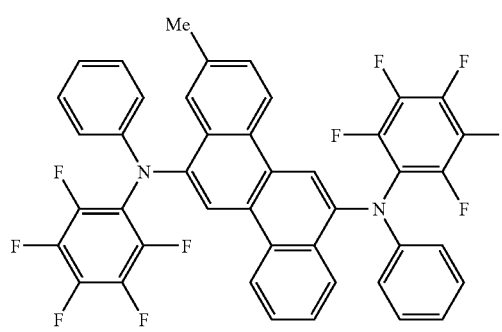

(105)
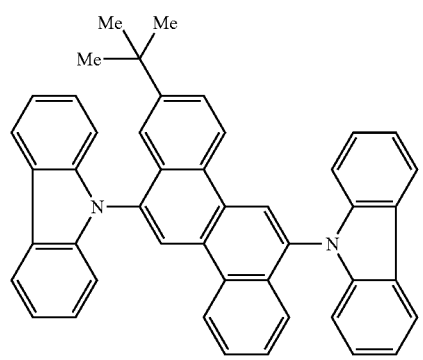
(106)
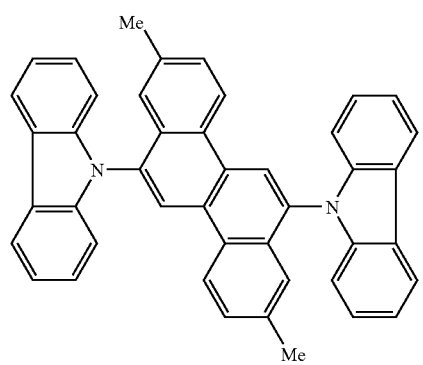
(107)
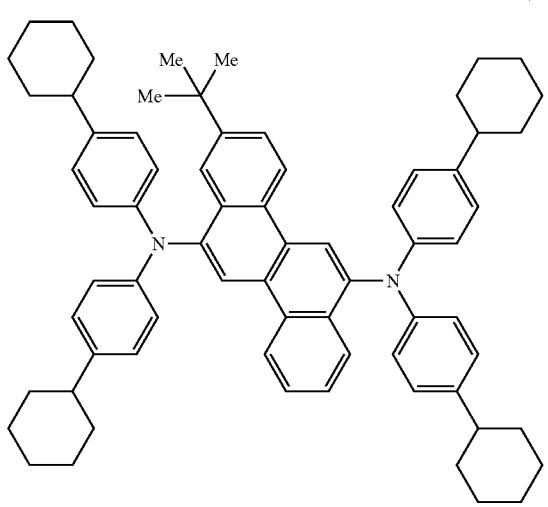
(108)
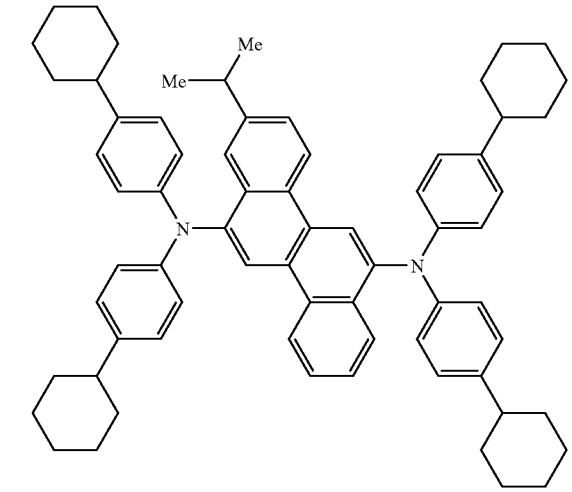
(109)
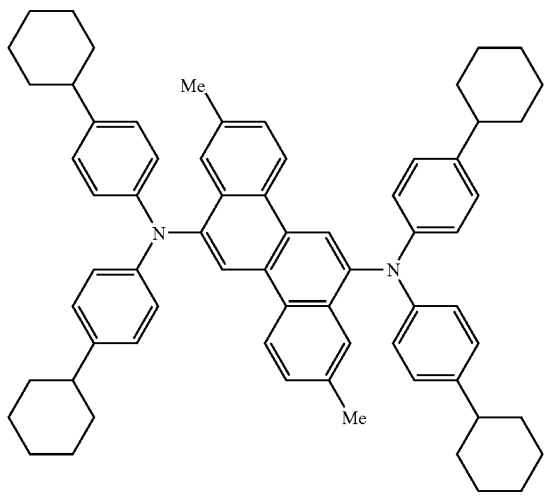
(110)
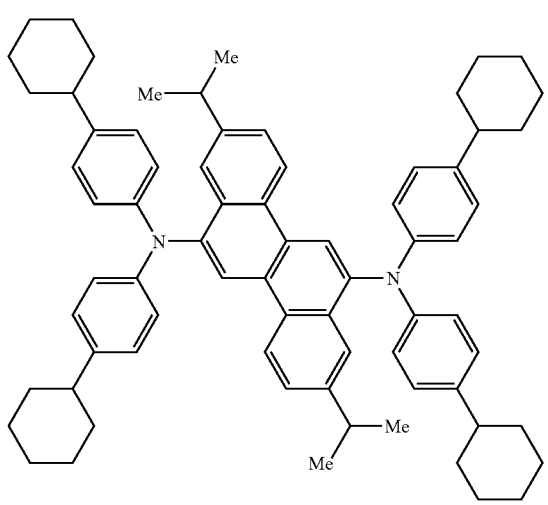

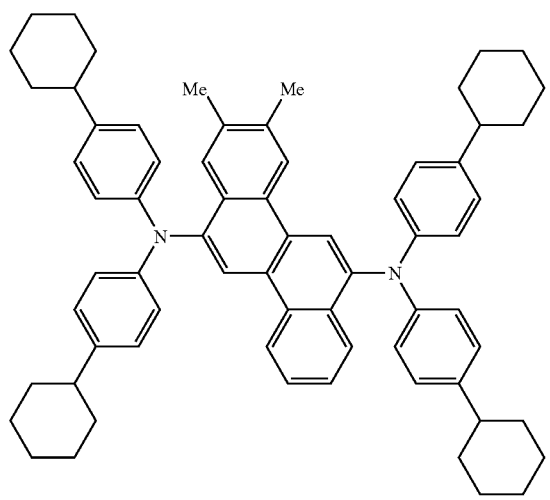
(111)
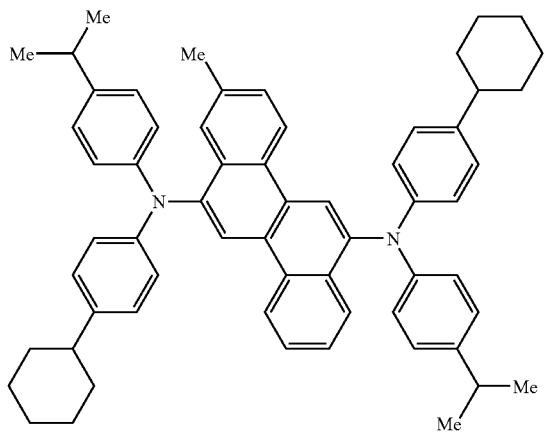
(114)
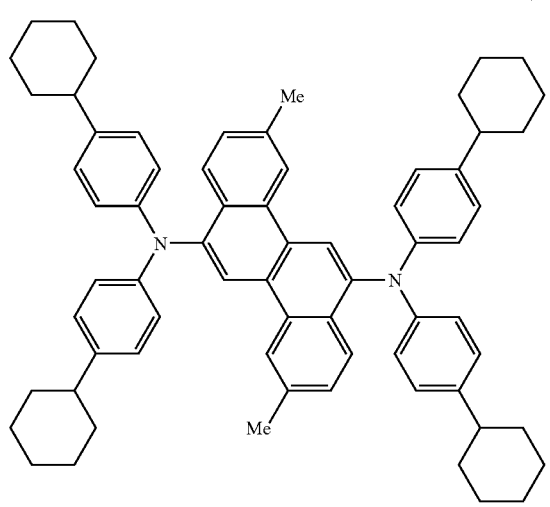
(112)
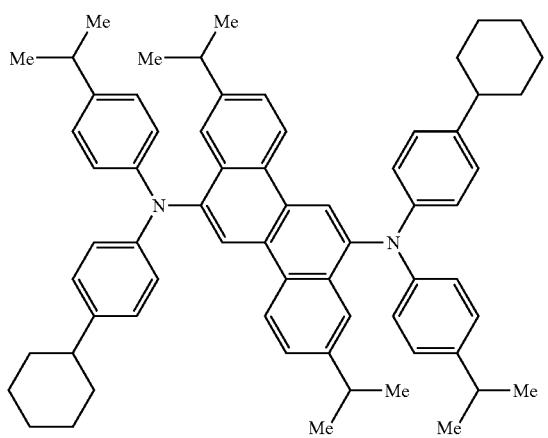
(115)
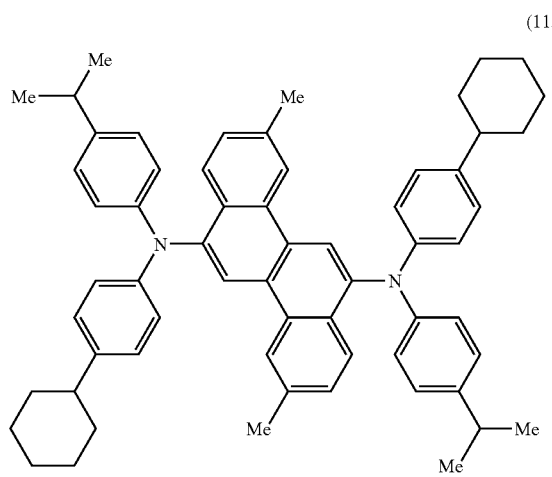
(113)
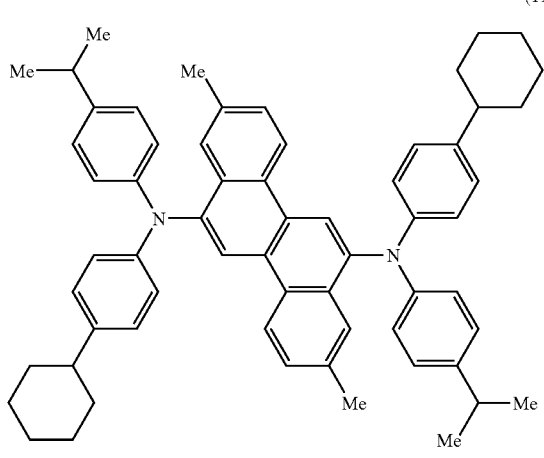
(116)

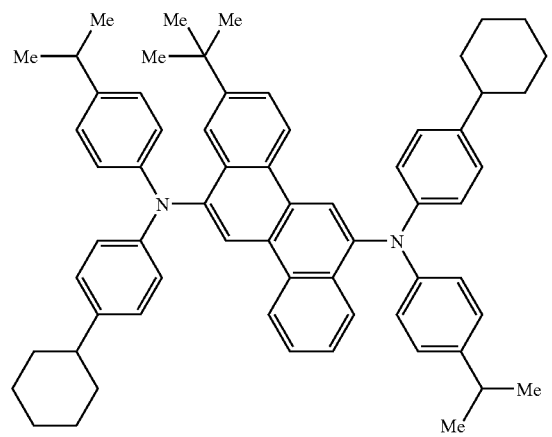
(117)
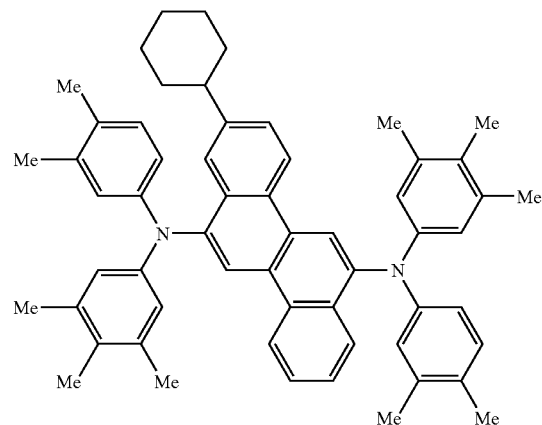
(120)
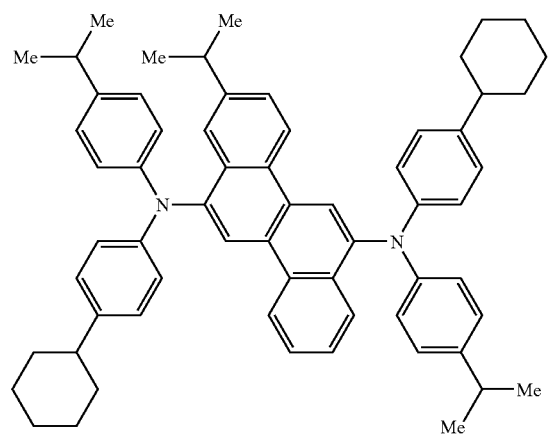
(118)
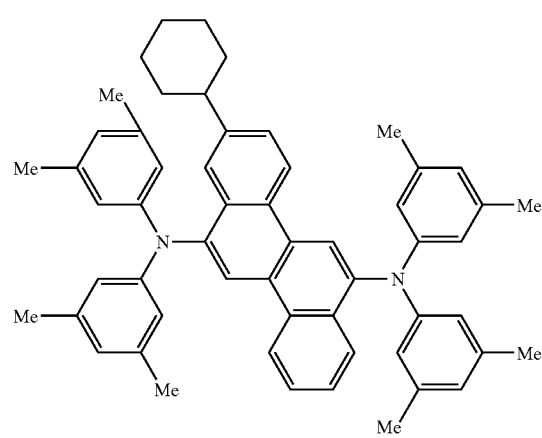
(121)
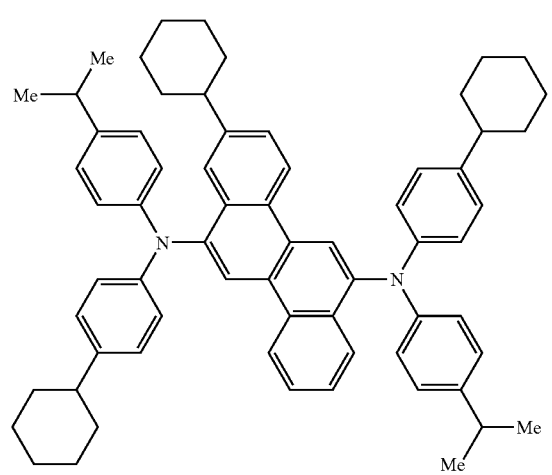
(119)
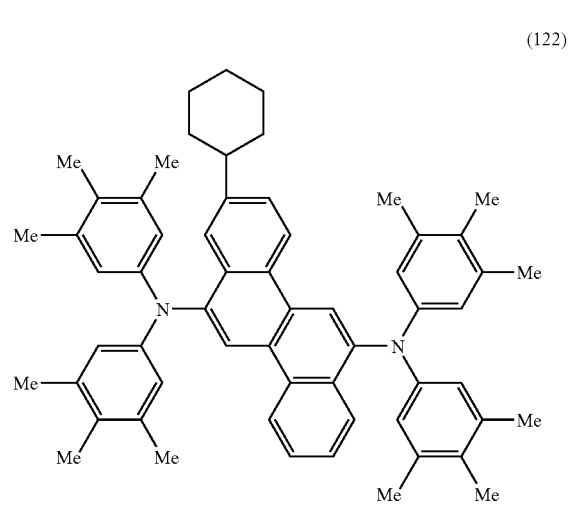
(122)

-continued
(123)
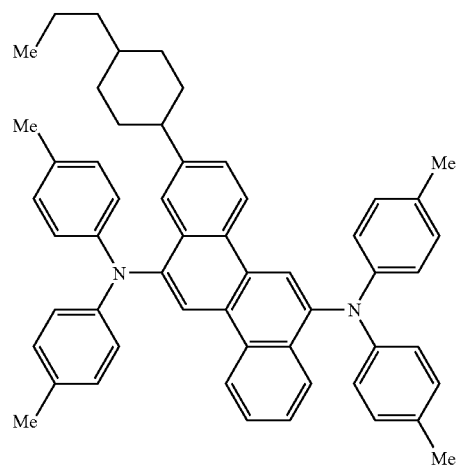
(124)
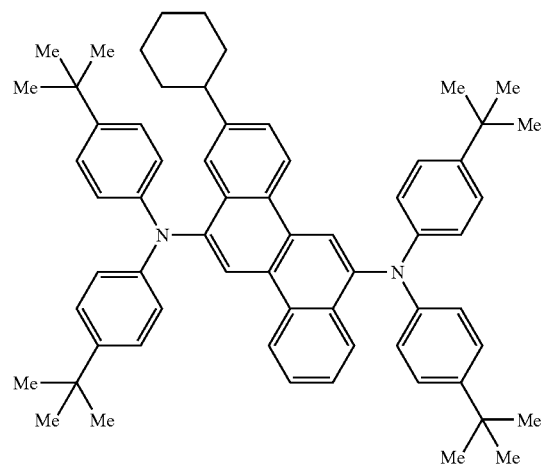
(125)
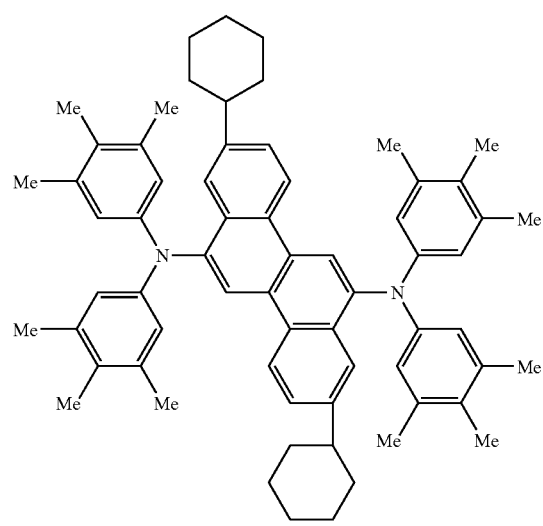
(126)
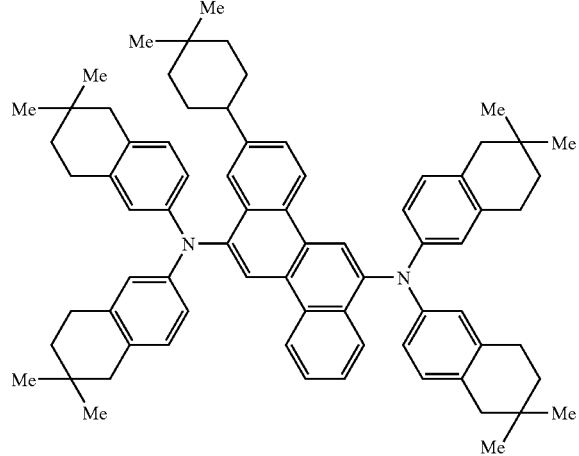
(127)
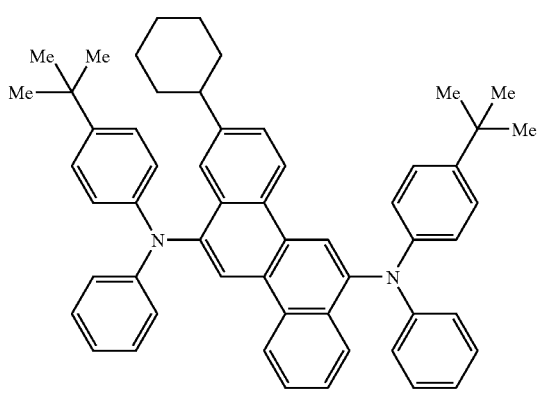
(128)
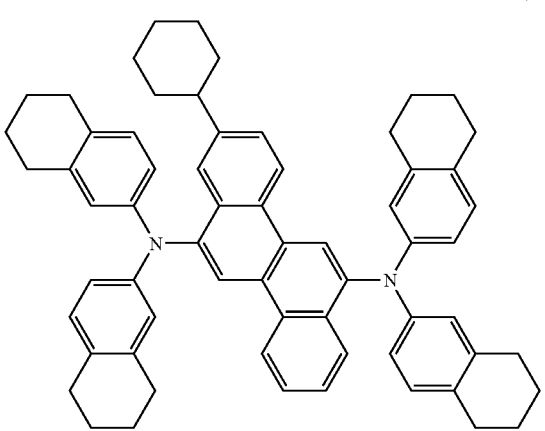

(129)
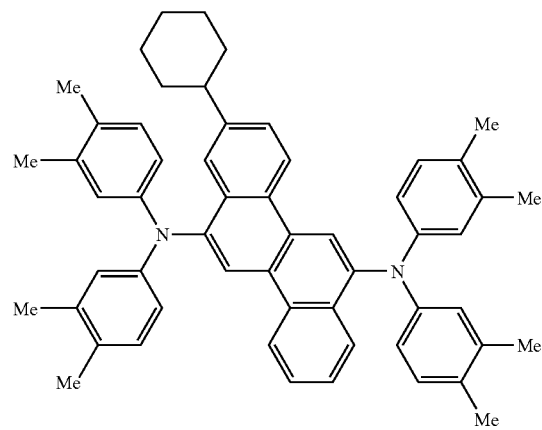
(130)
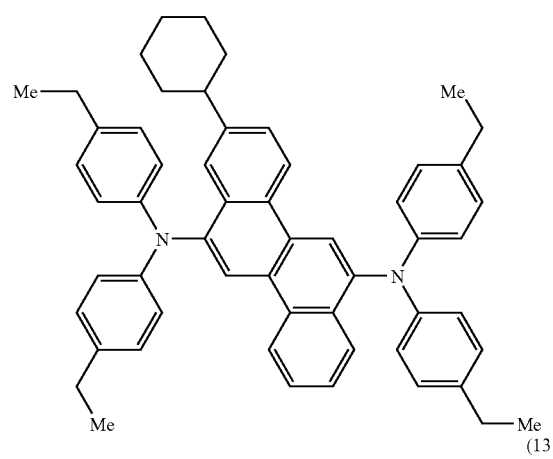
(131)
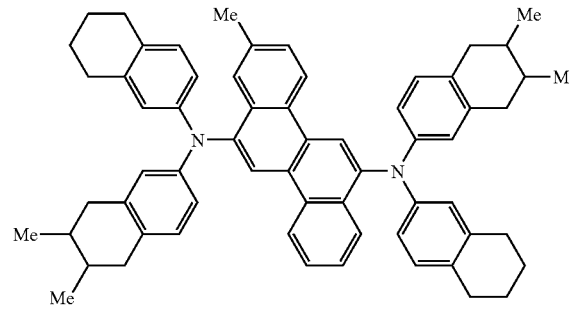
(132)
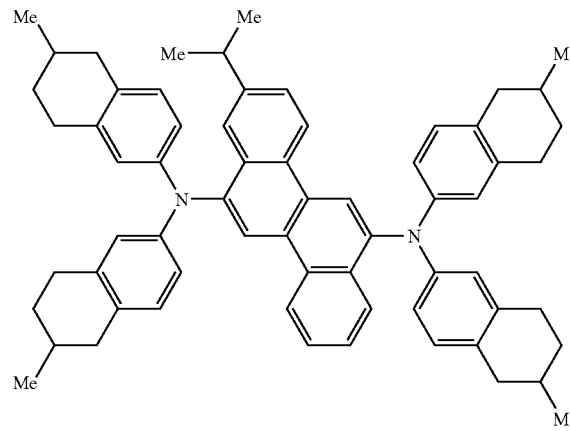
(133)
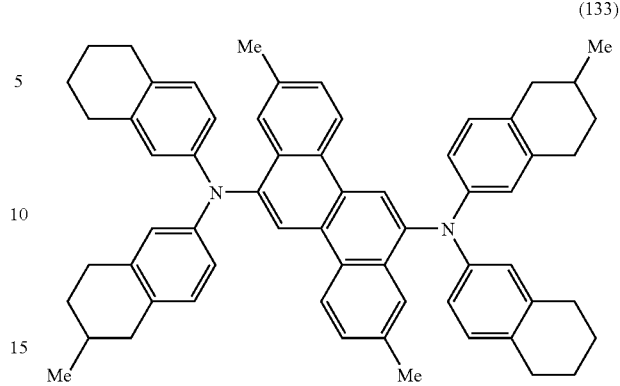
(134)
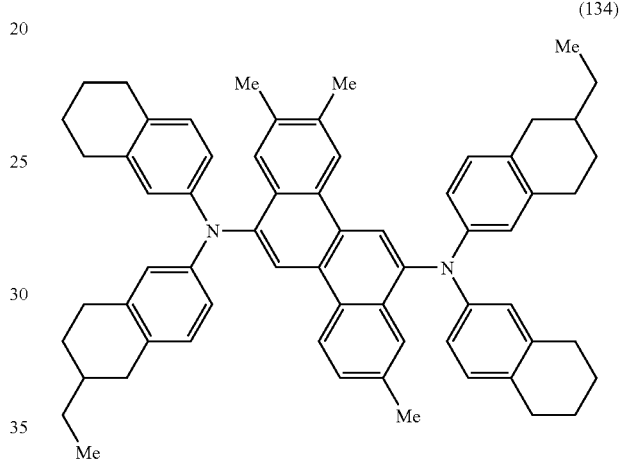
(135)
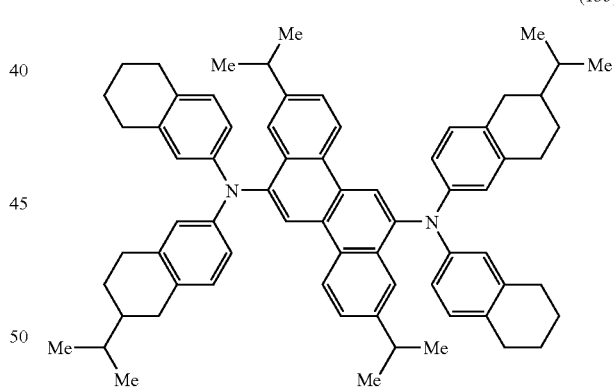
(136)
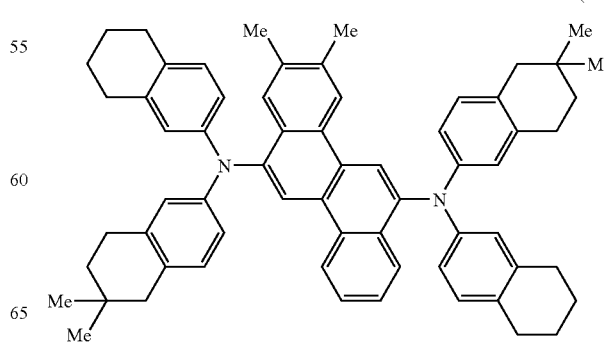

(137)
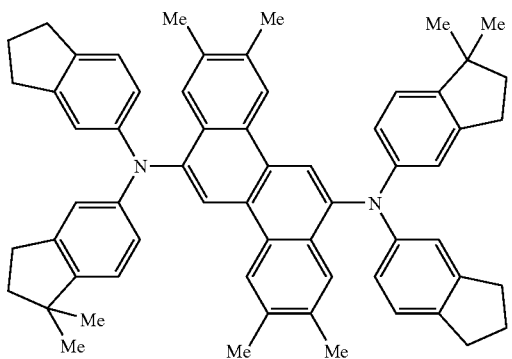
(138)
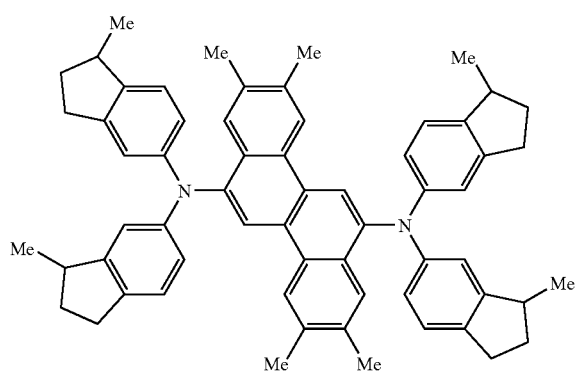
(139)
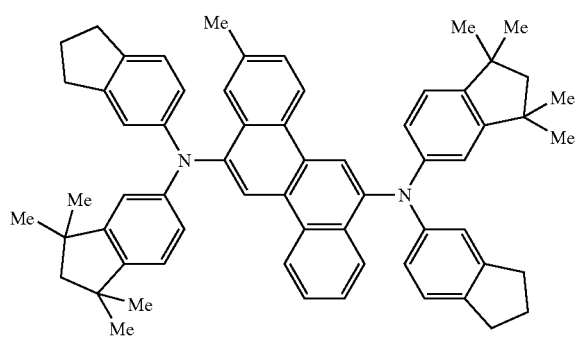
(140)
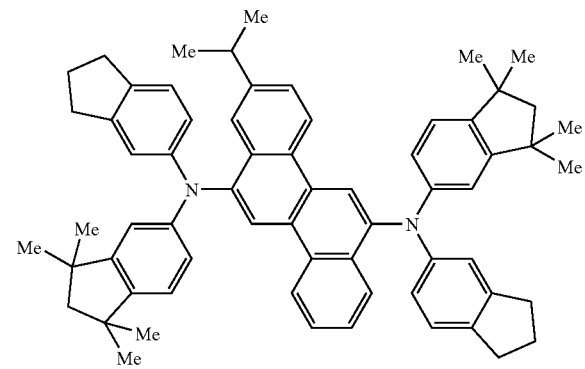
(141)
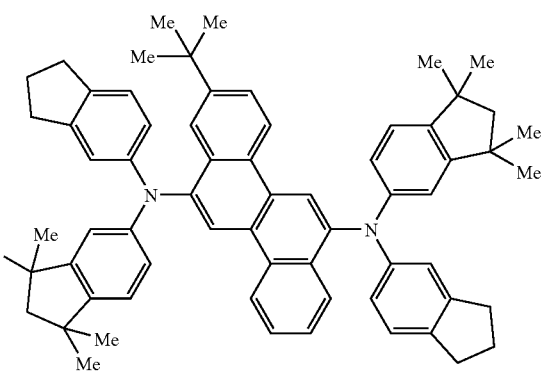
(142)
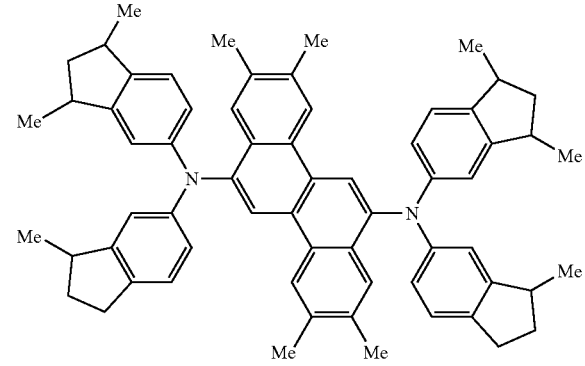
(143)
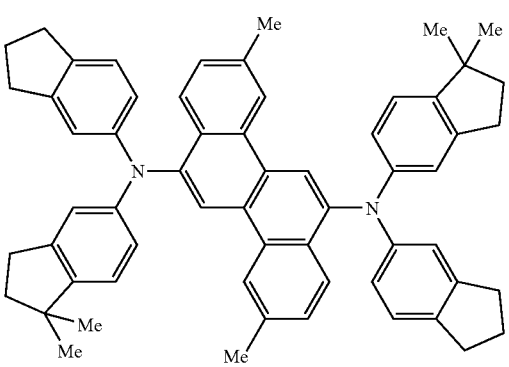

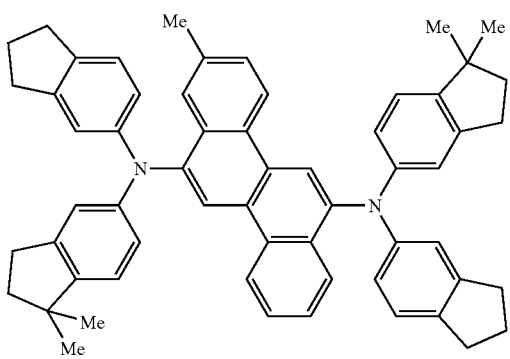
(144)
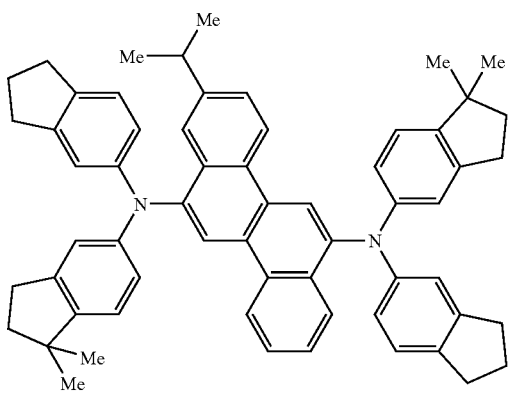
(145)
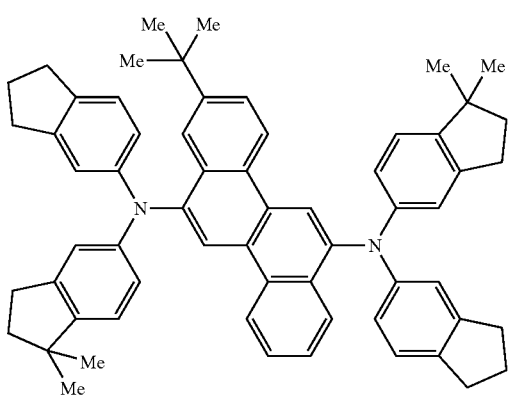
(146)
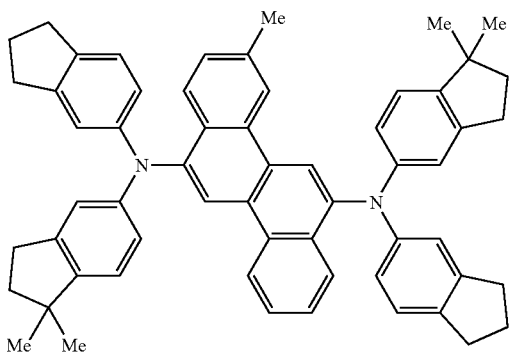
(147)
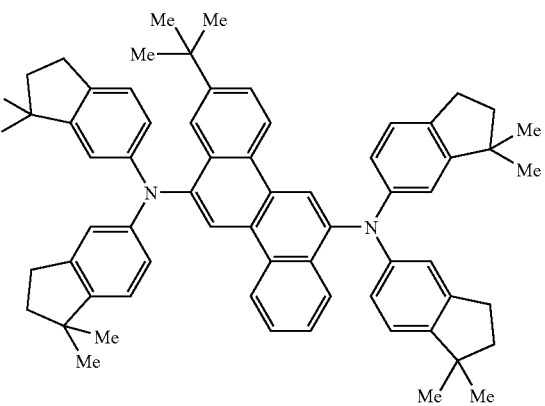
(148)
(149)
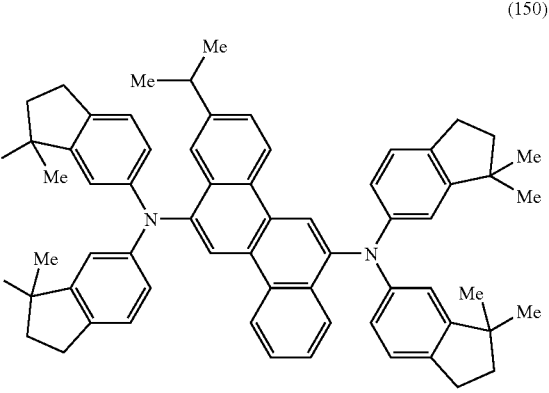
(150)

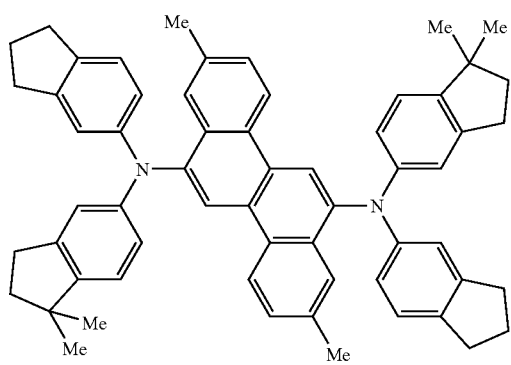
(151)
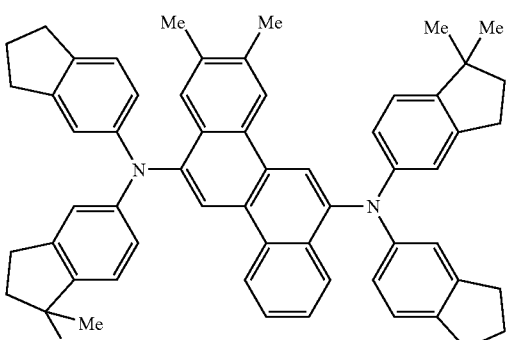
(153)
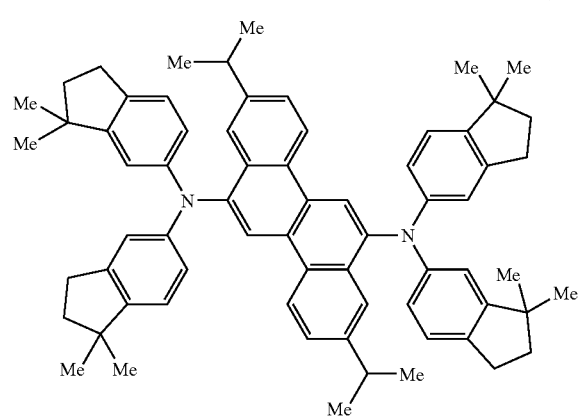
(152)
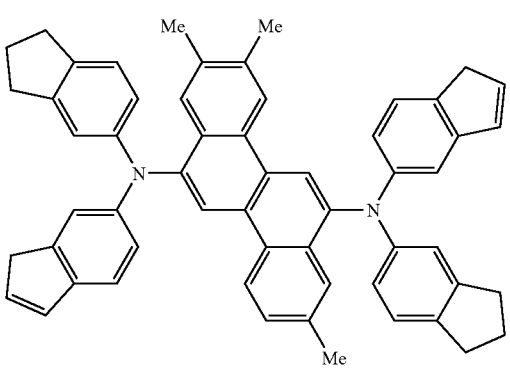
(154)
TABLE 1
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-1 | Methyl | H | H | H | phenyl | o-tolyl | phenyl | o-tolyl |
| D-2 | Methyl | H | H | H | phenyl | m-tolyl | phenyl | m-tolyl |
| D-3 | Methyl | H | H | H | m-tolyl | o-tolyl | m-tolyl | o-tolyl |
| D-4 | Methyl | H | H | H | phenyl | p-tolyl | phenyl | p-tolyl |

TABLE 1-continued

| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-5 | Methyl | H | H | H | 3,5-dimethylphenyl | 2,4-dimethylphenyl | 3,5-dimethylphenyl | 2,4-dimethylphenyl |
| D-6 | Methyl | H | H | H | 2,4,6-trimethylphenyl | 3,5-dimethylphenyl | 2,4,6-trimethylphenyl | 3,5-dimethylphenyl |
| D-7 | Methyl | H | H | H | 4-methylphenyl | 4-methylphenyl | 4-methylphenyl | 4-methylphenyl |
| D-8 | Methyl | H | H | H | 4-isopropylphenyl | 3,5-dimethylphenyl | 4-isopropylphenyl | 3,5-dimethylphenyl |
| D-9 | Methyl | H | H | H | 4-isopropylphenyl | 4-isopropylphenyl | 4-isopropylphenyl | 4-isopropylphenyl |
| D-10 | Methyl | H | H | H | 4-tert-butylphenyl | 4-tert-butylphenyl | 4-tert-butylphenyl | 4-tert-butylphenyl |
| D-11 | Methyl | H | H | H | 4-methylphenyl | 4-tert-butylphenyl | 4-methylphenyl | 4-tert-butylphenyl |
| D-12 | Methyl | H | H | H | 4-methylphenyl | 4-isopropylphenyl | 4-methylphenyl | 4-isopropylphenyl |

TABLE 2
| | $R_1$ | $R_2$ | $R_3$ | $R_4$ |  (A₁)a |  (A₂)b |  (A₃)c |  (A₄)d |
|---|---|---|---|---|---|---|---|---|
| D-13 | Methyl | H | H | H |  |  |  |  |
| D-14 | Methyl | H | H | H |  |  |  |  |
| D-15 | Methyl | H | H | H |  |  | 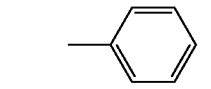 |  |
| D-16 | Methyl | H | H | H |  |  |  |  |
| D-17 | Methyl | H | H | H |  | | | |
| D-18 | Methyl | H | H | H |  | | | |
| D-19 | Methyl | H | H | H |  |  | | |

TABLE 2-continued
| | $R_1$ | $R_2$ | $R_3$ | $R_4$ | $-(A_1)a$ | $-(A_2)b$ | $-(A_3)c$ | $-(A_4)d$ |
|---|---|---|---|---|---|---|---|---|
| D-20 | Methyl | H | H | H | 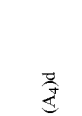 | 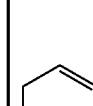 |  |  |
| D-21 | Methyl | H | H | H |  |  |  |  |
| D-22 | Methyl | H | H | H | 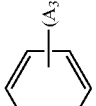 | 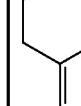 | 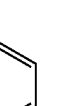 | 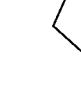 |
| D-23 | Methyl | H | H | H |  |  |  |  |
| D-24 | Methyl | H | H | H | 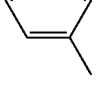 |  | 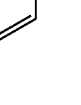 |  |

TABLE 3

| | (A₁)a | (A₂)b | (A₃)c | (A₄)d |
|---|---|---|---|---|
| | R₁ R₂ R₃ R₄ | | | |
| D-25 | Methyl H H H | | | |
| D-26 | Methyl H H H | | | |
| D-27 | Methyl H H H | | | |
| D-28 | Methyl H H H | | | |
| D-29 | Methyl H H H | | | |
| D-30 | Methyl H H H | | | |
| D-31 | Methyl H H H | | | |

TABLE 3-continued

TABLE 4
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-37 | Methyl | H | H | H | 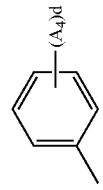 |  | 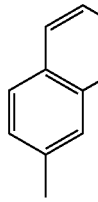 | 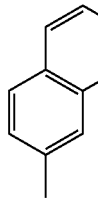 |
| D-38 | Methyl | H | H | H | 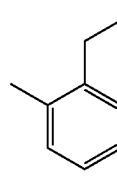 | 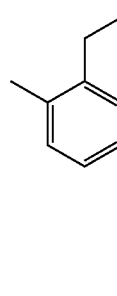 | 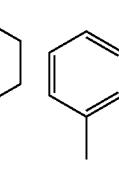 | 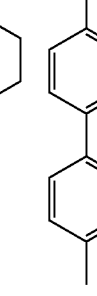 |
| D-39 | Methyl | H | H | H | 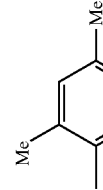 | 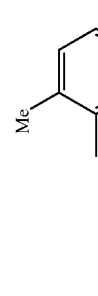 | 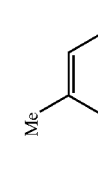 | 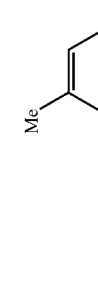 |
| D-40 | Methyl | H | H | H | | | | |
| D-41 | Methyl | H | H | H | | | | |
| D-42 | Methyl | H | H | H | | | | |

TABLE 4-continued

| | R₁ | R₂ | R₃ | R₄ | (A₁)a | (A₂)b | (A₃)c | (A₄)d |
|---|---|---|---|---|---|---|---|---|
| D-43 | Methyl | H | H | H | | | | |
| D-44 | Methyl | H | H | H | | | | |
| D-45 | Methyl | H | H | H | | | | |
| D-46 | Methyl | H | H | H | | | | |
| D-47 | Methyl | H | H | H | | | | |
| D-48 | Methyl | H | H | H | | | | |

TABLE 5
| | R₁ | R₂ | R₃ | R₄ | (A₁)a | (A₂)b | (A₃)c | (A₄)d |
|---|---|---|---|---|---|---|---|---|
| D-49 | Iso-propyl | H | H | H | 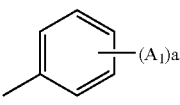 |  |  |  |
| D-50 | Iso-propyl | H | H | H | 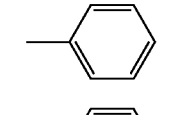 |  | 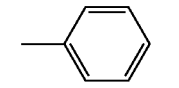 |  |
| D-51 | Iso-propyl | H | H | H | 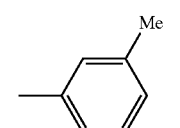 | 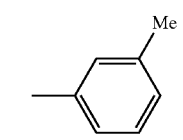 |  |  |
| D-52 | Iso-propyl | H | H | H | 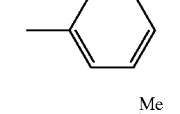 | 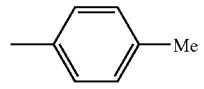 |  | 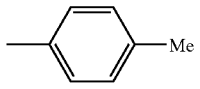 |
| D-53 | Iso-propyl | H | H | H |  | 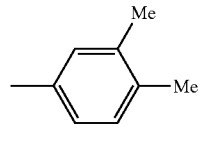 | 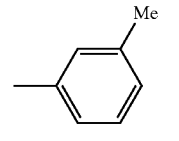 | 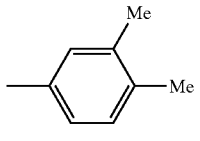 |
| D-54 | Iso-propyl | H | H | H | 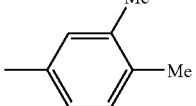 |  |  | 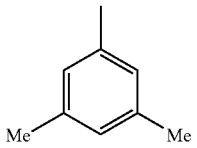 |
| D-55 | Iso-propyl | H | H | H |  | 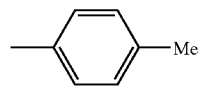 | 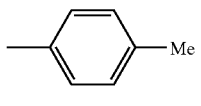 | 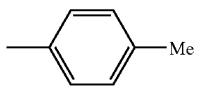 |
| D-56 | Iso-propyl | H | H | H |  |  | 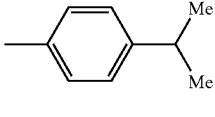 | 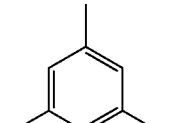 |
| D-57 | Iso-propyl | H | H | H | 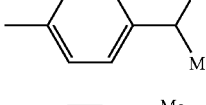 | 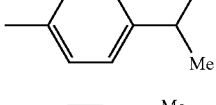 | 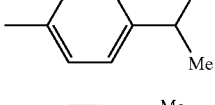 | 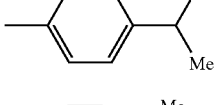 |
| D-58 | Iso-propyl | H | H | H | 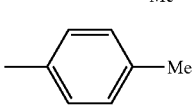 | 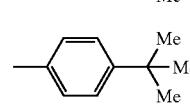 | 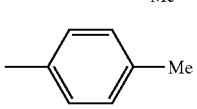 | 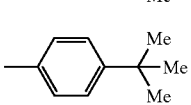 |
| D-59 | Iso-propyl | H | H | H | 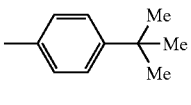 | 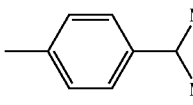 | 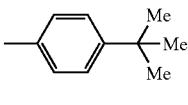 | 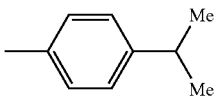 |
| D-60 | Iso-propyl | H | H | H |  |  |  |  |

TABLE 6

TABLE 6-continued
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-68 | Isopropyl | H | H | H | 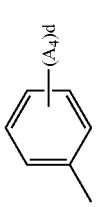 |  | 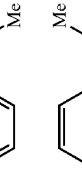 |  |
| D-69 | Isopropyl | H | H | H | 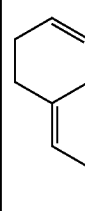 |  |  |  |
| D-70 | Isopropyl | H | H | H | 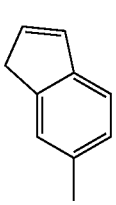 |  |  |  |
| D-71 | Isopropyl | H | H | H | 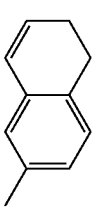 | 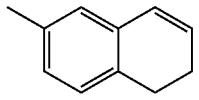 | 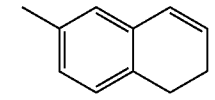 | 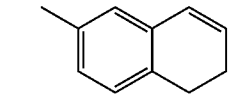 |
| D-72 | Isopropyl | H | H | H | 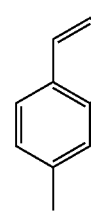 |  |  |  |

TABLE 7

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-73 | Isopropyl | H | H | H | 2,6-Me,4-Me-phenyl | 2,4-diMe-phenyl | 2,6-diMe,4-Me-phenyl | 2,4-diMe-phenyl |
| D-74 | Isopropyl | H | H | H | phenyl | 4-(2-Me-2-Me-propyl)phenyl | phenyl | 4-(2-Me-2-Me-propyl)phenyl |
| D-75 | Isopropyl | H | H | H | 6-Me-naphthyl | 4-(1-Me-ethyl)phenyl | 6-Me-naphthyl | 4-(1-Me-ethyl)phenyl |
| D-76 | Isopropyl | H | H | H | 4-(2-Me-2-Me-propyl)phenyl | 4-cyclohexylphenyl | 4-(2-Me-2-Me-propyl)phenyl | 4-cyclohexylphenyl |
| D-77 | Isopropyl | H | H | H | 4-cyclohexylphenyl | 6-tetrahydronaphthyl | 4-cyclohexylphenyl | 6-tetrahydronaphthyl |
| D-78 | Isopropyl | H | H | H | 9,9-diMe-fluorenyl | 9,9-diMe-fluorenyl | 9,9-diMe-fluorenyl | 9,9-diMe-fluorenyl |

TABLE 7-continued
| | $R_1$ | $R_2$ | $R_3$ | $R_4$ | (A₁)a | (A₂)b | (A₃)c | (A₄)d |
|---|---|---|---|---|---|---|---|---|
| D-79 | Isopropyl | H | H | H | 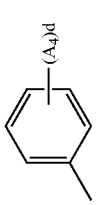 | 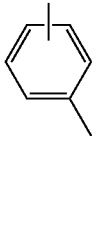 |  |  |
| D-80 | Isopropyl | H | H | H |  |  |  |  |
| D-81 | Isopropyl | H | H | H | 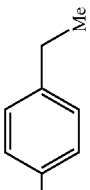 | 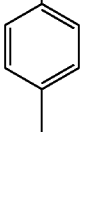 |  |  |
| D-82 | Isopropyl | H | H | H | 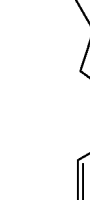 | 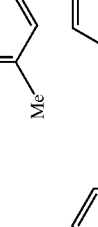 |  |  |
| D-83 | Isopropyl | H | H | H | 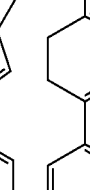 | 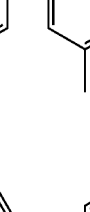 |  |  |
| D-84 | Isopropyl | H | H | H | 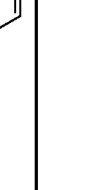 | 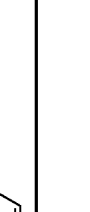 |  |  |

TABLE 8

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-85 | Isopropyl | H | H | H | 3,5-dimethylphenyl | 2,4-dimethylphenyl | 3,5-dimethylphenyl | 2,4-dimethylphenyl |
| D-86 | Isopropyl | H | H | H | phenyl | 4-(2-methylpropan-2-yl)phenyl | 4-methylphenyl | 4-(2-methylpropan-2-yl)phenyl |
| D-87 | Isopropyl | H | H | H | 6-methylnaphthyl | 4-(propan-2-yl)phenyl | 6-methylnaphthyl | 4-(propan-2-yl)phenyl |
| D-88 | Isopropyl | H | H | H | 4-cyclohexylphenyl | 4-cyclohexylphenyl | 4-cyclohexylphenyl | 4-cyclohexylphenyl |
| D-89 | Isopropyl | H | H | H | 4-cyclohexylphenyl | 6-tetralinyl | 4-cyclohexylphenyl | 6-tetralinyl |
| D-90 | Isopropyl | H | H | H | 9,9-dimethylfluorenyl | 9,9-dimethylfluorenyl | 9,9-dimethylfluorenyl | 9,9-dimethylfluorenyl |

TABLE 8-continued
| | R₁ | R₂ | R₃ | R₄ | (A₁)a | (A₂)b | (A₃)c | (A₄)d |
|---|---|---|---|---|---|---|---|---|
| D-91 | Isopropyl | H | H | H | 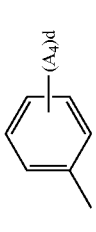 | 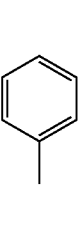 | 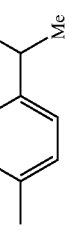 |  |
| D-92 | Isopropyl | H | H | H | 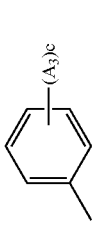 | 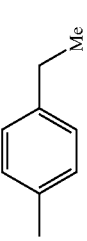 | 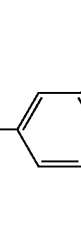 | 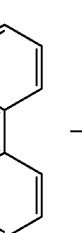 |
| D-93 | Isopropyl | H | H | H | 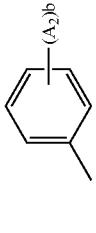 | 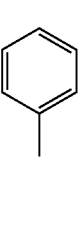 | 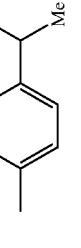 | 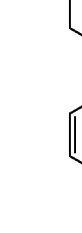 |
| D-94 | Isopropyl | H | H | H | 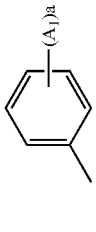 | 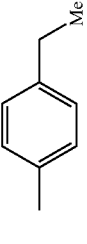 | 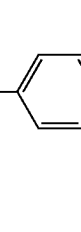 | 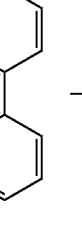 |
| D-95 | Isopropyl | H | H | H |  |  |  |  |
| D-96 | Isopropyl | H | H | H |  |  |  |  |

TABLE 9

| | $R_1$ | $R_2$ | $R_3$ | $R_4$ | $(A_1)_a$ | $(A_2)_b$ | $(A_3)_c$ | $(A_4)_d$ |
|---|---|---|---|---|---|---|---|---|
| D-97 | t-butyl | H | H | H | phenyl | phenyl | phenyl | phenyl |
| D-98 | t-butyl | H | H | H | phenyl | 3-methylphenyl | phenyl | 3-methylphenyl |
| D-99 | t-butyl | H | H | H | 3-methylphenyl | 3-methylphenyl | 3-methylphenyl | 3-methylphenyl |
| D-100 | t-butyl | H | H | H | phenyl | 4-methylphenyl | phenyl | 4-methylphenyl |
| D-101 | t-butyl | H | H | H | 3-methylphenyl | 3,4-dimethylphenyl | 3-methylphenyl | 3,4-dimethylphenyl |
| D-102 | t-butyl | H | H | H | 2,3,4-trimethylphenyl | 2,3,4-trimethylphenyl | 2,3,4-trimethylphenyl | 2,3,4-trimethylphenyl |
| D-103 | t-butyl | H | H | H | 4-methylphenyl | 4-methylphenyl | 4-methylphenyl | 4-methylphenyl |
| D-104 | t-butyl | H | H | H | 4-isopropylphenyl | 3,5-dimethylphenyl | 4-isopropylphenyl | 3,5-dimethylphenyl |
| D-105 | t-butyl | H | H | H | 4-isopropylphenyl | 4-isopropylphenyl | 4-isopropylphenyl | 4-isopropylphenyl |
| D-106 | t-butyl | H | H | H | 4-t-butylphenyl | 4-t-butylphenyl | 4-t-butylphenyl | 4-t-butylphenyl |
| D-107 | t-butyl | H | H | H | 4-methylphenyl | 4-t-butylphenyl | 4-methylphenyl | 4-t-butylphenyl |
| D-108 | t-butyl | H | H | H | 4-methylphenyl | 4-isopropylphenyl | 4-methylphenyl | 4-isopropylphenyl |

TABLE 10

| | R1 | R2 | R3 | R4 | (A1)a | (A2)b | (A3)c | (A4)d |
|---|---|---|---|---|---|---|---|---|
| D-109 | t-butyl | H | H | H | | | | |
| D-110 | t-butyl | H | H | H | | | | |
| D-111 | t-butyl | H | H | H | | | | |
| D-112 | t-butyl | H | H | H | | | | |
| D-113 | t-butyl | H | H | H | | | | |
| D-114 | t-butyl | H | H | H | | | | |
| D-115 | t-butyl | H | H | H | | | | |

TABLE 10-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-116 | t-butyl | H | H | H | 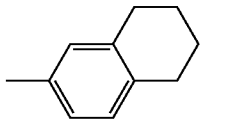 |  |  |  |
| D-117 | t-butyl | H | H | H |  | 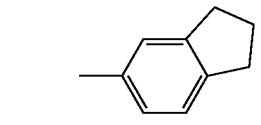 |  |  |
| D-118 | t-butyl | H | H | H |  |  |  |  |
| D-119 | t-butyl | H | H | H |  |  |  |  |
| D-120 | t-butyl | H | H | H |  |  |  |  |

TABLE 11

| | R1 | R2 | R3 | R4 | (A1)a | (A2)b | (A3)c | (A4)d |
|---|---|---|---|---|---|---|---|---|
| D-121 | t-butyl | H | H | H | | | | |
| D-122 | t-butyl | H | H | H | | | | |
| D-123 | t-butyl | H | H | H | | | | |
| D-124 | t-butyl | H | H | H | | | | |
| D-125 | t-butyl | H | H | H | | | | |
| D-126 | t-butyl | H | H | H | | | | |
| D-127 | t-butyl | H | H | H | | | | |

TABLE 11-continued

| | R₁ | R₂ | R₃ | R₄ | (A₁)a | (A₂)b | (A₃)c | (A₄)d |
|---|---|---|---|---|---|---|---|---|
| D-128 | t-butyl | H | H | H | | | | |
| D-129 | t-butyl | H | H | H | | | | |
| D-130 | t-butyl | H | H | H | | | | |
| D-131 | t-butyl | H | H | H | | | | |
| D-132 | t-butyl | H | H | H | | | | |

TABLE 12

| | $R_1$ | $R_2$ | $R_3$ | $R_4$ | (A₁)a | (A₂)b | (A₃)c | (A₄)d |
|---|---|---|---|---|---|---|---|---|
| D-133 | t-butyl | H | H | H | | | | |
| D-134 | t-butyl | H | H | H | | | | |
| D-135 | t-butyl | H | H | H | | | | |
| D-136 | t-butyl | H | H | H | | | | |
| D-137 | t-butyl | H | H | H | | | | |
| D-138 | t-butyl | H | H | H | | | | |
| D-139 | t-butyl | H | H | H | | | | |

TABLE 12-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-140 | t-butyl | H | H | H | 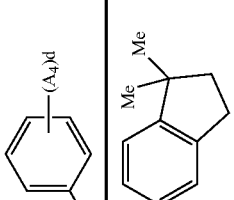 | 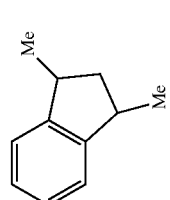 | 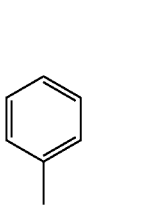 | 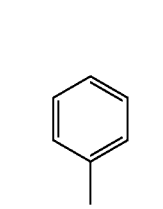 |
| D-141 | t-butyl | H | H | H | 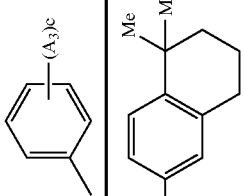 | 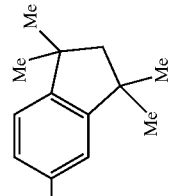 | 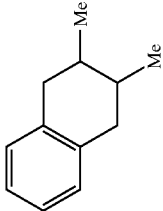 | 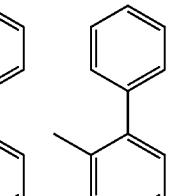 |
| D-142 | t-butyl | H | H | H | 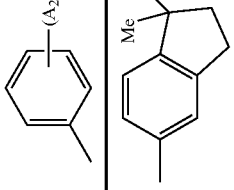 | 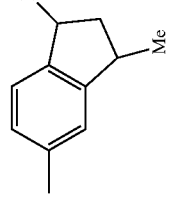 | 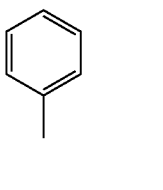 | 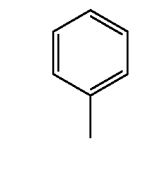 |
| D-143 | t-butyl | H | H | H | 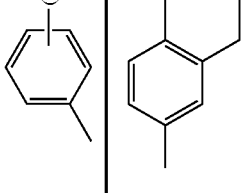 | 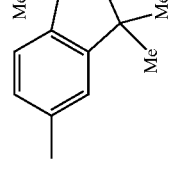 | 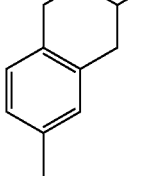 | 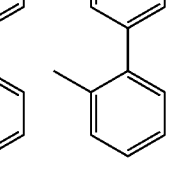 |
| D-144 | t-butyl | H | H | H | 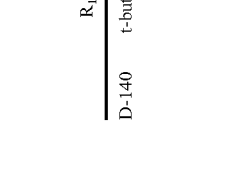 | 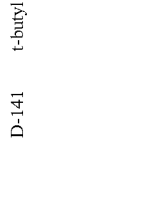 | 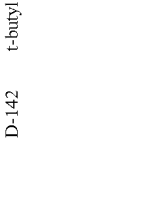 | 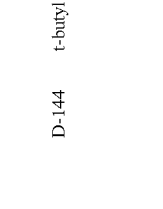 |

TABLE 13

| | R₁ | R₂ | R₃ | R₄ | (A₁)a | (A₂)b | (A₃)c | (A₄)d |
|---|---|---|---|---|---|---|---|---|
| D-145 | Phenyl | H | H | H | Phenyl | Phenyl | Phenyl | Phenyl |
| D-146 | Phenyl | H | H | H | Phenyl | 3-methylphenyl | Phenyl | 3-methylphenyl |
| D-147 | Phenyl | H | H | H | 3-methylphenyl | 3-methylphenyl | 3-methylphenyl | 3-methylphenyl |
| D-148 | Phenyl | H | H | H | Phenyl | 4-methylphenyl | Phenyl | 4-methylphenyl |
| D-149 | Phenyl | H | H | H | 2,4-dimethylphenyl | 2,4-dimethylphenyl | 2,4-dimethylphenyl | 2,4-dimethylphenyl |
| D-150 | Phenyl | H | H | H | 2,4,6-trimethylphenyl | 2,4,6-trimethylphenyl | 2,4,6-trimethylphenyl | 2,4,6-trimethylphenyl |
| D-151 | Phenyl | H | H | H | 4-methylphenyl | 4-methylphenyl | 4-methylphenyl | 4-methylphenyl |

TABLE 13-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-152 | Phenyl | H | H | H |  |  |  |  |
| D-153 | Phenyl | H | H | H |  | 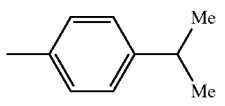 |  |  |
| D-154 | Phenyl | H | H | H |  | 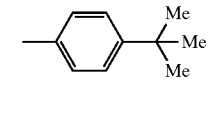 |  |  |
| D-155 | Phenyl | H | H | H |  |  |  |  |
| D-156 | Phenyl | H | H | H |  |  | 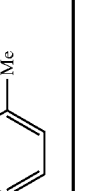 |  |

TABLE 14
| | R₁ | R₂ | R₃ | R₄ | (A₁)a | (A₂)b | (A₃)c | (A₄)d |
|---|---|---|---|---|---|---|---|---|
| D-157 | 1-naphtyl | H | H | H | | | | |
| D-158 | 1-naphtyl | H | H | H | | | | |
| D-159 | 1-naphtyl | H | H | H | | | | |
| D-160 | 1-naphtyl | H | H | H | | | | |
| D-161 | 1-naphtyl | H | H | H | | | | |
| D-162 | 1-naphtyl | H | H | H | | | | |
| D-163 | 1-naphtyl | H | H | H | | | | |

TABLE 14-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-164 | 1-naphtyl | H | H | H |  |  | 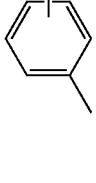 | 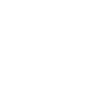 |
| D-165 | 1-naphtyl | H | H | H | 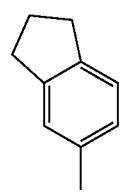 |  |  | 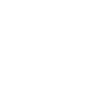 |
| D-166 | 1-naphtyl | H | H | H | 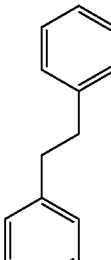 |  |  |  |
| D-167 | 1-naphtyl | H | H | H |  |  |  |  |
| D-168 | 1-naphtyl | H | H | H |  |  | 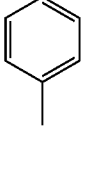 | 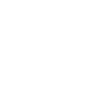 |

TABLE 15
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-169 | 2-naphtyl | H | H | H | 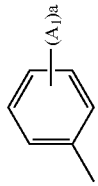 | 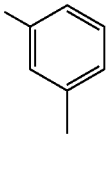 |  | 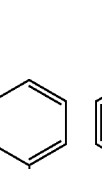 |
| D-170 | 2-naphtyl | H | H | H | 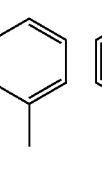 |  |  | 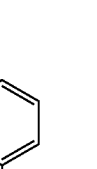 |
| D-171 | 2-naphtyl | H | H | H | 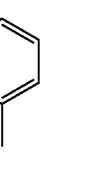 | 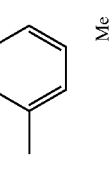 |  | 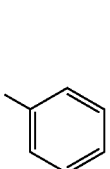 |
| D-172 | 2-naphtyl | H | H | H | 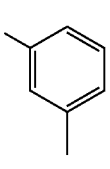 | 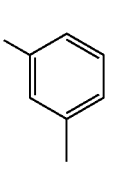 | 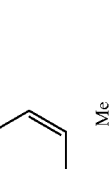 |  |
| D-173 | 2-naphtyl | H | H | H | 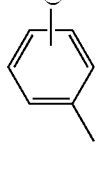 | 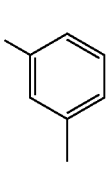 | 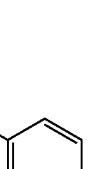 |  |
| D-174 | 2-naphtyl | H | H | H | 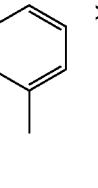 |  | 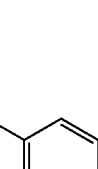 |  |
| D-175 | 2-naphtyl | H | H | H | 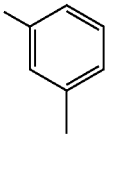 |  | 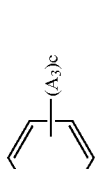 | 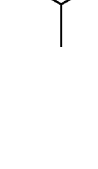 |

TABLE 15-continued
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-176 | 2-naphtyl | H | H | H |  |  |  |  |
| D-177 | 2-naphtyl | H | H | H |  |  |  |  |
| D-178 | 2-naphtyl | H | H | H |  |  |  |  |
| D-179 | 2-naphtyl | H | H | H | 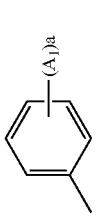 | 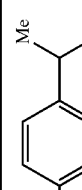 |  |  |
| D-180 | 2-naphtyl | H | H | H | 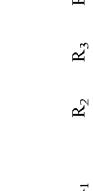 |  |  |  |

TABLE 16
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-181 | Cyano | H | H | H | 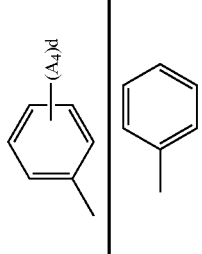 | 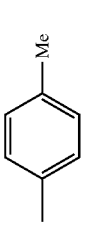 | 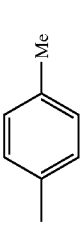 | 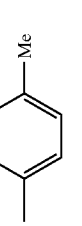 |
| D-182 | Cyano | H | H | H | 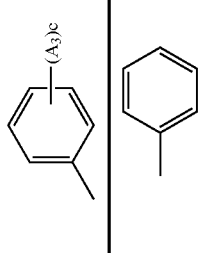 | 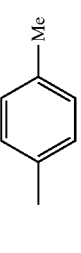 | 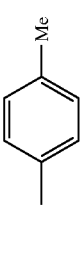 | 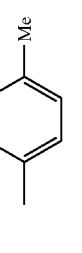 |
| D-183 | Dimethylamino | H | H | H | 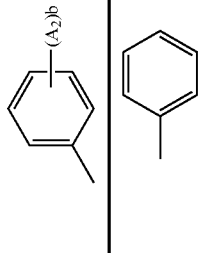 | 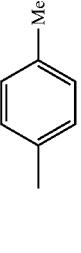 | 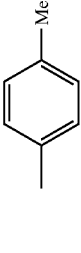 | 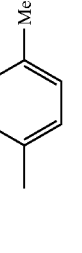 |
| D-184 | Dimethylamino | H | H | H | 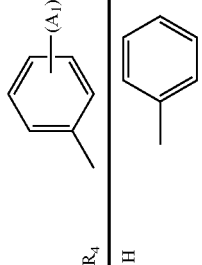 | 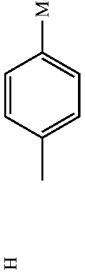 | 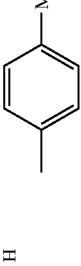 | 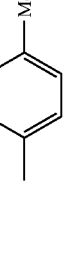 |
| D-185 | Dimethylamino | H | H | H | 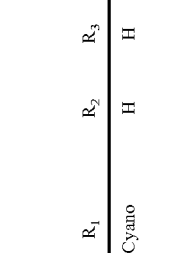 | 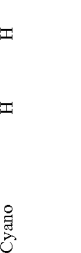 |  |  |
| D-186 | 2-methyl phenyl | H | H | H | 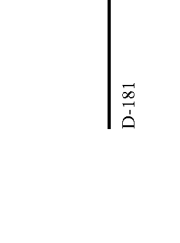 |  | | |
| D-187 | 2-methyl phenyl | H | H | H |  |  | | |

TABLE 16-continued

| | R$_1$ | R$_2$ | R$_3$ | R$_4$ | (A$_1$)a | (A$_2$)b | (A$_3$)c | (A$_4$)d |
|---|---|---|---|---|---|---|---|---|
| D-188 | 2-methylphenyl | H | H | H | 4-tBu-C$_6$H$_4$ | 4-tBu-C$_6$H$_4$ | 4-tBu-C$_6$H$_4$ | 4-tBu-C$_6$H$_4$ |
| D-189 | 2-biphenyl | H | H | H | phenyl | phenyl | phenyl | phenyl |
| D-190 | 2-biphenyl | H | H | H | 4-methylphenyl | 4-methylphenyl | 4-methylphenyl | 4-methylphenyl |
| D-191 | 2-biphenyl | H | H | H | 4-tBu-C$_6$H$_4$ | 4-tBu-C$_6$H$_4$ | 4-tBu-C$_6$H$_4$ | 4-tBu-C$_6$H$_4$ |
| D-192 | 2-biphenyl | H | H | H | phenyl | 2-naphthyl | phenyl | 2-naphthyl |

TABLE 17

| | $R_1$ | $R_2$ | $R_3$ | $R_4$ | (A₁)a | (A₂)b | (A₃)c | (A₄)d |
|---|---|---|---|---|---|---|---|---|
| D-193 | Methyl | Methyl | H | H | phenyl | phenyl | phenyl | phenyl |
| D-194 | Methyl | Methyl | H | H | phenyl | 3-methylphenyl | phenyl | 3-methylphenyl |
| D-195 | Methyl | Methyl | H | H | 3-methylphenyl | 3-methylphenyl | 3-methylphenyl | 3-methylphenyl |
| D-196 | Methyl | Methyl | H | H | phenyl | 4-methylphenyl | phenyl | 4-methylphenyl |
| D-197 | Methyl | Methyl | H | H | 2,4-dimethylphenyl | 2,4-dimethylphenyl | 2,4-dimethylphenyl | 2,4-dimethylphenyl |
| D-198 | Methyl | Methyl | H | H | 3,5-dimethylphenyl | 3,4,5-trimethylphenyl | 3,5-dimethylphenyl | 3,4,5-trimethylphenyl |
| D-199 | Methyl | Methyl | H | H | 4-methylphenyl | 4-methylphenyl | 4-methylphenyl | 4-methylphenyl |

TABLE 17-continued
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-200 | Methyl | Methyl | H | H |  | 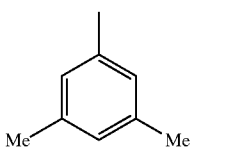 | 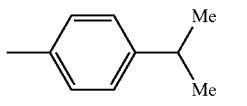 |  |
| D-200 | Methyl | Methyl | H | H |  |  | 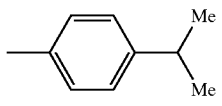 |  |
| D-201 | Methyl | Methyl | H | H |  |  |  |  |
| D-202 | Methyl | Methyl | H | H |  |  |  | 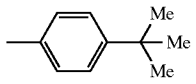 |
| D-203 | Methyl | Methyl | H | H |  |  |  |  |
| D-204 | Methyl | Methyl | H | H |  |  |  |  |

TABLE 18
| | R₁ | R₂ | R₃ | R₄ | (A₁)a | (A₂)b | (A₃)c | (A₄)d |
|---|---|---|---|---|---|---|---|---|
| D-205 | Methyl | Methyl | H | H |  |  |  |  |
| D-206 | Methyl | Methyl | H | H |  |  |  |  |
| D-207 | Methyl | Methyl | H | H |  |  |  |  |
| D-208 | Methyl | Methyl | H | H |  |  |  | 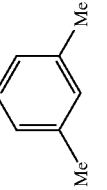 |
| D-209 | Methyl | Methyl | H | H | 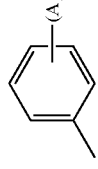 | 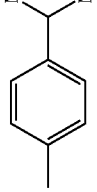 | 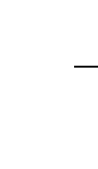 | 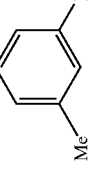 |
| D-210 | Methyl | Methyl | H | H | 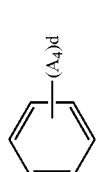 | 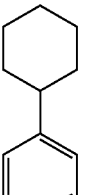 |  | 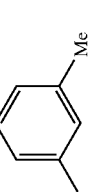 |
| D-211 | Methyl | Methyl | H | H | 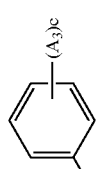 | 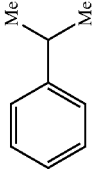 |  | 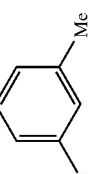 |

TABLE 18-continued
| | | | | | |
|---|---|---|---|---|---|
| D-212 | Methyl | Methyl | H |  |  |  |  |
| D-213 | Methyl | Methyl | H |  |  | 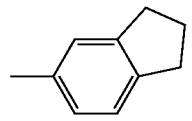 |  |
| D-214 | Methyl | Methyl | H |  |  |  |  |
| D-215 | Methyl | Methyl | H |  | 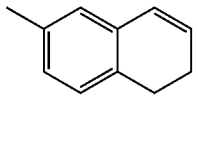 |  |  |
| D-216 | Methyl | Methyl | H |  |  |  |  |

TABLE 19
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-217 | Methyl | Methyl | H | H |  |  |  |  |
| D-218 | Methyl | Methyl | H | H |  |  |  |  |
| D-219 | Methyl | Methyl | H | H |  |  |  |  |
| D-220 | Methyl | Methyl | H | H |  | | | |
| D-221 | Methyl | Methyl | H | H |  |  | | 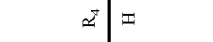 |
| D-222 | Methyl | Methyl | H | H | 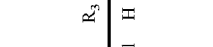 | 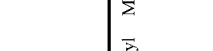 |  |  |
| D-223 | Methyl | Methyl | H | H |  | | | |

TABLE 19-continued

| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-224 | Methyl | Methyl | H | H | | | | |
| D-225 | Methyl | Methyl | H | H | | | | |
| D-226 | Methyl | Methyl | H | H | | | | |
| D-227 | Methyl | Methyl | H | H | | | | |
| D-228 | Methyl | Methyl | H | H | | | | |

TABLE 20
| | $R_1$ | $R_2$ | $R_3$ | $R_4$ | (A$_1$)a | (A$_2$)b | (A$_3$)c | (A$_4$)d |
|---|---|---|---|---|---|---|---|---|
| D-229 | Methyl | Methyl | H | H |  | 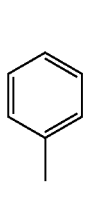 |  |  |
| D-230 | Methyl | Methyl | H | H | 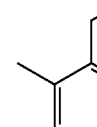 | 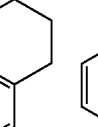 | 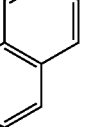 | 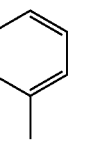 |
| D-231 | Methyl | Methyl | H | H | 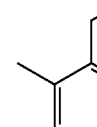 | 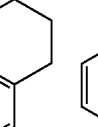 | 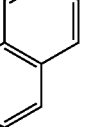 | 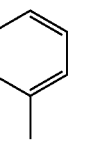 |
| D-232 | Methyl | Methyl | H | H | 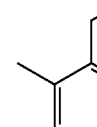 | 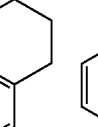 | 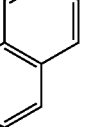 | 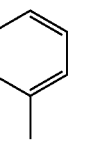 |
| D-233 | Methyl | Methyl | H | H | 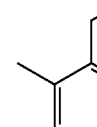 | 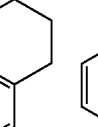 | 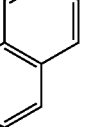 | 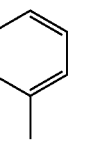 |
| D-234 | Methyl | Methyl | H | H | 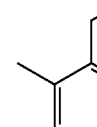 | 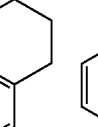 | 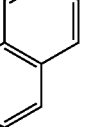 | 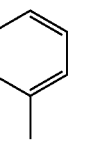 |
| D-235 | Methyl | Methyl | H | H | 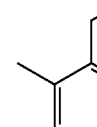 | 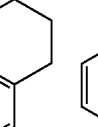 | 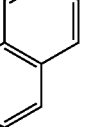 | 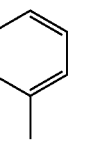 |

TABLE 20-continued

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-236 | Methyl | Methyl | H | H | | | | |
| D-237 | Methyl | Methyl | H | H | | | | |
| D-238 | Methyl | Methyl | H | H | | | | |
| D-239 | Methyl | Methyl | H | H | | | | |
| D-240 | Methyl | Methyl | H | H | | | | |

TABLE 21

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-241 | Methyl | Methyl | Methyl | Methyl | Phenyl | Phenyl | Phenyl | Phenyl |
| D-242 | Methyl | Methyl | Methyl | Methyl | Phenyl | 3-Methylphenyl | Phenyl | 3-Methylphenyl |
| D-243 | Methyl | Methyl | Methyl | Methyl | 3-Methylphenyl | 3-Methylphenyl | 3-Methylphenyl | 3-Methylphenyl |
| D-244 | Methyl | Methyl | Methyl | Methyl | Phenyl | 4-Methylphenyl | Phenyl | 4-Methylphenyl |
| D-245 | Methyl | Methyl | Methyl | Methyl | 3-Methylphenyl | 2,4-Dimethylphenyl | 3-Methylphenyl | 2,4-Dimethylphenyl |
| D-246 | Methyl | Methyl | Methyl | Methyl | 2,6-Dimethylphenyl | 3,5-Dimethylphenyl | 2,6-Dimethylphenyl | 3,5-Dimethylphenyl |
| D-247 | Methyl | Methyl | Methyl | Methyl | 4-Methylphenyl | 2-Naphthyl | 4-Methylphenyl | 2-Naphthyl |

TABLE 21-continued

| | | | | | |
|---|---|---|---|---|---|
| D-248 | Methyl | Methyl | Methyl | 4-MeC6H4-CH(Me)- | 3,5-Me2C6H3- | 4-MeC6H4-CH(Me)- |
| D-249 | Methyl | Methyl | Methyl | 4-MeC6H4-CH(Me)- | 4-MeC6H4-CH(Me)- | 4-MeC6H4-CH(Me)- |
| D-250 | Methyl | Methyl | Methyl | 4-MeC6H4-C(Me)2- | 4-MeC6H4-C(Me)2- | 4-MeC6H4-C(Me)2- |
| D-251 | Methyl | Methyl | Methyl | 4-MeC6H4- | 4-MeC6H4-C(Me)2- | 4-MeC6H4-C(Me)2- |
| D-252 | Methyl | Methyl | Methyl | 4-MeC6H4- | 4-MeC6H4-CH(Me)- | 4-MeC6H4-CH(Me)- |

TABLE 22
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-253 | Methyl | Methyl | Methyl | Methyl | 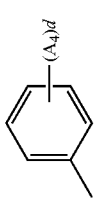 |  | 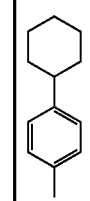 | 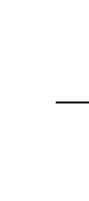 |
| D-254 | Methyl | Methyl | Methyl | Methyl |  | 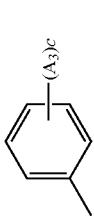 | 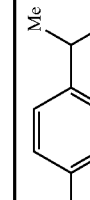 | 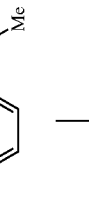 |
| D-255 | Methyl | Methyl | Methyl | Methyl |  | 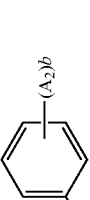 | 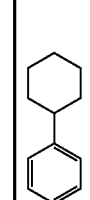 |  |
| D-256 | Methyl | Methyl | Methyl | Methyl |  | 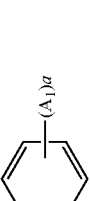 | 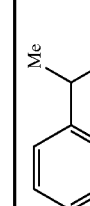 |  |
| D-257 | Methyl | Methyl | Methyl | Methyl |  | 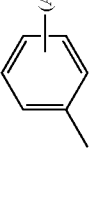 | 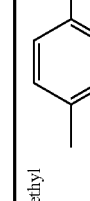 | 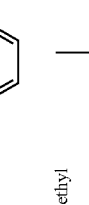 |
| D-258 | Methyl | Methyl | Methyl | Methyl |  | 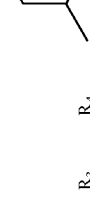 | 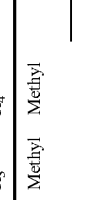 |  |
| D-259 | Methyl | Methyl | Methyl | Methyl |  | 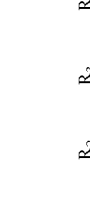 | 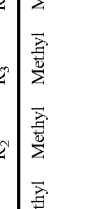 |  |

TABLE 22-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-260 | Methyl | Methyl | Methyl | Methyl |  |  |  |  |
| D-261 | Methyl | Methyl | Methyl | Methyl | | | | |
| D-262 | Methyl | Methyl | Methyl | Methyl | | | | |
| D-263 | Methyl | Methyl | Methyl | Methyl | | | | |
| D-264 | Methyl | Methyl | Methyl | Methyl |  |  |  |  |

TABLE 23

| | $R_1$ | $R_2$ | $R_3$ | $R_4$ | $-(A_1)a$ | $-(A_2)b$ | $-(A_3)c$ | $-(A_4)d$ |
|---|---|---|---|---|---|---|---|---|
| D-253 | Methyl | Methyl | Methyl | Methyl | | | | |
| D-254 | Methyl | Methyl | Methyl | Methyl | | | | |
| D-255 | Methyl | Methyl | Methyl | Methyl | | | | |
| D-256 | Methyl | Methyl | Methyl | Methyl | | | | |
| D-257 | Methyl | Methyl | Methyl | Methyl | | | | |
| D-258 | Methyl | Methyl | Methyl | Methyl | | | | |
| D-259 | Methyl | Methyl | Methyl | Methyl | | | | |

TABLE 23-continued
| | $R_1$ | $R_2$ | $R_3$ | $R_4$ | (A$_1$)a | (A$_2$)b | (A$_3$)c | (A$_4$)d |
|---|---|---|---|---|---|---|---|---|
| D-260 | Methyl | Methyl | Methyl | Methyl | 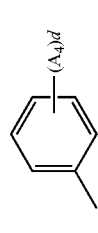 | 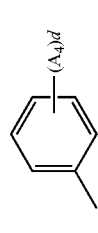 | 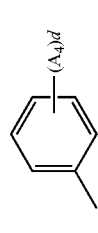 | 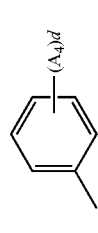 |
| D-261 | Methyl | Methyl | Methyl | Methyl | 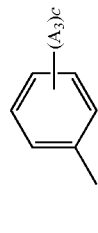 | 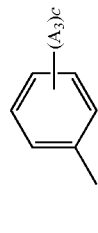 | 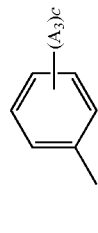 | 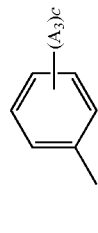 |
| D-262 | Methyl | Methyl | Methyl | Methyl | 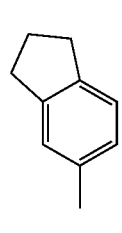 | 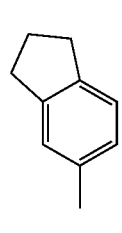 | 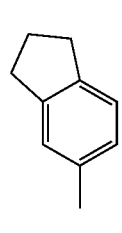 | 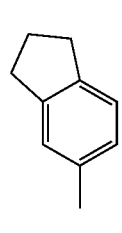 |
| D-263 | Methyl | Methyl | Methyl | Methyl | 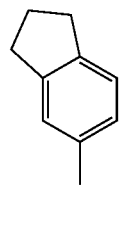 | 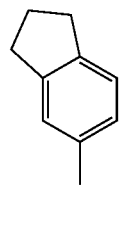 | 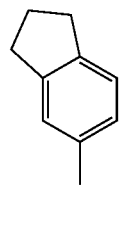 | 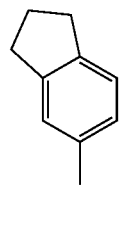 |
| D-264 | Methyl | Methyl | Methyl | Methyl | 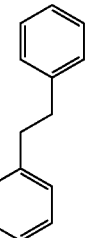 | 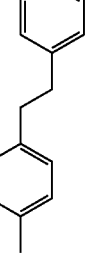 | 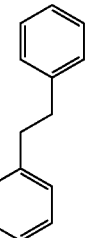 | 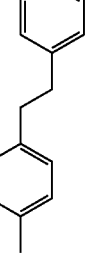 |

TABLE 24

| | R₁ | R₂ | R₃ | R₄ | —⟨⟩—(A₁)a | —⟨⟩—(A₂)b | —⟨⟩—(A₃)c | —⟨⟩—(A₄)d |
|---|---|---|---|---|---|---|---|---|
| D-277 | Diphenyl Amino | H | H | H | –Ph | –Ph | –Ph | –Ph |
| D-278 | Diphenyl Amino | H | H | H | –Ph | –C₆H₄-3-Me | –Ph | –C₆H₄-3-Me |
| D-279 | Diphenyl Amino | H | H | H | –C₆H₄-3-Me | –C₆H₄-3-Me | –C₆H₄-3-Me | –C₆H₄-3-Me |
| D-280 | Diphenyl Amino | H | H | H | –Ph | –C₆H₄-4-Me | –Ph | –C₆H₄-4-Me |
| D-281 | Diphenyl Amino | H | H | H | –C₆H₃-2,4-Me₂ | –C₆H₃-2,4-Me₂ | –C₆H₃-2,4-Me₂ | –C₆H₃-2,4-Me₂ |
| D-282 | Diphenyl Amino | H | H | H | –C₆H₂-2,3,4-Me₃ | –C₆H₂-2,3,4-Me₃ | –C₆H₂-2,3,4-Me₃ | –C₆H₂-2,3,4-Me₃ |
| D-283 | Diphenyl Amino | H | H | H | –C₆H₄-4-Me | –C₆H₄-4-Me | –C₆H₄-4-Me | –C₆H₄-4-Me |
| D-284 | Diphenyl Amino | H | H | H | –C₆H₄-4-CHMe₂ | –C₆H₃-3,5-Me₂ | –C₆H₄-4-CHMe₂ | –C₆H₃-3,5-Me₂ |
| D-285 | Diphenyl Amino | H | H | H | –C₆H₄-4-CHMe₂ | –C₆H₄-4-CHMe₂ | –C₆H₄-4-CHMe₂ | –C₆H₄-4-CHMe₂ |
| D-286 | Diphenyl Amino | H | H | H | –C₆H₄-4-CMe₃ | –C₆H₄-4-CMe₃ | –C₆H₄-4-CMe₃ | –C₆H₄-4-CMe₃ |
| D-287 | Diphenyl Amino | H | H | H | –C₆H₄-4-Me | –C₆H₄-4-CMe₃ | –C₆H₄-4-Me | –C₆H₄-4-CMe₃ |
| D-288 | Diphenyl Amino | H | H | H | –C₆H₄-4-Me | –C₆H₄-4-CHMe₂ | –C₆H₄-4-Me | –C₆H₄-4-CHMe₂ |

TABLE 25

| | R₁ | R₂ | R₃ | R₄ | ⟨Ar⟩–(A₁)a | ⟨Ar⟩–(A₂)b | ⟨Ar⟩–(A₃)c | ⟨Ar⟩–(A₄)d |
|---|---|---|---|---|---|---|---|---|
| D-289 | Methyl | H | Methyl | H | phenyl | phenyl | phenyl | phenyl |
| D-290 | Methyl | H | Methyl | H | phenyl | 3-Me-phenyl | phenyl | 3-Me-phenyl |
| D-291 | Methyl | H | Methyl | H | 3-Me-phenyl | 3-Me-phenyl | 3-Me-phenyl | 3-Me-phenyl |
| D-292 | Methyl | H | Methyl | H | 4-Me-phenyl | 6-Me-tetralinyl | 4-Me-phenyl | 6-Me-tetralinyl |
| D-293 | Methyl | H | Methyl | H | 3-Me-phenyl | 3,4-diMe-phenyl | 3-Me-phenyl | 3,4-diMe-phenyl |
| D-294 | Methyl | H | Methyl | H | 3,4,5-triMe-phenyl | 3,5-diMe-phenyl | 3,4,5-triMe-phenyl | 3,5-diMe-phenyl |
| D-295 | Methyl | H | Methyl | H | 4-Me-phenyl | 4-Me-phenyl | 4-Me-phenyl | 4-Me-phenyl |
| D-296 | Methyl | H | Methyl | H | 4-iPr-phenyl | 3,5-diMe-phenyl | 4-iPr-phenyl | 3,5-diMe-phenyl |
| D-297 | Methyl | H | Methyl | H | 4-iPr-phenyl | 4-iPr-phenyl | 4-iPr-phenyl | 4-iPr-phenyl |
| D-298 | Methyl | H | Methyl | H | 4-tBu-phenyl | 4-tBu-phenyl | 4-tBu-phenyl | 4-tBu-phenyl |
| D-299 | Methyl | H | Methyl | H | 4-Me-phenyl | 4-tBu-phenyl | 4-Me-phenyl | 4-tBu-phenyl |

TABLE 25-continued

| | R₁ | R₂ | R₃ | R₄ | (A₁)a | (A₂)b | (A₃)c | (A₄)d |
|---|---|---|---|---|---|---|---|---|
| D-300 | Methyl | H | Methyl | H | —C₆H₄—Me (p) | —C₆H₄—CMe₂H (p) | —C₆H₄—Me (p) | —C₆H₄—CMe₂H (p) |

TABLE 26

| | R₁ | R₂ | R₃ | R₄ | (A₁)a | (A₂)b | (A₃)c | (A₄)d |
|---|---|---|---|---|---|---|---|---|
| D-301 | Methyl | H | Methyl | H | —C₆H₄—CMe₂H (p) | —C₆H₄—C₆H₁₁ (p) | —C₆H₄—CMe₂H (p) | —C₆H₄—C₆H₁₁ (p) |
| D-302 | Methyl | H | Methyl | H | 3,5-Me₂-C₆H₃— | 3,5-Me₂-C₆H₃— | 3,5-Me₂-C₆H₃— | 3,5-Me₂-C₆H₃— |
| D-303 | Methyl | H | Methyl | H | —C₆H₅ | —C₆H₄—C₆H₅ | —C₆H₅ | —C₆H₄—C₆H₅ |
| D-304 | Methyl | H | Methyl | H | —C₆H₅ | 2-naphthyl | —C₆H₅ | 2-naphthyl |
| D-305 | Methyl | H | Methyl | H | 2-naphthyl | 2-naphthyl | 2-naphthyl | 2-naphthyl |
| D-306 | Methyl | H | Methyl | H | —C₆H₄—C₆H₅ | —C₆H₄—C₆H₅ | —C₆H₄—C₆H₅ | —C₆H₄—C₆H₅ |

TABLE 26-continued
| | R₁ | R₂ | R₃ | R₄ | (A₁)a | (A₂)b | (A₃)c | (A₄)d |
|---|---|---|---|---|---|---|---|---|
| D-307 | Methyl | H | Methyl | H | 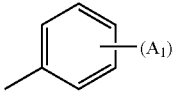 | 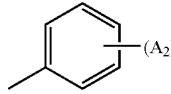 | 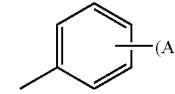 | 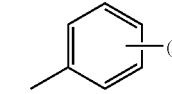 |
| D-308 | Methyl | H | Methyl | H | 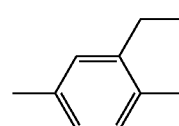 | 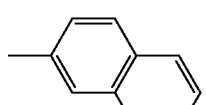 | 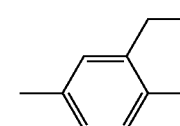 | 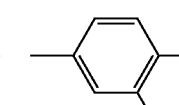 |
| D-309 | Methyl | H | Methyl | H | 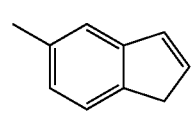 | 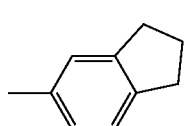 | 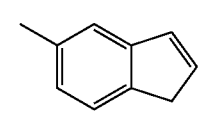 | 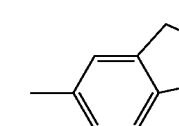 |
| D-310 | Methyl | H | Methyl | H | 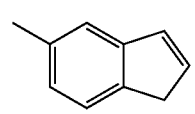 | 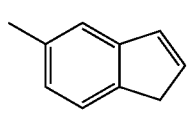 | 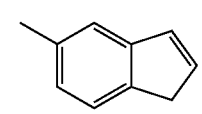 | 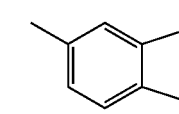 |
| D-311 | Methyl | H | Methyl | H | 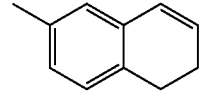 | 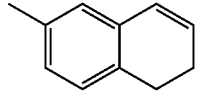 | 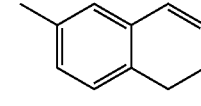 | 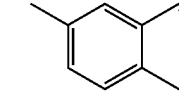 |
| D-312 | Methyl | H | Methyl | H | 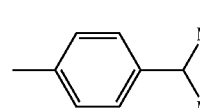 | 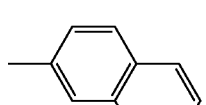 | 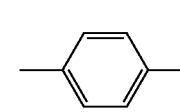 | 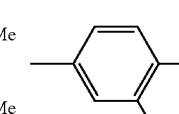 |

TABLE 27
| | $R_1$ | $R_2$ | $R_3$ | $R_4$ | (A₁)a | (A₂)b | (A₃)c | (A₄)d |
|---|---|---|---|---|---|---|---|---|
| D-313 | Methyl | H | Methyl | H | 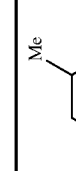 | 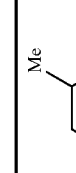 | 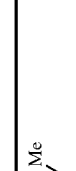 | 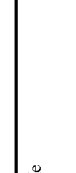 |
| D-314 | Methyl | H | Methyl | H | 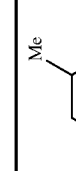 | 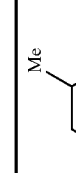 | 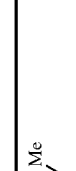 | 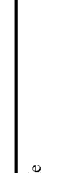 |
| D-315 | Methyl | H | Methyl | H | 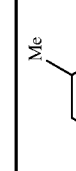 | 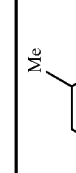 | 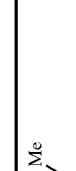 | 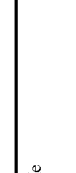 |
| D-316 | Methyl | H | Methyl | H | 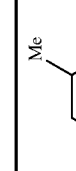 | 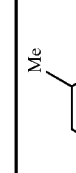 | 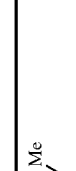 | 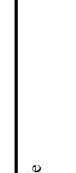 |
| D-317 | Methyl | H | Methyl | H | 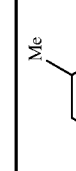 |  |  |  |
| D-318 | Methyl | H | Methyl | H | 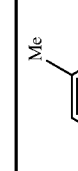 | 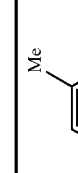 |  |  |

TABLE 27-continued
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-319 | Methyl | H | Methyl | H |  |  |  |  |
| D-320 | Methyl | H | Methyl | H |  |  |  |  |
| D-321 | Methyl | H | Methyl | H |  |  |  |  |
| D-322 | Methyl | H | Methyl | H |  |  |  |  |
| D-323 | Methyl | H | Methyl | H | | | | |
| D-324 | Methyl | H | Methyl | H |  | |  | |

TABLE 28

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-325 | Methyl | H | Methyl | H | 4-biphenyl | phenyl | 4-terphenyl | phenyl |
| D-326 | Methyl | H | Methyl | H | 5-methyl-tetrahydronaphthyl | 5-methyl-tetrahydronaphthyl | 5-methyl-tetrahydronaphthyl | 5-methyl-tetrahydronaphthyl |
| D-327 | Methyl | H | Methyl | H | 4-methylphenyl | 4-methylphenyl | 4-methylphenyl | 4-methylphenyl |
| D-328 | Methyl | H | Methyl | H | 4-methoxy-4'-methylphenyl | 4-methylphenyl | 4-methoxy-4'-methylphenyl | 4-methylphenyl |
| D-329 | Methyl | H | Methyl | H | 4-(N,N-dimethylamino)-4'-methylphenyl | 4-(N,N-dimethylamino)-4'-methylphenyl | 4-(N,N-dimethylamino)-4'-methylphenyl | 4-(N,N-dimethylamino)-4'-methylphenyl |
| D-330 | Methyl | H | Methyl | H | 4-trifluoromethyl-4'-methylphenyl | 4-fluoro-4'-methylphenyl | 4-trifluoromethyl-4'-methylphenyl | 4-fluoro-4'-methylphenyl |

TABLE 28-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-331 | Methyl | H | Methyl | H |  |  |  | 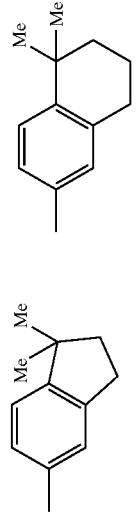 |
| D-332 | Methyl | H | Methyl | H |  |  | 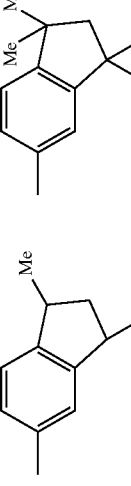 | 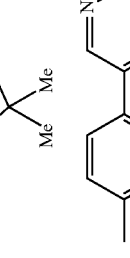 |
| D-333 | Methyl | H | Methyl | H | 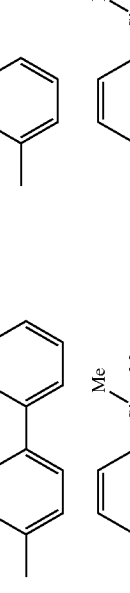 | 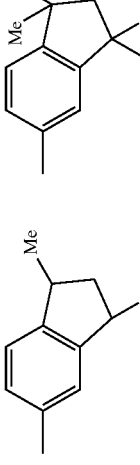 | 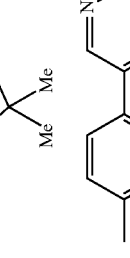 | 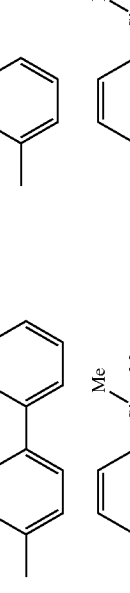 |
| D-334 | Methyl | H | Methyl | H | 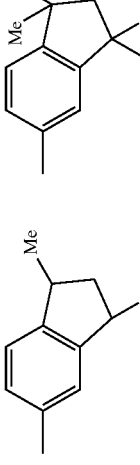 | 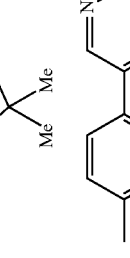 | 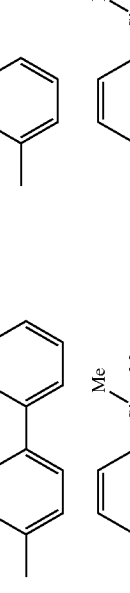 | 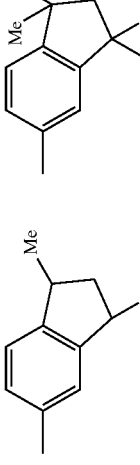 |
| D-335 | Methyl | H | Methyl | H | 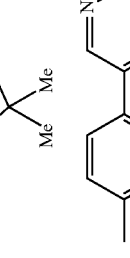 | | | |
| D-336 | Methyl | H | Methyl | H | 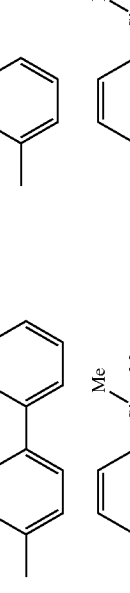 | | | |

TABLE 29

| | R₁ | R₂ | R₃ | R₄ | (A₁)a | (A₂)b | (A₃)c | (A₄)d |
|---|---|---|---|---|---|---|---|---|
| D-337 | Iso-propyl | H | Iso-propyl | H | Ph | Ph | Ph | Ph |
| D-338 | Iso-propyl | H | Iso-propyl | H | Ph | 3-Me-C₆H₄ | Ph | 3-Me-C₆H₄ |
| D-339 | Iso-propyl | H | Iso-propyl | H | 3-Me-C₆H₄ | 3-Me-C₆H₄ | 3-Me-C₆H₄ | 3-Me-C₆H₄ |
| D-340 | Iso-propyl | H | Iso-propyl | H | Ph | 4-Me-C₆H₄ | Ph | 4-Me-C₆H₄ |
| D-341 | Iso-propyl | H | Iso-propyl | H | 3-Me-C₆H₄ | 2,4-Me₂-C₆H₃ | 3-Me-C₆H₄ | 2,4-Me₂-C₆H₃ |
| D-342 | Iso-propyl | H | Iso-propyl | H | 2,3,4-Me₃-C₆H₂ | 3,5-Me₂-C₆H₃ | 2,3,4-Me₃-C₆H₂ | 3,5-Me₂-C₆H₃ |
| D-343 | Iso-propyl | H | Iso-propyl | H | 4-Me-C₆H₄ | 4-Me-C₆H₄ | 4-Me-C₆H₄ | 4-Me-C₆H₄ |
| D-344 | Iso-propyl | H | Iso-propyl | H | 4-iPr-C₆H₄ | 3,5-Me₂-C₆H₃ | 4-iPr-C₆H₄ | 3,5-Me₂-C₆H₃ |
| D-345 | Iso-propyl | H | Iso-propyl | H | 4-iPr-C₆H₄ | 4-iPr-C₆H₄ | 4-iPr-C₆H₄ | 4-iPr-C₆H₄ |
| D-346 | Iso-propyl | H | Iso-propyl | H | 4-tBu-C₆H₄ | 4-tBu-C₆H₄ | 4-tBu-C₆H₄ | 4-tBu-C₆H₄ |
| D-347 | Iso-propyl | H | Iso-propyl | H | 4-Me-C₆H₄ | 4-tBu-C₆H₄ | 4-Me-C₆H₄ | 4-tBu-C₆H₄ |
| D-348 | Iso-propyl | H | Iso-propyl | H | 4-tBu-C₆H₄ | 4-iPr-C₆H₄ | 4-tBu-C₆H₄ | 4-iPr-C₆H₄ |

TABLE 30
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-349 | Isopropyl | H | Isopropyl | H | 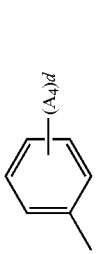 | 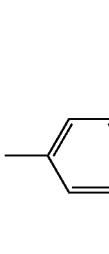 | 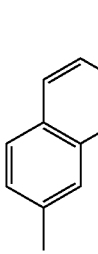 | 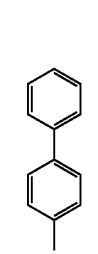 |
| D-350 | Isopropyl | H | Isopropyl | H | 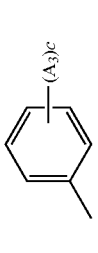 | 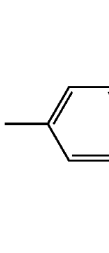 | 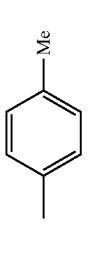 | 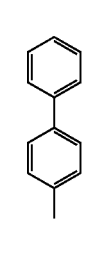 |
| D-351 | Isopropyl | H | Isopropyl | H | 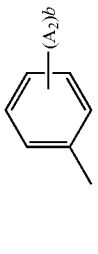 | 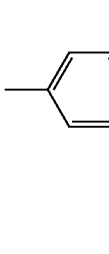 | 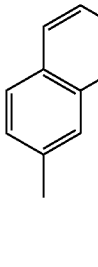 | 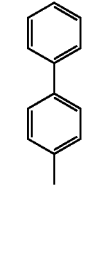 |
| D-352 | Isopropyl | H | Isopropyl | H | 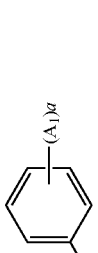 | 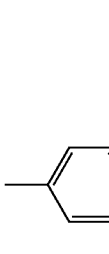 | 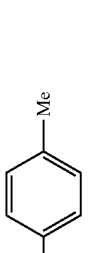 | 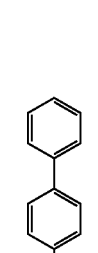 |
| D-353 | Isopropyl | H | Isopropyl | H | 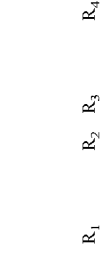 |  |  | 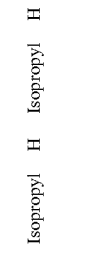 |
| D-354 | Isopropyl | H | Isopropyl | H |  |  |  |  |
| D-355 | Isopropyl | H | Isopropyl | H | | | | |

TABLE 30-continued
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-356 | Isopropyl | H | Isopropyl | H |  |  |  |  |
| D-357 | Isopropyl | H | Isopropyl | H |  |  |  |  |
| D-358 | Isopropyl | H | Isopropyl | H |  | 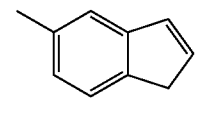 | 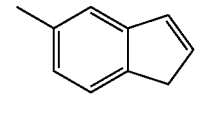 |  |
| D-359 | Isopropyl | H | Isopropyl | H |  |  |  |  |
| D-360 | Isopropyl | H | Isopropyl | H |  |  |  |  |

TABLE 31
| | $R_1$ | $R_2$ | $R_3$ | $R_4$ | (A₁)a | (A₂)b | (A₃)c | (A₄)d |
|---|---|---|---|---|---|---|---|---|
| D-361 | Isopropyl | H | Isopropyl | H | 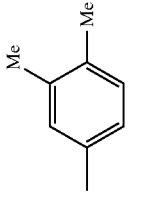 | 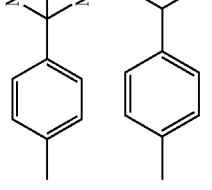 | 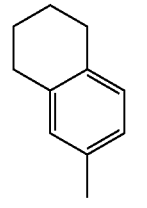 | 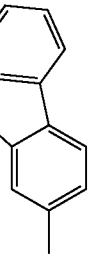 |
| D-362 | Isopropyl | H | Isopropyl | H |  | 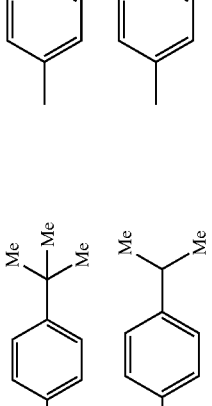 | 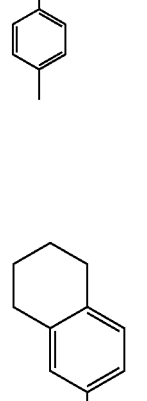 | 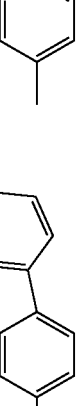 |
| D-363 | Isopropyl | H | Isopropyl | H | 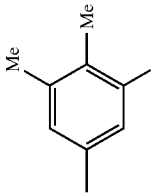 | 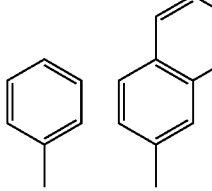 | 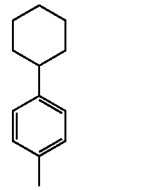 | 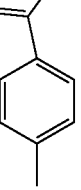 |
| D-364 | Isopropyl | H | Isopropyl | H |  | 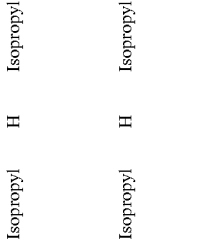 | 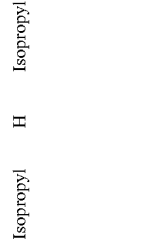 |  |
| D-365 | Isopropyl | H | Isopropyl | H |  |  |  |  |
| D-366 | Isopropyl | H | Isopropyl | H | | | | |

TABLE 31-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-367 | Isopropyl | H | Isopropyl | H |  |  | 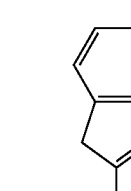 |  |
| D-368 | Isopropyl | H | Isopropyl | H | 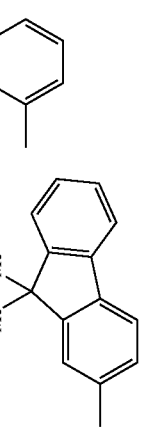 |  | 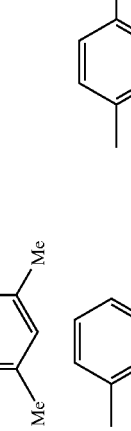 |  |
| D-369 | Isopropyl | H | Isopropyl | H | 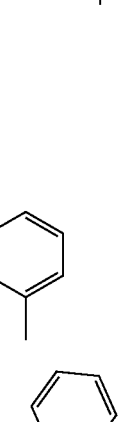 |  | 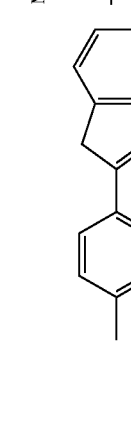 |  |
| D-370 | Isopropyl | H | Isopropyl | H | 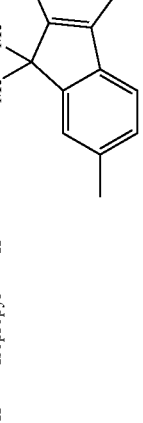 |  | 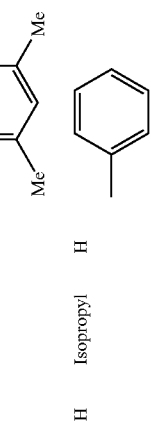 |  |
| D-371 | Isopropyl | H | Isopropyl | H |  | 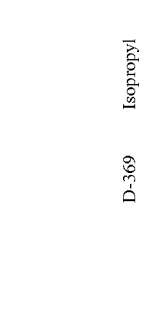 | 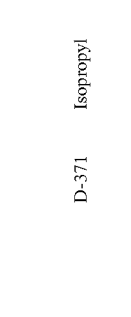 |  |
| D-372 | Isopropyl | H | Isopropyl | H | | | | |

TABLE 32

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-373 | Isopropyl | H | Isopropyl | H | tolyl (1p:2p) | tolyl | 2-methylnaphthyl | 2-methylnaphthyl |
| D-374 | Isopropyl | H | Isopropyl | H | 5-methyl-tetralinyl | 5-methyl-tetralinyl | 5-methyl-tetralinyl | 5-methyl-tetralinyl |
| D-375 | Isopropyl | H | Isopropyl | H | 4-methyl-p-terphenyl | 4-methyl-biphenyl | 4-methyl-p-terphenyl | 4-methyl-biphenyl |
| D-376 | Isopropyl | H | Isopropyl | H | o-tolyl (Me) | tolyl | tolyl | tolyl |
| D-377 | Isopropyl | H | Isopropyl | H | o-tolyl (Me) | o-tolyl (Me) | o-tolyl (Me) | o-tolyl (Me) |
| D-378 | Isopropyl | H | Isopropyl | H | 2-methylbiphenyl | 2-methylbiphenyl | tolyl | tolyl |

TABLE 32-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-379 | Isopropyl | H | Isopropyl | H | 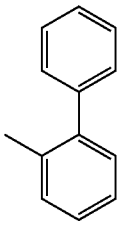 |  |  |  |
| D-380 | Isopropyl | H | Isopropyl | H | 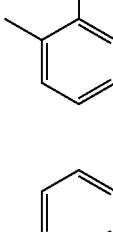 |  |  |  |
| D-381 | Isopropyl | H | Isopropyl | H | 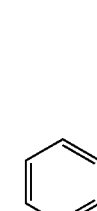 | 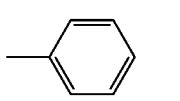 |  |  |
| D-382 | Isopropyl | H | Isopropyl | H | 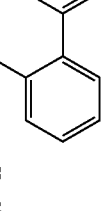 |  |  |  |
| D-383 | Isopropyl | H | Isopropyl | H | 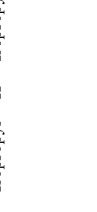 |  | 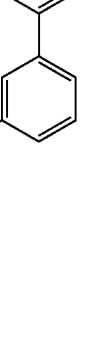 | 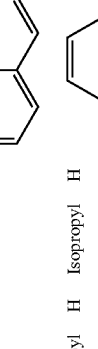 |
| D-384 | Isopropyl | H | Isopropyl | H |  |  |  |  |

TABLE 33

| | R₁ | R₂ | R₃ | R₄ | ─⟨⟩─(A₁)a | ─⟨⟩─(A₂)b | ─⟨⟩─(A₃)c | ─⟨⟩─(A₄)d |
|---|---|---|---|---|---|---|---|---|
| D-385 | t-butyl | H | t-butyl | H | Ph | Ph | Ph | Ph |
| D-386 | t-butyl | H | t-butyl | H | Ph | 3-Me-Ph | Ph | 3-Me-Ph |
| D-387 | t-butyl | H | t-butyl | H | 3-Me-Ph | 3-Me-Ph | 3-Me-Ph | 3-Me-Ph |
| D-388 | t-butyl | H | t-butyl | H | Ph | 4-Me-Ph | Ph | 4-Me-Ph |
| D-389 | t-butyl | H | t-butyl | H | 3,4-diMe-Ph | 3,4-diMe-Ph | 3,4-diMe-Ph | 3,4-diMe-Ph |
| D-390 | t-butyl | H | t-butyl | H | 3,4,5-triMe-Ph | 3,4,5-triMe-Ph | 3,4,5-triMe-Ph | 3,4,5-triMe-Ph |
| D-391 | t-butyl | H | t-butyl | H | 4-Me-Ph | 4-Me-Ph | 4-Me-Ph | 4-Me-Ph |
| D-392 | t-butyl | H | t-butyl | H | 4-iPr-Ph | 3,5-diMe-Ph | 4-iPr-Ph | 3,5-diMe-Ph |
| D-393 | t-butyl | H | t-butyl | H | Ph | 4-iPr-Ph | Ph | 4-iPr-Ph |
| D-394 | t-butyl | H | t-butyl | H | 4-tBu-Ph | 4-tBu-Ph | 4-tBu-Ph | 4-tBu-Ph |
| D-395 | t-butyl | H | t-butyl | H | 4-Me-Ph | 4-tBu-Ph | 4-Me-Ph | 4-Me-Ph |
| D-396 | t-butyl | H | t-butyl | H | 4-Me-Ph | 4-tBu-Ph | 4-Me-Ph | 4-tBu-Ph |

TABLE 34
| | $R_1$ | $R_2$ | $R_3$ | $R_4$ | $(A_1)a$ | $(A_2)b$ | | |
|---|---|---|---|---|---|---|---|---|
| D-397 | t-butyl | H | t-butyl | H |  |  | | |
| D-398 | t-butyl | H | t-butyl | H | | | | |
| D-399 | t-butyl | H | t-butyl | H | | | | |
| D-400 | t-butyl | H | t-butyl | H | | | | |
| D-401 | t-butyl | H | t-butyl | H | | | | |
| D-402 | t-butyl | H | t-butyl | H | | | | |
| D-403 | t-butyl | H | t-butyl | H | | | | |

TABLE 34-continued
| | $R_1$ | $R_2$ | $R_3$ | $R_4$ | $(A_1)a$ | $(A_2)b$ | | |
|---|---|---|---|---|---|---|---|---|
| D-404 | t-butyl | H | t-butyl | H |  | 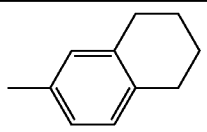 | 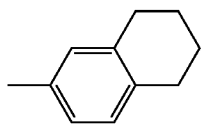 |  |
| D-404 | t-butyl | H | t-butyl | H |  |  |  | 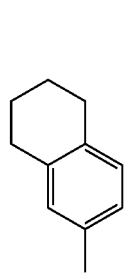 |
| D-405 | t-butyl | H | t-butyl | H | 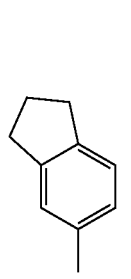 |  |  |  |
| D-406 | t-butyl | H | t-butyl | H |  |  |  |  |
| D-407 | t-butyl | H | t-butyl | H |  |  |  |  |
| D-408 | t-butyl | H | t-butyl | H | 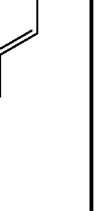 | | | |

TABLE 35

| | R₁ | R₂ | R₃ | R₄ | (A₁)a | (A₂)b | (A₃)c | (A₄)d |
|---|---|---|---|---|---|---|---|---|
| D-409 | t-butyl | H | t-butyl | H | | | | |
| D-410 | t-butyl | H | t-butyl | H | | | | |
| D-411 | t-butyl | H | t-butyl | H | | | | |
| D-412 | t-butyl | H | t-butyl | H | | | | |
| D-413 | t-butyl | H | t-butyl | H | | | | |
| D-414 | t-butyl | H | t-butyl | H | | | | |

TABLE 35-continued

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-415 | t-butyl | H | t-butyl | H | 9,9-dimethylfluorenyl (methyl-substituted) | phenyl | 9,9-dimethylfluorenyl (methyl-substituted) | phenyl |
| D-416 | t-butyl | H | t-butyl | H | 4-methylbenzyl (tolyl-CH2-) | tolyl | 4-methylbenzyl (tolyl-CH2-) | tolyl |
| D-417 | t-butyl | H | t-butyl | H | 4-methylbenzyl | 4-methylbenzyl | 4-methylbenzyl | 4-methylbenzyl |
| D-418 | t-butyl | H | t-butyl | H | 3,5-dimethylphenyl (tolyl) | 4-(isopropyl)tolyl | 3,5-dimethylphenyl (tolyl) | 4-(isopropyl)tolyl |
| D-419 | t-butyl | H | t-butyl | H | 10-methylphenanthryl (tolyl) | tolyl | 10-methylphenanthryl (tolyl) | tolyl |
| D-420 | t-butyl | H | t-butyl | H | 3,5-dicyclohexyltolyl | 4-cyclohexylphenyl-tolyl | 3,5-dicyclohexyltolyl | 4-cyclohexylphenyl-tolyl |

TABLE 36
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-421 | t-butyl | H | t-butyl | H | 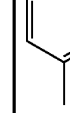 |  |  |  |
| D-422 | t-butyl | H | t-butyl | H | | | | |
| D-423 | t-butyl | H | t-butyl | H | | | | |
| D-424 | t-butyl | H | t-butyl | H | | | | |
| D-425 | t-butyl | H | t-butyl | H | | | | |
| D-426 | t-butyl | H | t-butyl | H |  | |  | |

TABLE 36-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-427 | t-butyl | H | t-butyl | H | 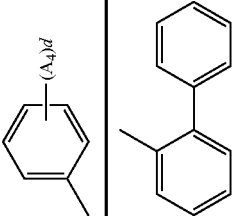 | 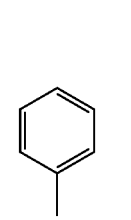 | 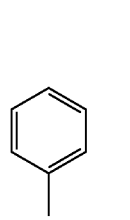 | 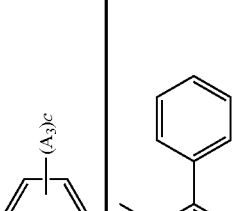 |
| D-428 | t-butyl | H | t-butyl | H | 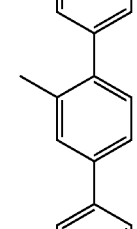 |  | 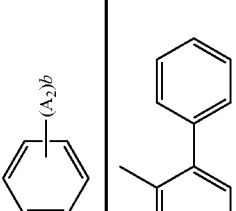 | 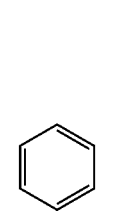 |
| D-429 | t-butyl | H | t-butyl | H | 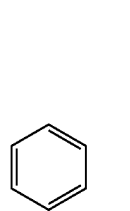 | 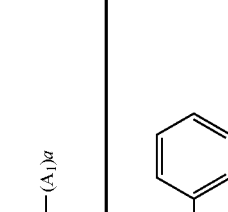 | 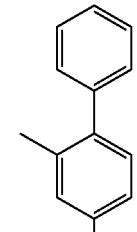 |  |
| D-430 | t-butyl | H | t-butyl | H | 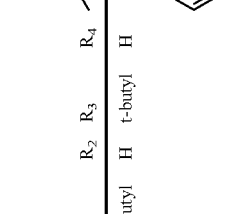 | 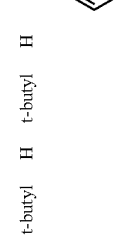 | 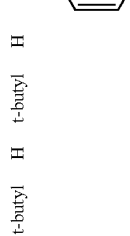 |  |
| D-431 | t-butyl | H | t-butyl | H |  | | | |
| D-432 | t-butyl | H | t-butyl | H |  | | | |

TABLE 37

| | R₁ | R₂ | R₃ | R₄ | —(A₁)a | —(A₂)b | —(A₃)c | —(A₄)d |
|---|---|---|---|---|---|---|---|---|
| D-433 | Phenyl | H | Phenyl | H | Phenyl | Phenyl | Phenyl | Phenyl |
| D-434 | Phenyl | H | Phenyl | H | Phenyl | 3-Me-phenyl | Phenyl | 3-Me-phenyl |
| D-435 | Phenyl | H | Phenyl | H | 3-Me-phenyl | 3-Me-phenyl | 3-Me-phenyl | 3-Me-phenyl |
| D-436 | Phenyl | H | Phenyl | H | Phenyl | 4-Me-phenyl | Phenyl | 4-Me-phenyl |
| D-437 | Phenyl | H | Phenyl | H | 3-Me-phenyl | 3,4-Me₂-phenyl | 3-Me-phenyl | 3,4-Me₂-phenyl |
| D-438 | Phenyl | H | Phenyl | H | 3,4,5-Me₃-phenyl | 3,5-Me₂-phenyl | 3,4,5-Me₃-phenyl | 3,5-Me₂-phenyl |
| D-439 | Phenyl | H | Phenyl | H | 4-Me-phenyl | 4-Me-phenyl | 4-Me-phenyl | 4-Me-phenyl |
| D-440 | Phenyl | H | Phenyl | H | 4-iPr-phenyl | 3,5-Me₂-phenyl | 4-iPr-phenyl | 3,5-Me₂-phenyl |
| D-441 | Phenyl | H | Phenyl | H | Phenyl | 4-iPr-phenyl | Phenyl | 4-iPr-phenyl |
| D-442 | Phenyl | H | Phenyl | H | 4-tBu-phenyl | 4-tBu-phenyl | 4-tBu-phenyl | 4-tBu-phenyl |
| D-443 | Phenyl | H | Phenyl | H | 4-Me-phenyl | 4-tBu-phenyl | 4-Me-phenyl | 4-tBu-phenyl |
| D-444 | Phenyl | H | Phenyl | H | 4-Me-phenyl | 4-iPr-phenyl | 4-Me-phenyl | 4-iPr-phenyl |

TABLE 38
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-445 | Phenyl | H | Phenyl | H | 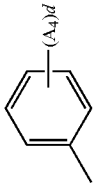 | 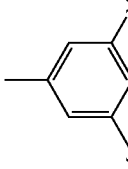 | 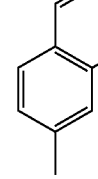 | 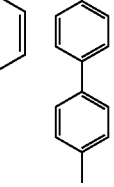 |
| D-446 | Phenyl | H | Phenyl | H | 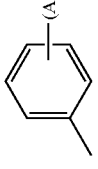 | 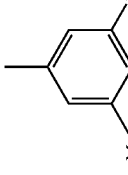 | 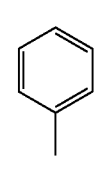 | 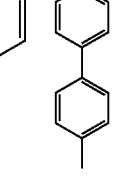 |
| D-447 | Phenyl | H | Phenyl | H | 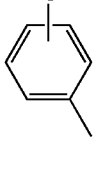 | 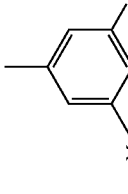 | 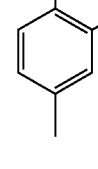 | 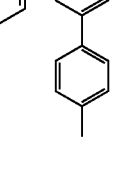 |
| D-448 | Phenyl | H | Phenyl | H | | | | |
| D-449 | Phenyl | H | Phenyl | H | 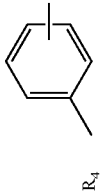 | 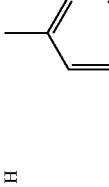 | 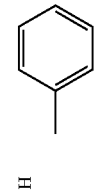 | 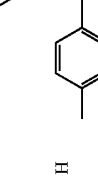 |
| D-450 | Phenyl | H | Phenyl | H |  |  | |  |
| D-451 | Phenyl | H | Phenyl | H |  | | | |

TABLE 38-continued
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-452 | Phenyl | H | Phenyl | H | 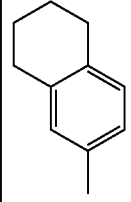 | 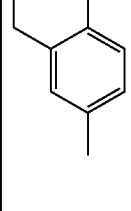 | 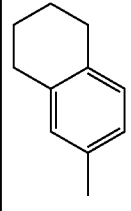 |  |
| D-453 | Phenyl | H | Phenyl | H | 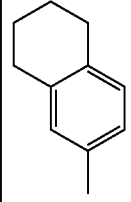 | 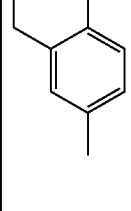 | 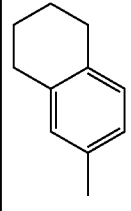 |  |
| D-454 | Phenyl | H | Phenyl | H | 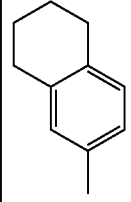 | 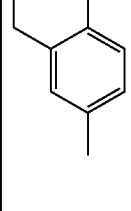 | 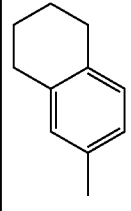 |  |
| D-455 | Phenyl | H | Phenyl | H | 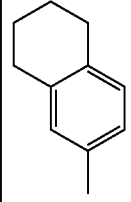 | 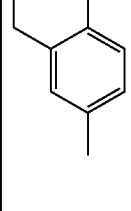 | 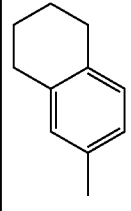 |  |
| D-456 | Phenyl | H | Phenyl | H | 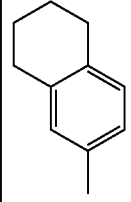 | 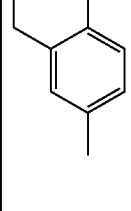 | 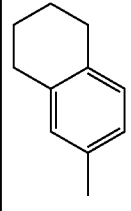 |  |

TABLE 39
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-457 | Phenyl | H | Phenyl | H | 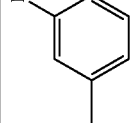 |  | 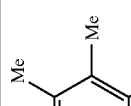 | 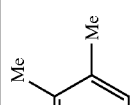 |
| D-458 | Phenyl | H | Phenyl | H | 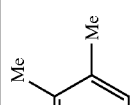 | 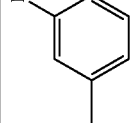 |  | 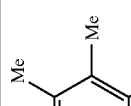 |
| D-459 | Phenyl | H | Phenyl | H | 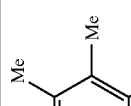 | 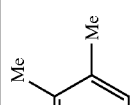 | 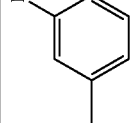 |  |
| D-460 | Phenyl | H | Phenyl | H |  | 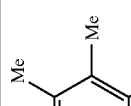 | 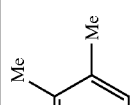 | 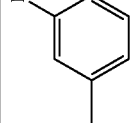 |
| D-461 | Phenyl | H | Phenyl | H | 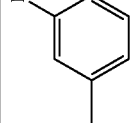 |  | 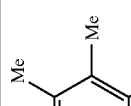 | 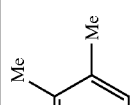 |
| D-462 | Phenyl | H | Phenyl | H | 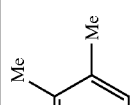 | 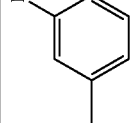 |  | 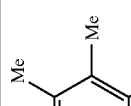 |
| D-463 | Phenyl | H | Phenyl | H | 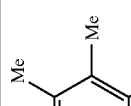 | 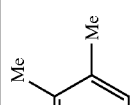 | 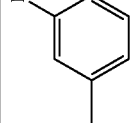 |  |

TABLE 39-continued

| | R₁ | R₂ | R₃ | R₄ | (A₁)a | (A₂)b | (A₃)c | (A₄)d |
|---|---|---|---|---|---|---|---|---|
| D-464 | Phenyl | H | Phenyl | H | 4-(1-methylethyl)phenyl | 4-(cumyl)phenyl | 4-(cumyl)phenyl | 4-(cumyl)phenyl |
| D-465 | Phenyl | H | Phenyl | H | pentafluorophenyl | phenyl | pentafluorophenyl | phenyl |
| D-466 | Phenyl | H | Phenyl | H | 3,5-dimethylphenyl | 4-(1-methylethyl)phenyl | 3,5-dimethylphenyl | 4-(1-methylethyl)phenyl |
| D-467 | Phenyl | H | Phenyl | H | 10-methylphenanthren-9-yl | phenyl | 10-methylphenanthren-9-yl | phenyl |
| D-468 | Phenyl | H | Phenyl | H | 3,5-dicyclohexylphenyl | 4-cyclohexylphenyl | 3,5-dicyclohexylphenyl | 4-cyclohexylphenyl |

TABLE 40
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-469 | Phenyl | H | Phenyl | H |  | 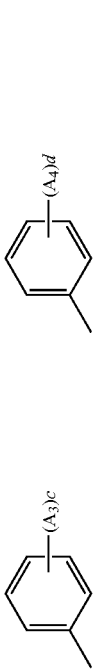 | 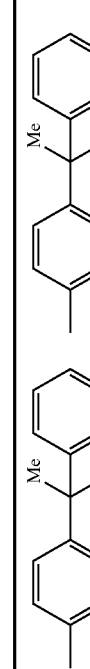 |  |
| D-470 | Phenyl | H | | H |  | 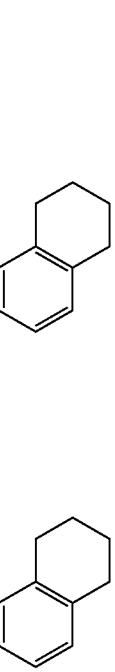 |  | 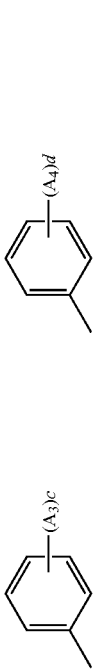 |
| D-471 | Phenyl | H | Phenyl | H | 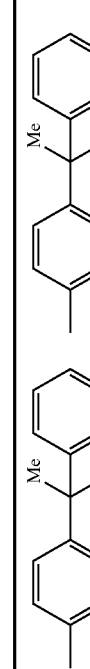 |  |  | 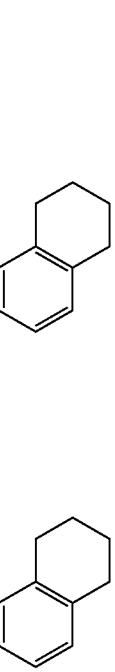 |
| D-472 | Phenyl | H | Phenyl | H |  | 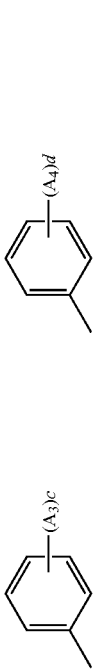 | 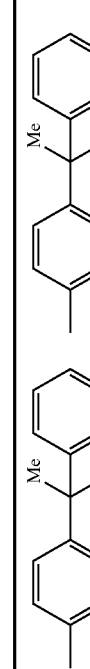 |  |
| D-473 | Phenyl | H | Phenyl | H |  | 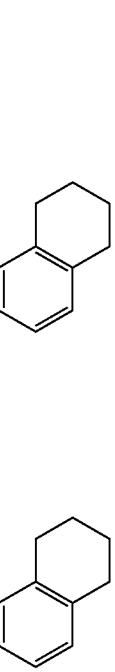 |  | 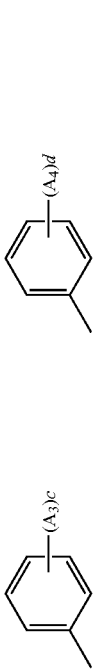 |

TABLE 40-continued

|  | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-474 | Phenyl | H | Phenyl | H | 4-CF₃-C₆H₄ | 4-F-C₆H₄ | 4-CF₃-C₆H₄ | 4-F-C₆H₄ |
| D-476 | Phenyl | H | Phenyl | H | 1,1-dimethyl-6-methyl-tetrahydronaphthyl | 1,1-dimethyl-6-methyl-indanyl | 1,1-dimethyl-6-methyl-tetrahydronaphthyl | 1,1-dimethyl-6-methyl-indanyl |
| D-477 | Phenyl | H | Phenyl | H | tetramethyl-methyl-indanyl | 1,3-dimethyl-5-methyl-indanyl | tetramethyl-methyl-indanyl | 1,3-dimethyl-5-methyl-indanyl |
| D-478 | Phenyl | H | Phenyl | H | 4-(pyridin-3-yl)-phenyl | 4-methylphenyl | 4-(pyridin-3-yl)-phenyl | 4-methylphenyl |
| D-479 | Phenyl | H | Phenyl | H | 4-(trimethylsilyl)-phenyl | 4-(trimethylsilyl)-phenyl | 4-(trimethylsilyl)-phenyl | 4-(trimethylsilyl)-phenyl |
| D-480 | Phenyl | H | Phenyl | H | 4-methylphenyl | 4-(3-methylbutyl)-phenyl | 4-methylphenyl | 4-(3-methylbutyl)-phenyl |

TABLE 41

| | R₁ | R₂ | R₃ | R₄ | (A₁)a | (A₂)b | (A₃)c | (A₄)d |
|---|---|---|---|---|---|---|---|---|
| D-481 | H | Methyl | H | H | Ph | Ph | Ph | Ph |
| D-482 | H | Methyl | H | H | Ph | 3-MeC₆H₄ | Ph | 3-MeC₆H₄ |
| D-483 | H | Methyl | H | H | 3-MeC₆H₄ | 3-MeC₆H₄ | 3-MeC₆H₄ | 3-MeC₆H₄ |
| D-484 | H | Methyl | H | H | Ph | 2-MeC₆H₄ | Ph | 2-MeC₆H₄ |
| D-485 | H | Methyl | H | H | 2,4-Me₂C₆H₃ | 2,4-Me₂C₆H₃ | 2,4-Me₂C₆H₃ | 2,4-Me₂C₆H₃ |
| D-486 | H | Methyl | H | H | 2,4,6-Me₃C₆H₂ | 3,5-Me₂C₆H₃ | 2,4,6-Me₃C₆H₂ | 3,5-Me₂C₆H₃ |
| D-487 | H | Methyl | H | H | 4-MeC₆H₄ | 4-MeC₆H₄ | 4-MeC₆H₄ | 4-MeC₆H₄ |
| D-488 | H | Methyl | H | H | 4-iPrC₆H₄ | 3,5-Me₂C₆H₃ | 4-iPrC₆H₄ | 3,5-Me₂C₆H₃ |

TABLE 41-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-489 | H | Methyl | H | H | 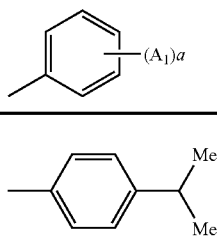 4-CHMe₂-C₆H₄ | 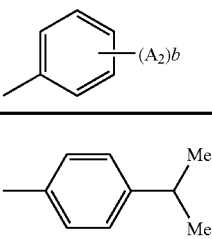 4-CHMe₂-C₆H₄ | 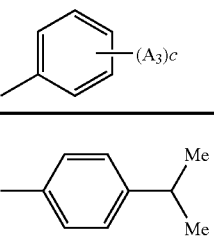 4-CHMe₂-C₆H₄ | 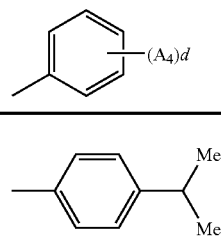 4-CHMe₂-C₆H₄ |
| D-490 | H | Methyl | H | H | 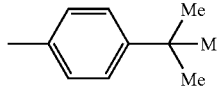 4-CMe₃-C₆H₄ | 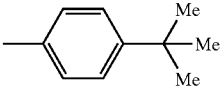 4-CMe₃-C₆H₄ | 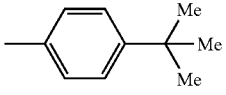 4-CMe₃-C₆H₄ | 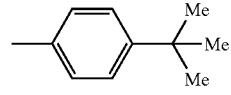 4-CMe₃-C₆H₄ |
| D-491 | H | Methyl | H | H | 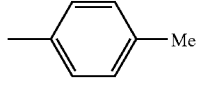 4-Me-C₆H₄ | 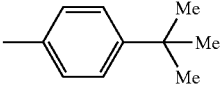 4-CMe₃-C₆H₄ | 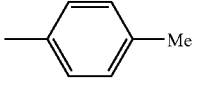 4-Me-C₆H₄ | 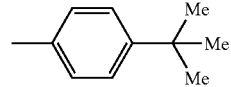 4-CMe₃-C₆H₄ |
| D-492 | H | Methyl | H | H | 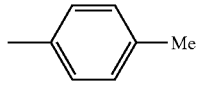 4-Me-C₆H₄ | 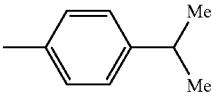 4-CHMe₂-C₆H₄ | 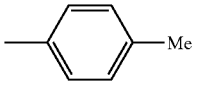 4-Me-C₆H₄ | 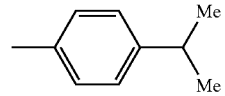 4-CHMe₂-C₆H₄ |

TABLE 42
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-493 | H | Methyl | H | H | 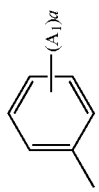 | 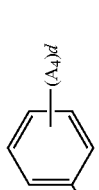 | 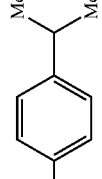 | 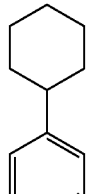 |
| D-494 | H | Methyl | H | H | 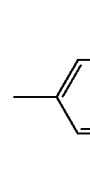 | 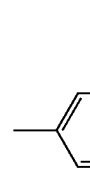 | 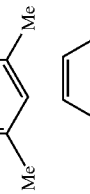 | 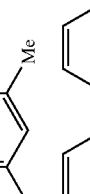 |
| D-495 | H | Methyl | H | H | | | | |
| D-496 | H | Methyl | H | H | | | | |
| D-497 | H | Methyl | H | H | | | | |
| D-498 | H | Methyl | H | H | | | | |
| D-499 | H | Methyl | H | H | 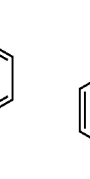 | 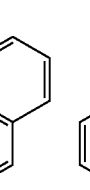 | 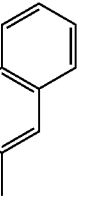 | 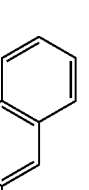 |

TABLE 42-continued

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-500 | H | Methyl | H | H | | | | |
| D-501 | H | Methyl | H | H | | | | |
| D-502 | H | Methyl | H | H | | | | |
| D-503 | H | Methyl | H | H | | | | |
| D-504 | H | Methyl | H | H | | | | |

TABLE 43
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-505 | H | Methyl | H | H | 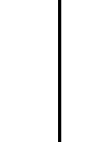 | 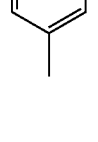 |  | 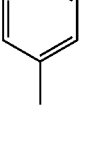 |
| D-506 | H | Methyl | H | H | 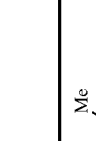 | 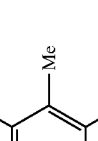 |  | 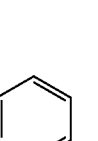 |
| D-507 | H | Methyl | H | H | 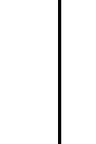 | 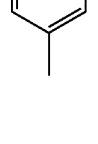 |  |  |
| D-508 | H | Methyl | H | H | 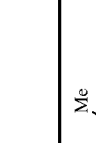 | 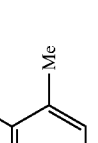 |  | 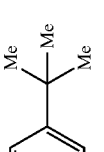 |
| D-509 | H | Methyl | H | H | 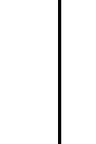 | 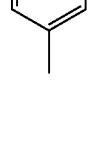 |  | 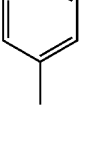 |
| D-510 | H | Methyl | H | H | 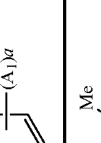 | 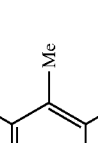 | 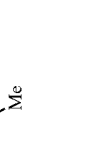 |  |

TABLE 43-continued
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-511 | H | Methyl | H | H |  |  |  |  |
| D-512 | H | Methyl | H | H |  |  |  |  |
| D-513 | H | Methyl | H | H |  |  |  |  |
| D-514 | H | Methyl | H | H |  |  |  |  |
| D-515 | H | Methyl | H | H |  |  |  |  |
| D-516 | H | Methyl | H | H |  |  |  |  |

TABLE 44
| | R₁ | R₂ | R₃ | R₄ | (A₁)a | (A₂)b | (A₃)c | (A₄)d |
|---|---|---|---|---|---|---|---|---|
| D-517 | H | Methyl | H | H |  |  |  |  |
| D-518 | H | Methyl | H | H |  |  |  |  |
| D-519 | H | Methyl | H | H |  |  |  |  |
| D-520 | H | Methyl | H | H |  |  |  |  |
| D-521 | H | Methyl | H | H |  |  |  |  |
| D-522 | H | Methyl | H | H |  |  |  |  |

TABLE 44-continued

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-523 | H | Methyl | H | H | 2-biphenyl | 2-biphenyl | 2-biphenyl | 2-biphenyl |
| D-524 | H | Methyl | H | H | 2-methyl-4-phenylbiphenyl | phenyl | 2-methyl-4-phenylbiphenyl | phenyl |
| D-525 | H | Methyl | H | H | 3'-methyl-4-biphenyl | phenyl | 3'-methyl-4-biphenyl | phenyl |
| D-526 | H | Methyl | H | H | 1-naphthyl | phenyl | 1-naphthyl | phenyl |
| D-527 | H | Methyl | H | H | 6-(4-methylphenyl)-2-naphthyl | phenyl | 6-(4-methylphenyl)-2-naphthyl | phenyl |
| D-528 | H | Methyl | H | H | phenyl | 4-(3-methylbutyl)phenyl | phenyl | 4-(3-methylbutyl)phenyl |

TABLE 45
| | $R_1$ | $R_2$ | $R_3$ | $R_4$ | (A$_1$)a | (A$_2$)b | (A$_3$)c | (A$_4$)d |
|---|---|---|---|---|---|---|---|---|
| D-529 | H | Isopropyl | H | H | 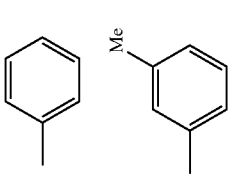 | 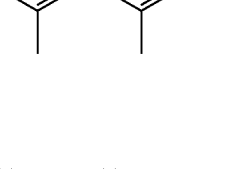 | 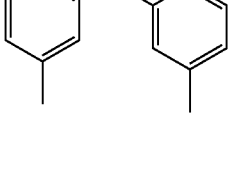 | 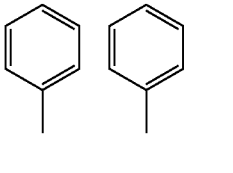 |
| D-530 | H | Isopropyl | H | H | 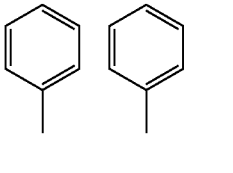 | 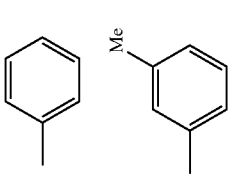 | 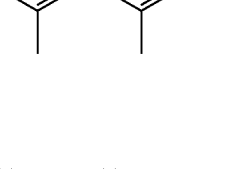 | 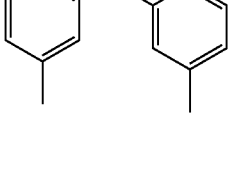 |
| D-531 | H | Isopropyl | H | H | 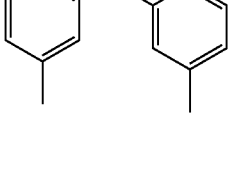 | 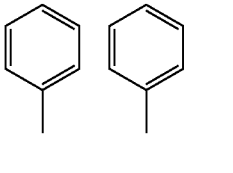 | 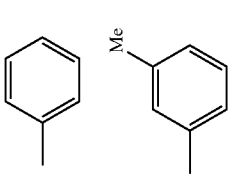 | 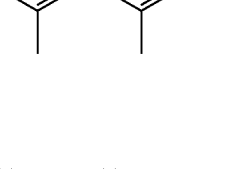 |
| D-532 | H | Isopropyl | H | H | 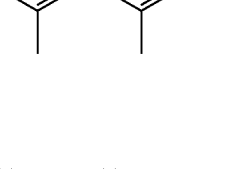 | 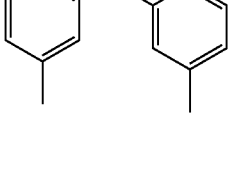 | 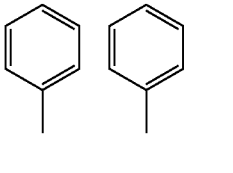 | 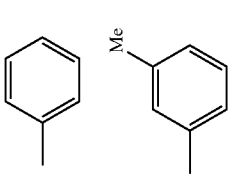 |
| D-533 | H | Isopropyl | H | H | 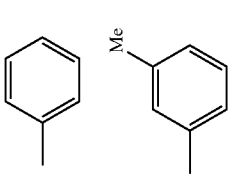 | 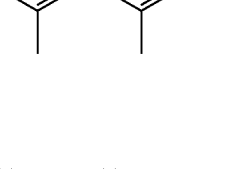 | 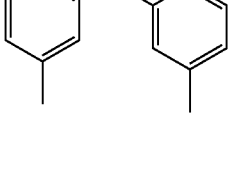 | 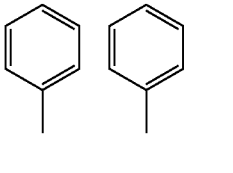 |
| D-534 | H | Isopropyl | H | H | 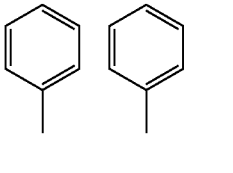 | 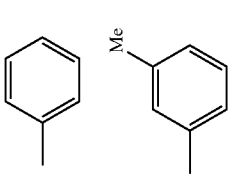 | 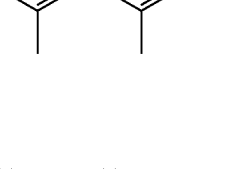 | 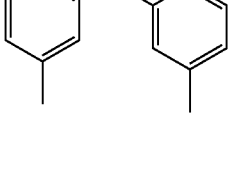 |
| D-535 | H | Isopropyl | H | H | 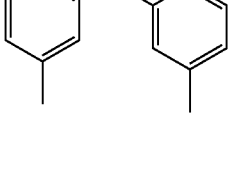 | 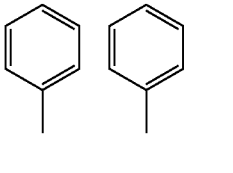 | 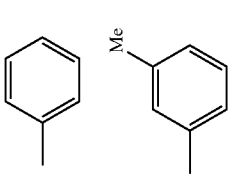 | 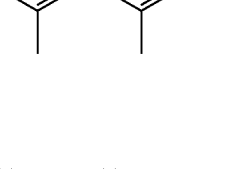 |

TABLE 45-continued

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-536 | H | Isopropyl | H | H | 4-(1-methylethyl)phenyl | 3,5-dimethylphenyl | 4-(1-methylethyl)phenyl | 3,5-dimethylphenyl |
| D-537 | H | Isopropyl | H | H | 4-(1-methylethyl)phenyl | 4-(1-methylethyl)phenyl | 4-(1-methylethyl)phenyl | 4-(1-methylethyl)phenyl |
| D-538 | H | Isopropyl | H | H | 4-(1,1-dimethylethyl)phenyl | 4-(1,1-dimethylethyl)phenyl | 4-(1,1-dimethylethyl)phenyl | 4-(1,1-dimethylethyl)phenyl |
| D-539 | H | Isopropyl | H | H | 4-methylphenyl | 4-(1,1-dimethylethyl)phenyl | 4-methylphenyl | 4-(1,1-dimethylethyl)phenyl |
| D-540 | H | Isopropyl | H | H | 4-methylphenyl | 4-(1-methylethyl)phenyl | 4-methylphenyl | 4-(1-methylethyl)phenyl |

TABLE 46

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-541 | H | Isopropyl | H | H | | | | |
| D-542 | H | Isopropyl | H | H | | | | |
| D-543 | H | Isopropyl | H | H | | | | |
| D-544 | H | Isopropyl | H | H | | | | |
| D-545 | H | Isopropyl | H | H | | | | |
| D-546 | H | Isopropyl | H | H | | | | |
| D-547 | H | Isopropyl | H | H | | | | |

TABLE 46-continued
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-548 | H | Isopropyl | H | H | 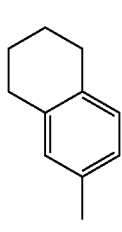 | 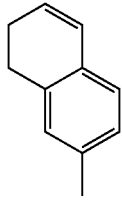 | 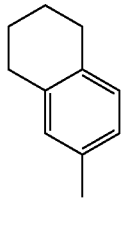 | 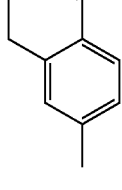 |
| D-549 | H | Isopropyl | H | H | 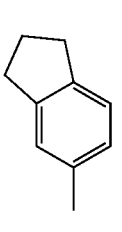 | 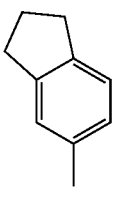 | 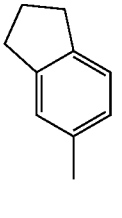 | 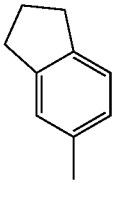 |
| D-550 | H | Isopropyl | H | H | 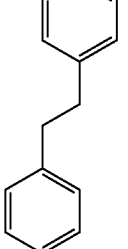 | 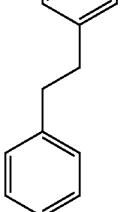 | 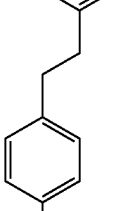 | 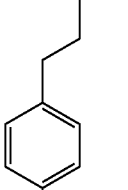 |
| D-551 | H | Isopropyl | H | H | 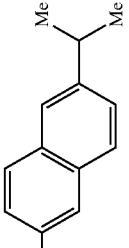 | 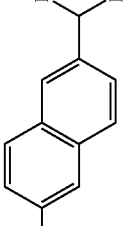 | 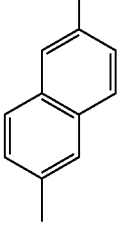 | 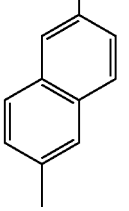 |
| D-552 | H | Isopropyl | H | H | 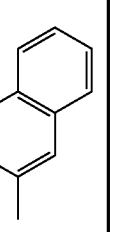 | 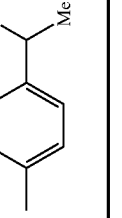 | 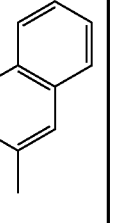 | 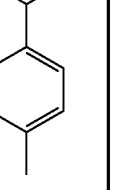 |

TABLE 47
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-553 | H | Isopropyl | H | H | 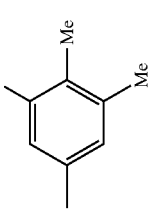 | 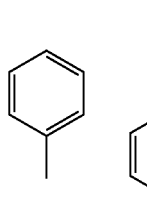 | 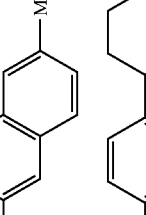 | 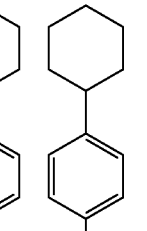 |
| D-554 | H | Isopropyl | H | H | 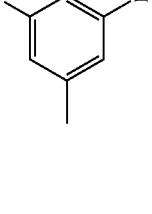 | 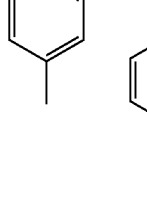 | 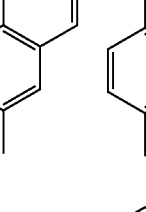 | 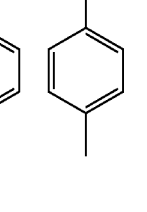 |
| D-555 | H | Isopropyl | H | H | 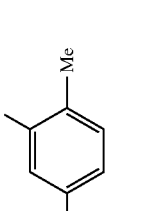 | 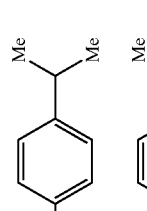 | 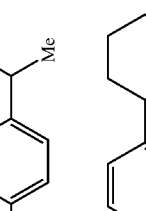 | 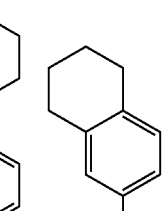 |
| D-556 | H | Isopropyl | H | H |  |  |  |  |
| D-557 | H | Isopropyl | H | H |  |  | 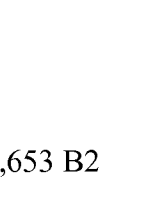 |  |
| D-558 | H | Isopropyl | H | H | 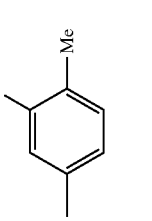 | 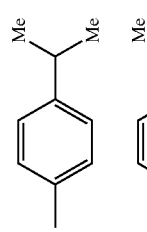 | 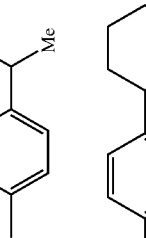 | 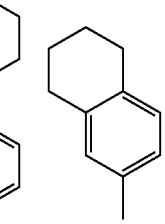 |

TABLE 47-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-559 | H | Isopropyl | H | H | 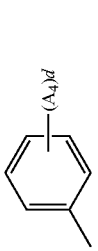 | 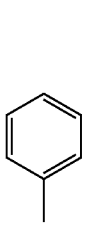 | 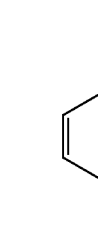 | 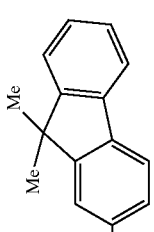 |
| D-560 | H | Isopropyl | H | H | 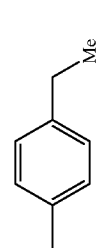 | 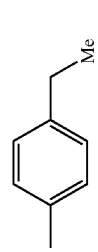 | 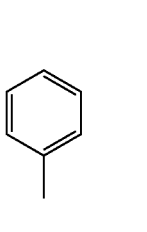 | 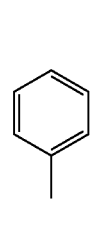 |
| D-561 | H | Isopropyl | H | H | 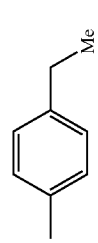 | 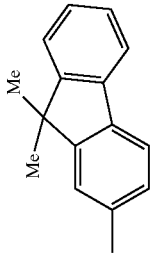 | 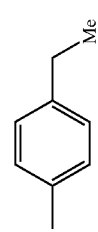 | 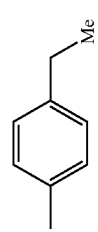 |
| D-562 | H | Isopropyl | H | H |  |  | | |
| D-563 | H | Isopropyl | H | H |  |  | | |
| D-564 | H | Isopropyl | H | H |  |  | | |

TABLE 48

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-565 | H | Isopropyl | H | H | phenyl | phenyl | 2-naphthyl | 2-naphthyl |
| D-566 | H | Isopropyl | H | H | 5-tetrahydronaphthyl | 5-tetrahydronaphthyl | 5-tetrahydronaphthyl | 5-tetrahydronaphthyl |
| D-567 | H | Isopropyl | H | H | 4-biphenyl | phenyl | 4-biphenyl | phenyl |
| D-568 | H | Isopropyl | H | H | o-tolyl | phenyl | o-tolyl | phenyl |
| D-569 | H | Isopropyl | H | H | o-tolyl | o-tolyl | o-tolyl | o-tolyl |
| D-570 | H | Isopropyl | H | H | 2-biphenyl | phenyl | 2-biphenyl | phenyl |

TABLE 48-continued

| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-571 | H | Isopropyl | H | H | 2-methylbiphenyl | 2-methylbiphenyl | 2-methylbiphenyl | 2-methylbiphenyl |
| D-572 | H | Isopropyl | H | H | 2-methyl-4-phenylbiphenyl | tolyl | 2-methyl-4-phenylbiphenyl | tolyl |
| D-573 | H | Isopropyl | H | H | 3-methyl-4-phenylbiphenyl | tolyl | 3-methyl-4-phenylbiphenyl | tolyl |
| D-574 | H | Isopropyl | H | H | 8-methylnaphthyl | tolyl | 8-methylnaphthyl | tolyl |
| D-575 | H | Isopropyl | H | H | 4-methyl-2-phenylnaphthyl | tolyl | 4-methyl-2-phenylnaphthyl | tolyl |
| D-576 | H | Isopropyl | H | H | tolyl | 4-(3-methylbutyl)phenyl | tolyl | 4-(3-methylbutyl)phenyl |

TABLE 49
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-577 | H | t-butyl | H | H | 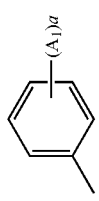 | 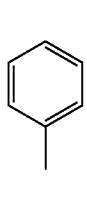 | 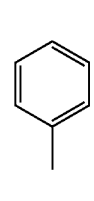 | 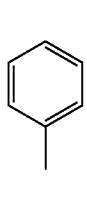 |
| D-578 | H | t-butyl | H | H | 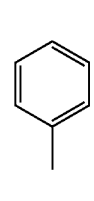 |  | 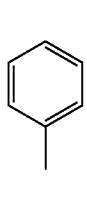 | 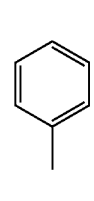 |
| D-579 | H | t-butyl | H | H |  | 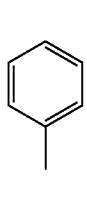 | 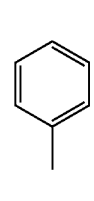 |  |
| D-580 | H | t-butyl | H | H | 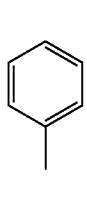 | 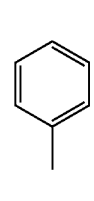 |  | 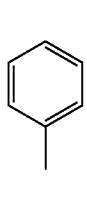 |
| D-581 | H | t-butyl | H | H | 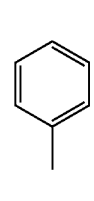 |  | 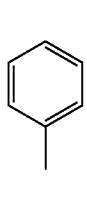 | 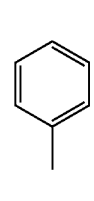 |
| D-582 | H | t-butyl | H | H |  | 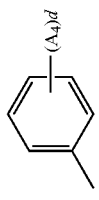 | 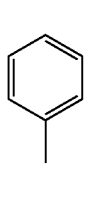 | 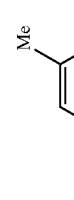 |
| D-583 | H | t-butyl | H | H | | | | |

TABLE 49-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-584 | H | t-butyl | H | H | 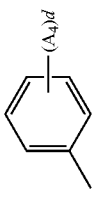 | 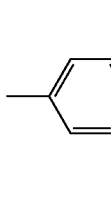 | 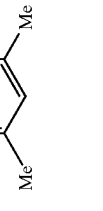 |  |
| D-585 | H | t-butyl | H | H | 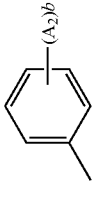 | 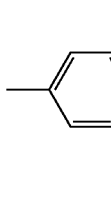 |  |  |
| D-586 | H | t-butyl | H | H | 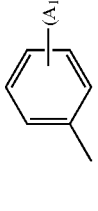 | 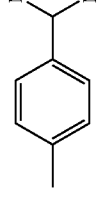 |  |  |
| D-587 | H | t-butyl | H | H | 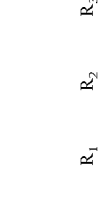 |  |  |  |
| D-588 | H | t-butyl | H | H |  | 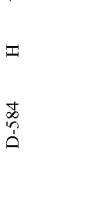 |  | 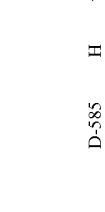 |

TABLE 50
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-589 | H | t-butyl | H | H | 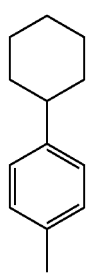 | 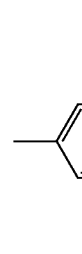 | 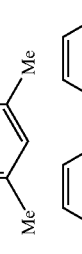 | 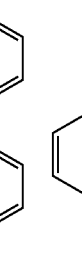 |
| D-590 | H | t-butyl | H | H | 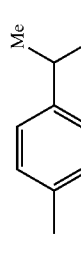 | 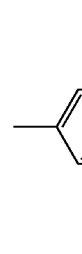 | 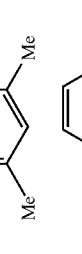 | 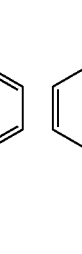 |
| D-591 | H | t-butyl | H | H | 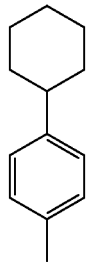 | 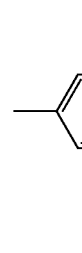 | 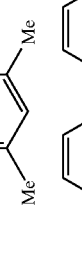 | 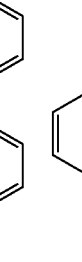 |
| D-592 | H | t-butyl | H | H | | | | 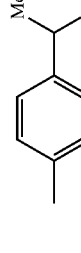 |
| D-593 | H | t-butyl | H | H | 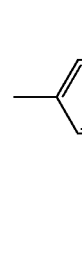 | 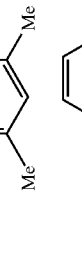 | 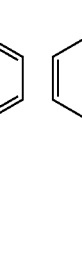 | 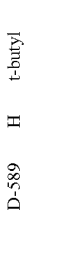 |
| D-594 | H | t-butyl | H | H |  | | |  |
| D-595 | H | t-butyl | H | H |  | | | |

TABLE 50-continued

| | $R_1$ | $R_2$ | $R_3$ | $R_4$ | (A$_1$)a | (A$_2$)b | (A$_3$)c | (A$_4$)d |
|---|---|---|---|---|---|---|---|---|
| D-596 | H | t-butyl | H | H | tetralin-Me | tetralin-Me | tetralin-Me | tetralin-Me |
| D-597 | H | t-butyl | H | H | indane-Me | indane-Me | indane-Me | indane-Me |
| D-598 | H | t-butyl | H | H | biphenyl-Me | biphenyl-Me | biphenyl-Me | biphenyl-Me |
| D-599 | H | t-butyl | H | H | naphthyl-CHMe$_2$ | naphthyl-CHMe$_2$ | naphthyl-CHMe$_2$ | naphthyl-CHMe$_2$ |
| D-600 | H | t-butyl | H | H | tolyl-CHMe$_2$ | naphthyl-Me | tolyl-CHMe$_2$ | naphthyl-Me |

TABLE 51

| | $R_1$ | $R_2$ | $R_3$ | $R_4$ | (A₁)a | (A₂)b | (A₃)c | (A₄)d |
|---|---|---|---|---|---|---|---|---|
| D-601 | H | t-butyl | H | H | | | | |
| D-602 | H | t-butyl | H | H | | | | |
| D-603 | H | t-butyl | H | H | | | | |
| D-604 | H | t-butyl | H | H | | | | |
| D-605 | H | t-butyl | H | H | | | | |
| D-606 | H | t-butyl | H | H | | | | |

TABLE 51-continued
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-607 | H | t-butyl | H | H | 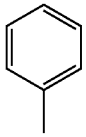 | 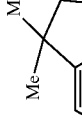 |  | 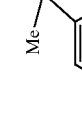 |
| D-608 | H | t-butyl | H | H | 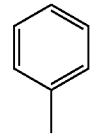 | 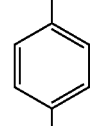 | 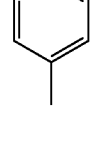 | 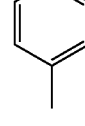 |
| D-609 | H | t-butyl | H | H | 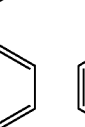 | 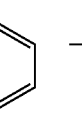 | 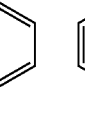 | 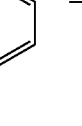 |
| D-610 | H | t-butyl | H | H | 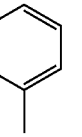 | 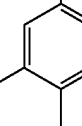 | | |
| D-611 | H | t-butyl | H | H | 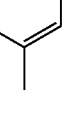 | | 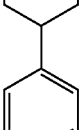 | |
| D-612 | H | t-butyl | H | H | 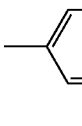 | | 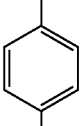 | |

TABLE 52

| | $R_1$ | $R_2$ | $R_3$ | $R_4$ | (A₁)a | (A₂)b | (A₃)c | (A₄)d |
|---|---|---|---|---|---|---|---|---|
| D-613 | H | t-butyl | H | H | phenyl | phenyl | 2-naphthyl | 2-naphthyl |
| D-614 | H | t-butyl | H | H | 5-tetrahydronaphthyl | 5-tetrahydronaphthyl | 5-tetrahydronaphthyl | 5-tetrahydronaphthyl |
| D-615 | H | t-butyl | H | H | 4'-methylbiphenyl | phenyl | 4-biphenyl | phenyl |
| D-616 | H | t-butyl | H | H | o-tolyl | phenyl | o-tolyl | phenyl |
| D-617 | H | t-butyl | H | H | o-tolyl | o-tolyl | o-tolyl | o-tolyl |
| D-618 | H | t-butyl | H | H | 2-biphenyl | phenyl | 2-biphenyl | phenyl |

TABLE 52-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-619 | H | t-butyl | H | H | 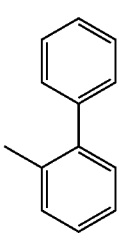 | 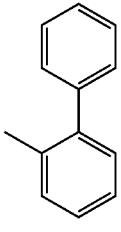 | 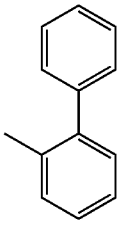 | 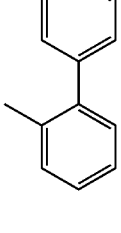 |
| D-620 | H | t-butyl | H | H | 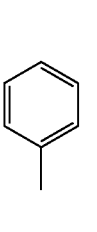 | 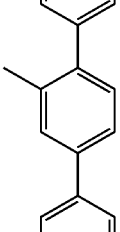 | 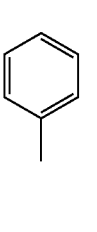 | 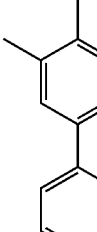 |
| D-621 | H | t-butyl | H | H | 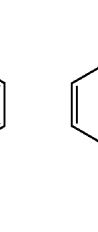 | 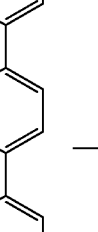 | 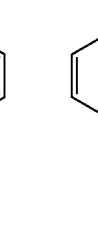 | 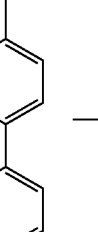 |
| D-622 | H | t-butyl | H | H | 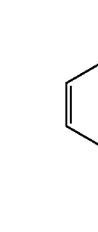 | 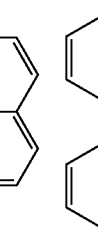 | 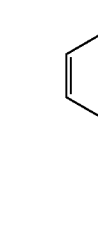 | 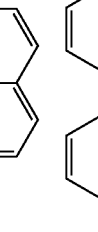 |
| D-623 | H | t-butyl | H | H | 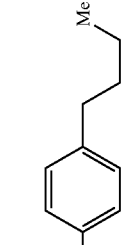 | 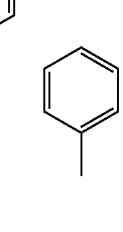 | 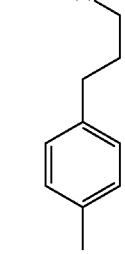 | 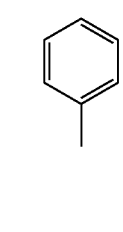 |
| D-624 | H | t-butyl | H | H |  |  |  |  |

TABLE 53

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-625 | H | Phenyl | H | H | Phenyl | Phenyl | Phenyl | Phenyl |
| D-626 | H | Phenyl | H | H | Phenyl | 3-Me-phenyl | Phenyl | 3-Me-phenyl |
| D-627 | H | Phenyl | H | H | 3-Me-phenyl | 3-Me-phenyl | 3-Me-phenyl | 3-Me-phenyl |
| D-628 | H | Phenyl | H | H | Phenyl | 4-Me-phenyl | Phenyl | 4-Me-phenyl |
| D-629 | H | Phenyl | H | H | 2,3-diMe-phenyl | 2,3-diMe-phenyl | 2,3-diMe-phenyl | 2,3-diMe-phenyl |
| D-630 | H | Phenyl | H | H | 3,5-diMe-phenyl | 3,5-diMe-phenyl | 3,5-diMe-phenyl | 3,5-diMe-phenyl |
| D-631 | H | Phenyl | H | H | 4-Me-phenyl | 4-Me-phenyl | 4-Me-phenyl | 4-Me-phenyl |

TABLE 53-continued

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-632 | H | Phenyl | H | H | 4-(1-methylethyl)phenyl | 3,5-dimethylphenyl | 4-(1-methylethyl)phenyl | 3,5-dimethylphenyl |
| D-633 | H | Phenyl | H | H | 4-(1-methylethyl)phenyl | 4-(1-methylethyl)phenyl | 4-(1-methylethyl)phenyl | 4-(1-methylethyl)phenyl |
| D-634 | H | Phenyl | H | H | 4-tert-butylphenyl | 4-tert-butylphenyl | 4-tert-butylphenyl | 4-tert-butylphenyl |
| D-635 | H | Phenyl | H | H | 4-methylphenyl | 4-tert-butylphenyl | 4-methylphenyl | 4-tert-butylphenyl |
| D-636 | H | Phenyl | H | H | 4-methylphenyl | 4-(1-methylethyl)phenyl | 4-methylphenyl | 4-(1-methylethyl)phenyl |

TABLE 54

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-637 | H | Phenyl | H | H | | | | |
| D-638 | H | Phenyl | H | H | | | | |
| D-639 | H | Phenyl | H | H | | | | |
| D-640 | H | Phenyl | H | H | | | | |
| D-641 | H | Phenyl | H | H | | | | |
| D-642 | H | Phenyl | H | H | | | | |
| D-643 | H | Phenyl | H | H | | | | |

TABLE 54-continued

| | $R_1$ | $R_2$ | $R_3$ | $R_4$ | (A$_1$)a | (A$_2$)b | (A$_3$)c | (A$_4$)d |
|---|---|---|---|---|---|---|---|---|
| D-644 | H | Phenyl | H | H | | | | |
| D-645 | H | Phenyl | H | H | | | | |
| D-646 | H | Phenyl | H | H | | | | |
| D-647 | H | Phenyl | H | H | | | | |
| D-648 | H | Phenyl | H | H | | | | |

TABLE 55

| | $R_1$ | $R_2$ | $R_3$ | $R_4$ | (A₁)a | (A₂)b | (A₃)c | (A₄)d |
|---|---|---|---|---|---|---|---|---|
| D-649 | H | Phenyl | H | H | mesityl | 2,4-dimethylphenyl | mesityl | 2,4-dimethylphenyl |
| D-650 | H | Phenyl | H | H | p-tolyl | 4-tert-butyl-p-tolyl | p-tolyl | 4-tert-butyl-p-tolyl |
| D-651 | H | Phenyl | H | H | 6-methyl-2-naphthyl | 4-isopropyl-p-tolyl | 6-methylnaphthyl | 4-isopropyl-p-tolyl |
| D-652 | H | Phenyl | H | H | 4-cyclohexyl-phenyl | 4-cyclohexyl-phenyl | 4-cyclohexyl-phenyl | 4-cyclohexyl-phenyl |
| D-653 | H | Phenyl | H | H | 4-cyclohexyl-phenyl | 6-methyl-tetralinyl | 4-cyclohexyl-phenyl | 6-methyl-tetralinyl |
| D-654 | H | Phenyl | H | H | 9,9-dimethylfluorenyl | 9,9-dimethylfluorenyl | 9,9-dimethylfluorenyl | 9,9-dimethylfluorenyl |

TABLE 55-continued
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-655 | H | Phenyl | H | H | 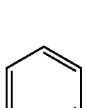 | 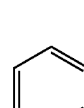 | 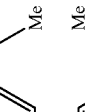 |  |
| D-656 | H | Phenyl | H | H |  |  |  |  |
| D-657 | H | Phenyl | H | H | 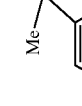 | 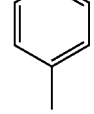 | 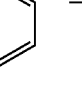 | 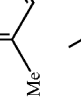 |
| D-658 | H | Phenyl | H | H | 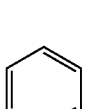 | 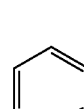 | 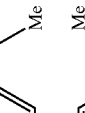 |  |
| D-659 | H | Phenyl | H | H |  |  |  |  |
| D-660 | H | Phenyl | H | H | 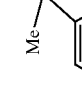 | 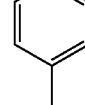 | 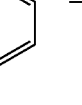 | 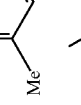 |

TABLE 56

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-661 | H | Phenyl | H | H | phenyl | phenyl | 2-naphthyl | 2-naphthyl |
| D-662 | H | Phenyl | H | H | 5-tetrahydronaphthyl | 5-tetrahydronaphthyl | 5-tetrahydronaphthyl | 5-tetrahydronaphthyl |
| D-663 | H | Phenyl | H | H | 4-(4-methylphenyl)phenyl | phenyl | 4-(4-methylphenyl)phenyl | phenyl |
| D-664 | H | Phenyl | H | H | 2-methylphenyl | phenyl | 2-methylphenyl | phenyl |
| D-665 | H | Phenyl | H | H | 2-methylphenyl | 2-methylphenyl | 2-methylphenyl | 2-methylphenyl |
| D-666 | H | Phenyl | H | H | 2-biphenyl | phenyl | 2-biphenyl | phenyl |

TABLE 56-continued
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-667 | H | Phenyl | H | H | 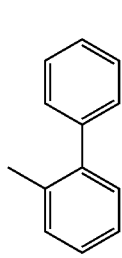 | 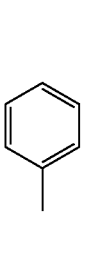 | 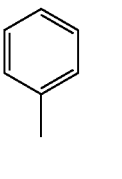 | 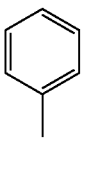 |
| D-668 | H | Phenyl | H | H | 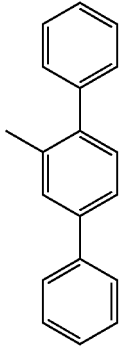 | | 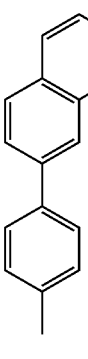 | |
| D-669 | H | Phenyl | H | H | | | | |
| D-670 | H | Phenyl | H | H | 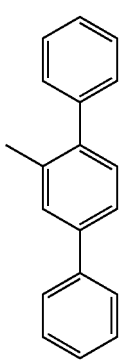 | | 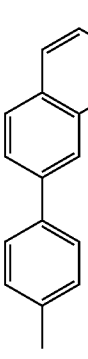 | |
| D-671 | H | Phenyl | H | H |  | |  | |
| D-672 | H | Phenyl | H | H | |  | |  |

TABLE 57

| | $R_1$ | $R_2$ | $R_3$ | $R_4$ | (A₁)a | (A₂)b | (A₃)c | (A₄)d |
|---|---|---|---|---|---|---|---|---|
| D-673 | H | Methyl | H | Methyl | Ph | Ph | Ph | Ph |
| D-674 | H | Methyl | H | Methyl | Ph | 3-MeC₆H₄ | Ph | 3-MeC₆H₄ |
| D-675 | H | Methyl | H | Methyl | 3-MeC₆H₄ | 3-MeC₆H₄ | 3-MeC₆H₄ | 3-MeC₆H₄ |
| D-676 | H | Methyl | H | Methyl | Ph | 4-MeC₆H₄ | Ph | 4-MeC₆H₄ |
| D-677 | H | Methyl | H | Methyl | 3-MeC₆H₄ | 2,3-Me₂C₆H₃ | 3-MeC₆H₄ | 2,3-Me₂C₆H₃ |
| D-678 | H | Methyl | H | Methyl | 2,6-Me₂-4-... | 3,5-Me₂C₆H₃ | 2,6-Me₂-4-... | 3,5-Me₂C₆H₃ |
| D-679 | H | Methyl | H | Methyl | 4-MeC₆H₄ | 4-MeC₆H₄ | 4-MeC₆H₄ | 4-MeC₆H₄ |

TABLE 57-continued

| | $R_1$ | $R_2$ | $R_3$ | $R_4$ | —(A₁)a | —(A₂)b | —(A₃)c | —(A₄)d |
|---|---|---|---|---|---|---|---|---|
| D-680 | H | Methyl | H | Methyl | 4-(1-methylethyl)phenyl | 3,5-dimethylphenyl | 4-(1-methylethyl)phenyl | 3,5-dimethylphenyl |
| D-681 | H | Methyl | H | Methyl | 4-(1-methylethyl)phenyl | 4-(1-methylethyl)phenyl | 4-(1-methylethyl)phenyl | 4-methylphenyl |
| D-682 | H | Methyl | H | Methyl | 4-(1,1-dimethylethyl)phenyl | 4-(1,1-dimethylethyl)phenyl | 4-(1,1-dimethylethyl)phenyl | 4-methylphenyl |
| D-683 | H | Methyl | H | Methyl | 4-methylphenyl | 4-(1,1-dimethylethyl)phenyl | 4-methylphenyl | 4-(1,1-dimethylethyl)phenyl |
| D-684 | H | Methyl | H | Methyl | 4-methylphenyl | 4-(1-methylethyl)phenyl | 4-methylphenyl | 4-(1-methylethyl)phenyl |

TABLE 58
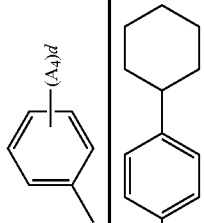

TABLE 58-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-692 | H | Methyl | H | Methyl | 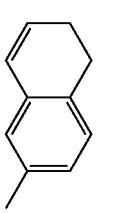 | 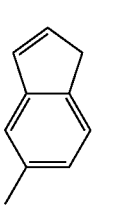 |  |  |
| D-693 | H | Methyl | H | Methyl |  |  |  | 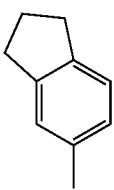 |
| D-694 | H | Methyl | H | Methyl |  | 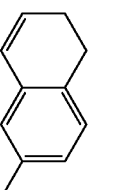 | 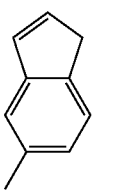 | 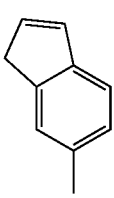 |
| D-695 | H | Methyl | H | Methyl | 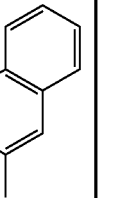 | 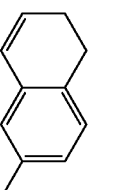 | 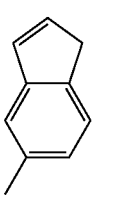 | 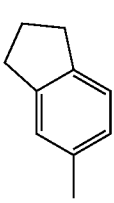 |
| D-696 | H | Methyl | H | Methyl |  | 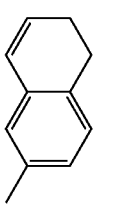 |  | 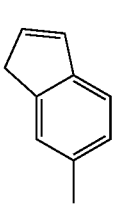 |

TABLE 59

| | R₁ | R₂ | R₃ | R₄ | (A₁)a | (A₂)b | (A₃)c | (A₄)d |
|---|---|---|---|---|---|---|---|---|
| D-697 | H | Methyl | H | Methyl | 2,6-dimethylphenyl | 2,4-dimethylphenyl | 3,4,5-trimethylphenyl | 2,4-dimethylphenyl |
| D-698 | H | Methyl | H | Methyl | 4-methylphenyl | 4-(2-methylprop-2-yl)phenyl | 4-methylphenyl | 4-(2-methylprop-2-yl)phenyl |
| D-699 | H | Methyl | H | Methyl | 6-methylnaphth-2-yl | 4-(propan-2-yl)phenyl | 6-methylnaphth-2-yl | 4-(propan-2-yl)phenyl |
| D-700 | H | Methyl | H | Methyl | 4-(2-methylprop-2-yl)phenyl | 4-cyclohexylphenyl | 4-(2-methylprop-2-yl)phenyl | 4-cyclohexylphenyl |
| D-701 | H | Methyl | H | Methyl | 4-cyclohexylphenyl | 6-methyl-1,2,3,4-tetrahydronaphth-2-yl | 4-cyclohexylphenyl | 6-methyl-1,2,3,4-tetrahydronaphth-2-yl |
| D-702 | H | Methyl | H | Methyl | 9,9-dimethyl-3-methylfluoren-2-yl | 9,9-dimethyl-3-methylfluoren-2-yl | 9,9-dimethyl-3-methylfluoren-2-yl | 9,9-dimethyl-3-methylfluoren-2-yl |

TABLE 59-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-703 | H | Methyl | H | Methyl | 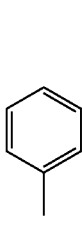 | 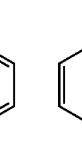 | 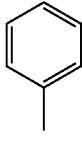 | 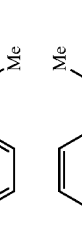 |
| D-704 | H | Methyl | H | Methyl | 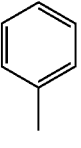 | 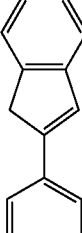 | 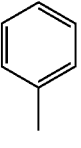 | 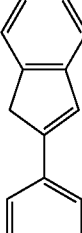 |
| D-705 | H | Methyl | H | Methyl | 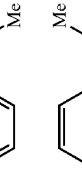 | 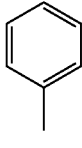 | 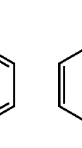 | 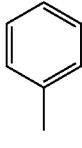 |
| D-706 | H | Methyl | H | Methyl | 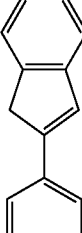 | 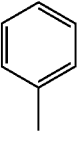 | 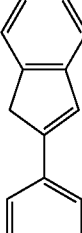 | 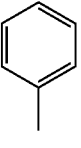 |
| D-707 | H | Methyl | H | Methyl | 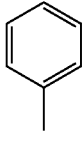 | 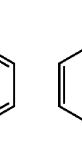 | 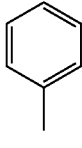 | 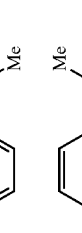 |
| D-708 | H | Methyl | H | Methyl | 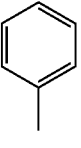 | 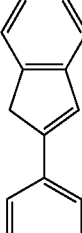 | 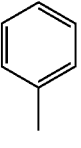 | 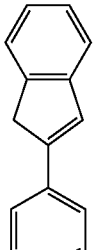 |

TABLE 60
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-709 | H | Methyl | H | Methyl | 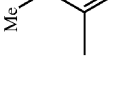 |  | 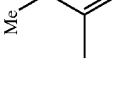 |  |
| D-710 | H | Methyl | H | Methyl | | | | |
| D-711 | H | Methyl | H | Methyl | | | | |
| D-712 | H | Methyl | H | Methyl | | | | |
| D-713 | H | Methyl | H | Methyl | | | | |
| D-714 | H | Methyl | H | Methyl | | | | |

TABLE 60-continued

| | R₁ | R₂ | R₃ | R₄ | —(A₁)a | —(A₂)b | —(A₃)c | —(A₄)d |
|---|---|---|---|---|---|---|---|---|
| D-715 | H | Methyl | H | Methyl | 2-biphenyl | 2-biphenyl | 2-biphenyl | 2-biphenyl |
| D-716 | H | Methyl | H | Methyl | 2-methyl-4-phenylbiphenyl | phenyl | 2-methyl-4-phenylbiphenyl | phenyl |
| D-717 | H | Methyl | H | Methyl | 3-methyl-4'-phenylbiphenyl | phenyl | 3-methyl-4'-phenylbiphenyl | phenyl |
| D-718 | H | Methyl | H | Methyl | 1-methylnaphthyl | phenyl | 1-methylnaphthyl | phenyl |
| D-719 | H | Methyl | H | Methyl | 4-(2-naphthyl)-methylphenyl | phenyl | 4-(2-naphthyl)-methylphenyl | phenyl |
| D-720 | H | Methyl | H | Methyl | phenyl | 4-(3-methylbutyl)phenyl | phenyl | 4-(3-methylbutyl)phenyl |

TABLE 61

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-721 | H | Isopropyl | H | Isopropyl | Ph | Ph | Ph | Ph |
| D-722 | H | Isopropyl | H | Isopropyl | Ph | 3-Me-Ph | Ph | 3-Me-Ph |
| D-723 | H | Isopropyl | H | Isopropyl | 3-Me-Ph | 3-Me-Ph | 3-Me-Ph | 3-Me-Ph |
| D-724 | H | Isopropyl | H | Isopropyl | Ph | 4-Me-Ph | Ph | 4-Me-Ph |
| D-725 | H | Isopropyl | H | Isopropyl | 2,4-diMe-Ph | 2,4-diMe-Ph | 2,4-diMe-Ph | 2,4-diMe-Ph |
| D-726 | H | Isopropyl | H | Isopropyl | 3,5-diMe-Ph | 3,5-diMe-Ph | 3,5-diMe-Ph | 3,5-diMe-Ph |
| D-727 | H | | H | Isopropyl | 4-Me-Ph | 4-Me-Ph | 4-Me-Ph | 4-Me-Ph |

TABLE 61-continued

| | R₁ | R₂ | R₃ | R₄ | (A₁)a | (A₂)b | (A₃)c | (A₄)d |
|---|---|---|---|---|---|---|---|---|
| D-728 | H | Isopropyl | H | Isopropyl | 4-(1-methylethyl)phenyl | 3,5-dimethylphenyl | 4-(1-methylethyl)phenyl | 3,5-dimethylphenyl |
| D-729 | H | Isopropyl | H | Isopropyl | phenyl | 4-(1-methylethyl)phenyl | phenyl | 4-(1-methylethyl)phenyl |
| D-730 | H | Isopropyl | H | Isopropyl | 4-tert-butylphenyl | 4-tert-butylphenyl | 4-tert-butylphenyl | 4-tert-butylphenyl |
| D-731 | H | Isopropyl | H | Isopropyl | 4-methylphenyl | 4-tert-butylphenyl | 4-methylphenyl | 4-tert-butylphenyl |
| D-732 | H | Isopropyl | H | Isopropyl | 4-methylphenyl | 4-(1-methylethyl)phenyl | 4-methylphenyl | 4-(1-methylethyl)phenyl |

TABLE 62

| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-733 | H | Isopropyl | H | Isopropyl | 4-isopropylbenzyl-p-tolyl | 4-cyclohexylphenyl | 4-isopropylbenzyl-p-tolyl | 4-cyclohexylphenyl |
| D-734 | H | Isopropyl | H | Isopropyl | 3,5-dimethylphenyl | 3,5-dimethylphenyl | 3,5-dimethylphenyl | 3,5-dimethylphenyl |
| D-735 | H | Isopropyl | H | Isopropyl | p-tolyl | 4-biphenyl | p-tolyl | 4-biphenyl |
| D-736 | H | Isopropyl | H | Isopropyl | p-tolyl | 6-methyl-2-naphthyl | p-tolyl | 6-methyl-2-naphthyl |
| D-737 | H | Isopropyl | H | Isopropyl | 6-methyl-2-naphthyl | 6-methyl-2-naphthyl | 6-methyl-2-naphthyl | 6-methyl-2-naphthyl |
| D-738 | H | Isopropyl | H | Isopropyl | 4-biphenyl | 4-biphenyl | 4-biphenyl | 4-biphenyl |
| D-739 | H | Isopropyl | H | Isopropyl | tetrahydronaphthyl | p-tolyl | tetrahydronaphthyl | p-tolyl |

TABLE 62-continued
| | $R_1$ | $R_2$ | $R_3$ | $R_4$ | $-(A_1)a$ | $-(A_2)b$ | $-(A_3)c$ | $-(A_4)d$ |
|---|---|---|---|---|---|---|---|---|
| D-740 | H | Isopropyl | H | Isopropyl | 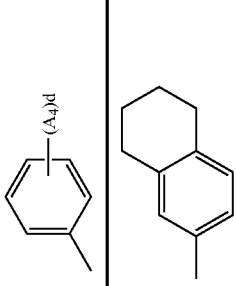 | 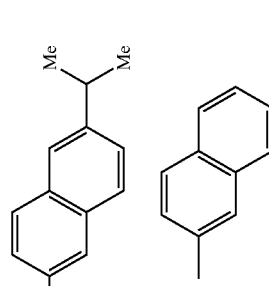 | 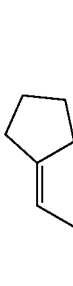 | 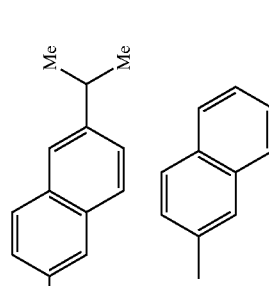 |
| D-741 | H | Isopropyl | H | Isopropyl | indane | indane | indane | indane |
| D-742 | H | Isopropyl | H | Isopropyl | biphenylmethyl | biphenylmethyl | biphenylmethyl | biphenylmethyl |
| D-743 | H | Isopropyl | H | Isopropyl | 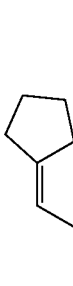 | 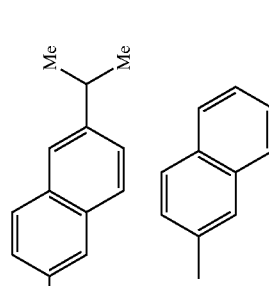 | 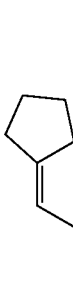 | 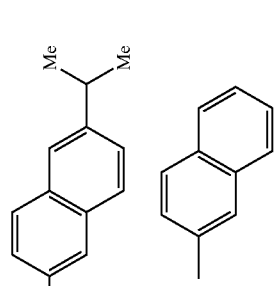 |
| D-744 | H | Isopropyl | H | Isopropyl | 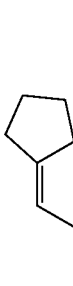 | 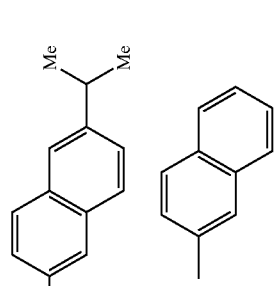 | methylnaphthyl | methylnaphthyl |

TABLE 63
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-745 | H | Isopropyl | H | Isopropyl | 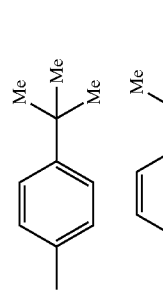 | 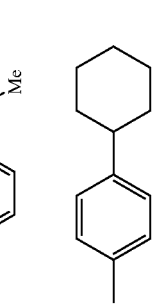 | 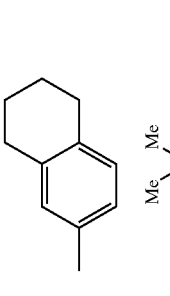 | 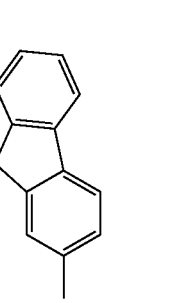 |
| D-746 | H | Isopropyl | H | Isopropyl | 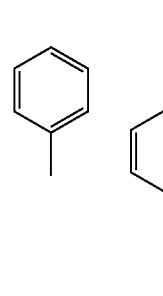 | 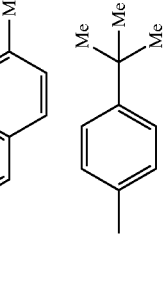 | 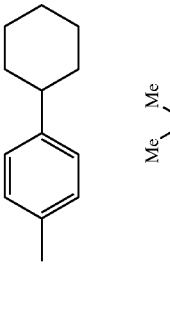 | 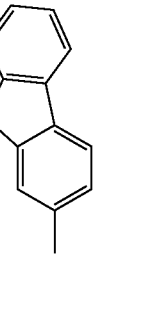 |
| D-747 | H | Isopropyl | H | Isopropyl | 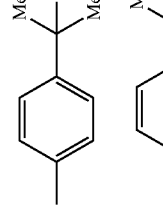 | 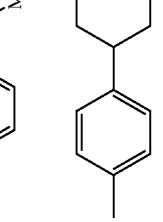 | 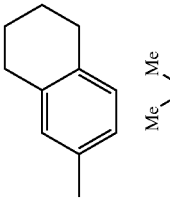 | 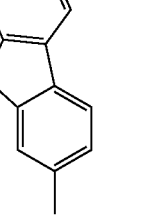 |
| D-748 | H | Isopropyl | H | Isopropyl | 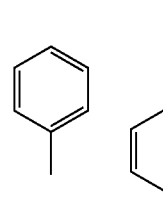 | 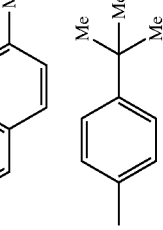 | 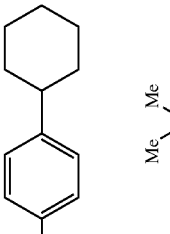 | 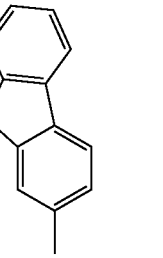 |
| D-749 | H | Isopropyl | H | Isopropyl |  |  |  |  |
| D-750 | H | Isopropyl | H | Isopropyl | | | | |

TABLE 63-continued
| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-751 | H | Isopropyl | H | Isopropyl |  | 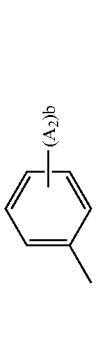 | 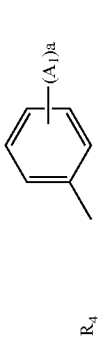 | 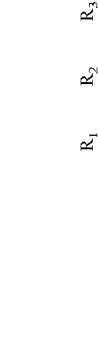 |
| D-752 | H | Isopropyl | H | Isopropyl |  | 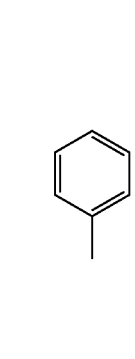 | 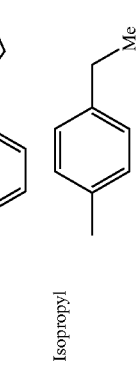 | 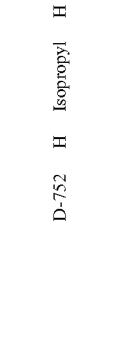 |
| D-753 | H | Isopropyl | H | Isopropyl | 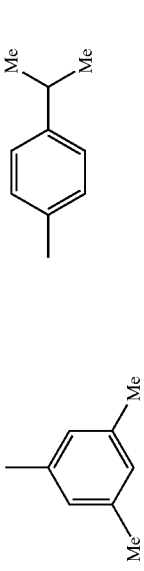 | 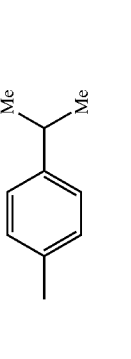 | 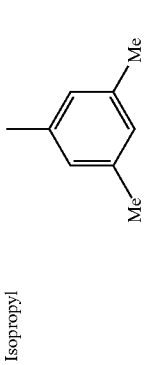 | 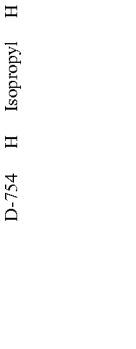 |
| D-754 | H | Isopropyl | H | Isopropyl | 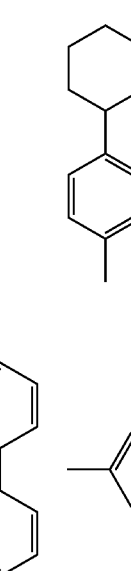 | 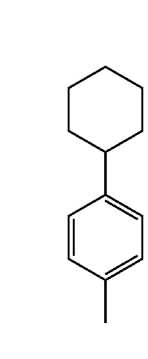 | 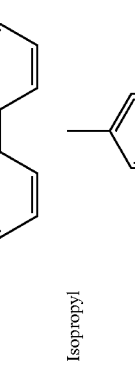 | 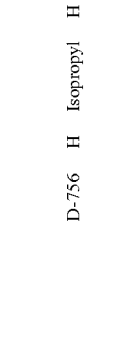 |
| D-755 | H | Isopropyl | H | Isopropyl | | | | |
| D-756 | H | Isopropyl | H | Isopropyl | | | | |

TABLE 64

| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-757 | H | Isopropyl | H | Isopropyl | tolyl | phenyl | 2-methylnaphthyl | 2-methylnaphthyl |
| D-758 | H | Isopropyl | H | Isopropyl | methyltetrahydronaphthyl | methyltetrahydronaphthyl | methyltetrahydronaphthyl | methyltetrahydronaphthyl |
| D-759 | H | Isopropyl | H | Isopropyl | methyl-p-terphenyl | tolyl | methyl-p-terphenyl | tolyl |
| D-760 | H | Isopropyl | H | Isopropyl | o-methyl-tolyl | tolyl | o-methyl-tolyl | tolyl |
| D-761 | H | Isopropyl | H | Isopropyl | o-methyl-tolyl | o-methyl-tolyl | o-methyl-tolyl | o-methyl-tolyl |
| D-762 | H | Isopropyl | H | Isopropyl | 2-methylbiphenyl | tolyl | 2-methylbiphenyl | tolyl |

TABLE 64-continued

| | R₁ | R₂ | R₃ | R₄ | —(A₁)a | —(A₂)b | —(A₃)c | —(A₄)d |
|---|---|---|---|---|---|---|---|---|
| D-763 | H | Isopropyl | H | Isopropyl | 2-biphenyl | 2-biphenyl | 2-biphenyl | 2-biphenyl |
| D-764 | H | Isopropyl | H | Isopropyl | 2,4-diphenylphenyl | phenyl | 2,4-diphenylphenyl | phenyl |
| D-765 | H | Isopropyl | H | Isopropyl | 3'-methylbiphenyl-4-yl | phenyl | 3'-methylbiphenyl-4-yl | phenyl |
| D-766 | H | Isopropyl | H | Isopropyl | 1-naphthyl | phenyl | 1-naphthyl | phenyl |
| D-767 | H | Isopropyl | H | Isopropyl | 4-(2-naphthyl)phenyl | phenyl | 4-(2-naphthyl)phenyl | phenyl |
| D-768 | H | Isopropyl | H | Isopropyl | 4-(3-methylbutyl)phenyl | 4-(3-methylbutyl)phenyl | phenyl | 4-(3-methylbutyl)phenyl |

TABLE 65

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-769 | Cyclohexyl | H | H | H | Phenyl | Phenyl | Phenyl | Phenyl |
| D-770 | Cyclohexyl | H | H | H | Phenyl | 3-Methylphenyl | Phenyl | 3-Methylphenyl |
| D-771 | Cyclohexyl | H | H | H | 3-Methylphenyl | 3-Methylphenyl | 3-Methylphenyl | 3-Methylphenyl |
| D-772 | Cyclohexyl | H | H | H | Phenyl | 4-Methylphenyl | Phenyl | 4-Methylphenyl |
| D-773 | Cyclohexyl | H | H | H | 3-Methylphenyl | 2,3-Dimethylphenyl | 3-Methylphenyl | 2,3-Dimethylphenyl |
| D-774 | Cyclohexyl | H | H | H | 2,6-Dimethyl-4-... | 3,5-Dimethylphenyl | 2,4,6-Trimethylphenyl | 3,5-Dimethylphenyl |
| D-775 | Cyclohexyl | H | H | H | 4-Methylphenyl | 4-Methylphenyl | 4-Methylphenyl | 4-Methylphenyl |

TABLE 65-continued

| | R₁ | R₂ | R₃ | R₄ | —(A₁)a | —(A₂)b | —(A₃)c | —(A₄)d |
|---|---|---|---|---|---|---|---|---|
| D-776 | Cyclohexyl | H | H | H | 4-(1-methylethyl)phenyl | 3,5-dimethylphenyl | 4-(1-methylethyl)phenyl | 3,5-dimethylphenyl |
| D-777 | Cyclohexyl | H | H | H | 4-(1-methylethyl)phenyl | 4-(1-methylethyl)phenyl | 4-(1-methylethyl)phenyl | 4-(1-methylethyl)phenyl |
| D-778 | Cyclohexyl | H | H | H | 4-methylphenyl | 4-(1,1-dimethylethyl)phenyl | phenyl | 4-(1,1-dimethylethyl)phenyl |
| D-779 | Cyclohexyl | H | H | H | 4-methylphenyl | 4-(1,1-dimethylethyl)phenyl | 4-methylphenyl | 4-(1,1-dimethylethyl)phenyl |
| D-780 | Cyclohexyl | H | H | H | 4-methylphenyl | 4-(1-methylethyl)phenyl | 4-methylphenyl | 4-(1-methylethyl)phenyl |

TABLE 66
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-781 | Cyclohexyl | H | H | H | 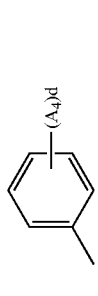 | 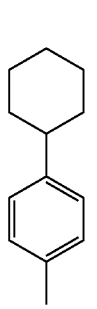 | 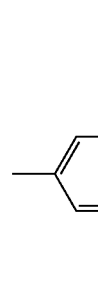 | 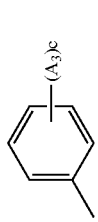 |
| D-782 | Cyclohexyl | H | H | H | 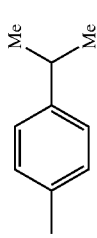 | 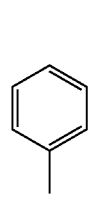 | 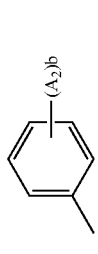 | 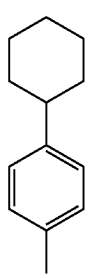 |
| D-783 | Cyclohexyl | H | H | H | 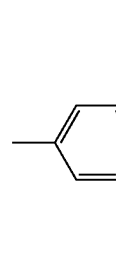 | 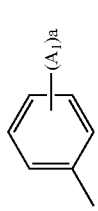 | 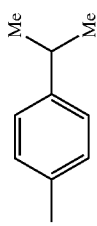 | 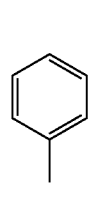 |
| D-784 | Cyclohexyl | H | H | H |  |  |  |  |
| D-785 | Cyclohexyl | H | H | H |  | | | |
| D-786 | Cyclohexyl | H | H | H |  | | | |
| D-787 | Cyclohexyl | H | H | H |  |  | | |

TABLE 66-continued

| | R₁ | R₂ | R₃ | R₄ | (A₁)a | (A₂)b | (A₃)c | (A₄)d |
|---|---|---|---|---|---|---|---|---|
| D-788 | Cyclohexyl | H | H | H | 6-methyl-tetralinyl | 6-methyl-tetralinyl | 6-methyl-dihydronaphthyl | 6-methyl-tetralinyl |
| D-789 | Cyclohexyl | H | H | H | 5-methyl-indanyl | 5-methyl-indanyl | 5-methyl-indanyl | 5-methyl-indanyl |
| D-790 | Cyclohexyl | H | H | H | 4-methylphenyl-CH₂CH₂-phenyl | 4-methylphenyl-CH₂CH₂-phenyl | 4-methylphenyl-CH₂CH₂-phenyl | 4-methylphenyl-CH₂CH₂-phenyl |
| D-791 | Cyclohexyl | H | H | H | 6-(CHMe₂)-naphthyl | 6-(CHMe₂)-naphthyl | 6-(CHMe₂)-naphthyl | 6-(CHMe₂)-naphthyl |
| D-792 | Cyclohexyl | H | H | H | 4-(CHMe₂)-methylphenyl | 6-methylnaphthyl | 4-(CHMe₂)-methylphenyl | 6-methylnaphthyl |

TABLE 67

| | $R_1$ | $R_2$ | $R_3$ | $R_4$ | (A$_1$)a | (A$_2$)b | (A$_3$)c | (A$_4$)d |
|---|---|---|---|---|---|---|---|---|
| D-793 | Cyclohexyl | H | Cyclohexyl | H | phenyl | phenyl | phenyl | phenyl |
| D-794 | Cyclohexyl | H | Cyclohexyl | H | phenyl | 3-Me-phenyl | phenyl | 3-Me-phenyl |
| D-795 | Cyclohexyl | H | Cyclohexyl | H | 3-Me-phenyl | 3-Me-phenyl | 3-Me-phenyl | 3-Me-phenyl |
| D-796 | Cyclohexyl | H | Cyclohexyl | H | phenyl | 4-Me-phenyl | phenyl | 4-Me-phenyl |
| D-797 | Cyclohexyl | H | Cyclohexyl | H | 3-Me-phenyl | 2,4-Me$_2$-phenyl | 3-Me-phenyl | 2,4-Me$_2$-phenyl |
| D-798 | Cyclohexyl | H | Cyclohexyl | H | 3,5-Me$_2$-phenyl | 3,4,5-Me$_3$-phenyl | 3,4,5-Me$_3$-phenyl | 3,4,5-Me$_3$-phenyl |
| D-799 | Cyclohexyl | H | Cyclohexyl | H | 4-Me-phenyl | 4-Me-phenyl | 4-Me-phenyl | 4-Me-phenyl |

TABLE 67-continued

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-800 | Cyclohexyl | H | Cyclohexyl | H | 4-(1-methylethyl)phenyl | 3,5-dimethylphenyl | 4-(1-methylethyl)phenyl | 3,5-dimethylphenyl |
| D-801 | Cyclohexyl | H | Cyclohexyl | H | 4-(1-methylethyl)phenyl | 4-(1-methylethyl)phenyl | 4-(1-methylethyl)phenyl | 4-(1-methylethyl)phenyl |
| D-802 | Cyclohexyl | H | Cyclohexyl | H | 4-tert-butylphenyl | 4-tert-butylphenyl | 4-tert-butylphenyl | 4-tert-butylphenyl |
| D-803 | Cyclohexyl | H | Cyclohexyl | H | 4-methylphenyl | 4-tert-butylphenyl | 4-methylphenyl | 4-methylphenyl |
| D-804 | Cyclohexyl | H | Cyclohexyl | H | 4-methylphenyl | 4-(1-methylethyl)phenyl | 4-methylphenyl | 4-(1-methylethyl)phenyl |

TABLE 68

TABLE 68-continued

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-812 | Cyclohexyl | H | Cyclohexyl | H | tetrahydronaphthyl | tetrahydronaphthyl | tetrahydronaphthyl | tetrahydronaphthyl |
| D-813 | Cyclohexyl | H | Cyclohexyl | H | indanyl | indanyl | indanyl | indanyl |
| D-814 | Cyclohexyl | H | Cyclohexyl | H | 4-benzylphenyl-CH₂ | 4-benzylphenyl-CH₂ | 4-benzylphenyl-CH₂ | 4-benzylphenyl-CH₂ |
| D-815 | Cyclohexyl | H | Cyclohexyl | H | 6-isopropylnaphthyl | 6-isopropylnaphthyl | 6-isopropylnaphthyl | 6-isopropylnaphthyl |
| D-816 | Cyclohexyl | H | Cyclohexyl | H | 4-isopropylphenyl | naphthyl | 4-isopropylphenyl | naphthyl |

TABLE 69
| | R$_1$ | R$_2$ | R$_3$ | R$_4$ | (A$_1$)a | (A$_2$)b | (A$_3$)c | (A$_4$)d |
|---|---|---|---|---|---|---|---|---|
| D-817 | 4-t-butylphenyl | H | H | H |  |  |  |  |
| D-818 | 4-t-butylphenyl | H | H | H |  |  |  |  |
| D-819 | 4-t-butylphenyl | H | H | H |  |  |  |  |
| D-820 | 4-t-butylphenyl | H | H | H |  |  |  |  |
| D-821 | 4-t-butylphenyl | H | H | H |  |  |  |  |
| D-822 | 4-t-butylphenyl | H | H | H |  |  |  |  |
| D-823 | 4-trimethylsilylphenyl | H | H | H |  |  |  |  |

TABLE 69-continued

| | R₁ | R₂ | R₃ | R₄ | (A₁)a | (A₂)b | (A₃)c | (A₄)d |
|---|---|---|---|---|---|---|---|---|
| D-824 | 4-trimethylsilylphenyl | H | H | H | 4-(1-methylethyl)phenyl | 3,5-dimethylphenyl | 4-(1-methylethyl)phenyl | 3,5-dimethylphenyl |
| D-825 | 4-trimethylsilylphenyl | H | H | H | 4-(1-methylethyl)phenyl | 4-(1-methylethyl)phenyl | 4-(1-methylethyl)phenyl | 4-(1-methylethyl)phenyl |
| D-826 | 4-trimethylsilylphenyl | H | H | H | 4-tert-butylphenyl | 4-tert-butylphenyl | 4-tert-butylphenyl | 4-tert-butylphenyl |
| D-827 | 4-trimethylsilylphenyl | H | H | H | 4-methylphenyl | 4-tert-butylphenyl | 4-methylphenyl | 4-tert-butylphenyl |
| D-828 | 4-trimethylsilylphenyl | H | H | H | 4-methylphenyl | 4-(1-methylethyl)phenyl | 4-methylphenyl | 4-(1-methylethyl)phenyl |

TABLE 70
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-829 | 4-cyanophenyl | H | H | H | 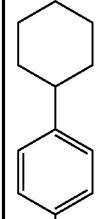 | 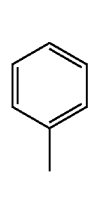 | 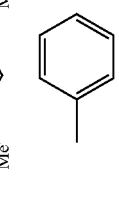 |  |
| D-830 | 4-cyanophenyl | H | H | H | 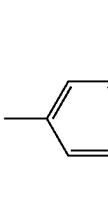 | 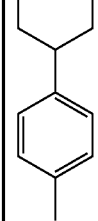 | 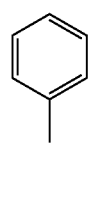 |  |
| D-831 | 4-cyanophenyl | H | H | H | 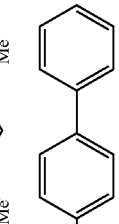 | 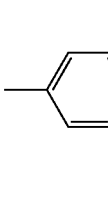 |  |  |
| D-832 | 4-cyanophenyl | H | H | H | 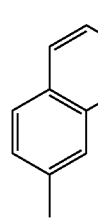 | 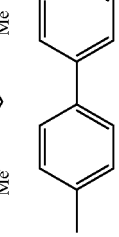 |  | 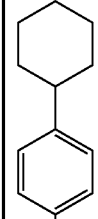 |
| D-833 | 4-cyanophenyl | H | H | H | 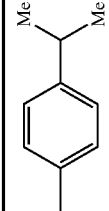 | 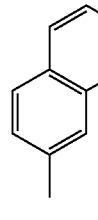 |  | 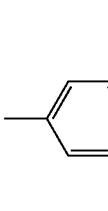 |
| D-834 | 4-cyanophenyl | H | H | H | 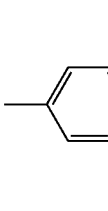 | 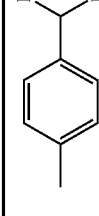 |  | 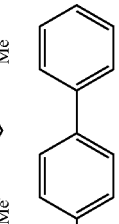 |
| D-835 | 4-trifluoromethylphenyl | H | H | H | 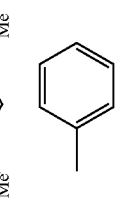 | 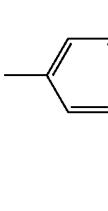 |  | 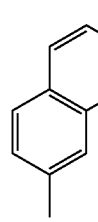 |

TABLE 70-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-836 | 4-trifluoromethylphenyl | H | H | H | 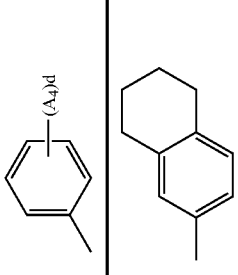 | 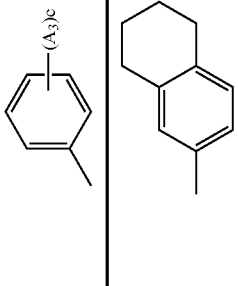 | 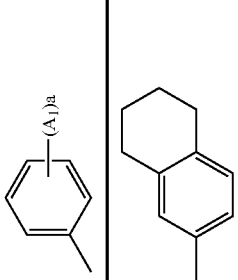 | 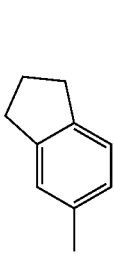 |
| D-837 | 4-trifluoromethylphenyl | H | H | H | 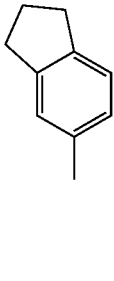 | 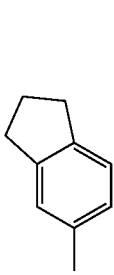 | 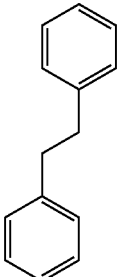 | 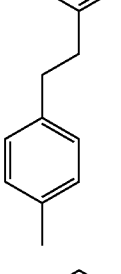 |
| D-838 | 4-trifluoromethylphenyl | H | H | H | 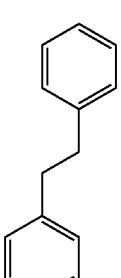 | 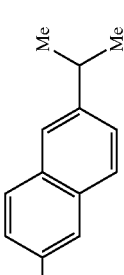 | 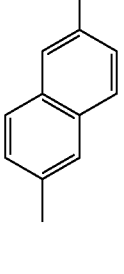 | 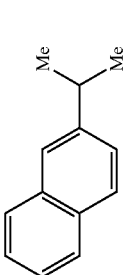 |
| D-839 | 4-trifluoromethylphenyl | H | H | H | 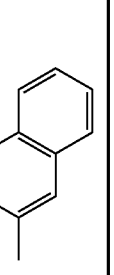 | 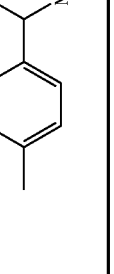 | 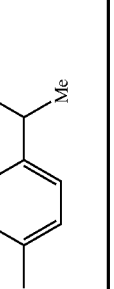 |  |
| D-840 | 4-trifluoromethylphenyl | H | H | H |  |  |  |  |

TABLE 71
| | $R_1$ | $R_2$ | $R_3$ | $R_4$ | —(A$_1$)a 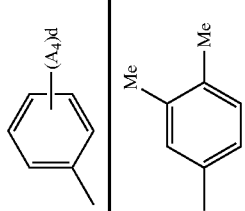 | —(A$_2$)b 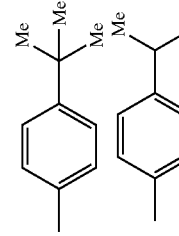 | —(A$_3$)c 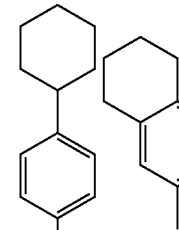 | —(A$_4$)d 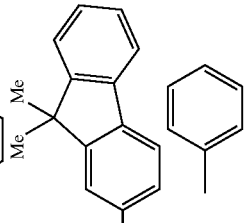 |
|---|---|---|---|---|---|---|---|---|
| D-841 | 2-quinolyl | H | H | H | 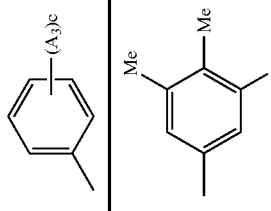 | 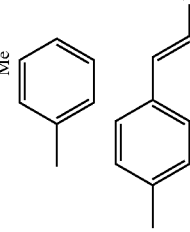 | 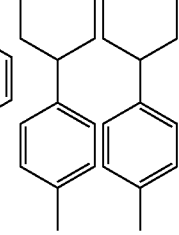 | 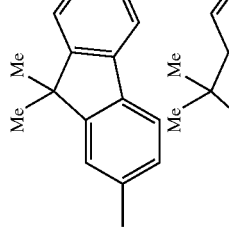 |
| D-842 | 2-quinolyl | H | H | H | 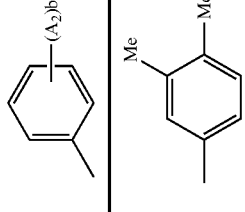 | 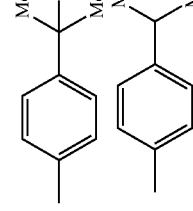 | 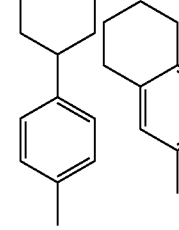 | 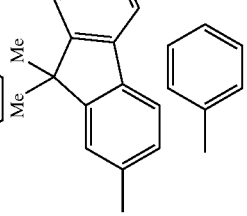 |
| D-843 | 2-quinolyl | H | H | H | 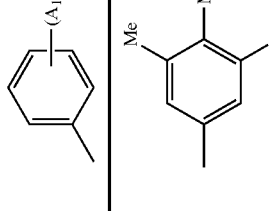 | 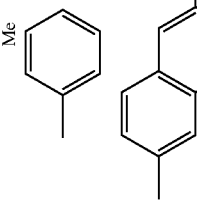 | 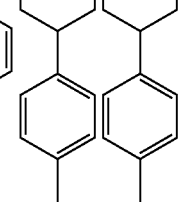 | 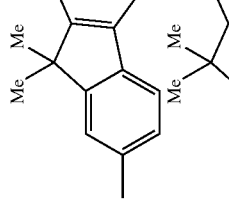 |
| D-844 | 2-quinolyl | H | H | H | 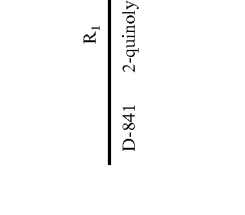 | 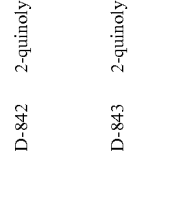 | 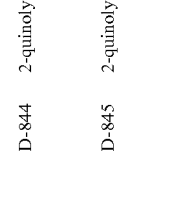 | 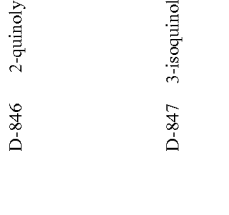 |
| D-845 | 2-quinolyl | H | H | H | | | | |
| D-846 | 2-quinolyl | H | H | H |  | 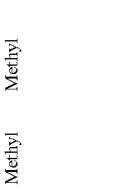 |  |  |
| D-847 | 3-isoquinolyl | H | H | H | | | |  |

TABLE 71-continued

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-848 | 3-isoquinolyl | H | H | H | 4-isopropylphenyl | 4-(2-phenylpropan-2-yl)phenyl | 4-isopropylphenyl | 4-(2-phenylpropan-2-yl)phenyl |
| D-849 | 3-isoquinolyl | H | H | H | pentafluorophenyl | phenyl | pentafluorophenyl | phenyl |
| D-850 | 3-isoquinolyl | H | H | H | 3,5-dimethylphenyl | 4-isopropylphenyl | 3,5-dimethylphenyl | 4-isopropylphenyl |
| D-851 | 3-isoquinolyl | H | H | H | 10-methylphenanthren-9-yl | phenyl | 10-methylphenanthren-9-yl | phenyl |
| D-852 | 3-isoquinolyl | H | H | H | 3,5-dicyclohexylphenyl | 4-cyclohexylphenyl | 3,5-dicyclohexylphenyl | 4-cyclohexylphenyl |

TABLE 72

| | R₁ | R₂ | R₃ | R₄ | (A₁)a | (A₂)b | (A₃)c | (A₄)d |
|---|---|---|---|---|---|---|---|---|
| D-853 | 1-adamanthyl | H | H | H | CMe₂(Ph)(p-tolyl) | CMe₂(Ph)(p-tolyl) | CMe₂(Ph)(p-tolyl) | CMe₂(Ph)(p-tolyl) |
| D-854 | 1-adamanthyl | H | H | H | 8-methyl-tetralinyl | 8-methyl-tetralinyl | 8-methyl-tetralinyl | 8-methyl-tetralinyl |
| D-855 | 1-pyrenyl | H | H | H | phenyl (methyl) | phenyl (methyl) | 2-methylnaphthyl | 2-methylnaphthyl |
| D-856 | 1-pyrenyl | H | H | H | 4-methoxyphenyl | phenyl (methyl) | 4-methoxyphenyl | phenyl (methyl) |
| D-857 | 1-pyrenyl | H | H | H | 4-(NMe₂)phenyl | 4-(NMe₂)phenyl | 4-(NMe₂)phenyl | 4-(NMe₂)phenyl |
| D-858 | 1-pyrenyl | H | H | H | 4-CF₃-phenyl | 4-F-phenyl | 4-CF₃-phenyl | 4-F-phenyl |
| D-859 | 1-pyrenyl | H | H | H | 4-CN-phenyl | 4-CN-phenyl | 4-CN-phenyl | 4-CN-phenyl |

TABLE 72-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-860 | 1-pyrenyl | H | H | H | 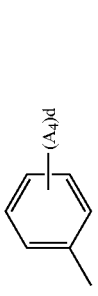 | 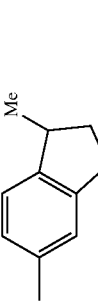 | 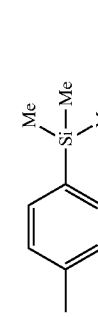 | 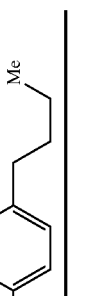 |
| D-861 | 1-pyrenyl | H | H | H | 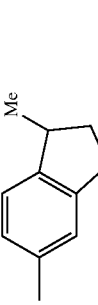 | 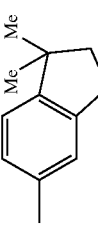 | 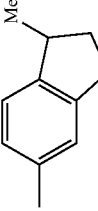 | 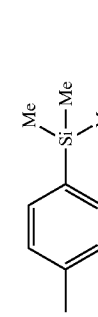 |
| D-862 | 1-pyrenyl | H | H | H | 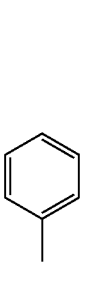 | 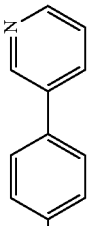 | 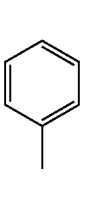 | 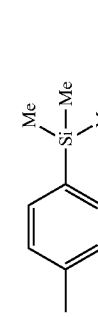 |
| D-863 | 1-pyrenyl | H | H | H | 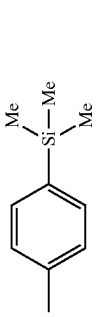 | 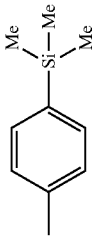 | 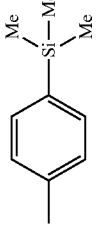 | 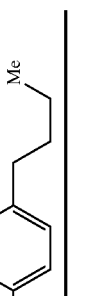 |
| D-864 | 1-pyrenyl | H | H | H | 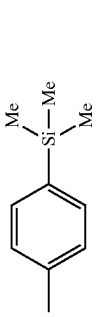 | 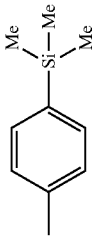 | 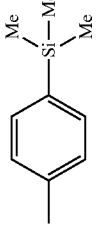 | 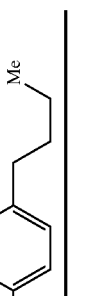 |

TABLE 73

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-865 | H | Cyclohexyl | H | H | Phenyl | Phenyl | Phenyl | Phenyl |
| D-866 | H | Cyclohexyl | H | H | Phenyl | 3-Me-phenyl | Phenyl | 3-Me-phenyl |
| D-867 | H | Cyclohexyl | H | H | 3-Me-phenyl | 3-Me-phenyl | 3-Me-phenyl | 3-Me-phenyl |
| D-868 | H | Cyclohexyl | H | H | Phenyl | 4-Me-phenyl | Phenyl | 4-Me-phenyl |
| D-869 | H | Cyclohexyl | H | H | 2,4-diMe-phenyl | 2,4-diMe-phenyl | 2,4-diMe-phenyl | 2,4-diMe-phenyl |
| D-870 | H | Cyclohexyl | H | H | 3,5-diMe-phenyl | 3,5-diMe-phenyl | 3,5-diMe-phenyl | 3,5-diMe-phenyl |
| D-871 | H | Cyclohexyl | H | H | 4-Me-phenyl | 4-Me-phenyl | 4-Me-phenyl | 4-Me-phenyl |

TABLE 73-continued
| | R₁ | R₂ | R₃ | R₄ | (A₁)a | (A₂)b | (A₃)c | (A₄)d |
|---|---|---|---|---|---|---|---|---|
| D-872 | H | Cyclohexyl | H | H | 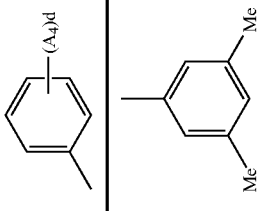 |  | 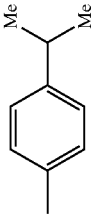 | 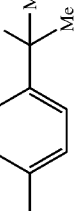 |
| D-873 | H | Cyclohexyl | H | H | 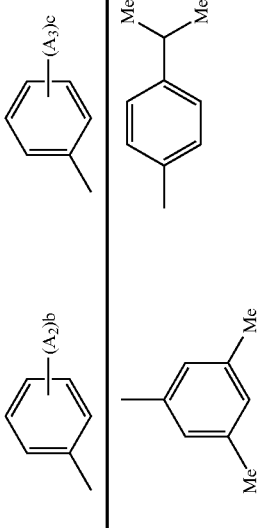 | 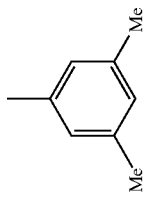 |  | 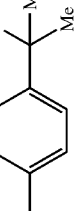 |
| D-874 | H | Cyclohexyl | H | H | 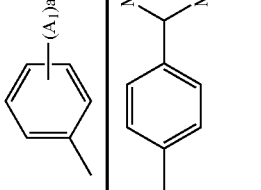 |  |  |  |
| D-875 | H | Cyclohexyl | H | H | 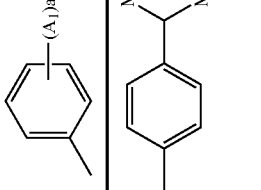 |  |  | 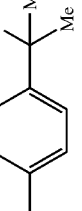 |
| D-876 | H | Cyclohexyl | H | H | 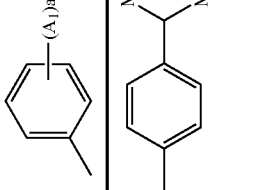 |  |  | 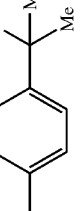 |

TABLE 74
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-877 | H | Cyclohexyl | H | H |  | 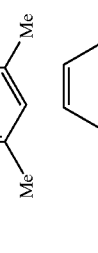 | 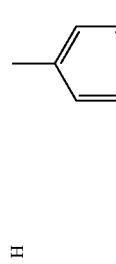 | 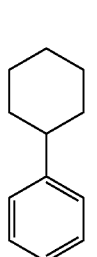 |
| D-878 | H | Cyclohexyl | H | H | 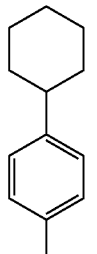 | 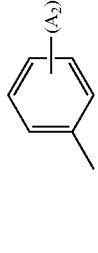 | 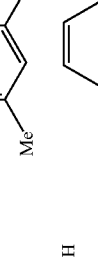 | 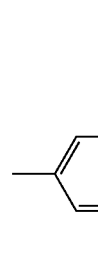 |
| D-879 | H | Cyclohexyl | H | H | 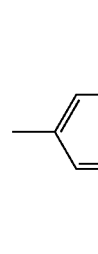 | 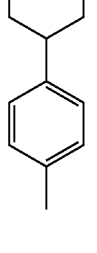 |  | 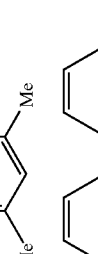 |
| D-880 | H | Cyclohexyl | H | H | 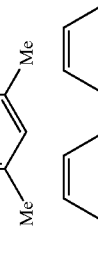 | 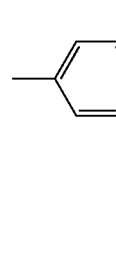 |  | 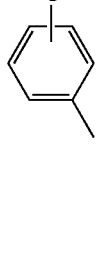 |
| D-881 | H | Cyclohexyl | H | H | 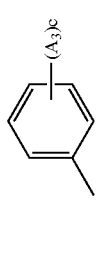 | 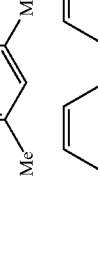 |  | 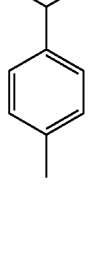 |
| D-882 | H | Cyclohexyl | H | H | 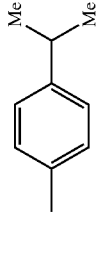 | 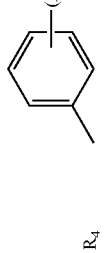 |  |  |
| D-883 | H | Cyclohexyl | H | H | 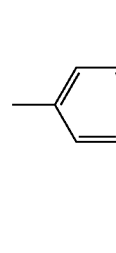 | 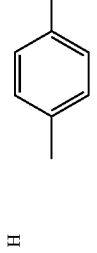 | 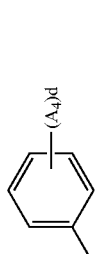 | 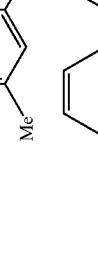 |

TABLE 74-continued

| | R₁ | R₂ | R₃ | R₄ | (A₁)a | (A₂)b | (A₃)c | (A₄)d |
|---|---|---|---|---|---|---|---|---|
| D-884 | H | Cyclohexyl | H | H | 6-methyl-tetralinyl | 6-methyl-tetralinyl | 6-methyl-tetralinyl | 6-methyl-tetralinyl |
| D-885 | H | Cyclohexyl | H | H | 5-methyl-indanyl | 5-methyl-indanyl | 5-methyl-indanyl | 5-methyl-indanyl |
| D-886 | H | Cyclohexyl | H | H | 4-(2-phenylethyl)phenyl | 4-(2-phenylethyl)phenyl | 4-(2-phenylethyl)phenyl | 4-(2-phenylethyl)phenyl |
| D-887 | H | Cyclohexyl | H | H | 6-(1-methylethyl)naphthyl | 6-(1-methylethyl)naphthyl | 6-(1-methylethyl)naphthyl | 6-(1-methylethyl)naphthyl |
| D-888 | H | Cyclohexyl | H | H | 4-(1-methylethyl)-methylphenyl | 6-methyl-naphthyl | 4-(1-methylethyl)-methylphenyl | 6-methyl-naphthyl |

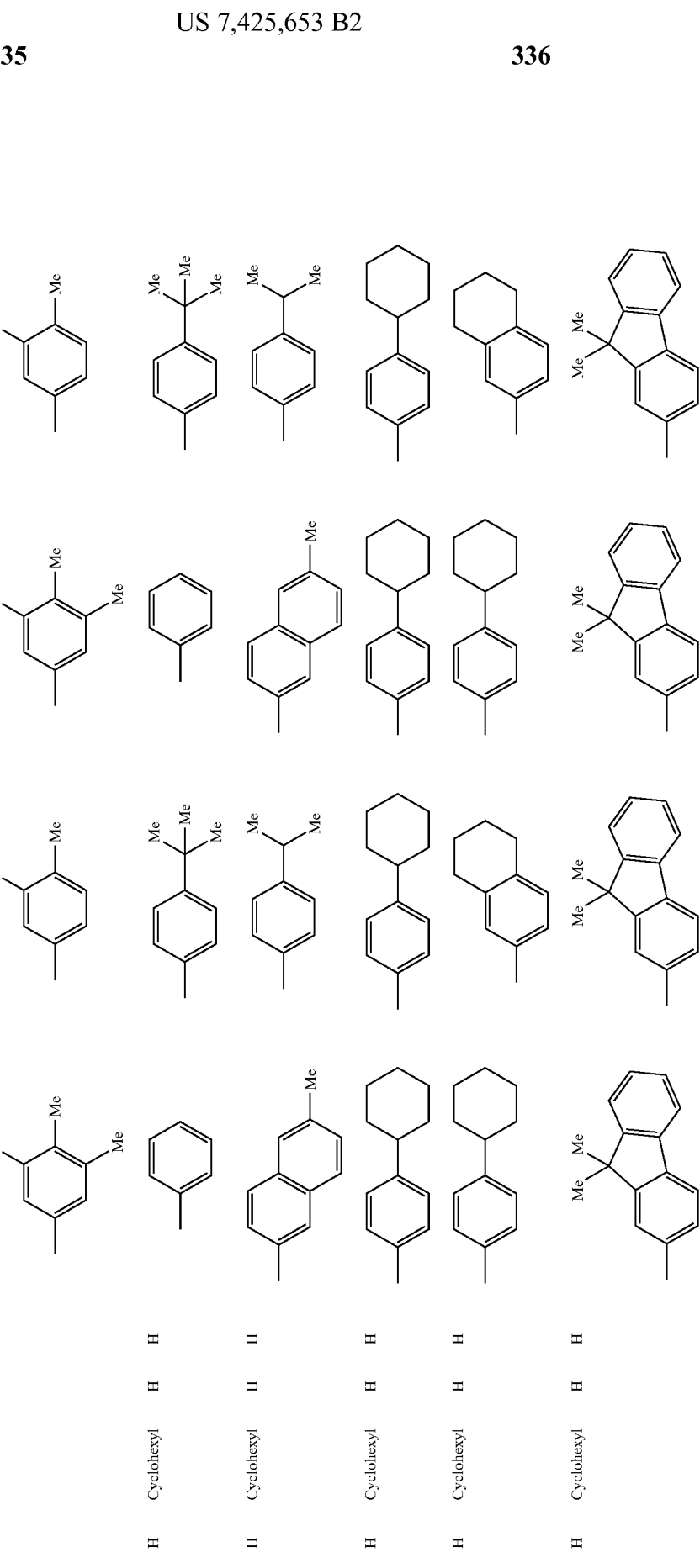

TABLE 75-continued
| H | Cyclohexyl | H | 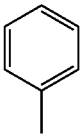 |  | 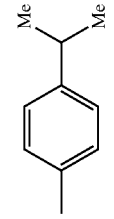 | 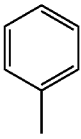 |
| H | Cyclohexyl | H |  | 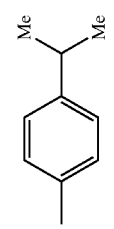 | 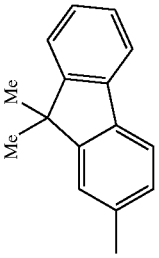 | 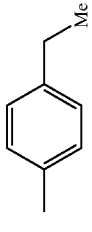 |
| H | Cyclohexyl | H | 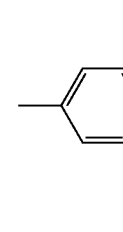 | 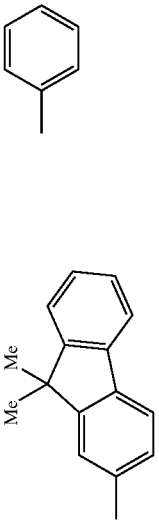 |  |  |
| H | Cyclohexyl | H | 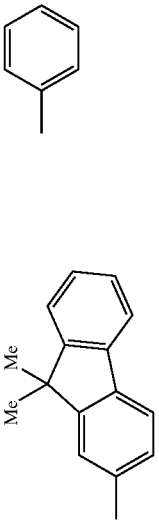 |  |  | 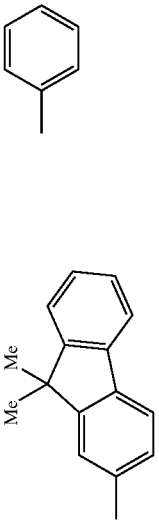 |
| H | Cyclohexyl | H |  |  | 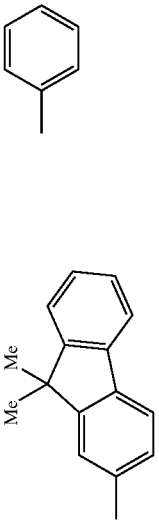 |  |
| H | Cyclohexyl | H |  | 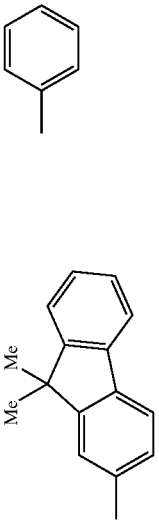 |  |  |

TABLE 76

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-901 | H | Cyclohexyl | H | H | | | | |
| D-902 | H | Cyclohexyl | H | H | | | | |
| D-903 | H | Cyclohexyl | H | H | | | | |
| D-904 | H | Cyclohexyl | H | H | | | | |
| D-905 | H | Cyclohexyl | H | H | | | | |
| D-906 | H | Cyclohexyl | H | H | | | | |

TABLE 76-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-907 | H | Cyclohexyl | H | H | 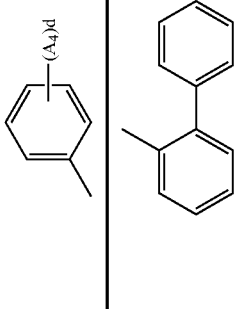 | 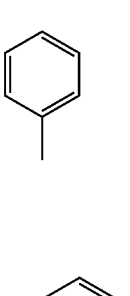 | 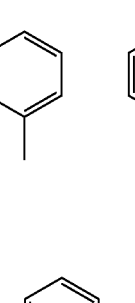 | 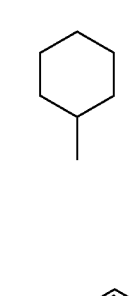 |
| D-908 | H | Cyclohexyl | H | H | 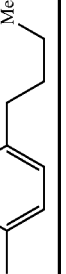 | 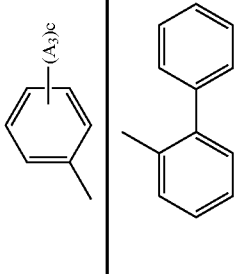 | 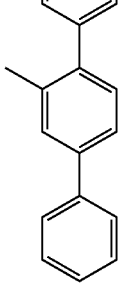 | 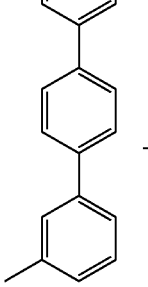 |
| D-909 | H | Cyclohexyl | H | H | 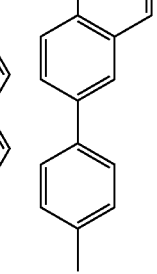 | 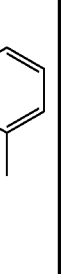 | 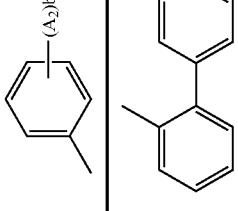 | 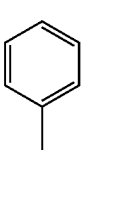 |
| D-910 | H | Cyclohexyl | H | H | 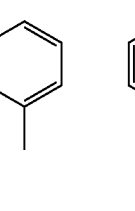 | 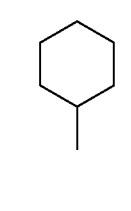 | 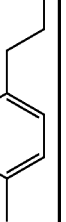 | 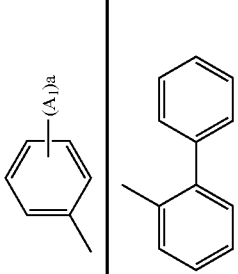 |
| D-911 | H | Cyclohexyl | H | H | 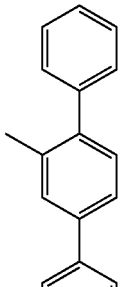 | 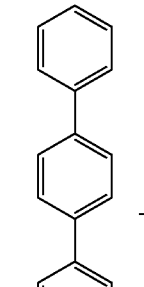 | 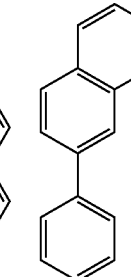 | 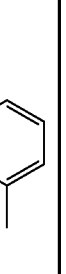 |
| D-912 | H | Cyclohexyl | H | H | 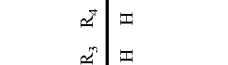 |  |  | 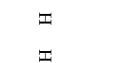 |

TABLE 77

| | R₁ | R₂ | R₃ | R₄ | (A₁)a | (A₂)b | (A₃)c | (A₄)d |
|---|---|---|---|---|---|---|---|---|
| D-913 | Methyl | H | Isopropyl | H | Ph | Ph | Ph | Ph |
| D-914 | Methyl | H | Isopropyl | H | Ph | 3-MeC₆H₄ | Ph | 3-MeC₆H₄ |
| D-915 | Methyl | H | Isopropyl | H | 3-MeC₆H₄ | 3-MeC₆H₄ | 3-MeC₆H₄ | 3-MeC₆H₄ |
| D-916 | Methyl | H | Isopropyl | H | Ph | 4-MeC₆H₄ | Ph | 4-MeC₆H₄ |
| D-917 | Methyl | H | Isopropyl | H | 2,4-Me₂C₆H₃ | 2,4-Me₂C₆H₃ | 2,4-Me₂C₆H₃ | 2,4-Me₂C₆H₃ |
| D-918 | Methyl | | | | 3,5-Me₂C₆H₃ | 3,5-Me₂C₆H₃ | 3,5-Me₂C₆H₃ | 3,5-Me₂C₆H₃ |
| D-919 | Methyl | H | Isopropyl | H | 4-MeC₆H₄ | 4-MeC₆H₄ | 4-MeC₆H₄ | 4-MeC₆H₄ |

TABLE 77-continued
| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-920 | Methyl | H | Isopropyl | H | 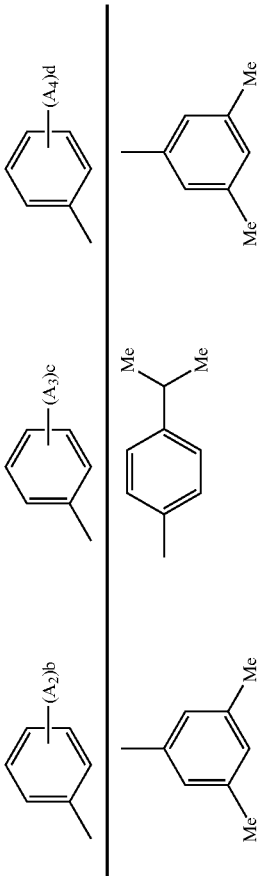 | 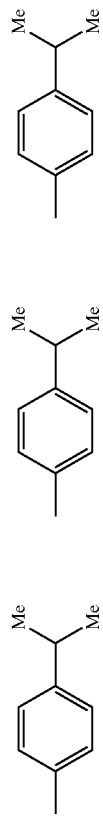 | 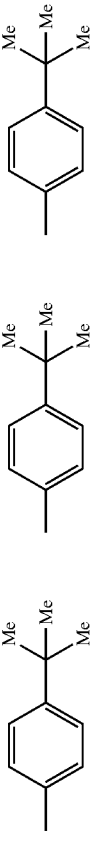 | 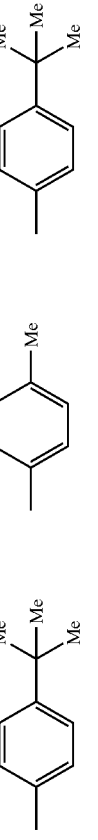 |
| D-921 | Methyl | H | Isopropyl | H | 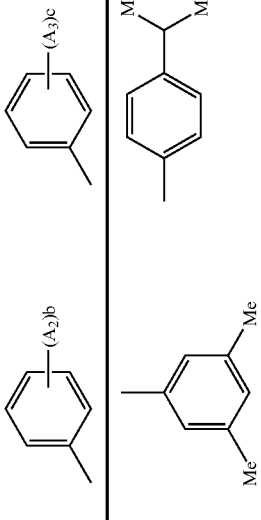 |  |  | 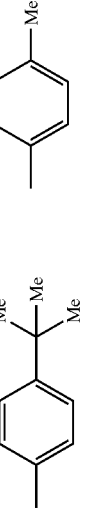 |
| D-922 | Methyl | H | Isopropyl | H | 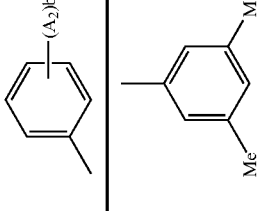 | 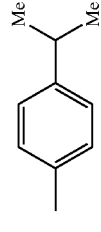 | 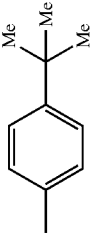 | 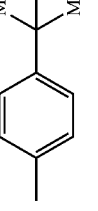 |
| D-923 | Methyl | H | Isopropyl | H | 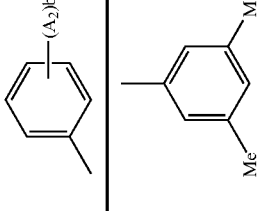 | 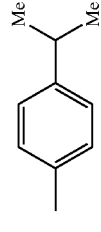 | 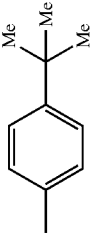 | 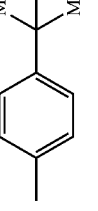 |
| D-924 | Methyl | H | Isopropyl | H | 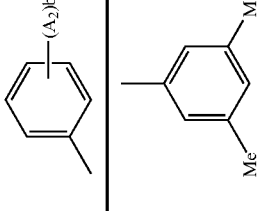 | 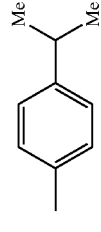 | 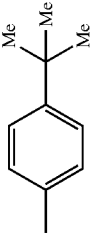 | 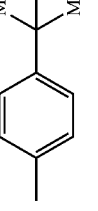 |

TABLE 78

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-925 | Methyl | H | Isopropyl | H | 4-(isopropyl)phenyl | 4-cyclohexylphenyl | 4-(isopropyl)phenyl | 4-cyclohexylphenyl |
| D-926 | Methyl | H | Isopropyl | H | 3,5-dimethylphenyl | 3,5-dimethylphenyl | 3,5-dimethylphenyl | 3,5-dimethylphenyl |
| D-927 | Methyl | H | Isopropyl | H | phenyl | biphenyl | phenyl | biphenyl |
| D-928 | Methyl | H | Isopropyl | H | phenyl | naphthyl | phenyl | naphthyl |
| D-929 | Methyl | H | Isopropyl | H | naphthyl | naphthyl | naphthyl | naphthyl |
| D-930 | Methyl | H | Isopropyl | H | biphenyl | biphenyl | naphthyl | biphenyl |
| D-931 | Methyl | H | Isopropyl | H | tetrahydronaphthyl | phenyl | tetrahydronaphthyl | phenyl |

TABLE 78-continued

| | $R_1$ | $R_2$ | $R_3$ | $R_4$ | —(A$_1$)a | —(A$_2$)b | —(A$_3$)c | —(A$_4$)d |
|---|---|---|---|---|---|---|---|---|
| D-932 | Methyl | H | Isopropyl | H | 6-methyl-tetralinyl | 6-methyl-tetralinyl | 6-methyl-tetralinyl | 6-methyl-tetralinyl |
| D-933 | Methyl | H | Isopropyl | H | 5-methyl-indanyl | 5-methyl-indanyl | 5-methyl-indanyl | 5-methyl-indanyl |
| D-934 | Methyl | H | Isopropyl | H | 4-benzyl-phenyl (4′-methyl) | 4-benzyl-phenyl (4′-methyl) | 4-benzyl-phenyl (4′-methyl) | 4-benzyl-phenyl (4′-methyl) |
| D-935 | Methyl | H | Isopropyl | H | 6-(1-methylethyl)-naphthyl | 6-(1-methylethyl)-naphthyl | 6-(1-methylethyl)-naphthyl | 6-(1-methylethyl)-naphthyl |
| D-936 | Methyl | H | Isopropyl | H | 4-methylphenyl isopropyl | 6-methylquinolinyl | 4-methylphenyl isopropyl | 6-methylquinolinyl |

TABLE 79

| | $R_1$ | $R_2$ | $R_3$ | $R_4$ | $(A_1)a$ | $(A_2)b$ | $(A_3)c$ | $(A_4)d$ |
|---|---|---|---|---|---|---|---|---|
| D-937 | t-bytyl | H | Isopropyl | H | phenyl | phenyl | phenyl | phenyl |
| D-938 | t-bytyl | H | Isopropyl | H | phenyl | 3-Me-phenyl | phenyl | 3-Me-phenyl |
| D-939 | t-bytyl | H | Isopropyl | H | 3-Me-phenyl | 3-Me-phenyl | 3-Me-phenyl | 3-Me-phenyl |
| D-940 | t-bytyl | H | Isopropyl | H | phenyl | 4-Me-phenyl | phenyl | 4-Me-phenyl |
| D-941 | t-bytyl | H | Isopropyl | H | 3-Me-phenyl | 2,6-Me$_2$-phenyl | 3-Me-phenyl | 2,6-Me$_2$-phenyl |
| D-942 | t-bytyl | H | Isopropyl | H | 3,5-Me$_2$-phenyl | 3,5-Me$_2$-phenyl | 3,5-Me$_2$-phenyl | 3,5-Me$_2$-phenyl |
| D-943 | t-bytyl | H | Isopropyl | H | 4-Me-phenyl | 4-Me-phenyl | 4-Me-phenyl | 4-Me-phenyl |

TABLE 79-continued
| | | | | | |
|---|---|---|---|---|---|
| D-944 | t-bytyl | H | Isopropyl | 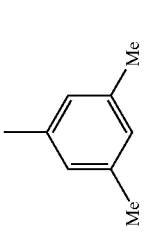 | 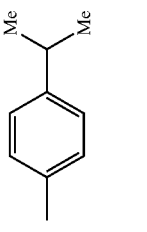 | 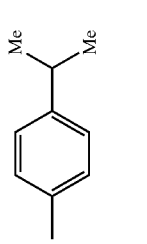 |
| D-945 | t-bytyl | H | Isopropyl | | | |
| D-946 | t-bytyl | H | Isopropyl | | | |
| D-947 | t-bytyl | H | Isopropyl | | | |
| D-948 | t-bytyl | H | Isopropyl | | | |

TABLE 80

| | R₁ | R₂ | R₃ | R₄ | (A₁)a | (A₂)b | (A₃)c | (A₄)d |
|---|---|---|---|---|---|---|---|---|
| D-949 | t-bytyl | H | Isopropyl | H | 4-isopropyl-methylphenyl (CHMe₂ on 4-methylphenyl) | 4-cyclohexylphenyl | 4-(1-methylethyl)phenyl | 4-cyclohexylphenyl |
| D-950 | t-bytyl | H | Isopropyl | H | 3,5-dimethylphenyl | 3,5-dimethylphenyl | 3,5-dimethylphenyl | 3,5-dimethylphenyl |
| D-951 | t-bytyl | H | Isopropyl | H | phenyl | 4-biphenyl | phenyl | 4-biphenyl |
| D-952 | t-bytyl | H | Isopropyl | H | phenyl | 2-naphthyl | phenyl | 2-naphthyl |
| D-953 | t-bytyl | H | Isopropyl | H | 2-naphthyl | 2-naphthyl | 2-naphthyl | 2-naphthyl |
| D-954 | t-bytyl | H | Isopropyl | H | 4-biphenyl | 4-biphenyl | phenyl | 4-biphenyl |
| D-955 | t-bytyl | H | Isopropyl | H | 5,6,7,8-tetrahydro-2-naphthyl | phenyl | 5,6,7,8-tetrahydro-2-naphthyl | phenyl |

TABLE 80-continued
| | R₁ | R₂ | R₃ | R₄ | —(A₁)a | —(A₂)b | —(A₃)c | —(A₄)d |
|---|---|---|---|---|---|---|---|---|
| D-956 | t-bytyl | H | Isopropyl | H | 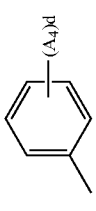 | 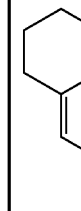 | 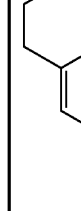 | 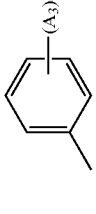 |
| D-957 | t-bytyl | H | Isopropyl | H | | | | |
| D-958 | t-bytyl | H | Isopropyl | H | | | | |
| D-959 | t-bytyl | H | Isopropyl | H | | | | |
| D-960 | t-bytyl | H | Isopropyl | H | 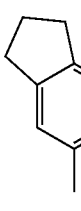 | 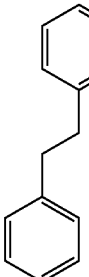 | 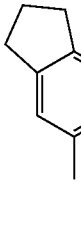 | 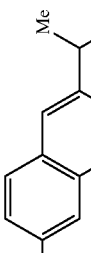 |

TABLE 81

| No | R$_5$ | R$_6$ | R$_7$ | R$_8$ | A$_5$ | A$_6$ | A$_7$ | A$_8$ |
|---|---|---|---|---|---|---|---|---|
| D-961 | —H | —H | —H | —H | —Me | —Me | —Me | —Me |
| D-962 | —H | —H | —H | —H | —Me | —Me | —Me | —Me |
| D-963 | —H | —H | —H | —H | —CH(Me)Me | —CH(Me)Me | —CH(Me)Me | —CH(Me)Me |
| D-964 | —H | —H | —H | —H | —CH$_2$Me | —Me | —CH$_2$Me | —Me |
| D-965 | —H | —H | —H | —H | —C(Me)$_2$Me | —C(Me)$_2$Me | —C(Me)$_2$Me | —C(Me)$_2$Me |
| D-966 | —Me | —H | —Me | —H | —C(Me)$_2$Me | —C(Me)$_2$Me | —C(Me)$_2$Me | —C(Me)$_2$Me |
| D-967 | —Me | —Me | —Me | —H | —CH(Me)Me | —CH(Me)Me | —CH(Me)Me | —CH(Me)Me |
| D-968 | —CH(Me)Me | —H | —CH(Me)Me | —Me | —Me | —CH(Me)Me | —Me | —CH(Me)Me |
| D-969 | —H | —Me | —H | —Me | —(CH$_2$)$_4$Me | —(CH$_2$)$_4$Me | —(CH$_2$)$_4$Me | —(CH$_2$)$_4$Me |
| D-970 | —Ph | —H | —Ph | —H | —C(Me)$_2$Me | —C(Me)$_2$Me | —C(Me)$_2$Me | —C(Me)$_2$Me |

TABLE 82
| No | R₅ | R₆ | R₇ | R₈ | A₅ | A₆ | A₇ | A₈ |
|---|---|---|---|---|---|---|---|---|
| D-971 | —H | —H | —H | —H | —Me | 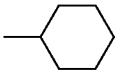 | —Me | 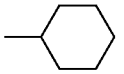 |
| D-972 | —H | —H | —H | —H | 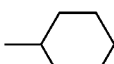 | 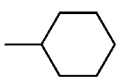 | 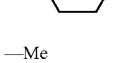 | 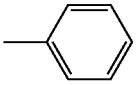 |
| D-973 | —H | —H | —H | —H | —Me | 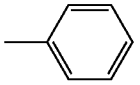 | —Me | 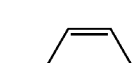 |
| D-974 | —H | —H | —H | —H | 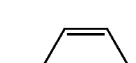 | 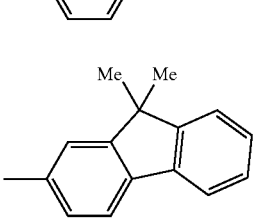 | 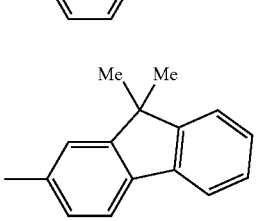 | 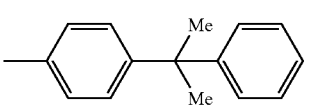 |
| D-975 | —H | —H | —H | —H | 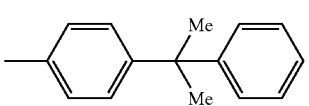 | 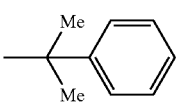 | 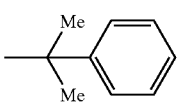 | 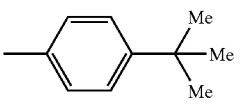 |
| D-976 | —H | —H | —H | —H | 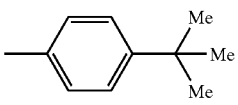 | 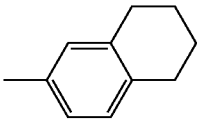 | 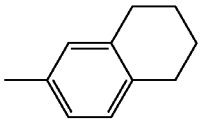 | 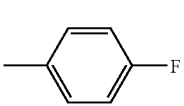 |
| D-977 | —H | —H | —H | —H | 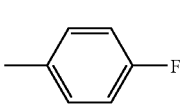 | 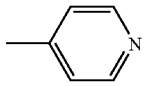 | 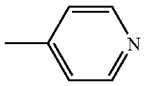 | 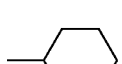 |
| D-978 | —Me | —H | —Me | —H | —Me | 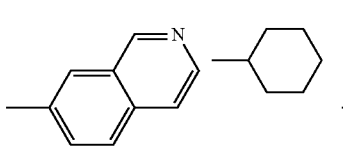 | —Me | 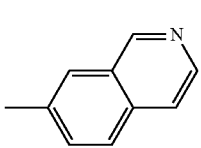 |
| D-979 | —Me | —Me | —Me | Me | | | | |
| D-980 | —Me | —H | —Me | —H | | | | |
TABLE 83
| No | R₅ | R₆ | R₇ | R₈ | A₅ | A₆ | A₇ | A₈ |
|---|---|---|---|---|---|---|---|---|
| D-981 | —H | —H | —H | —H | —Me | | —Me | |
| D-982 | —H | —H | —H | —H | | | | |

TABLE 83-continued

| No | R5 | R6 | R7 | R8 | A5 | A6 | A7 | A8 |
|---|---|---|---|---|---|---|---|---|
| D-983 | —H | —H | —H | —H | —Me | 2-pyridyl | —Me | 2-pyridyl |
| D-984 | —H | —H | —H | —H | isopropyl | 7-quinolinyl | isopropyl | 7-quinolinyl |
| D-985 | —H | —H | —H | —H | tert-butyl | 2,5-dimethylthiophen-3-yl | tert-butyl | 2,5-dimethylthiophen-3-yl |
| D-986 | —H | —H | —H | —H | isopropyl | 4-pyridyl | isopropyl | 4-pyridyl |
| D-987 | —H | —H | —H | —H | isopropyl | 2-pyridyl | isopropyl | 2-pyridyl |
| D-988 | —Me | —H | —Me | —H | —Me | isochroman-7-yl | —Me | isochroman-7-yl |
| D-989 | —H | —H | —H | —H | isopropyl | 3-pyridyl | isopropyl | 3-pyridyl |
| D-990 | —H | —H | —H | —H | tert-butyl | 6-quinoxalinyl | tert-butyl | 6-quinoxalinyl |

TABLE 84

| No | R5 | R6 | R7 | R8 | A5 | A6 | A7 | A8 |
|---|---|---|---|---|---|---|---|---|
| D-991 | —H | —H | —H | —H | phenyl | 4-pyridyl | phenyl | 4-pyridyl |
| D-992 | —H | —H | —H | —H | phenyl | 3-pyridyl | phenyl | 3-pyridyl |
| D-993 | —H | —H | —H | —H | phenyl | 2-pyridyl | phenyl | 2-pyridyl |
| D-994 | —H | —H | —H | —H | 4-methylphenyl | 4-pyridyl | 4-methylphenyl | 4-pyridyl |

TABLE 84-continued

| No | R₅ | R₆ | R₇ | R₈ | A₅ | A₆ | A₇ | A₈ |
|---|---|---|---|---|---|---|---|---|
| D-995 | —H | —H | —H | —H | -C₆H₄-Me (p) | 3-pyridyl | -C₆H₄-Me (p) | 3-pyridyl |
| D-996 | —H | —H | —H | —H | -C₆H₄-Me (p) | 2-pyridyl | -C₆H₄-Me (p) | 2-pyridyl |
| D-997 | —H | —H | —H | —H | -C₆H₄-CHMe₂ (p) | 4-pyridyl | -C₆H₄-CHMe₂ (p) | 4-pyridyl |
| D-998 | —H | —H | —H | —H | -C₆H₄-CHMe₂ (p) | 3-pyridyl | -C₆H₄-CHMe₂ (p) | 3-pyridyl |
| D-999 | —H | —H | —H | —H | -C₆H₄-CHMe₂ (p) | 2-pyridyl | -C₆H₄-CHMe₂ (p) | 2-pyridyl |
| D-1000 | —Me | —H | —H | —H | -C₆H₄-CHMe₂ (p) | 3-pyridyl | -C₆H₄-CHMe₂ (p) | 3-pyridyl |

TABLE 85

| No | R₅ | R₆ | R₇ | R₈ | A₅ | A₆ | A₇ | A₈ |
|---|---|---|---|---|---|---|---|---|
| D-1001 | —H | —H | —H | —H | -C₆H₄-CMe₃ (p) | 4-pyridyl | -C₆H₄-CMe₃ (p) | 4-pyridyl |
| D-1002 | —H | —H | —H | —H | -C₆H₄-CMe₃ (p) | 3-pyridyl | -C₆H₄-CMe₃ (p) | 3-pyridyl |
| D-1003 | —H | —H | —H | —H | -C₆H₄-CMe₃ (p) | 2-pyridyl | -C₆H₄-CMe₃ (p) | 2-pyridyl |
| D-1004 | —H | —H | —H | —H | 2-naphthyl | 4-pyridyl | 2-naphthyl | 4-pyridyl |
| D-1005 | —H | —H | —H | —H | 2-naphthyl | 3-pyridyl | 2-naphthyl | 3-pyridyl |
| D-1006 | —H | —H | —H | —H | 2-naphthyl | 2-pyridyl | 2-naphthyl | 2-pyridyl |

TABLE 85-continued
| No | R5 | R6 | R7 | R8 | A5 | A6 | A7 | A8 |
|---|---|---|---|---|---|---|---|---|
| D-1007 | —H | —H | —H | —H | 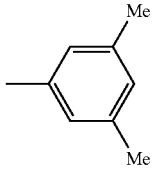 | 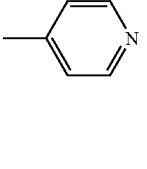 | 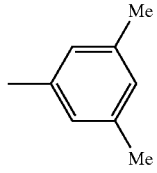 | 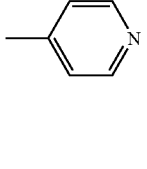 |
| D-1008 | —H | —H | —H | —H | 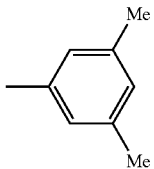 | 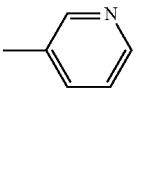 | 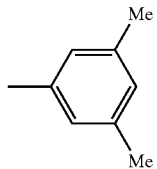 | 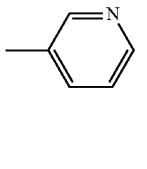 |
| D-1009 | —H | —H | —H | —H | 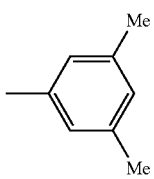 | 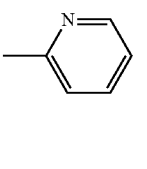 | 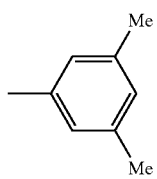 | 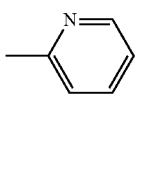 |
| D-1010 | —Me | —H | —Me | —H | 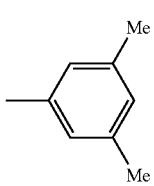 | 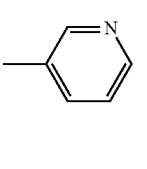 | 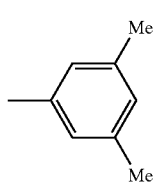 | 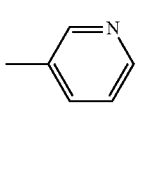 |
TABLE 86
| No | R5 | R6 | R7 | R8 | A5 | A6 | A7 | A8 |
|---|---|---|---|---|---|---|---|---|
| D-1011 | —H | —H | —H | —H | 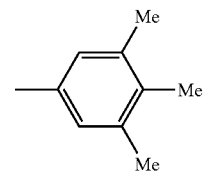 | 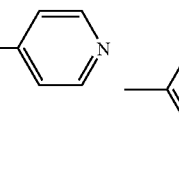 | 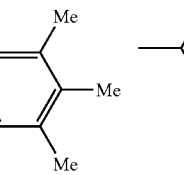 | 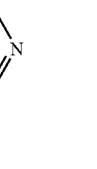 |
| D-1012 | —H | —H | —H | —H | 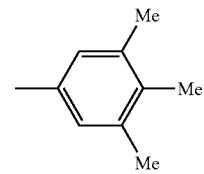 | 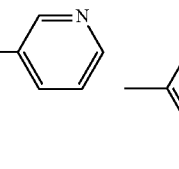 | 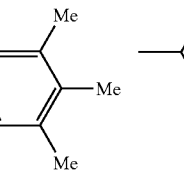 |  |
| D-1013 | —H | —H | —H | —H | 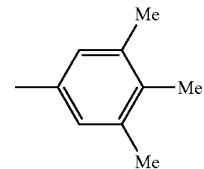 | 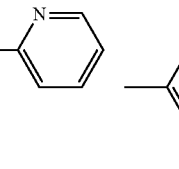 | 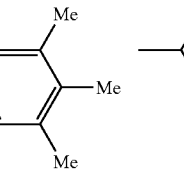 | 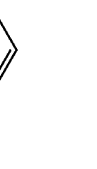 |
| D-1014 | —H | —H | —H | —H | 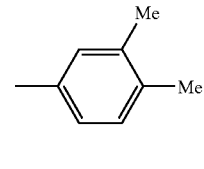 | 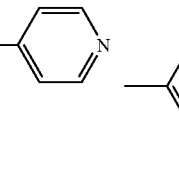 | 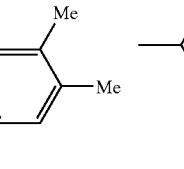 | 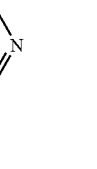 |

TABLE 86-continued
| No | R5 | R6 | R7 | R8 | A5 | A6 | A7 | A8 |
|---|---|---|---|---|---|---|---|---|
| D-1015 | —H | —H | —H | —H | 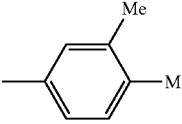 | 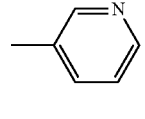 | 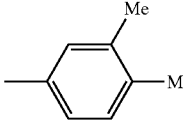 | 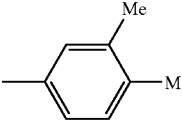 |
| D-1016 | —H | —H | —H | —H | 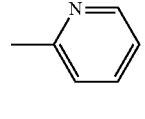 | 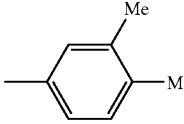 | 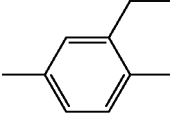 | 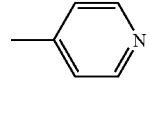 |
| D-1017 | —H | —H | —H | —H | 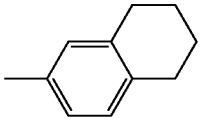 | 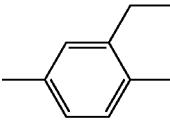 | 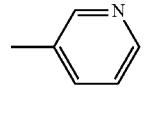 | 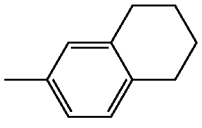 |
| D-1018 | —H | —H | —H | —H | 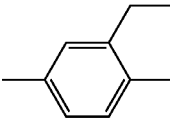 | 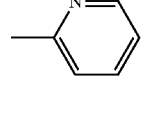 | 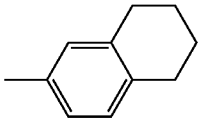 | 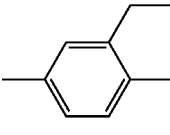 |
| D-1019 | —H | —H | —H | —H | 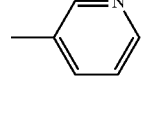 | 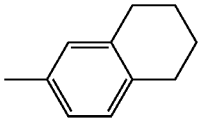 | 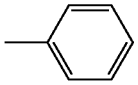 | 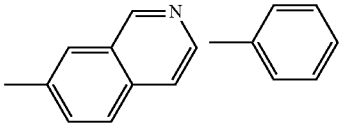 |
| D-1020 | —Me | —H | —Me | —H | 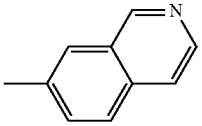 | 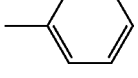 | 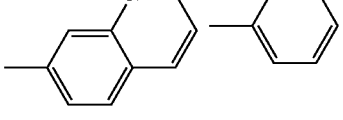 | 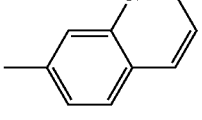 |
TABLE 87
| No | R5 | R6 | R7 | R8 | A5 | A6 | A7 | A8 |
|---|---|---|---|---|---|---|---|---|
| D-1021 | —H | —H | —H | —H | 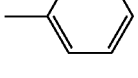 | 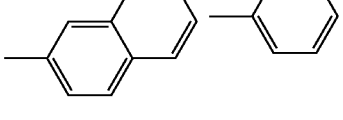 | 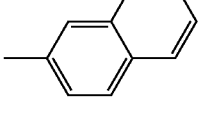 | 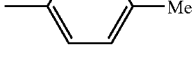 |
| D-1022 | —H | —H | —H | —H | | | | |
| D-1023 | —H | —H | —H | —H | | | | |
| D-1024 | —H | —H | —H | —H | 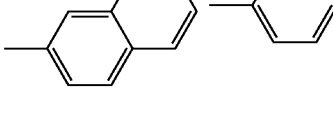 | | 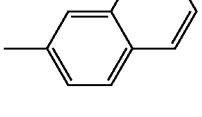 | |

TABLE 87-continued
| No | R5 | R6 | R7 | R8 | A5 | A6 | A7 | A8 |
|---|---|---|---|---|---|---|---|---|
| D-1025 | —H | —H | —H | —H | 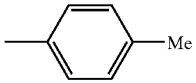 | 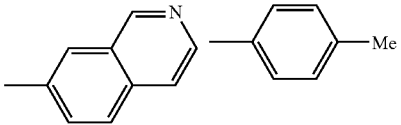 | 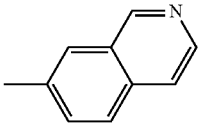 | 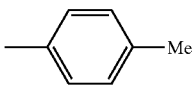 |
| D-1026 | —H | —H | —H | —H | 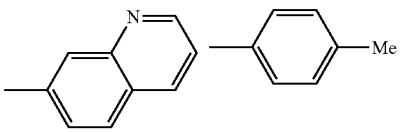 | 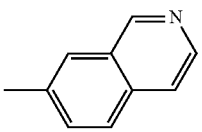 | 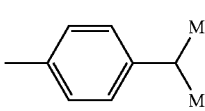 | 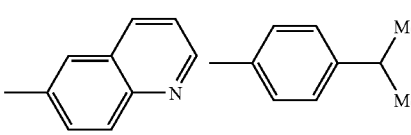 |
| D-1027 | —H | —H | —H | —H | 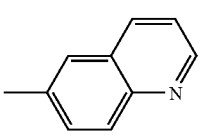 | 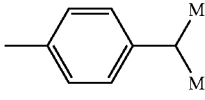 | 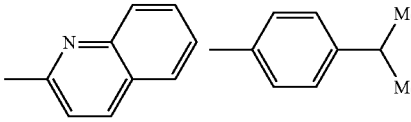 | 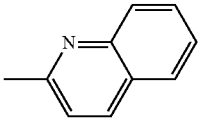 |
| D-1028 | Me | —H | Me | —H | 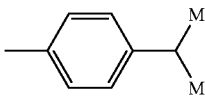 | 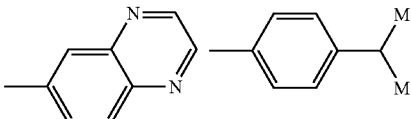 | 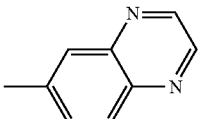 | 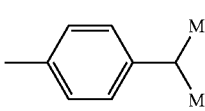 |
| D-1029 | —H | —H | —H | —H | 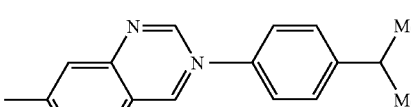 | 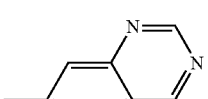 | 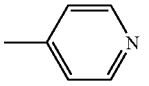 | 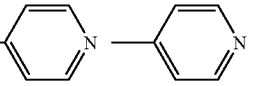 |
| D-1030 | —H | —H | —H | —H | 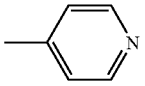 | 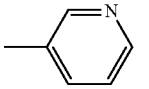 | 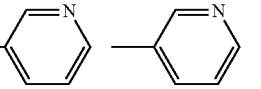 | 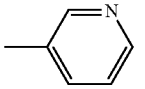 |
TABLE 88
| No | R5 | R6 | R7 | R8 | A5 | A6 | A7 | A8 |
|---|---|---|---|---|---|---|---|---|
| D-1031 | —H | —H | —H | —H | 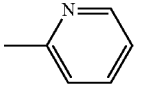 | 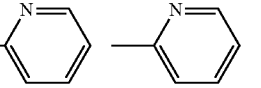 | | 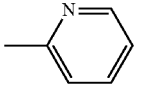 |
| D-1032 | —H | —H | —H | —H | 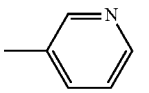 | | | |
| D-1033 | —H | —H | —H | —H | 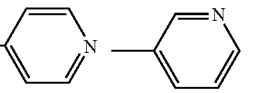 | | | |
| D-1034 | —H | —H | —H | —H | 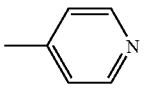 | 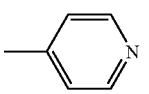 | | |
| D-1035 | —H | —H | —H | —H | 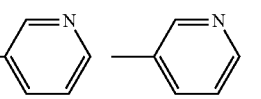 | 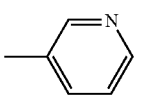 | | |

TABLE 88-continued
| No | R₅ | R₆ | R₇ | R₈ | A₅ | A₆ | A₇ | A₈ |
|---|---|---|---|---|---|---|---|---|
| D-1036 | —H | —H | —H | —H | 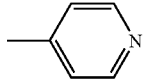 | 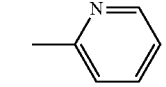 | 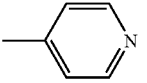 | 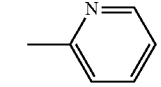 |
| D-1037 | —H | —H | —H | —H | | 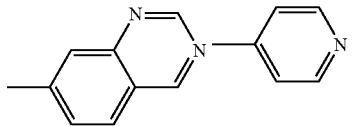 | | 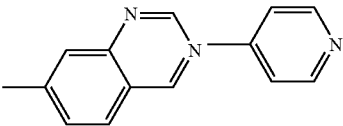 |
| D-1038 | —H | —H | —H | —H | | 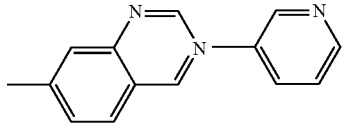 | | 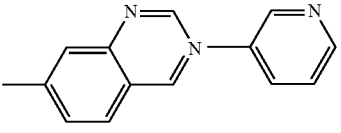 |
| D-1039 | —H | —H | —H | —H | | 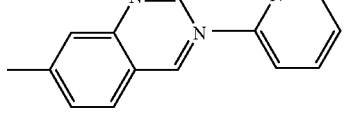 | | 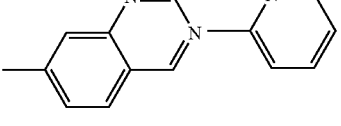 |
| D-1040 | —Me | —H | —Me | —H | | 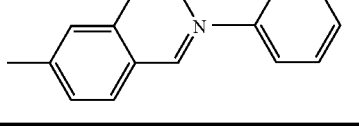 | | 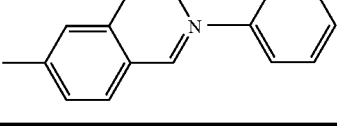 |
TABLE 89
| No | R₅ | R₆ | R₇ | R₈ | A₅ | A₆ | A₇ | A₈ |
|---|---|---|---|---|---|---|---|---|
| D-1041 | —H | —H | —H | —H | 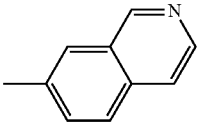 | 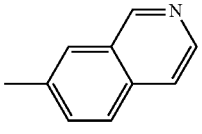 | 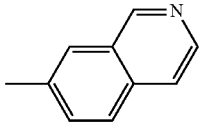 | 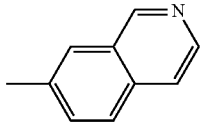 |
| D-1042 | —H | —H | —H | —H | 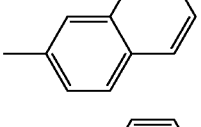 | 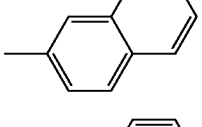 | 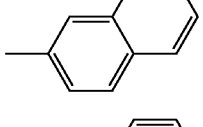 | 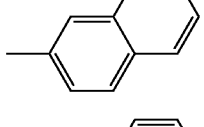 |
| D-1043 | —H | —H | —H | —H | 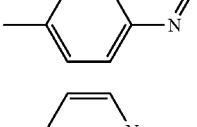 | 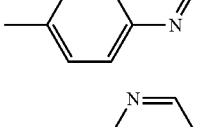 | 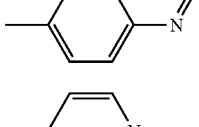 | 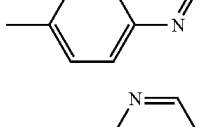 |
| D-1044 | —H | —H | —H | —H | 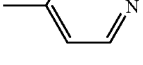 | 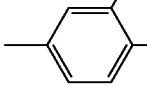 | 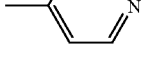 | 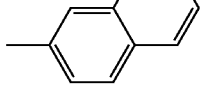 |
| D-1045 | —H | —H | —H | —H | 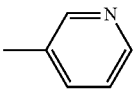 | 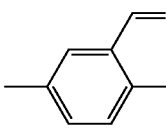 | 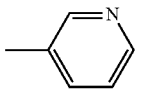 | 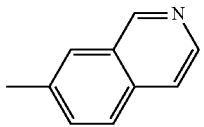 |

TABLE 89-continued

| No | $R_5$ | $R_6$ | $R_7$ | $R_8$ | $A_5$ | $A_6$ | $A_7$ | $A_8$ |
|---|---|---|---|---|---|---|---|---|
| D-1046 | —H | —H | —H | —H | 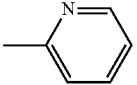 | 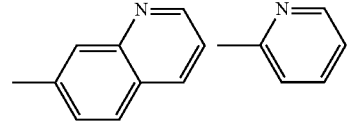 | 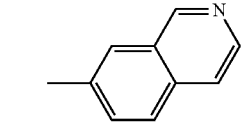 |  |
| D-1047 | —H | —H | —H | —H | 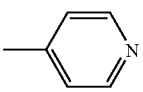 | 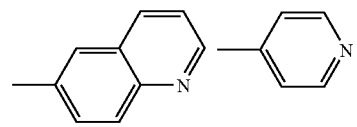 | 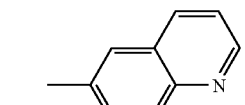 | 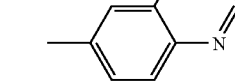 |
| D-1048 | Me | —H | Me | —H | 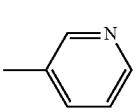 | 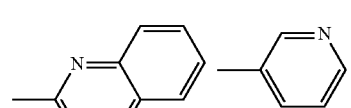 | 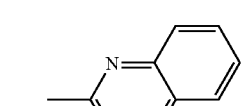 | 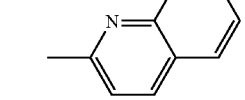 |
| D-1049 | —H | —H | —H | —H | 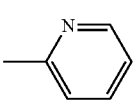 | 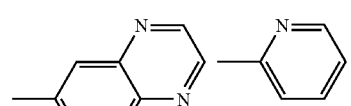 | 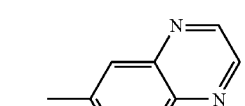 | 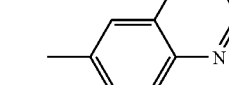 |
| D-1050 | —H | —H | —H | —H | 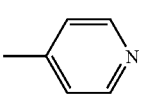 | 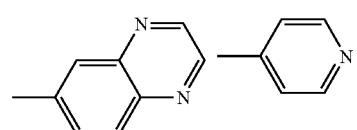 | 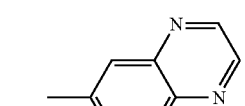 | 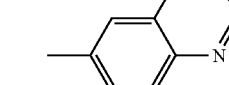 |

In the aromatic amine derivative of the present invention, since the aryl group (in particular, a benzene ring), the alkyl group, the cycroalkyl group or the heterocyclic group is connected to a diaminocrysene structure as a light emission center, an association between the compounds is prevented, resulting in a prolonged lifetime thereof. Moreover, because coupling a bulky substituent to the chrysene backbone structure increases a steric repulsion against the amine structure, the lifetime prolongs further.

Further, the aromatic amine derivatives have a strong fluorescence in a solid state, and are excellent in an electric field light emission, which leads to a fluorescent quantum efficiency as high as 0.3 or more. In addition, the aromatic amine derivatives of the present invention exhibit not only excellent capabilities of injecting and transporting holes from the metal electrode or organic thin film layers, but also excellent capabilities of injecting and transporting electrons from the metal electrode or organic thin film layers and, therefore, are usefully employable as light emitting materials, particularly doping materials for organic EL devices. Besides, the aromatic amine derivatives of the present invention may be used together with other hole transporting materials, electron transporting materials or doping materials.

The organic EL device of the present invention comprises one or plural organic thin film layers sandwiched between an anode and a cathode. In the case of one layer type, a light emitting layer as the organic thin film layer is sandwiched between the anode and cathode. The light emitting layer contains the light emitting material and may further contain a hole injecting material and an electron injecting material in order to transport holes injected from the anode or electrons injected from the cathode to the light emitting material. The aromatic amine derivatives of the present invention have an enhanced light emitting property and excellent hole injecting capability and hole transporting capability as well as excellent electron injecting capability and electron transporting capability and, therefore, can be employed as a light emitting material or a doping material in the light emitting layer.

In the organic EL device of the present invention, the light emitting layer contains the aromatic amine derivative of the present invention in an amount of preferably 0.1 to 20% by weight and more preferably 1 to 10% by weight. Further, the aromatic amine derivatives of the present invention exhibit not only an extremely high fluorescent quantum efficiency but also high hole transporting capability and electron transporting capability, and further are capable of forming a uniform thin film, so that the light emitting layer may be formed from the aromatic amine derivatives only.

On the other hand, in the case where the organic EL device of the present invention comprises two or more organic thin film layers having at least the light emitting layer which are sandwiched between the cathode and anode, the organic thin film layers preferably include an organic layer containing the aromatic amine derivative of the present invention as an essential component which is provided between the anode and the light emitting layer. Such an organic layer may be a hole injecting layer, a hole transporting layer, etc.

Further, in a case where the aromatic amine derivative of the present invention is employed as a doping material, it is preferable that at least one kind selected from the group consisting of anthracene derivatives of a following general formula (3), anthracene derivatives of a following general formula (4) and pyrene derivatives of a following general formula (5) is employed as a host material.

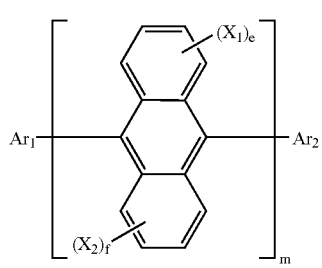

(3)

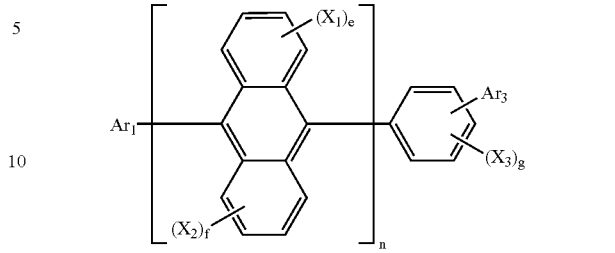

(4)

In the general formula (3), $X_1$ and $X_2$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 ring carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms or a halogen atom; e and f each independently represents an integer of 0 to 4; when e or f is 2 or greater, $X_1$ and $X_2$ may be the same with or different from each other.

$Ar_1$ and $Ar_2$ each independently represents a substituted or unsubstituted aryl group having 5 to 50 ring carbon atoms or a substituted or unsubstituted heterocyclic group having 5 to 50 ring carbon atoms; at least one of $Ar_1$ or $Ar_2$ represents a substituted or unsubstituted aryl group with a condensed ring and having 10 to 50 ring carbon atoms; and m represents an integer of 1 to 3. When m is 2 or greater, a group within the above parentheses: [ ] may be the same with or different from each other.

Specific examples and substituents of the $X_1$, $X_2$, $Ar_1$ and $Ar_2$ are the same as those explained about the foregoing general formula (1).

In the general formula (4), $X_1$ to $X_3$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms or a halogen atom; e, f, and g each independently represents an integer of 0 to 4. When e, f, or g is 2 or greater, $X_1$, $X_2$ and $X_3$ may be the same with or different from each other.

$Ar_1$ represents a substituted or unsubstituted aryl group with a condensed ring and having 10 to 50 ring carbon atoms and $Ar^3$ represents a substituted or unsubstituted aryl group having 5 to 50 ring carbon atoms; n represents an integer of 1 to 3. When n is 2 or greater, a group within the above parentheses: [ ] may be the same with or different from each other.

Specific examples and substituents of the $X_1$ to $X_3$, $Ar_1$ and $Ar_3$ are the same as those explained about the foregoing general formula (1).

Specific examples of anthracene derivative represented by the general formulae (3) and (4) will be illustrated below, though not particularly limited thereto.

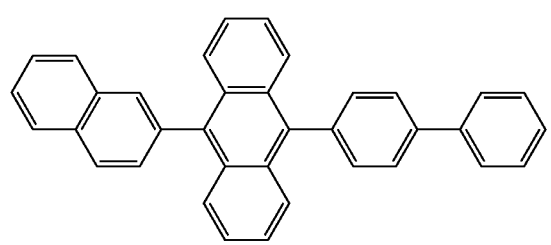

AN1

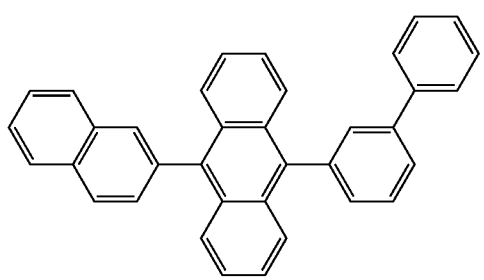

AN2

-continued
AN3
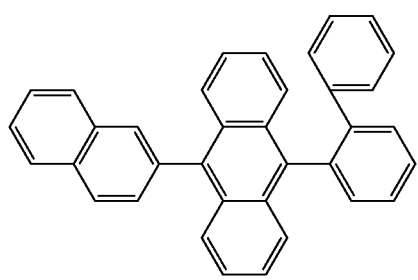
AN4
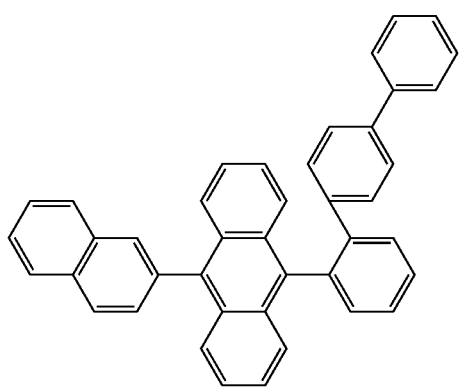
AN5
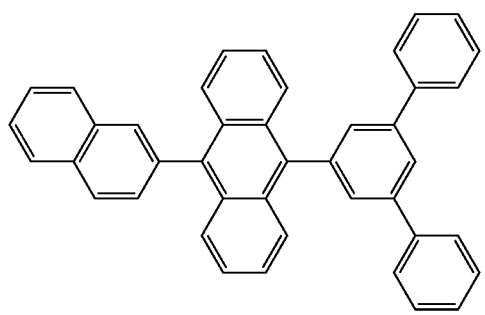
AN6
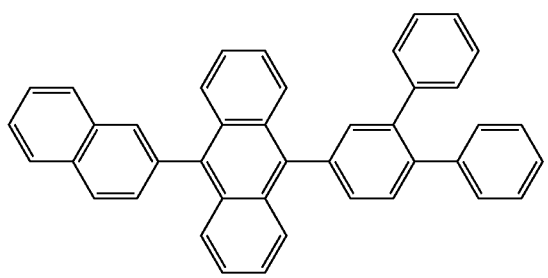
AN7
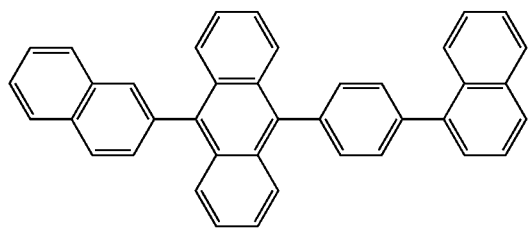
AN8
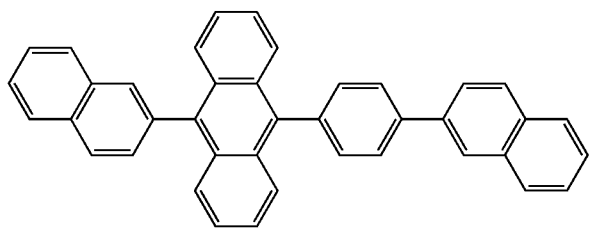
AN9
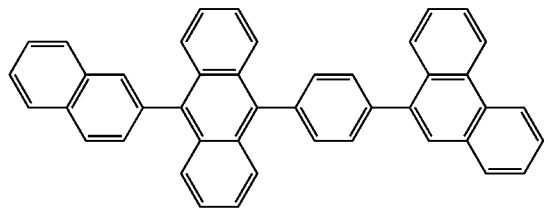
AN10
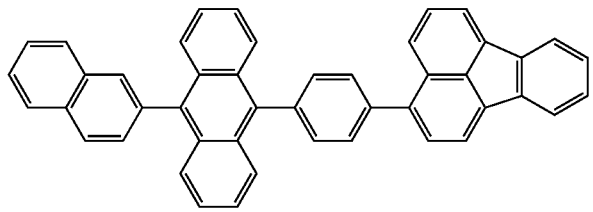
AN11
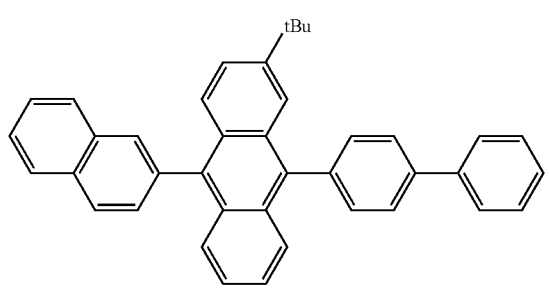
AN12
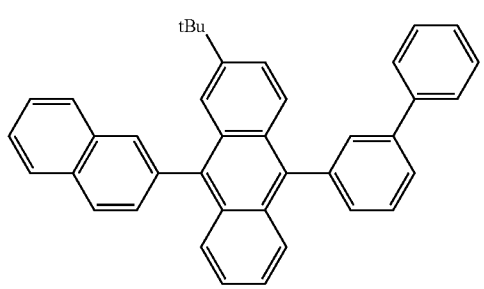

-continued
AN13
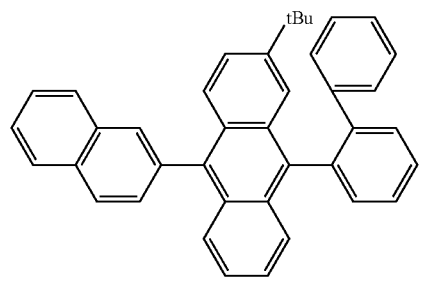
AN14
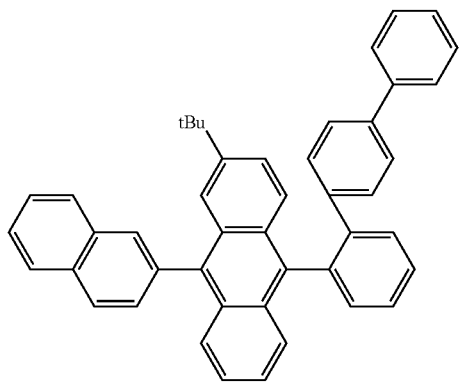
AN15
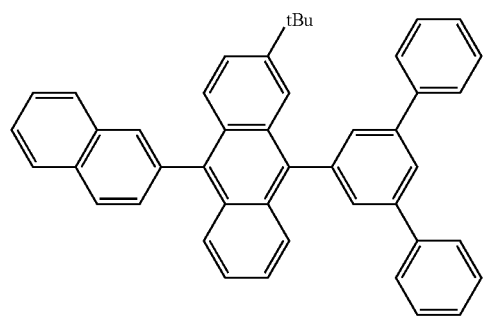
AN16
AN17
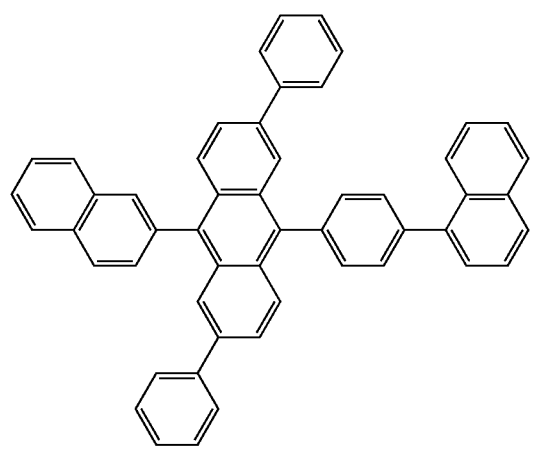
AN18
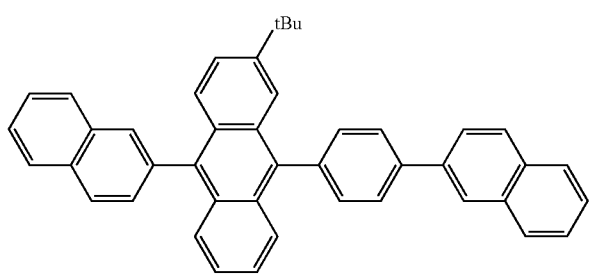
AN19
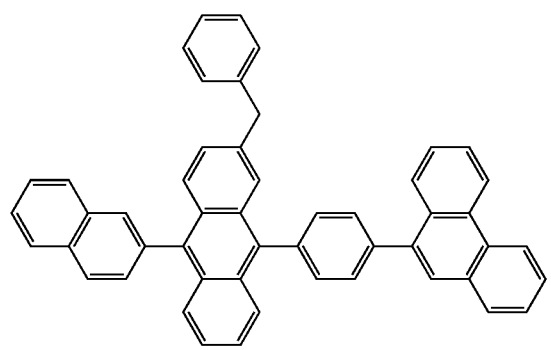
AN20
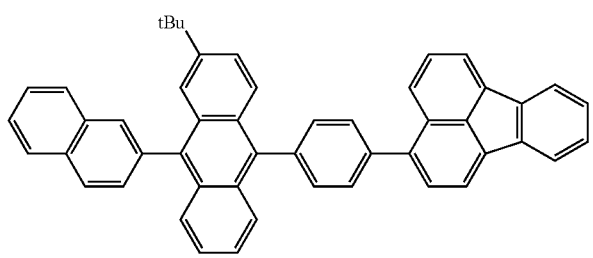

-continued
AN21
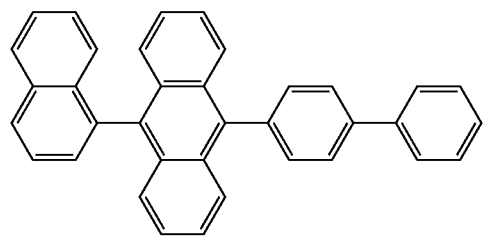
AN22
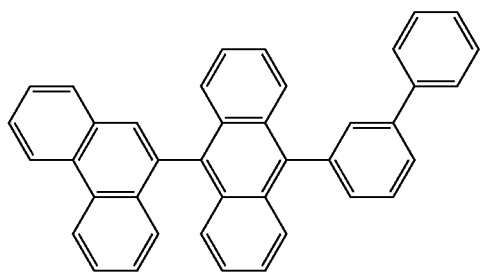
AN23
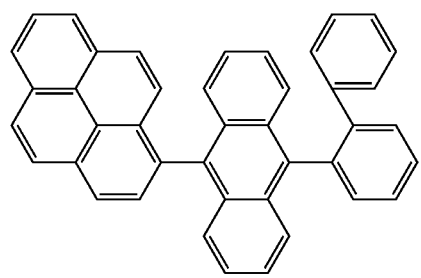
AN24
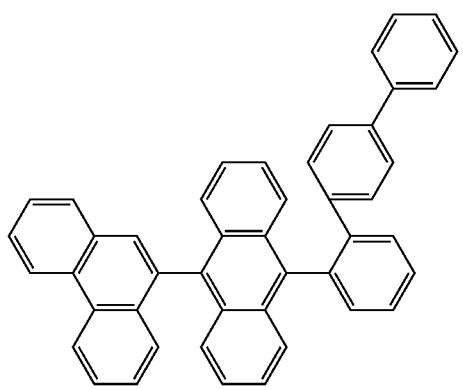
AN25
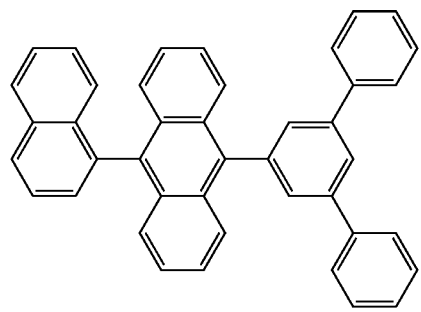
AN26
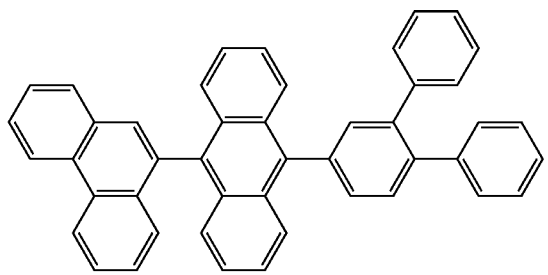
AN27
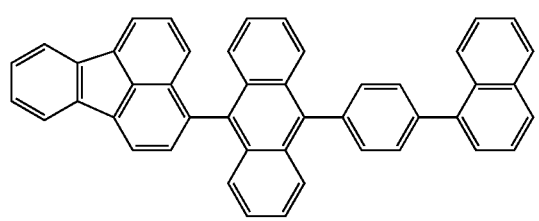
AN28
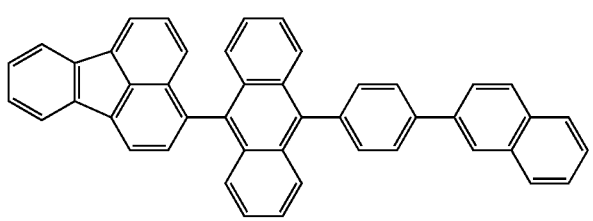
AN29
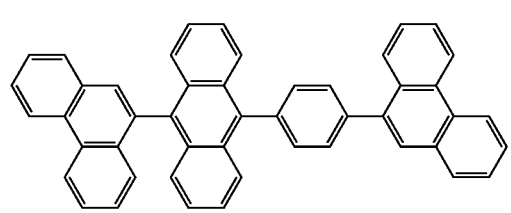
AN30
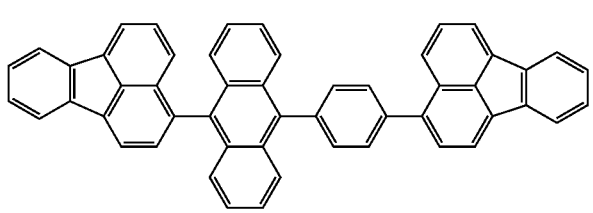

-continued
AN31
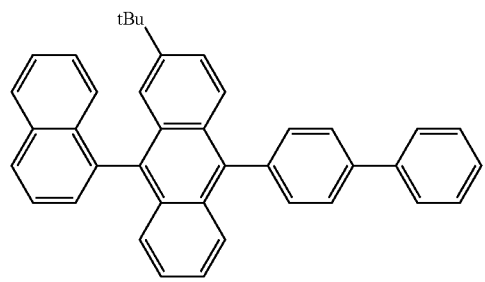
AN32
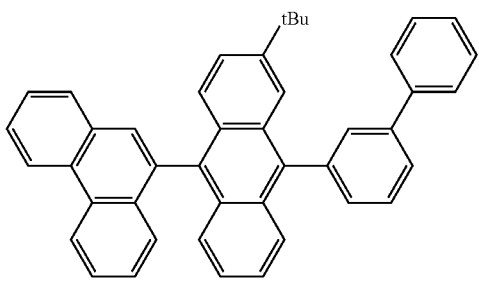
AN33
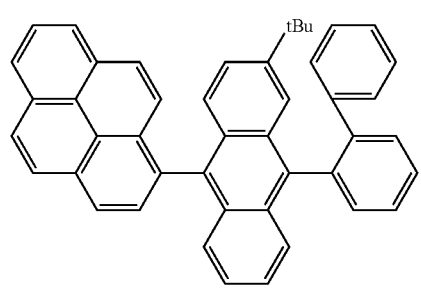
AN34
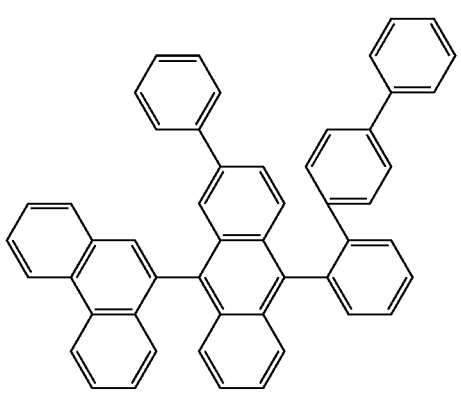
AN35
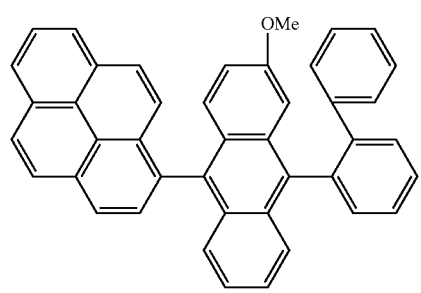
AN36
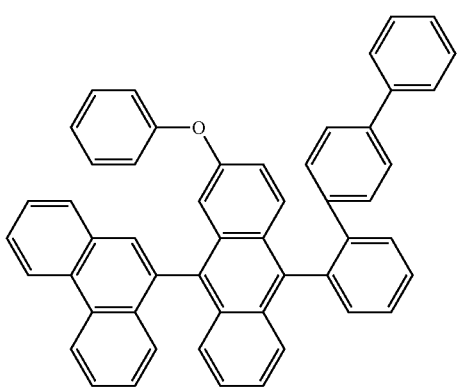
AN37
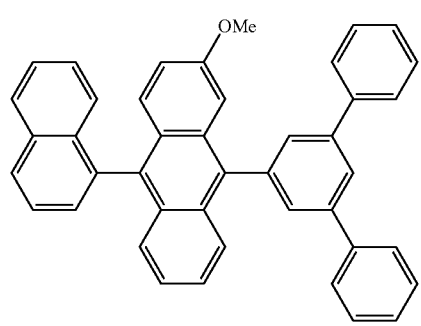
AN38
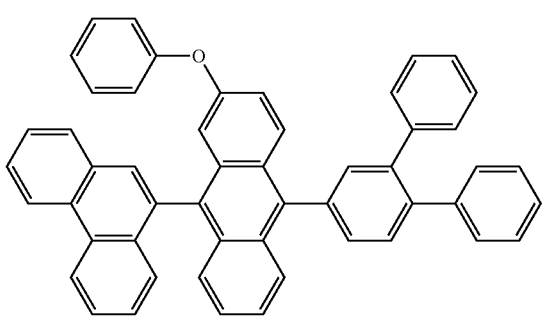

-continued
AN39
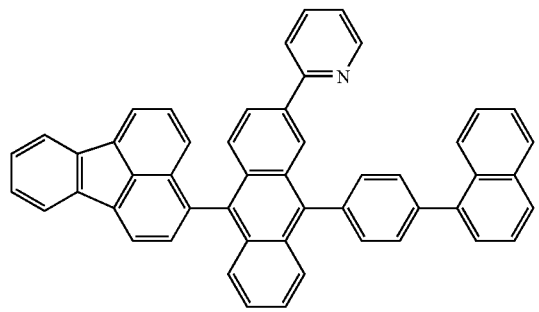
AN40
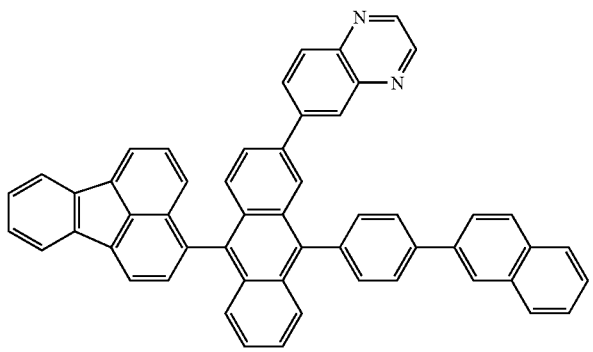
AN41
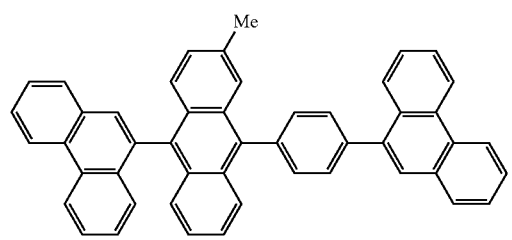
AN42
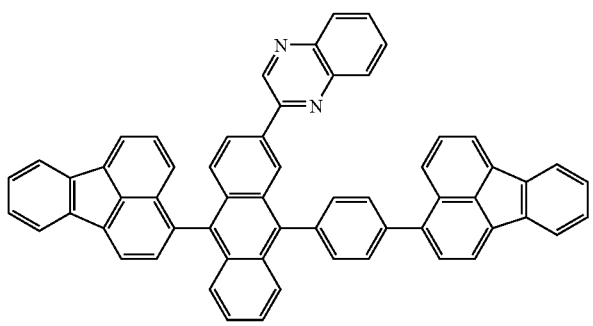
AN43
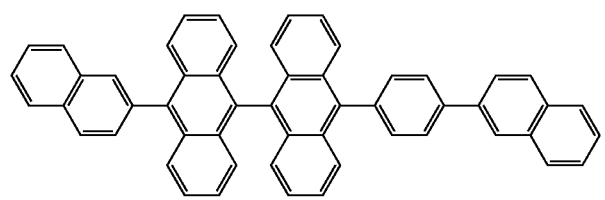
AN44
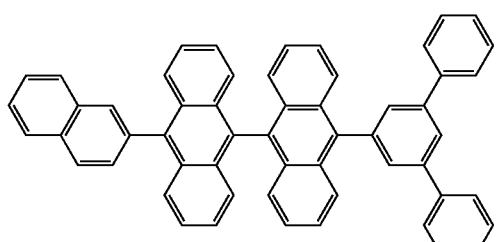
AN45
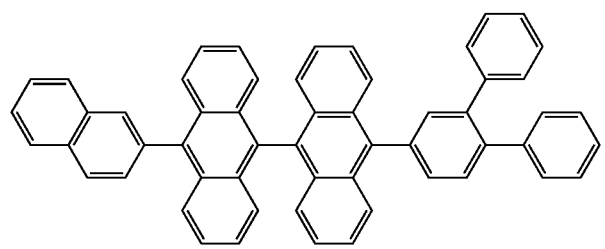
AN46
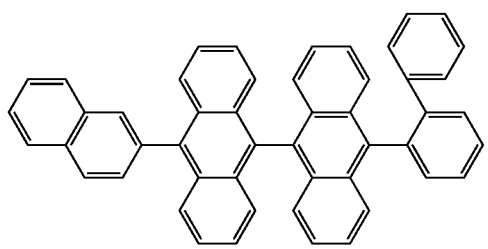
AN47
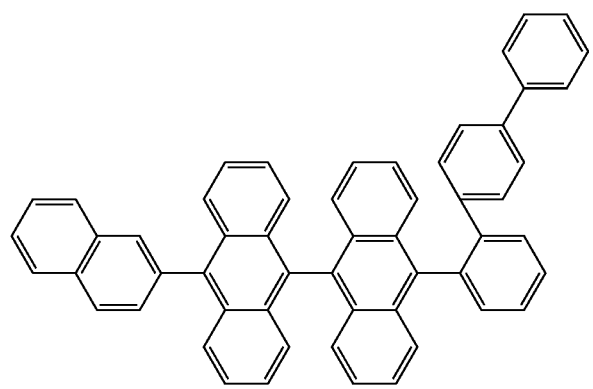

-continued

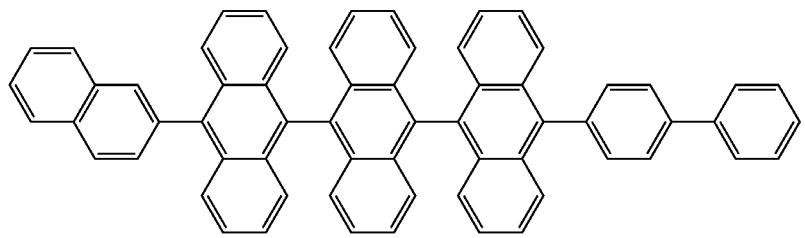

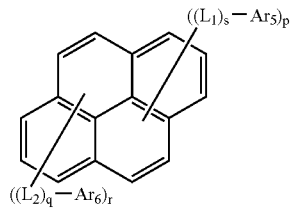

In the general formula (5), $Ar_5$ and $Ar_6$ each represents a substituted or unsubstituted aryl group having 6 to 50 ring carbon atoms;

$L_1$ and $L_2$ each independently represents a substituted or unsubstituted phenylene group, a substituted or unsubstituted naphthalenylene group, a substituted or unsubstituted fluorenylene group or a substituted or unsubstituted dibenzosilolylene group;

s represents an integer of 0 to 2, p represents an integer of 1 to 4, q represents an integer of 0 to 2 and r represents an integer of 0 to 4; and $L_1$ or $Ar_5$ bonds to any one of 1 to 5 position of pyrene, also $L_2$ or $Ar_6$ bonds to any one of 6 to 10 position thereof, however, when p+r is an even number, $Ar_5$, $Ar_6$, $L_1$ and $L_2$ satisfy a following requirement (1) or a requirement (2):

(1) $Ar_5 \ne Ar_6$ and/or $L_1 \ne L_2$ (wherein ≠means that each group has a different structure)

(2) when $Ar_5 = Ar_6$ and $L_1 = L_2$ (2-1) s≠q and/or p≠r, or (2-2) when s=q, and p=r, (2-2-1) both $L_1$ and $L_2$ or pyrene each bond respectively to different positions of $Ar_5$ and $Ar_6$, or (2-2-2) both $L_1$ and $L_2$ or pyrene each bonds respectively to the same position of $Ar_5$ and $Ar_6$, excluding a case where both $L_1$ and $L_2$ or both $Ar_5$ and $Ar_6$ bond to 1 and 6 positions thereof, or 2 and 7 positions thereof.

Specific examples and substituents of the $Ar_5$, $Ar_6$, $L_1$ and $L_2$ are the same as those explained about the foregoing general formula (1).

Specific examples of the pyrene derivative represented by the general formula (5) will be illustrated below, though not particularly limited thereto.

P1

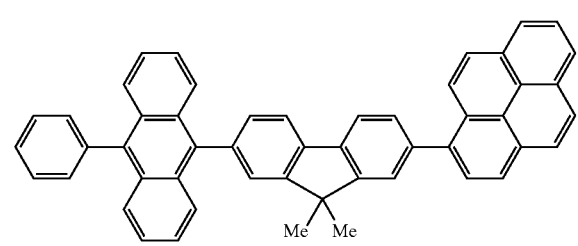

AN48

(5)

-continued

P2

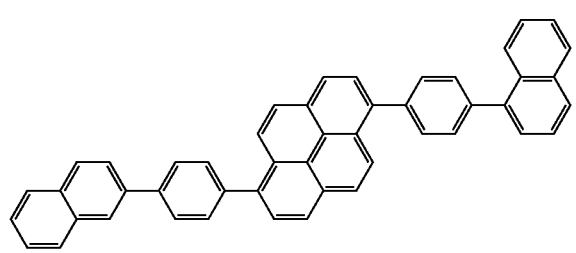

P3

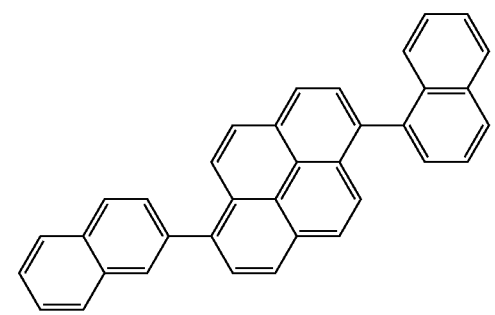

P4

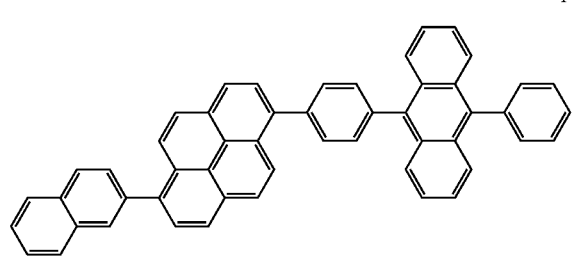

P5

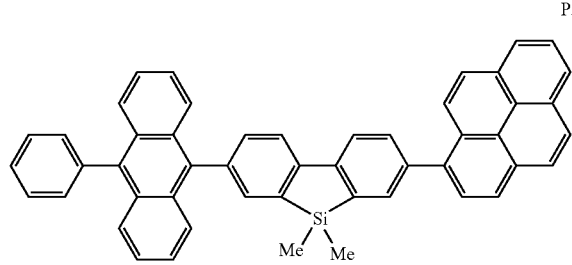

-continued
P6
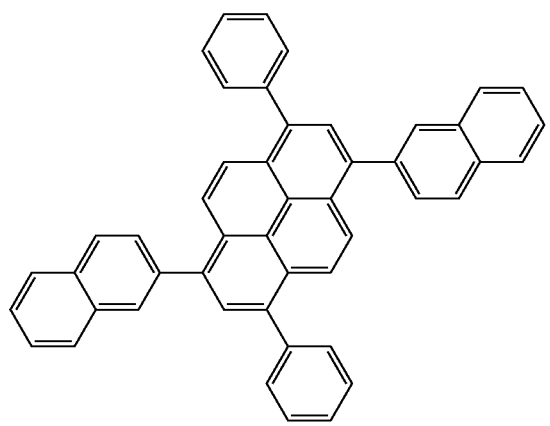
P7
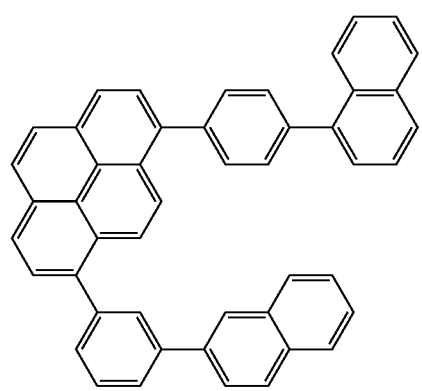
P8
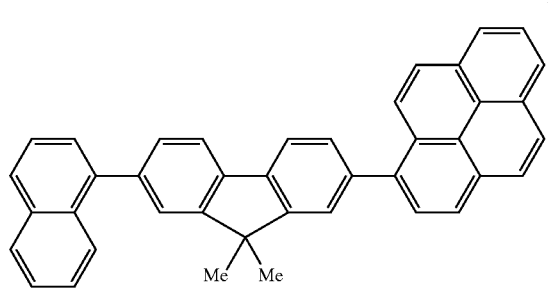
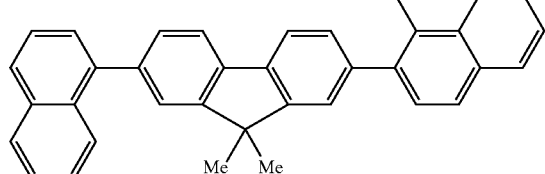
P9
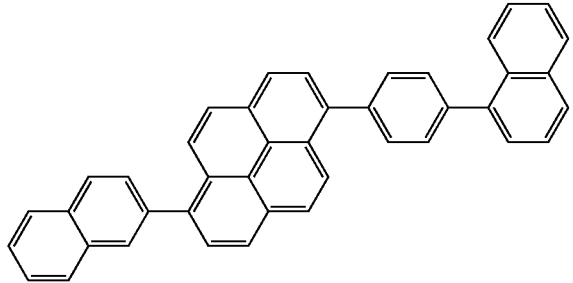
-continued
P10
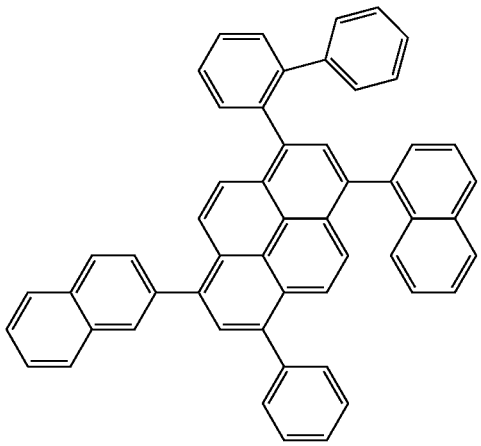
P11
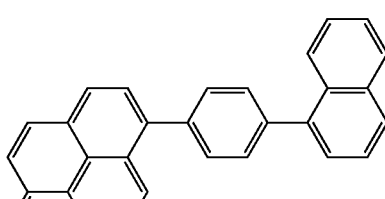
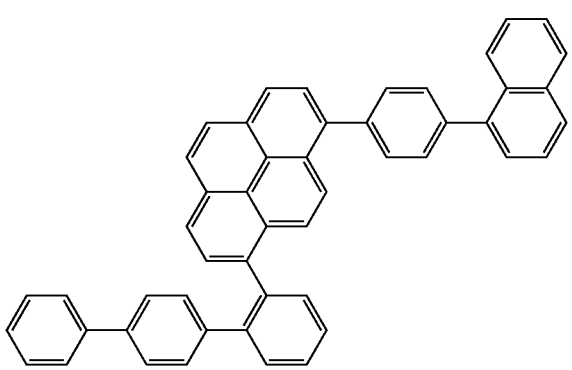
P12
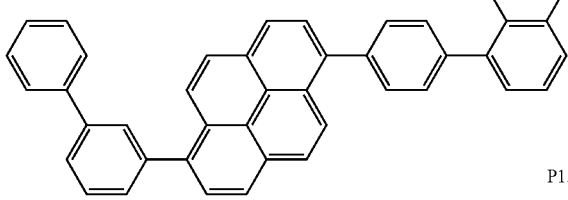
P13
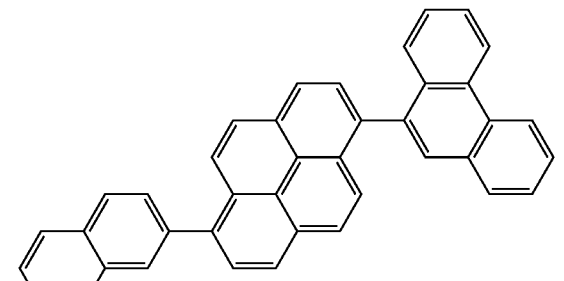
P14
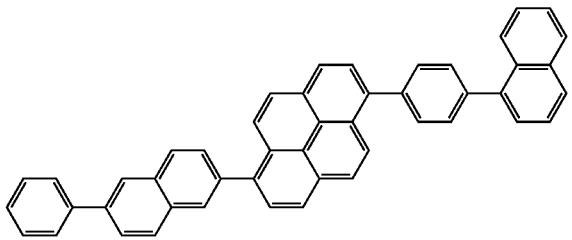

-continued

P15
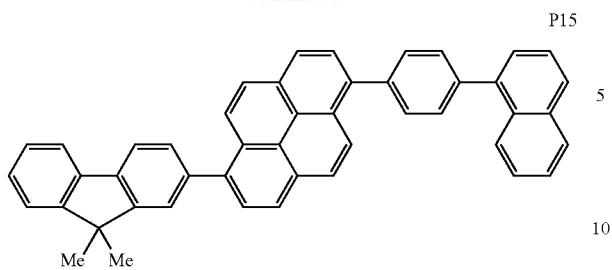

P16
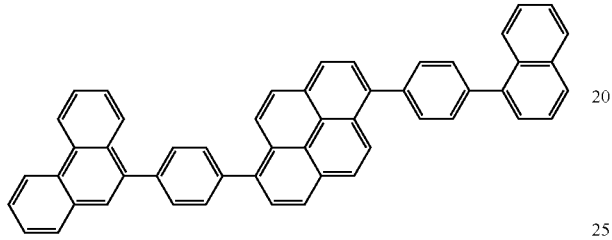

P17
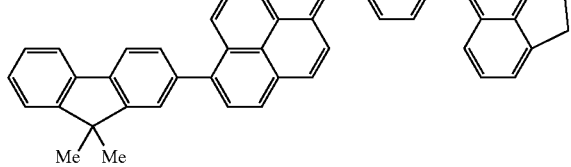

P18
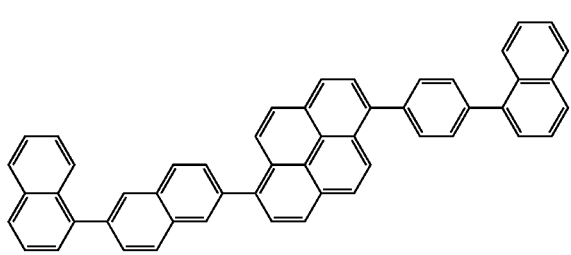

P19
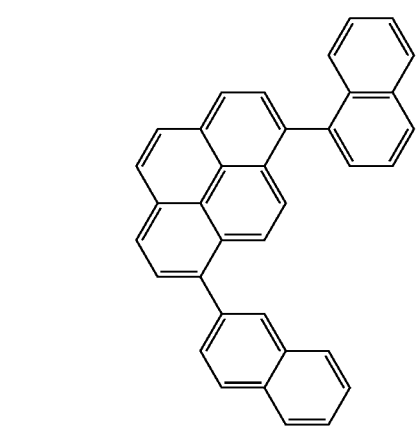

-continued

P20
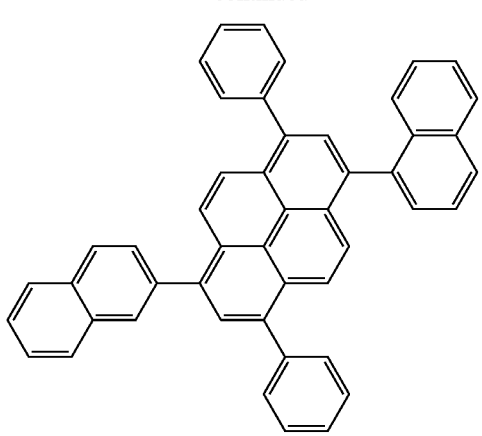

P21
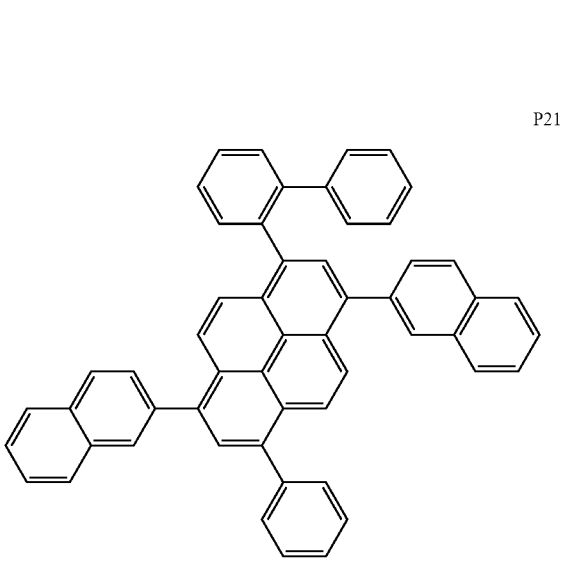

Examples of the organic EL device of a multilayer type include those having multilayer structures such as (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

The multilayers may also optionally contain, in addition to the aromatic amine derivatives of the present invention, conventionally known materials such as light emitting materials, doping materials, hole injecting materials and electron injecting materials according to requirements. The organic EL device having such a multilayer structure can be prevented from suffering from deterioration in luminance and lifetime due to quenching. If required, the light emitting materials, doping materials, hole injecting materials and electron injecting materials may be used in combination with each other. The use of the doping materials enables the resultant device to be improved in luminance of light emission and efficiency of light emission, and further emit a red color light or a blue color light. Further, in the organic EL device of the present invention, the hole injecting layer, the light emitting layer and the electron injecting layer may respectively have a multilayer structure including two or more layers. In these cases, a layer injecting holes from the electrode is called as a hole injecting layer, and a layer for accepting the holes from the hole injecting layer and transporting the holes to the light emitting layer is called as a hole transporting layer. Also, a layer injecting electrons the electrode is called as an electron injecting layer, and a layer transporting for accepting the electrons from the electron injecting layer and transporting the electrons to the light emitting layer is called as an electron transporting layer. Those respective layers may be selectively used according to various factors such as energy level of the materials used, heat resistance, and adhesion to the organic thin film layers or the metal electrodes.

Examples of the host material or the doping material besides the foregoing general formulae (3) to (5) employable for the light emitting layer together with the aromatic amine derivative of the present invention include condensed mass aromatic compound such as naphthalene, phenanthrene, rubrene, anthracene, tetracene, pyrene, perylene, chrysene, decacyclene, coronene, tetraphenylcyclopentadiene, pentaphenyl cyclopentadiene, fluorene, spiro fluorene, 9,10-diphenylanthracene, 9,10-bis(phenyl-ethynyl)anthracene, 1,4-bis(9'-ethynyl anthracenyl)benzene and those derivatives; organometallic complex such as tris(8-quinolinolat) aluminium, bis-(2-methyl-8-quinolinolat)-4-(phenylphenolinat)aluminum, etc.; triarylamine derivative, styryl amine derivative, stilbene derivative, coumarine derivative, pyran derivative, oxazone derivative, benzothiazole derivative, benzoxazole derivative, benzimidazole derivative, pyrazine derivative, cinnamate ester derivative, diketo pyrrolopyrrole derivative, acridone derivative, quinacridon derivative, etc.; though not particularly limited thereto.

The hole injecting material is preferably made of compounds which have a good hole transporting capability as well as excellent capabilities of accepting holes injected from the anode and injecting the holes into the light emitting layer or light emitting material, prevent excited particles produced in the light emitting layer from moving into the electron injecting layer or electron injecting material, and exhibit an excellent capability of forming a thin film. Specific examples of the hole injecting material include phthalocyanine derivatives, naphthalocyanine derivatives, porphyrin derivatives, oxazole, oxadiazole, triazole, imidazole, imidazolone, imidazole thione, pyrazoline, pyrazolone, tetrahydroimidazole, hydrazone, acyl hydrazone, polyaryl alkanes, stilbene, butadiene, benzidine-type triphenyl amine, styryl amine-type triphenyl amine, diamine-type triphenyl amine and derivatives thereof, as well as polyvinyl carbazoles, polysilanes, and high molecular materials such as electro-conductive polymers, though not particularly limited thereto.

Among those hole injecting materials usable in the organic EL device of the present invention, more effective hole injecting materials are aromatic tertiary amine derivatives and phthalocyanine derivatives.

Specific examples of the aromatic tertiary amine derivatives include triphenyl amine, tritolyl amine, tolyldiphenyl amine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cylcohexane, and oligomers and polymers having these aromatic tertiary amine skeletons, though not particularly limited thereto.

Specific examples of the phthalocyanine (Pc) derivatives include phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O—GaPc, as well as naphthalocyanine derivatives, though not particularly limited thereto.

Also, in the organic EL device of the present invention, between the light emitting layer and the anode, there is preferably formed a layer such as the above hole transporting layer or hole injecting layer containing those aromatic tertiary amine derivatives and/or phthalocyanine derivatives,.

The electron injecting material is preferably made of compounds which have a good electron transporting capability as well as excellent capabilities of accepting electrons injected from the cathode and injecting the electrons into the light emitting layer or light emitting material, prevent excited particles produced in the light emitting layer from moving into the hole injecting layer, and exhibit an excellent capability of forming a thin film. Specific examples of the electron injecting material include fluorenone, anthraquinodimethane, diphenoquinone, thiopyrane dioxide, oxazole, oxadiazole, triazole, imidazole, perylenetetracarboxylic acid, fluorenylidene methane, anthrone, and derivatives thereof, though not particularly limited thereto. Further, an electron accepting substance and an electron donating substance may be added to the hole injecting material and the electron injecting material, respectively, for enhanced sensitization thereof.

In the organic EL device of the present invention, among these electron injecting materials, more effective electron injecting materials are metal complex compounds and five-member ring derivatives having a nitrogen atom.

Specific examples of the metal complex compounds include 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium, though not particularly limited thereto.

The five-member ring derivatives having a nitrogen atom are preferably derivatives of oxazole, thiazole, oxadiazole, thiadiazole or triazole. Specific examples of the nitrogen-containing five-member ring derivatives include 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazolyl)]benzene, though not particularly limited thereto.

In the organic EL device of the present invention, the light emitting layer may also optionally contain, in addition to the aromatic amine derivatives represented by the general formula (1), at least one material selected from the group consisting of light emitting materials, doping materials, hole injecting materials and electron injecting materials. The organic EL device of the present invention may be further provided with a protective layer on a surface thereof, or the whole part thereof may be protected with silicone oil, resins, etc., in order to enhance stability thereof against temperature, humidity, atmosphere, etc.

The anode of the organic EL device according to the present invention may be suitably made of an electro-conductive material having a work function more than 4 eV. Examples of the electro-conductive material for the anode include carbon, aluminum, vanadium, iron, cobalt, nickel, tungsten, silver, gold, platinum, palladium and alloys thereof, metal oxides such as tin oxide and indium oxide which are used for ITO substrates or NESA substrates, and organic electro-conductive resins such as polythiophene and polypyrrole. The cathode of the organic EL device according to the present invention may be suitably made of an electro-conductive material having a work function of 4 eV or less. Examples of the electro-conductive material for the cathode include magnesium, calcium, tin, lead, titanium, yttrium, lithium, ruthenium, manganese, aluminum, lithium fluoride and alloys thereof, though not particularly limited thereto. Typical examples of the alloys include alloys of magnesium and silver, alloys of magnesium and indium, and alloys of lithium and aluminum, though not particularly limited thereto. The ratio between the constituting metals in the alloys may be controlled and appropriately determined depending upon temperature of vapor deposition sources, atmosphere, vacuum degree, etc. The anode and cathode may be constituted of two or more layers, if required.

At least one surface of the organic EL device of the present invention preferably exhibits a sufficient transparency in a wavelength range of light emitted therefrom in order to enhance an efficiency of light emission thereof. Further, the substrate for the device is also preferably transparent. The transparent electrode is formed using the above electro-conductive material by vapor deposition method, sputtering method, etc., so as to ensure a desirable transparency thereof. The electrode disposed on a light emitting surface of the device preferably has a light transmittance of 10% or greater. The substrate is not particularly limited as long as it suitably has a good mechanical and thermal strength as well as a good transparency. Examples of the substrate include glass substrates and transparent resin films. Specific examples of the transparent resin films include films made of polyethylene, ethylene-vinyl acetate copolymer, ethylene-vinyl alcohol copolymer, polypropylene, polystyrene, polymethyl methacrylate, polyvinyl chloride, polyvinyl alcohol, polyvinyl butyral, nylons, polyether ether ketones, polysulfones, polyether sulfones, tetrafluoroethylene-perfluoroalkylvinyl ether copolymer, polyvinyl fluoride, tetrafluoroethylene-ethylene copolymer, tetrafluororethylene-hexafluoropropylene copolymer, polychlorotrifluoroethylene, polyvinylidene fluoride, polyesters, polycarbonates, polyurethanes, polyimides, polyether imides and polypropylene.

The respective layers of the organic EL device of the present invention may be formed by either a dry film-forming process such as vacuum deposition, sputtering, plasma and ion-plating, or a wet film-forming process such as spin-coating, dipping and flow-coating. The thickness of the respective layers is not particularly limited, but should be adjusted to an appropriate range. When the thickness is too large, a large electric voltage must be applied to the device in order to achieve a predetermined light output, resulting in a poor efficiency of light emission. On the other hand, when the thickness is too small, pinholes tend to be formed in the layers, thereby failing to obtain a sufficient luminance of light emission even upon applying an electric field thereto. The suitable thickness of the respective layers is usually in the range of from 5 nm to 10 μm and preferably from 10 nm to 0.2 μm.

In the wet film-forming process, materials constituting the respective layers are dissolved or dispersed in a suitable solvent such as ethanol, chloroform, tetrahydrofuran and dioxane to form a thin film thereof. The solvent used for forming the respective layers is not particularly limited. Also, suitable resins or additives may be added to the respective organic thin film layers for the purposes of improving a film-forming property, preventing formation of pinholes in the resultant film, etc. Examples of the resins usable for the above purposes include insulating resins such as polystyrene, polycarbonates, polyarylates, polyesters, polyamides, polyurethanes, polysulfones, polymethyl methacrylate, polymethyl acrylate and celluloses as well as copolymers thereof, photoconductive resins such as poly-N-vinyl carbazole and polysilanes, and electro-conductive resins such as polythiophene and polypyrrole. Examples of the additives include antioxidants, ultraviolet absorbers and plasticizers.

The organic EL device of the present invention is suitably applied to, for example, planar light-emitting members such as a wall-hanging type television flat panel displays or so, light sources for copiers, printers, back light for liquid crystal displays and, measuring instruments, display panels, marker light, etc. Further, the material of the present invention can be used not only for organic EL devices but also in other applications such as electronic photographic members, photoelectric converter elements, solar cells, image sensors, etc.

EXAMPLE

The present invention will be described in more detail by reference to the following examples.

Synthesis Example 1

Synthesis of Chemical Compound (4)

(1-1) Synthesis of 2-bromo-6-methylnaphthalene

Under an atmospheric argon gas flow, trifluoromethane sulfonic acid-6-bromo-2-naphthyl ester in an amount of 32 g (90 mmol), dichloro(diphenylphosphinoferrocene)palladium in an amount of 3.6 g (5% by mol), lithium bromide in an amount of 7.8 g (90 mmol) and desiccated tetrahydrofuran in an amount of 100 milliliter were placed into a three neck flask with cooling pipe and having a capacity of 500 milliliter, and then, the resultant solution was cooled down to −20° C. After slowly dripping methylmagnesiumbromide in an amount of 90 milliliter (90 mmol, 1 mol/liter (tetrahydrofuran)) into the flask, the resultant solution was stirred under heating at the temperature of 80° C. for 4 hours. After the reaction terminated, adding dilute hydrochloric acid in an amount of 100 milliliter into the reacted solution, an organic layer was separated and washed with the use of sodium bicarbonate solution and sodium chloride solution, followed by drying with the use of magnesium sulfate. After removing the solvent by distillation by means of a rotary evaporator, the resultant crude product was refined by means of column chromatography (silicagel, hexane/dichloromethane=90/10), and as a result, 9.4 g of aimed compound (white crystal) was obtained (yield: 47%).

(1-2) Synthesis of 2-(6-methyl-2-naphthyl)benzaldehyde

Under an atmospheric argon gas flow, 2-bromo-6-methylnaphthalene in an amount of 6.6 g (30 mmol), 2-formylphenylboronic acid in an amount of 5.4 g (36 mmol), (tetrakistriphenylphosphine)palladium in an amount of 0.7 g (0.6 mmol), 2N sodium carbonate aqueous solution in an amount of 45 milliliter and dimethoxyethane in an amount of 90 milliliter were placed into a three neck flask with a cooling pipe and having a capacity of 500 milliliter, and the resultant solution was refluxed under heating for 8 hours. After the reaction terminated, adding water in an amount of 100 milliliter into the reacted solution, an organic layer was separated and washed with the use of sodium chloride solution, followed by drying with the use of magnesium sulfate. After removing the solvent by distillation by means of a rotary evaporator, the resultant crude product was refined by means of column chromatography (silicagel, hexane/dichloromethane=60/40), and as a result, 6.7 g of aimed compound (white crystal) was obtained (yield: 91%).

(1-3) Synthesis of 2-((2-methoxyvinyl)phenyl)-6-methylnaphthalene

Under an atmospheric argon gas flow, 2-(6-methyl-2-naphthyl)benzaldehyde in an amount of 13.7 g (55 mmol), (methoxymethyl)triphenylphosphoniumchloride in an amount of 21 g (61 mmol), t butoxy potassium in an amount of 7.5 g (67 mmol) and desiccated tetrahydrofuran in an amount of 250 milliliter were placed into a three neck flask with a cooling pipe and having a capacity of 500 milliliter, and the resultant solution was stirred at the room temperature for a night. After the reaction terminated, adding water in an amount of 100 milliliter into the reacted solution, an organic layer was separated, followed by drying with the use of magnesium sulfate. After removing the solvent by distillation by means of a rotary evaporator, the resultant crude product was refined by means of column chromatography (silicagel, hexane/dichloromethane=10/90), and as a result, 12.8 g of aimed compound (white crystal) was obtained (yield: 84%).

(1-4) Synthesis of 2-methylchrysene

Under an atmospheric argon gas flow, 2-((2-methoxyvinyl)phenyl)-6-methylnaphthalene in an amount of 12.8 g (46 mmol), several drops of methyl acid, and desiccated dichloromethane in an amount of 100 milliliter were placed into a three necked-flask equipped with a cooling pipe and having a capacity of 500 milliliter, and the resultant solution was stirred at the room temperature for 8 hours. After the reaction terminated, adding sodium bicarbonate solution in an amount of 100 milliliter into the reacted solution, crystals were separated by filtration. The resultant crude product was washed with the use of water and methanol, and then, it was vacuum dried at the temperature of 50° C. for 8 hours, and as a result, 8.2 g of aimed compound (white crystal) was obtained (yield: 73%).

(1-5) Synthesis of 2-methyl-6,12-dibromochrysene

Under an atmospheric argon gas flow, 2-methylchrysene in an amount of 8.2 g (34 mmol), N-bromosuccinimide in an amount of 14.5 g (81 mmol) and N,N-dimethylformamide in an amount of 400 milliliter were placed into a three neck flask with a cooling pipe and having a capacity of 1 liter, and the resultant solution was stirred at the room temperature for one night. After the reaction terminated, adding water in an amount of 300 milliliter into the reacted solution, crystals were separated by filtration. The resultant crude product was washed with the use of water and methanol, and then, it was re-crystallized in 100 milliliter of toluene, and as a result, 8.8 g of aimed compound (white crystal) was obtained (yield: 65%).

(1-6) Synthesis of Chemical Compound (4)

Under an atmospheric argon gas flow, 2-methyl-6,12-dibromochrysene in an amount of 4.0 g (10 mmol), bis(3,4-dimethylphenyl)amine in an amount of 5.6 g (25 mmol), palladium acetate in an amount of 0.03 g (1.5% by mol), tri-t-butylphosphine 0.06 g (3% by mol), t-butoxy sodium in an amount of 2.4 g (25 mmol) and desiccated toluene in an amount of 100 milliliter were placed into a three-necked flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 5.8 g of pale yellow powders were obtained. The pale yellow powders were identified as Compound (4) from the result in accordance with Field Desorption Mass Spectrum (FD-MS) measurement (yield: 85%).

Measurement by means of DRX-500 (Trade name; produced by Brucker Optics Inc.) was carried out using dimethylene chloride as a solvent and a result of $^1$H-NMR spectrum about the resultant Compound (4) is shown in FIG. 1. Further, the maximum absorption wavelength and the maximum fluorescence wavelength of Compound (4) among the toluene solvent were 400 nm and 456 nm respectively.

Synthesis Example 2

Synthesis of Compound (9)

(2-1) Synthesis of 2-isopropyl-6,12-dibromochrysene

An aimed compound was obtained in a similar manner as Synthesis Example 1 from the step (1-1) to the step (1-5) except that isopropylmagnesium bromide was employed instead of methylmagnesium bromide in the step (1-1).

(2-2) Synthesis of Compound (9)

Under an atmospheric argon gas flow, 2-isopropyl-6,12-dibromochrysene in an amount of 4.2 g (10 mmol), 4-isopropylphenyl-p-tolyl amine in an amount of 5.6 g (25 mmol), palladium acetate in an amount of 0.03 g (1.5% by mol), tri-t-butylphosphine 0.06 g (3% by mol), t-butoxy sodium in an amount of 2.4 g (25 mmol) and desiccated toluene in an amount of 100 milliliter were placed into a three-necked flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 6.4 g of pale yellow powders were obtained. The obtained product was identified to be Compound (9) in accordance with FD-MS measurement (yield: 90%).

Figure 2:
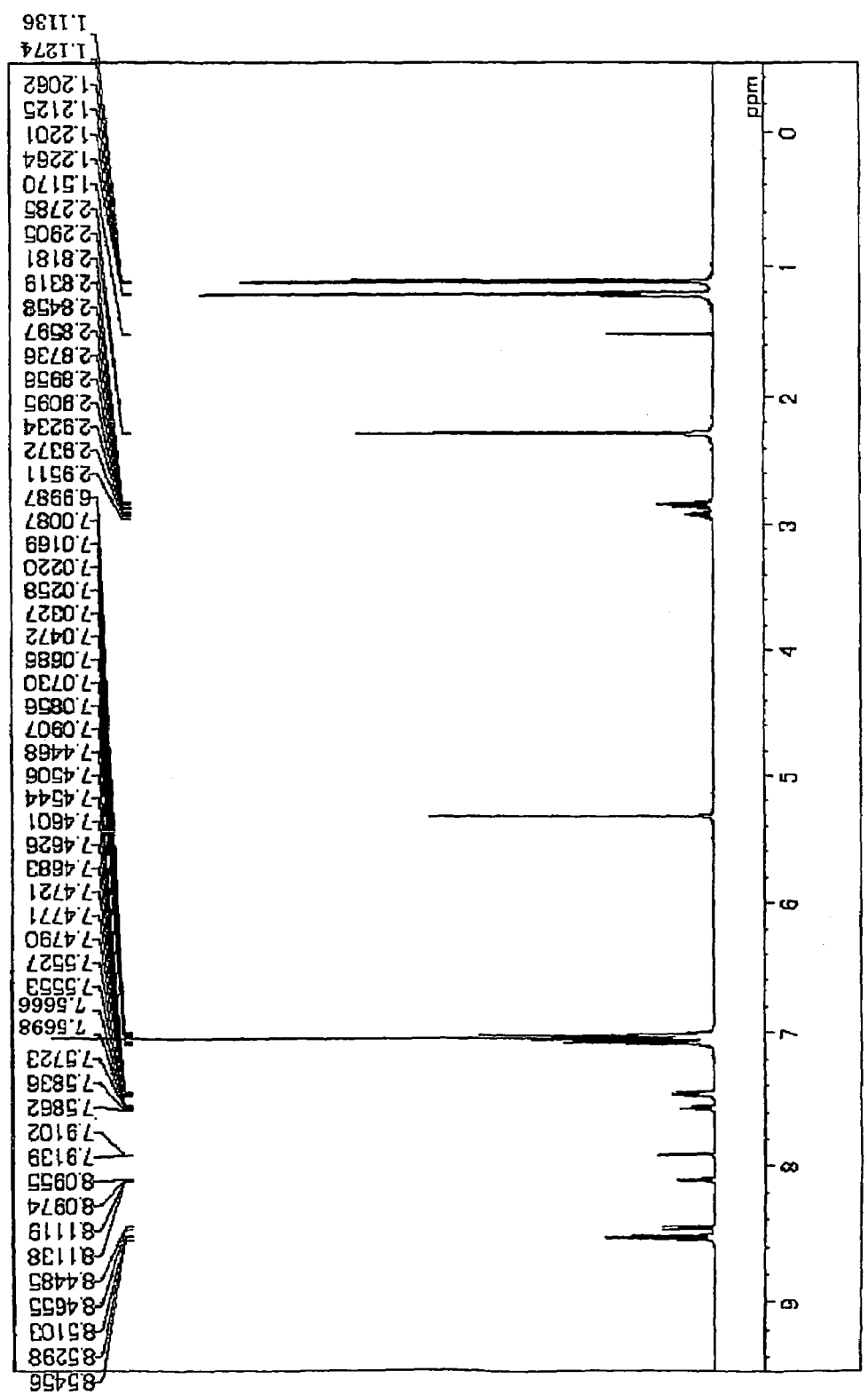
FIG. 2 is a chart showing a result of $^1$H-NMR measurement about Compound (9) obtained in Synthesis Example 2.

Measurement by means of DRX-500 (Trade name; produced by Brucker Optics Inc.) was carried out using dimethylene chloride as a solvent and a result of $^1$H-NMR spectrum about the resultant Compound (9) is shown in FIG. 2. Further, the maximum absorption wavelength and the maximum fluorescence wavelength of Compound (9) among the toluene solvent were 407 nm and 453 nm respectively.

Synthesis Example 3

Synthesis of Chemical Compound (20)

(3-1) Synthesis of 2-bromo-6-isopropylnaphthalene

Under an atmospheric argon gas flow, trifluoromethane sulfonic acid-6-bromo-2-naphthyl ester in an amount of 32 g (90 mmol), dichloro(diphenylphosphinoferrocene)palladium in an amount of 3.6 g (5% by mol), lithium bromide in an amount of 7.8 g (90 mmol) and desiccated tetrahydrofuran in an amount of 100 milliliter were placed into three necked-flask equipped with cooling pipe and having a capacity of 500 milliliter, and then, the resultant solution was cooled down to −20° C. After slowly dripping isopropylmagnesiumbromide in an amount of 90 milliliter (90 mmol, 1 mol/liter (tetrahydrofuran)) into the flask, the resultant solution was stirred under heating at the temperature of 80° C. for 4 hours. After the reaction terminated, adding dilute hydrochloric acid in an amount of 100 milliliter into the reacted solution, an organic layer was separated and washed with the use of sodium bicarbonate solution and sodium chloride solution, followed by drying with the use of magnesium sulfate. After removing the solvent by distillation by means of a rotary evaporator, the resultant crude product was refined by means of column chromatography (silicagel, hexane/dichloromethane=90/10), and as a result, 9.4 g of aimed compound (white crystal) was obtained (yield: 33%).

(3-2) Synthesis of 6-isopropylnaphthalene-2-boronic acid

Under an atmospheric argon gas flow, 2-bromo-6-isopropylnaphthalene in an amount of 9.4 g (38 mmol), desiccated ether in an amount of 100 milliliter and desiccated toluen in an amount of 50 milliliter were placed into a three necked-flask equipped with cooling pipe and having a capacity of 500 milliliter, and then, the resultant solution was cooled down to −40° C. After slowly dripping n-butyllithium in an amount of 25 milliliter (40 mmol, 1.58M (n-hexane)) into the flask, the resultant solution was stirred at a temperature of −20° C. for 2 hours. Subsequently, the solution was cooled down to −40° C. and then, slowly dripping boronic acid triisopropylester in an amount of 26 milliliter (114 mmol), the resultant solution was stirred at the room temperature for one night. After the reaction terminated, adding dilute hydrochloric acid in an amount of 100 milliliter into the reacted solution, an organic layer was separated and washed with the use of sodium chloride solution, followed by drying with the use of magnesium sulfate. After removing the solvent by distillation by means of a rotary evaporator, the resultant crude product was washed with the use of 100 milliliter of toluene and as a result, 5.0 g of an aimed compound (white crystal) was obtained (yield: 63%).

(3-3) Synthesis of 5-isopropyl-2-(6-isopropyl-2-naphthyl)benzaldehyde

Under an atmospheric argon gas flow, 2-hydroxy-5-isopropylbenzaldehyde in an amount of 4.4 g (27 mmol), trifluoromethane sulfonic acid anhydride in an amount of 11.2 g (40 mmol), pyridine in an amount of 6 milliliter (80 mmol) and dichloromethane in an amount of 100 milliliter were placed into a three necked-flask equipped with a cooling pipe and having a capacity of 500 milliliter, and the resultant solution was stirred at the room temperature for 2 hours. After the reaction terminated, the resultant was separated by filtration, and after washing the resultant crude product with the use of hexane and dichloromethane, the resultant solution was vacuum dried at a temperature of 50° C. for 8 hours and as a result, 6.0 g of 2-formyl-4-isopropylphenyltrifluoromethanesulfonate (white crystal) was obtained (yield: 75%). Subsequently, under an atmospheric argon gas flow, 2-formyl-4-isopropylphenyl trifluoromethanesulfonate in an amount of 5.9 g (20 mmol), 6-isopropylnaphthalene-2-boronic acid in an amount of 4.7 g (22 mmol), (tetrakistriphenylphosphine)palladium in an amount of 1.1 g (1 mmol), 2N sodium carbonate aqueous solution in an amount of 30 milliliter and dimethoxyethane in an amount of 40 milliliter were placed into a three necked-flask equipped with a cooling pipe and having a capacity of 500 milliliter, and the resultant solution was refluxed under heating for 8 hours. After the reaction terminated, adding water in an amount of 100 milliliter into the reacted solution, an organic layer was separated and washed with the use of sodium chloride solution, followed by drying with the use of magnesium sulfate. After removing the solvent by distillation by means of a rotary evaporator, the resultant crude product was refined by means of column chromatography (silicagel, hexane/dichloromethane=60/40), and as a result, 4.4 g of an aimed compound (white crystal) was obtained (yield: 70%).

(3-4) Synthesis of 2-isopropyl-6-(4-isopropyl-2-(2-methoxyvinyl)phenyl)naphthalene Under an atmospheric argon gas flow, 5-isopropyl-2-(6-isopropyl-2-naphthyl)benzaldehyde in an amount of 4.4 g (14 mmol), (methoxymethyl)triphenylphosphoniumchloride in an amount of 5.1 g (15 mmol), t-butoxypotassium in an amount of 1.7 g (15 mmol) and desiccated tetrahydrofuran in an amount of 100 milliliter were placed into a three-necked flask equipped with a cooling pipe and having a capacity of 500 milliliter, and the resultant solution was stirred under heating at the room temperature for one night. After the reaction terminated, adding water in an amount of 100 milliliter into the reacted solution, an organic layer was separated, followed by drying with the use of magnesium sulfate. After removing the solvent by distillation by means of a rotary evaporator, the resultant crude product was refined by means of column chromatography (silicagel, hexane/dichloromethane=10/90), and as a result, 4.3 g of an aimed compound (white crystal) was obtained (yield: 90%).

(3-5) Synthesis of 2,8-diisopropyl chrysene

Under an atmospheric argon gas flow, 2-isopropyl-6-(4-isopropyl-2-(2-methoxy vinyl)phenyl)naphthalene in an amount of 4.3 g (12 mmol), several drops of methyl acid, and desiccated dichloromethane in an amount of 50 milliliter were placed into a three necked-flask equipped with a cooling pipe and having a capacity of 300 milliliter, and the resultant solution was stirred at the room temperature for 8 hours. After the reaction terminated, adding sodium bicarbonate solution in an amount of 100 milliliter into the reacted solution, crystals were separated by filtration. The resultant crude product was washed with the use of water and methanol, and then, it was vacuum dried at the temperature of 50° C. for 8 hours, and as a result, 3.5 g of an aimed compound (white crystal) was obtained (yield: 90%).

(3-6) Synthesis of 2,8-diisopropyl-6,12-dibromochrysene

Under an atmospheric argon gas flow, 2,8-diisopropyl chrysene in an amount of 3.5 g (12 mmol), N-bromosuccinimide in an amount of 5.3 g (30 mmol) and N,N-dimethylformamide in an amount of 20 milliliter were placed into a three-neck flask equipped with a cooling pipe and having a capacity of 500 milliliter, and the resultant solution was stirred at the room temperature for one night. After the reaction terminated, adding water in an amount of 300 milliliter into the reacted solution, crystals were separated by filtration. The resultant crude product was washed with the use of water and methanol, and then, it was re-crystallized in 100 milliliter of toluene, and as a result, 4.7 g of an aimed compound (white crystal) was obtained (yield: 80%).

(3-7) Synthesis of Chemical Compound (20)

Under an atmospheric argon gas flow, 2,8-diisopropyl-6,12-dibromochrysene in an amount of 4.7 g (10 mmol), 4-isopropylphenyl-p-tolyl amine in an amount of 5.6 g (25 mmol), palladium acetate in an amount of 0.03 g (1.5% by mol), tri-t-butylphosphine 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 6.6 g of pale yellow powders were obtained. The obtained product was identified to be Compound (20) in accordance with FD-MS measurement (yield: 88%).

Figure 3:
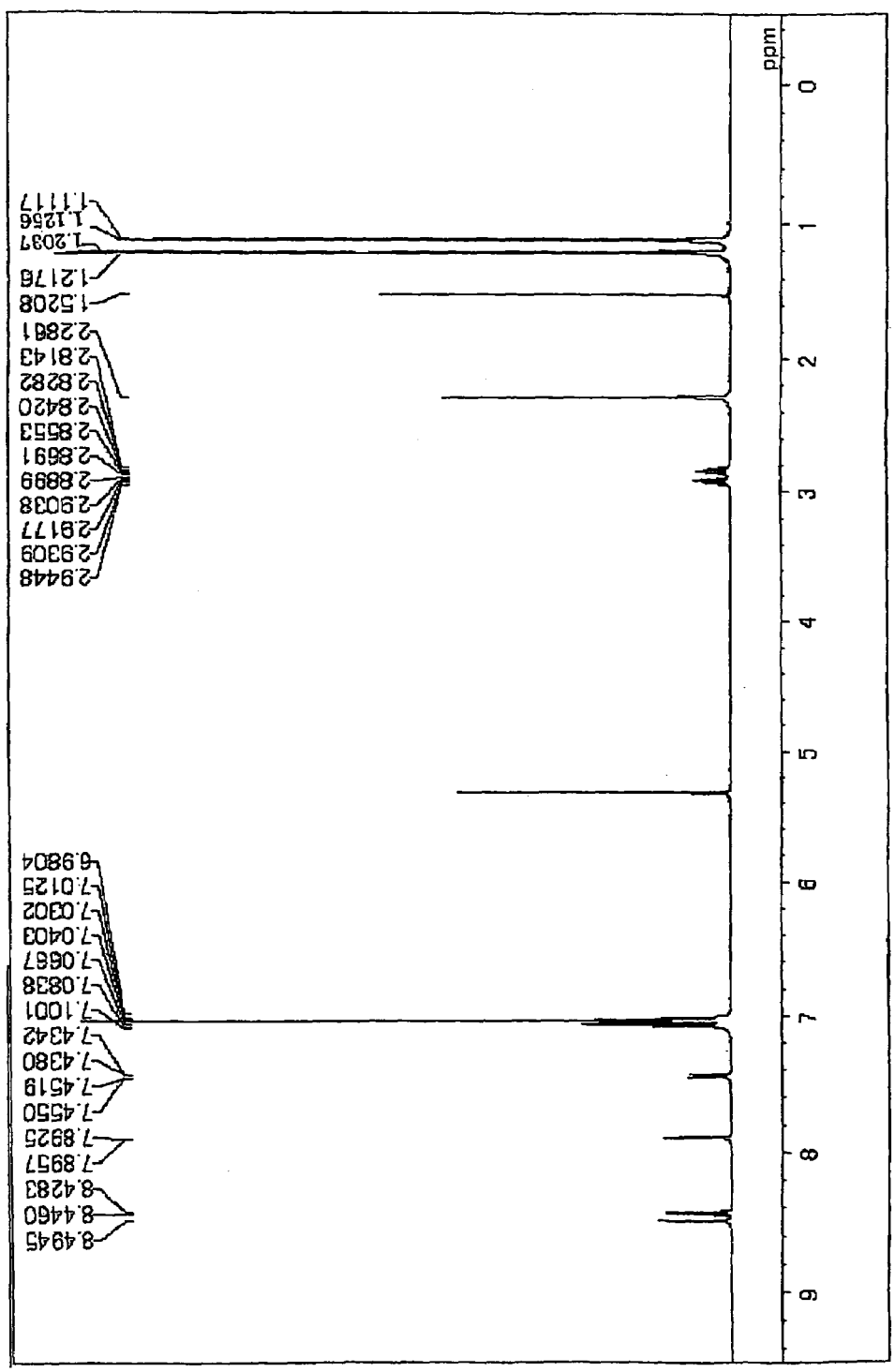
FIG. 3 is a chart showing a result of $^1$H-NMR measurement about Compound (20) obtained in Synthesis Example 3.

Measurement by means of DRX-500 (Trade name; produced by Brucker Optics Inc.) was carried out using dimethylene chloride as a solvent and a result of $^1$H-NMR spectrum about the resultant Compound (20) is shown in FIG. 3. Further, the maximum absorption wavelength and the maximum fluorescence wavelength of Compound (20) among the toluene solvent were 407 nm and 450 nm respectively.

Synthesis Example 4

Synthesis of Compound (23)

(4-1) Synthesis of 2-t-butyl-8-isopropyl-6,12-dibromochrysene

An aimed compound was obtained in a similar manner as Synthesis Example 3 from the step (3-1) to the step (3-6) except that 2-hydroxy-5-t-butyl benzaldehyde was employed instead of 2-hydroxy-5-isopropyl benzaldehyde in the step (3-3).

(4-2) Synthesis of Compound (23)

Under an atmospheric argon gas flow, 2-t-butyl-8-isopropyl-6,12-dibromo chrysene in an amount of 4.8 g (10 mmol), bis(3,4-dimethylphenyl)amine in an amount of 5.6 g (25 mmol), palladium acetate in an amount of 0.03 g (1.5% by mol), tri-t-butylphosphine 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluen and 100 milliliter of methanol, and as a result, 6.9 g of pale yellow powders were obtained. The obtained product was identified to be Compound (23) in accordance with FD-MS measurement (yield: 90%).

Figure 4:
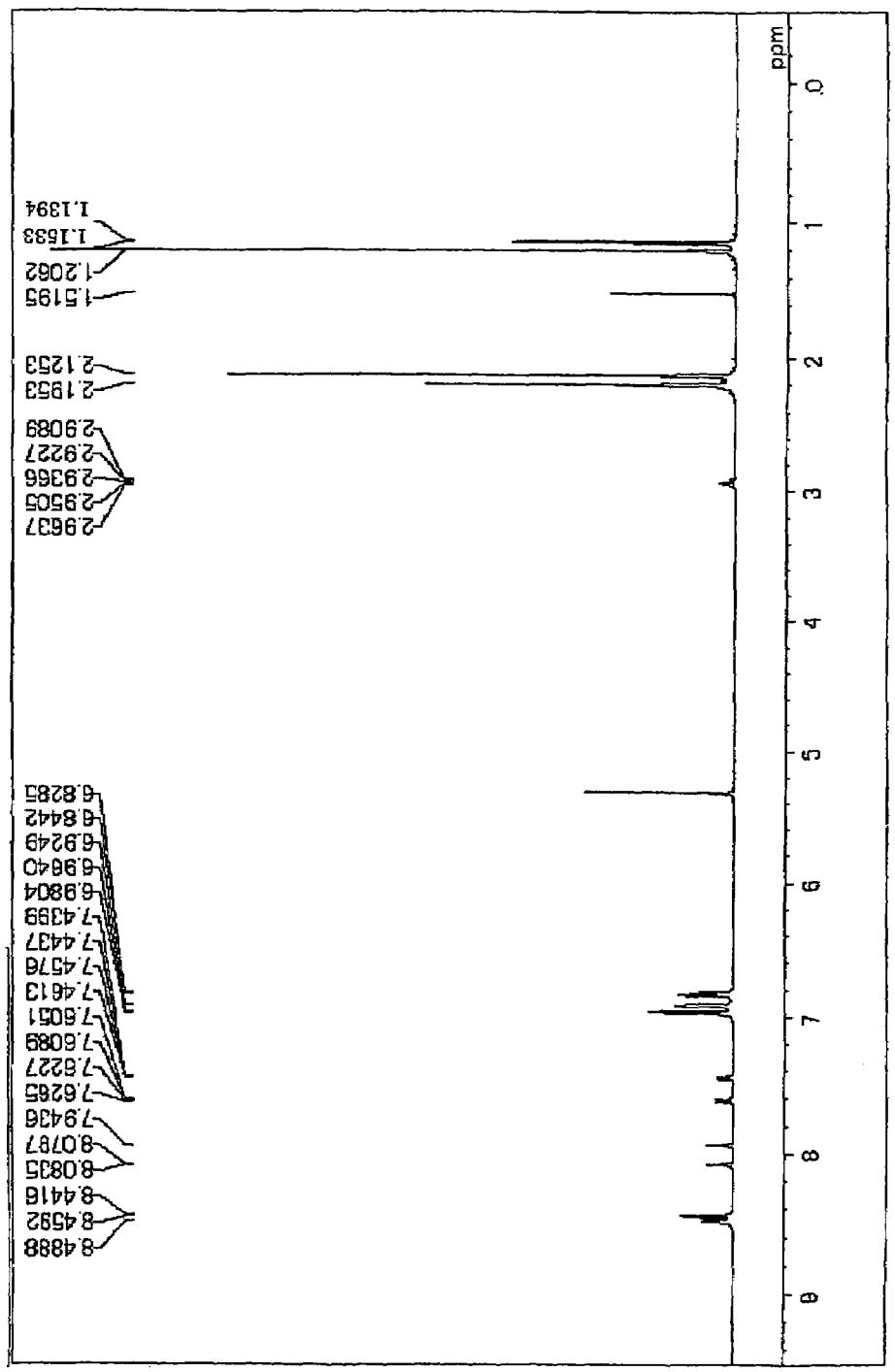
FIG. 4 is a chart showing a result of $^1$H-NMR measurement about Compound (23) obtained in Synthesis Example 4.

Measurement by means of DRX-500 (Trade name; produced by Brucker Optics Inc.) was carried out using dimethylene chloride as a solvent and a result of 1H-NMR spectrum about the resultant Compound (23) is shown in FIG. 4. Further, the maximum absorption wavelength and the maximum fluorescence wavelength of Compound (23) among the toluene solvent were 409 nm and 453 nm respectively.

Synthesis Example 5

Synthesis of Compound (25)

Under an atmospheric argon gas flow, 2-isopropyl-6,12-dibromo chrysene obtained in the step (2-1) in Synthesis Example 2 in an amount of 4.2 g (10 mmol), bis(3,4-dimethylphenyl)amine in an amount of 6.3 g (25 mmol), palladium acetate in an amount of 0.03 g (1.5% by mol), tri-t-butylphosphine in an amount of 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluen and 100 milliliter of methanol, and as a result, 6.8 g of pale yellow powders were obtained. The obtained product was identified to be Compound (25) in accordance with FD-MS measurement (yield: 88%).

Figure 5:
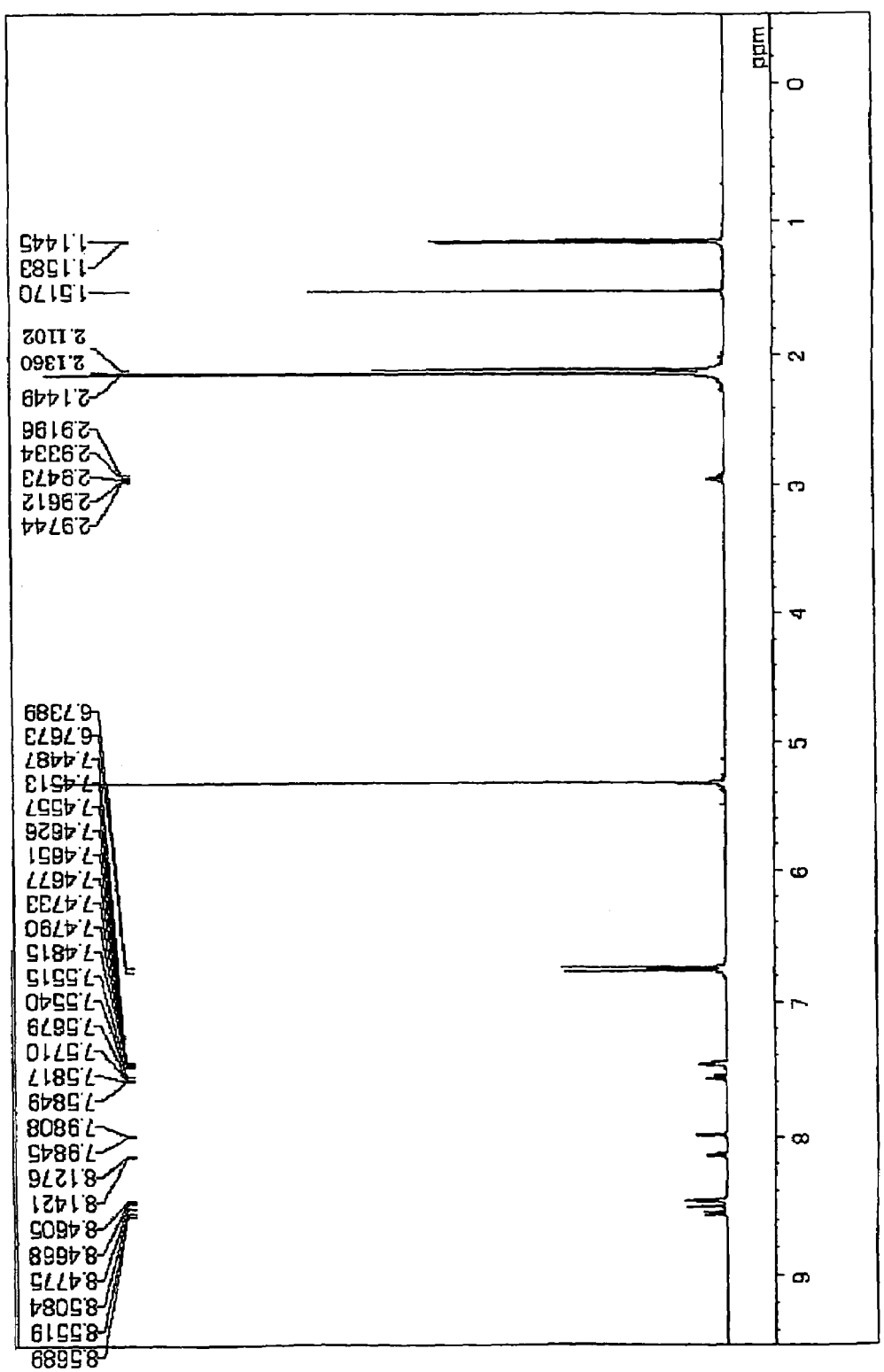
FIG. 5 is a chart showing a result of $^1$H-NMR measurement about Compound (25) obtained in Synthesis Example 5.

Measurement by means of DRX-500 (Trade name; produced by Brucker Optics Inc.) was carried out using dimethylene chloride as a solvent and a result of $^1$H-NMR spectrum about the resultant Compound (25) is shown in FIG. 5. Further, the maximum absorption wavelength and the maximum fluorescence wavelength of Compound (25) among the toluene solvent were 415 nm and 459 nm respectively.

Synthesis Example 6

Synthesis of Compound (39)

Under an atmospheric argon gas flow, 2-isopropyl-6,12-dibromo chrysene obtained in the step (2-1) in Synthesis Example 2 in an amount of 4.2 g (10 mmol), di(2-naphthyl)amine in an amount of 6.7 g (25 mmol), palladium acetate in an amount of 0.03 g (1.5% by mol), tri-t-butylphosphine in an amount of 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 6.8 g of pale yellow powders were obtained. The obtained product was identified to be Compound (39) in accordance with FD-MS measurement (yield: 85%).

Figure 6:
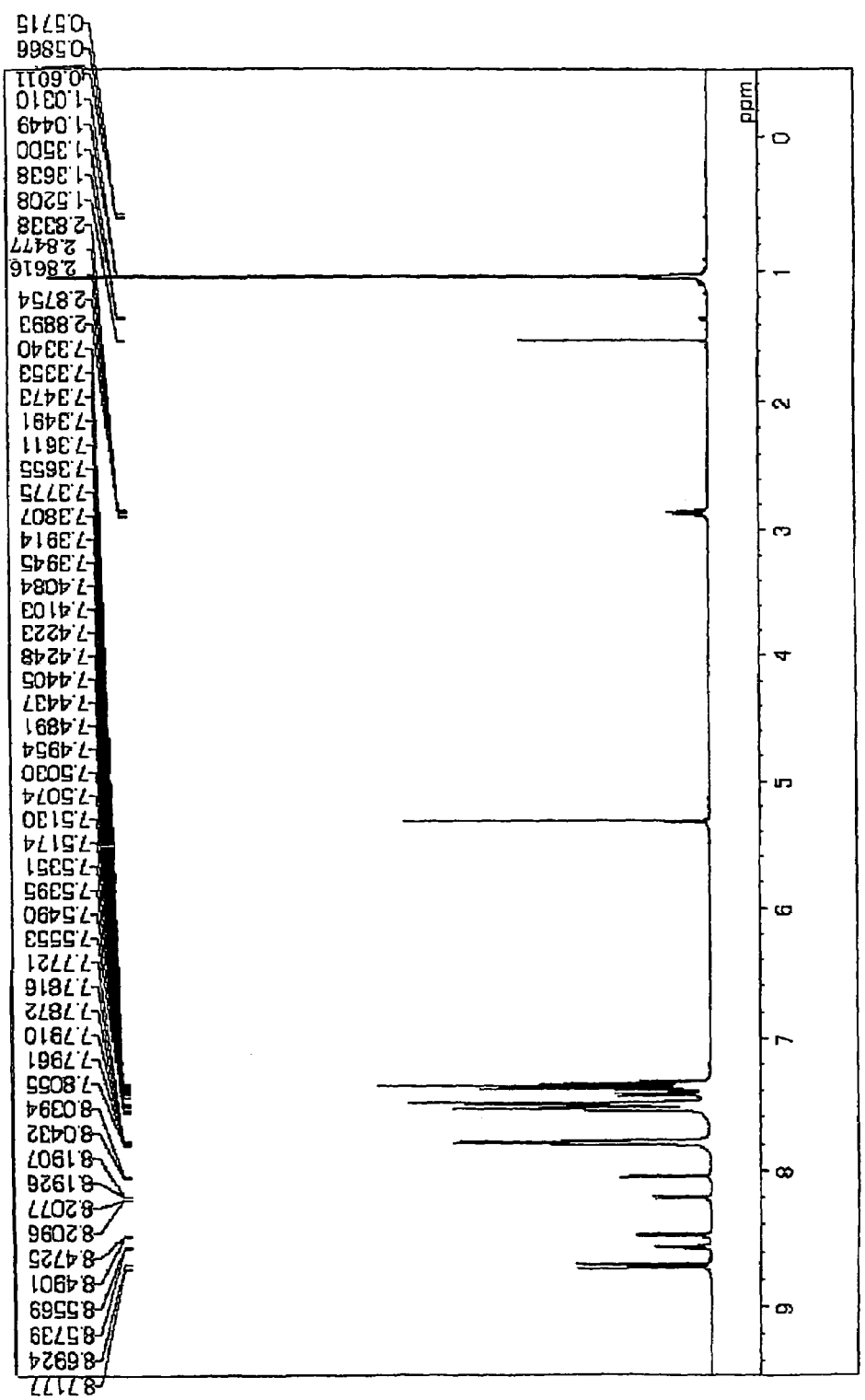
FIG. 6 is a chart showing a result of $^1$H-NMR measurement about Compound (39) obtained in Synthesis Example 6.

Measurement by means of DRX-500 (Trade name; produced by Brucker Optics Inc.) was carried out using dimethylene chloride as a solvent and a result of $^1$H-NMR spectrum about the resultant Compound (39) is shown in FIG. 6. Further, the maximum absorption wavelength and the maximum fluorescence wavelength of Compound (39) among the toluene solvent were 408 nm and 452 nm respectively.

Synthesis Example 7

Synthesis of Compound (57)

(7-1) Synthesis of 2-t-butyl-6,12-dibromochrysene

An aimed compound was obtained in a similar manner as Synthesis Example 1 from the step (1-1) to the step (1-5) except that t-butyl magnesium bromide was employed instead of methyl magnesium bromide in the step (1-1).

(7-2) Synthesis of Chemical Compound (57)

Under an atmospheric argon gas flow, 2-t-butyl-6,12-dibromochrysene in an amount of 4.4 g (10 mmol), bis(3,4-dimethylphenyl)amine in an amount of 5.6 g (25 mmol), palladium acetate in an amount of 0.03 g (1.5% by mol), tri-t-butylphosphine 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 6.5 g of pale yellow powders were obtained. The obtained product was identified to be Compound (57) in accordance with FD-MS measurement (yield: 90%).

Figure 7:
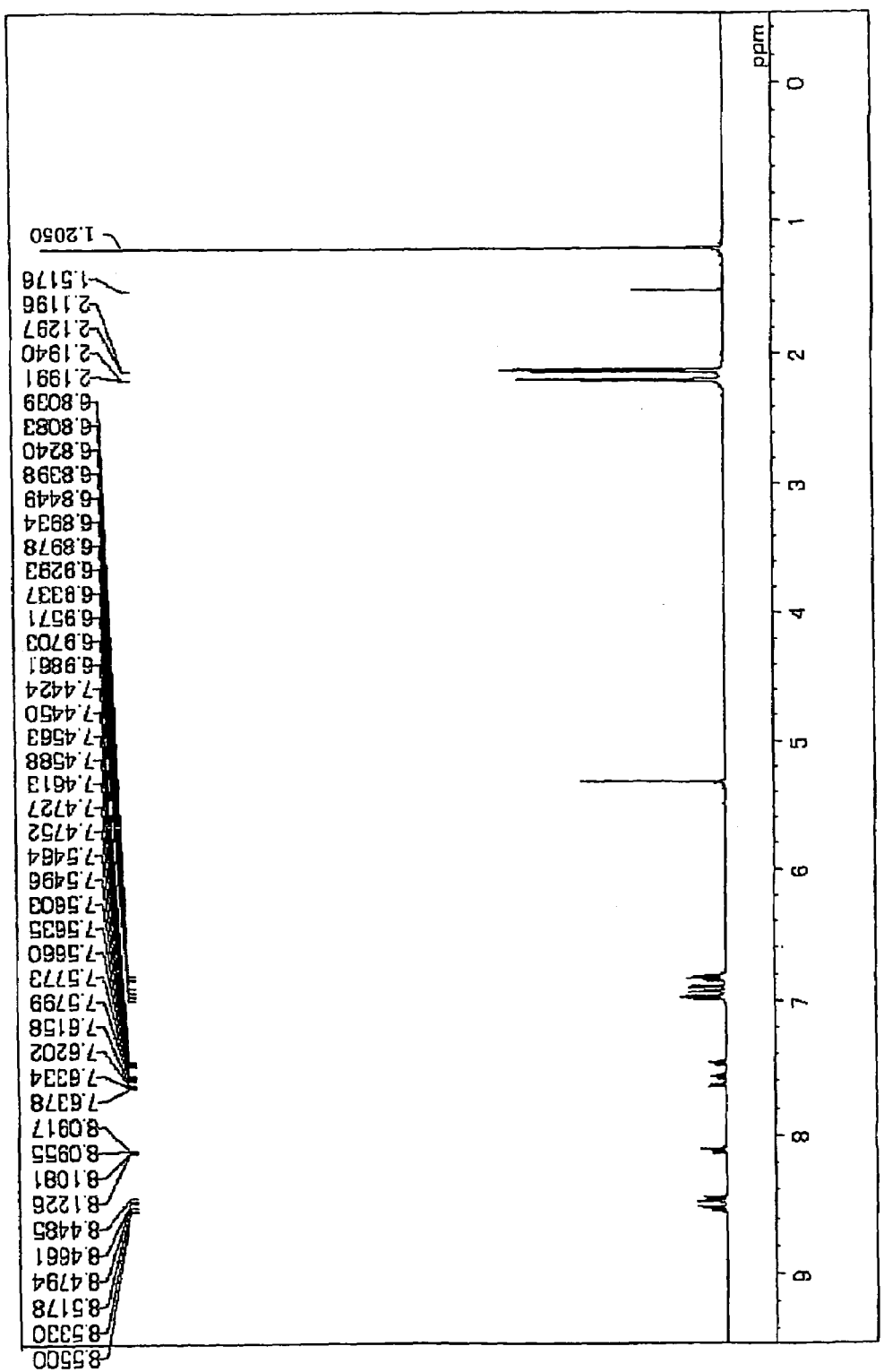
FIG. 7 is a chart showing a result of $^1$H-NMR measurement about Compound (57) obtained in Synthesis Example 7.

Measurement by means of DRX-500 (Trade name; produced by Brucker Optics Inc.) was carried out using dimethylene chloride as a solvent and a result of $^1$H-NMR spectrum about the resultant Compound (57) is shown in FIG. 7. Further, the maximum absorption wavelength and the maximum fluorescence wavelength of Compound (57) among the toluene solvent were 410 nm and 456 nm respectively.

Synthesis Example 8

Synthesis of Compound (95)

Under an atmospheric argon gas flow, 2-methyl-6,12-dibromochrysene obtained in the step (1-5) in Synthesis Example 1 in an amount of 4.0 g (10 mmol), di(4-cyclohexylphenyl)amine in an amount of 8.3 g (25 mmol), palladium acetate in an amount of 0.03 g (1.5% by mol), tri-t-butylphosphine 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 6.3 g of pale yellow powders were obtained. The obtained product was identified to be Compound (95) in accordance with FD-MS measurement yield: 70%).

Figure 8:
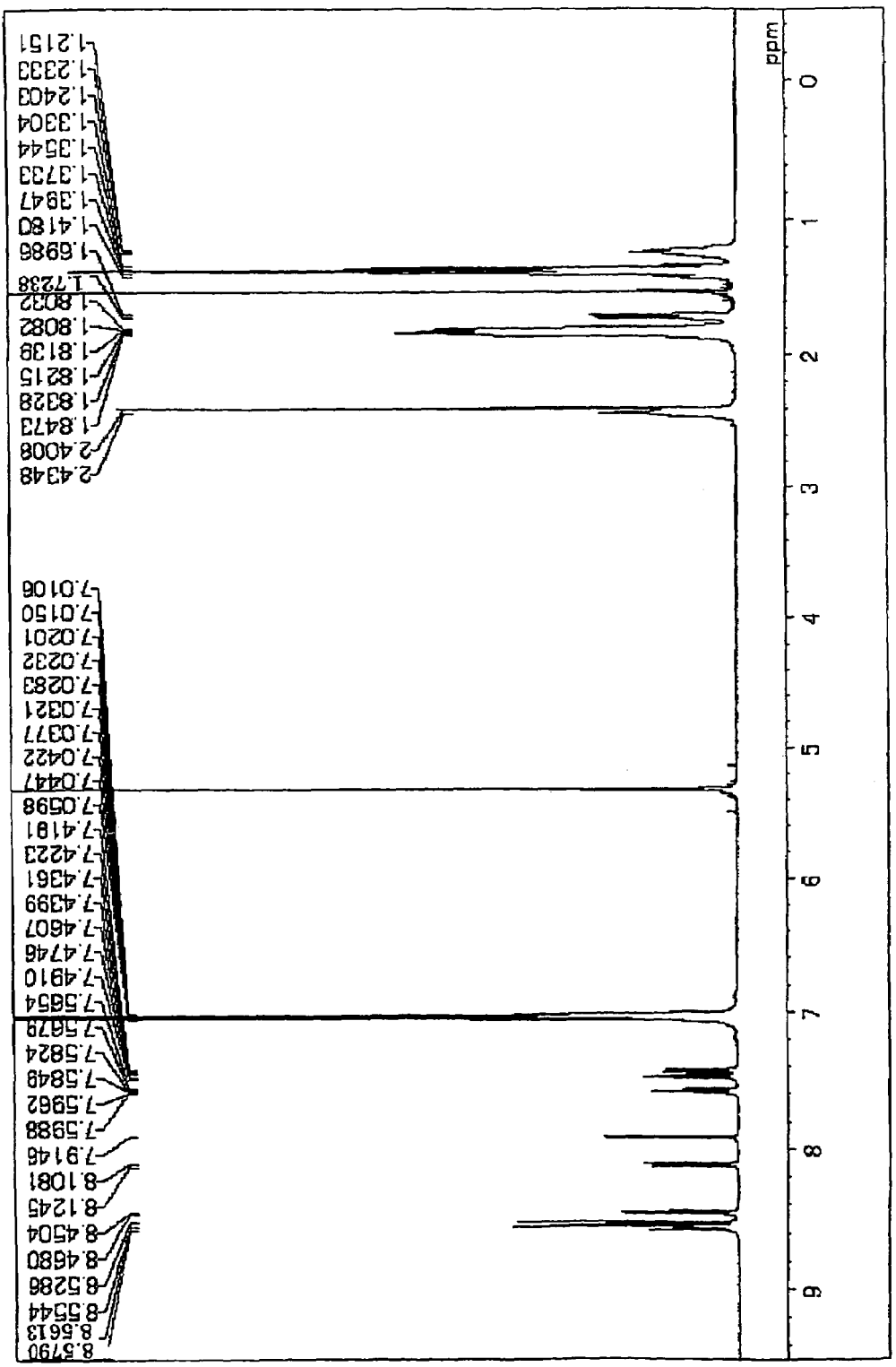
FIG. 8 is a chart showing a result of $^1$H-NMR measurement about Compound (95) obtained in Synthesis Example 8.

Measurement by means of DRX-500 (Trade name; produced by Brucker Optics Inc.) was carried out using dimethylene chloride as a solvent and a result of $^1$H-NMR spectrum about the resultant Compound (95) is shown in FIG. 8. Further, the maximum absorption wavelength and the maximum fluorescence wavelength of Compound (95) among the toluene solvent were 406 nm and 454 nm respectively.

Synthesis Example 9

Synthesis of Compound (D-973)

Under an atmospheric argon gas flow, 6,12-dibromochrysene in an amount of 3.8 g (10 mmol), N-methylaniline in an amount of 2.7 g (25 mmol, palladium acetate in an amount of 0.03 g (1.5% by mol), tri-t-butylphosphine 0.06 g (3% by mol), t-butoxy sodium in an amount of 2.4 g (25 mmol) and desiccated toluene in an amount of 100 milliliter were placed into a three-necked flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 2.2 g of white powders were obtained. The obtained product was identified to be Compound (D-973) in accordance with FD-MS measurement (yield: 50%).

Figure 9:
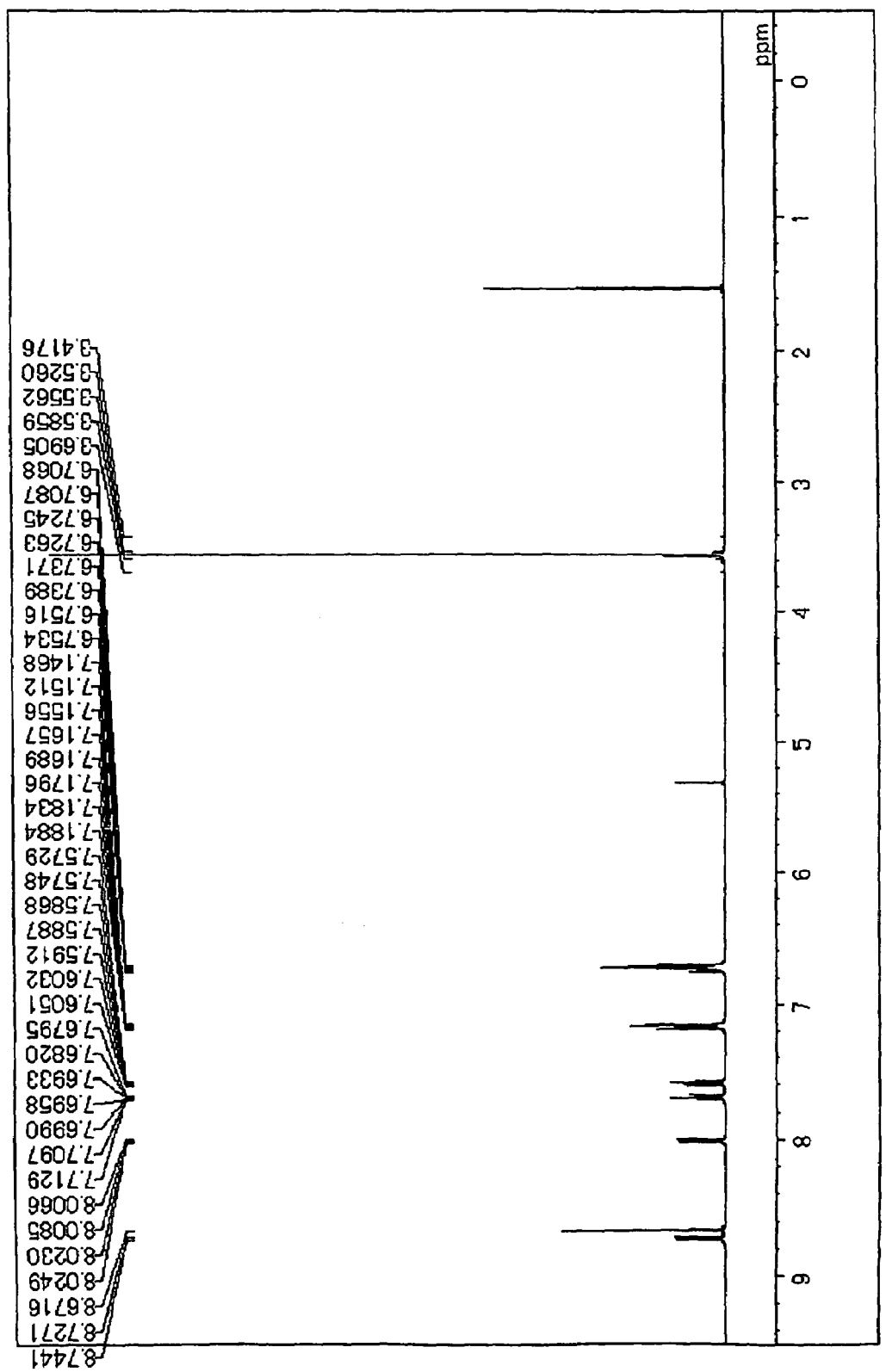
FIG. 9 is a chart showing a result of $^1$H-NMR measurement about Compound (D-973) obtained in Synthesis Example 9.

Measurement by means of DRX-500 (Trade name; produced by Brucker Optics Inc.) was carried out using dimethylene chloride as a solvent and a result of $^1$H-NMR spectrum about the resultant Compound (D-973) is shown in FIG. 9. Further, the maximum absorption wavelength and the maximum fluorescence wavelength of Compound (D-973) among the toluene solvent were 373 nm and 440 nm respectively.

Synthesis Example 10

Synthesis of Compound (D-974)

Under an atmospheric argon gas flow, 6,12-dibromochrysene in an amount of 3.8 g (10 mmol), N-isopropylaniline in an amount of 3.4 g (25 mmol, palladium acetate in an amount of 0.03 g (1.5% by mol), tri-t-butylphosphine 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 2.0 g of pale yellow powders were obtained. The obtained product was identified to be Compound (C-974) in accordance with FD-MS measurement (yield: 40%).

Figure 10:
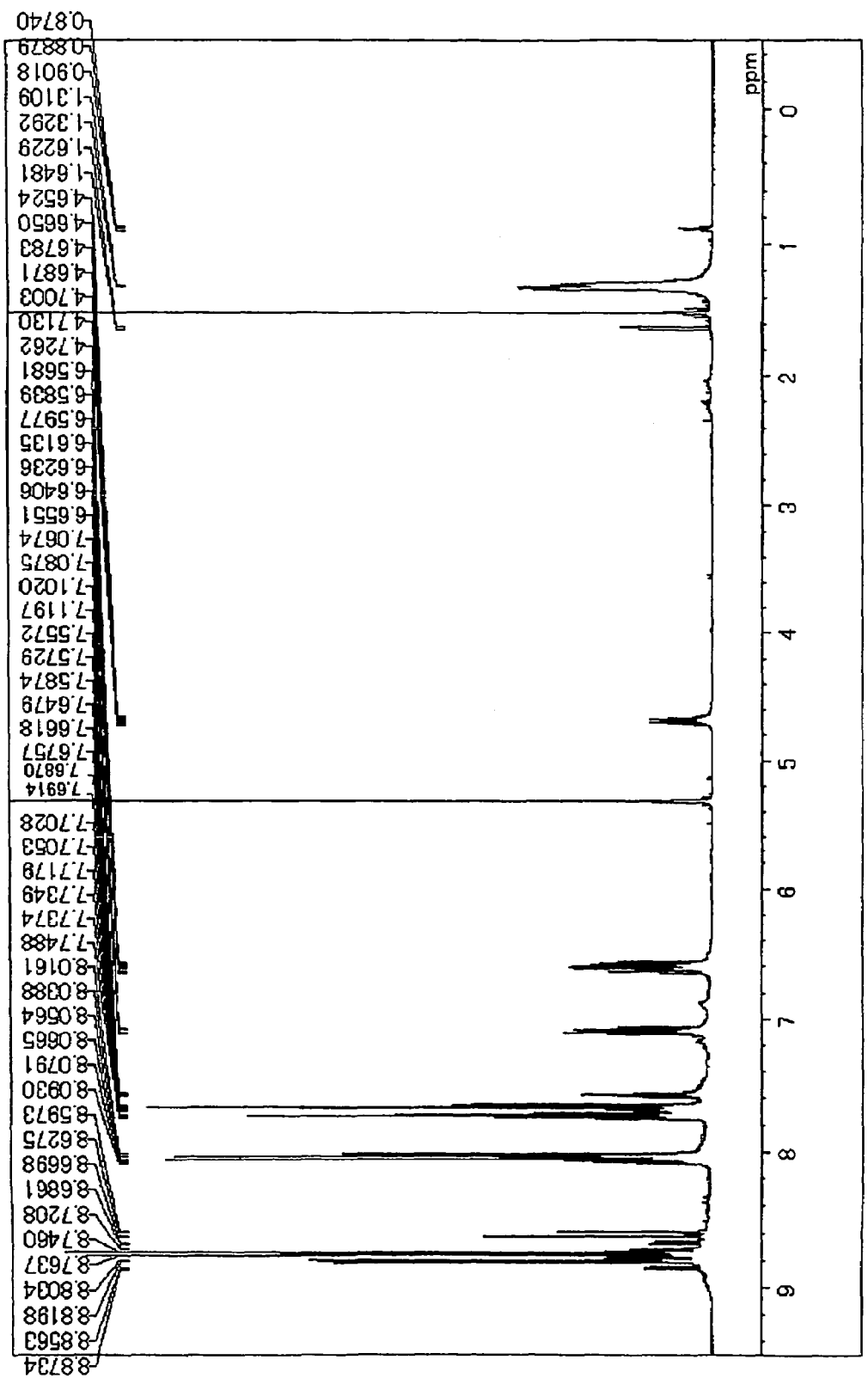
FIG. 10 is a chart showing a result of $^1$H-NMR measurement about Compound (D-974) obtained in Synthesis Example 10.

Measurement by means of DRX-500 (Trade name; produced by Brucker Optics Inc.) was carried out using dimethylene chloride as a solvent and a result of $^1$H-NMR spectrum about the resultant Compound (D-974) is shown in FIG. 10. Further, the maximum absorption wavelength and the maximum fluorescence wavelength of Compound (D-974) among the toluene solvent were 362 nm and 436 nm respectively.

Synthesis Example 11

Synthesis of Compound (D-998)

Under an atmospheric argon gas flow, 6,12-dibromochrysene in an amount of 3.8 g (10 mmol), N-(4-isopropylphenyl)pyridine-3-amine in an amount of 5.3 g (25 mmol), palladium acetate in an amount of 0.03 g (1.5% by mol), tri-t-butylphosphine 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 4.2 g of pale yellow powders were obtained. The obtained product was identified to be Compound (D-998) in accordance with FD-MS measurement (yield: 65%).

Figure 11:
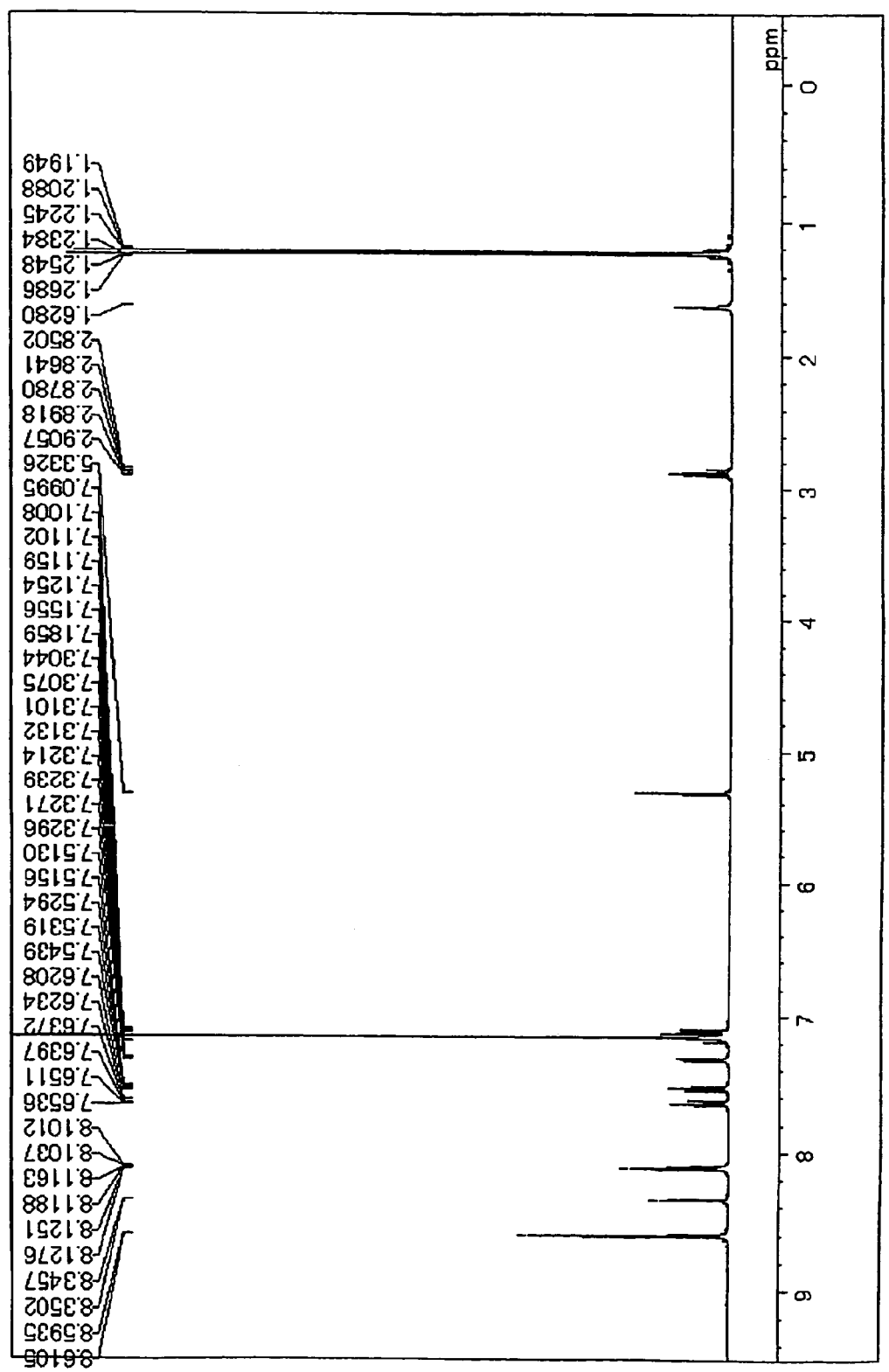
FIG. 11 is a chart showing a result of $^1$H-NMR measurement about Compound (D-998) obtained in Synthesis Example 11.

Measurement by means of DRX-500 (Trade name; produced by Brucker Optics Inc.) was carried out using dimethylene chloride as a solvent and a result of $^1$H-NMR spectrum about the resultant Compound (D-998) is shown in FIG. 11. Further, the maximum absorption wavelength and the maximum fluorescence wavelength of Compound (D-998) among the toluene solvent were 393 nm and 444 nm respectively.

Synthesis Example 12

Synthesis of Compound (D-1000)

Under an atmospheric argon gas flow, 2-methyl-6,12-dibromochrysene in an amount of 3.9 g (10 mmol), N-(4-isopropylphenyl)pyridine-3-amine in an amount of 5.3 g (25 mmol), palladium acetate in an amount of 0.03 g (1.5% by mol), tri-t-butylphosphine 0.06 g (3% by mol), t-butoxy sodium in an amount of 2.4 g (25 mmol) and desiccated toluene in an amount of 100 milliliter were placed into a three-neck flask equipped with a cooling pipe and having a capacity of 300 milliliter, and the resultant solution was stirred under heating at a temperature of 100° C. for one night. After the reaction terminated, precipitated crystals were separated by filtration and washed with the use of 50 milliliter of toluene and 100 milliliter of methanol, and as a result, 5.3 g of pale yellow powders were obtained. The obtained product was identified to be Compound (D-1000) in accordance with FD-MS measurement (yield: 80%).

Figure 12:
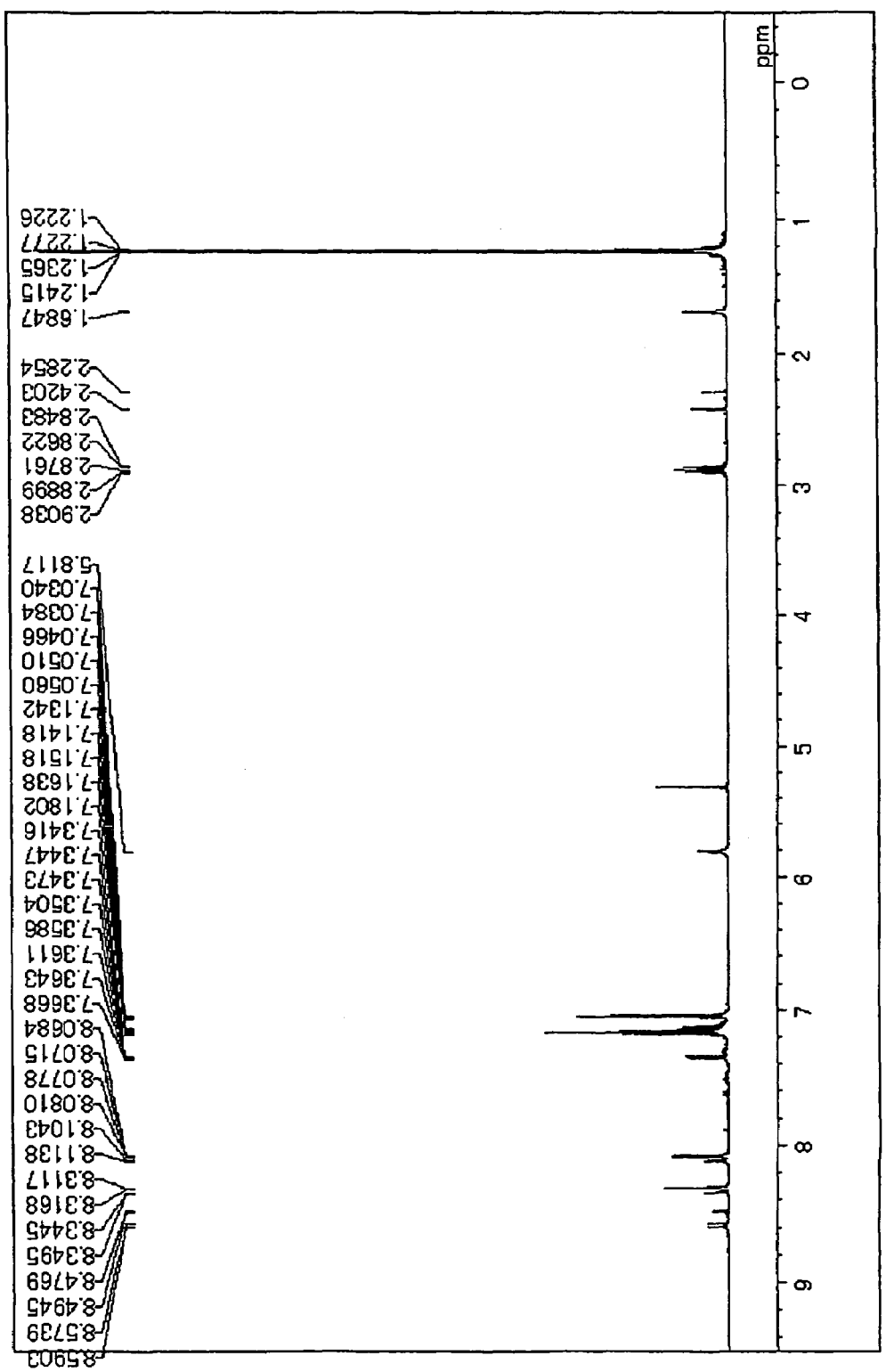
FIG. 12 is a chart showing a result of $^1$H-NMR measurement about Compound (D-1000) obtained in Synthesis Example 12.

Measurement by means of DRX-500 (Trade name; produced by Brucker Optics Inc.) was carried out using dimethylene chloride as a solvent and a result of $^1$H-NMR spectrum about the resultant Compound (D-1000) is shown in FIG. 12. Further, the maximum absorption wavelength and the maximum fluorescence wavelength of Compound (D-1000) among the toluene solvent were 385 nm and 440 nm respectively.

Example 1

A 120 nm-thick transparent electrode made of indium oxide was formed on a glass substrate having a size of 25 mm×75 mm×1.1 mm. The glass substrate with the transparent electrode was cleaned by irradiation of Ultra Violet ray and ozone. The thus cleaned glass substrate with the transparent electrode was mounted to a vacuum vapor deposition apparatus.

First, N',N'''-bis[4-(diphenylamino)phenyl]-N',N''-diphenylbiphenyl-4,4'-diamine was vapor-deposited to form a hole injecting layer having a thickness of 60 nm, and then N,N,N', N'-tetrakis(4-biphenyl)-4,4'-bendizine was vapor deposited on the hole injecting layer to form a hole transporting layer having a thickness of 20 nm. Then, 10,10'-bis[1,1',4',1"]terphenyl-2-yl-9,9'-bianthracenyl and the above Compound (9) were simultaneously vapor deposited at a weight ratio of 40:2 on the hole transporting layer to form a light emitting layer having a thickness of 40 nm.

Next, tris(8-hydroxyquinolinato)aluminum was vapor-deposited on the light emitting layer to form an electron injecting layer having a thickness of 10 nm. Then, tris(8-hydroxyquinolinato)aluminum and lithium was vapor-deposited at a weight ratio of 10:0.3 on the electron injecting layer to form a layer having a thickness of 10 nm, and further aluminum was vapor-deposited thereon to form an aluminum layer having a thickness of 150 nm. The aluminum layer functioned as a cathode. Thus, an organic EL device was fabricated.

As a result of subjecting the thus obtained organic EL device to a test by passing electric current, it was confirmed that a blue light with a luminance of 602 cd/m$^2$ (peak wavelength of light emission: 464 nm) and current efficiency of 6.0 cd/A was emitted at a voltage of 6.0 V and a current density of 10 mA/cm$^2$. Further, as a result of subjecting the device to a continuous test by passing DC electric current starting at an initial luminance of 500 cd/m$^2$, it was confirmed that the half lifetime thereof was 18900 hours.

Example 2

An organic EL device was fabricated in accordance with the same procedures as those conducted in Example 1 except that Compound (9) was replaced with Compound (23).

As a result of subjecting the thus obtained organic EL device to a test by passing electric current, it was confirmed that a blue light with a luminance of 664 cd/m$^2$ (peak wavelength of light emission: 462 nm) and current efficiency of 6.6 cd/A was emitted at a voltage of 6.5 V and a current density of 10 mA/cm$^2$. Further, as a result of subjecting the device to a continuous test by passing DC electric current starting at an initial luminance of 500 cd/m$^2$, it was confirmed that the half lifetime thereof was 16000 hours.

Example 3

An organic EL device was fabricated in accordance with the same procedures as those conducted in Example 1 except that 10,10'-bis[1,1',4',1']terphenyl-2-yl-9,9'-bianthracenyl was replaced with 10-(3-(naphthalen-1-yl)phenyl)-9-(naphthalen-2-yl)anthracene.

As a result of subjecting the thus obtained organic EL device to a test by passing electric current, it was confirmed that a blue light with a luminance of 631 cd/m$^2$ (peak wavelength of light emission: 464 nm) and current efficiency of 6.3 cd/A was emitted at a voltage of 6.5 V and a current density of 10 mA/cm$^2$. Further, as a result of subjecting the device to a continuous test by passing DC electric current starting at an initial luminance of 500 cd/m$^2$, it was confirmed that the half lifetime thereof was 20000 hours or longer.

Example 4

An organic EL device was fabricated in accordance with the same procedures as those conducted in Example 3 except that Compound (9) was replaced with Compound (23) for the doping material.

As a result of subjecting the thus obtained organic EL device to a test by passing electric current, it was confirmed that a blue light with a luminance of 710 cd/m$^2$ (peak wavelength of light emission: 465 nm) and current efficiency of 7.1 cd/A was emitted at a voltage of 6.5 V and a current density of 10 mA/cm$^2$. Further, as a result of subjecting the device to a continuous test by passing DC electric current starting at an initial luminance of 500 cd/m$^2$, it was confirmed that the half lifetime thereof was 20000 hours or longer.

Example 5

An organic EL device was fabricated in accordance with the same procedures as those conducted in Example 3 except that Compound (9) was replaced with Compound (25) for the doping material.

As a result of subjecting the thus obtained organic EL device to a test by passing electric current, it was confirmed that a blue light with a luminance of 793 cd/m$^2$ (peak wavelength of light emission: 469 nm) and current efficiency of 7.9 cd/A was emitted at a voltage of 6.5 V and a current density of 10 mA/cm$^2$. Further, as a result of subjecting the device to a continuous test by passing DC electric current starting at an initial luminance of 500 cd/m$^2$, it was confirmed that the half lifetime thereof was 20000 hours or longer.

Example 6

An organic EL device was fabricated in accordance with the same procedures as those conducted in Example 3 except that Compound (9) was replaced with Compound (10) for the doping material.

As a result of subjecting the thus obtained organic EL device to a test by passing electric current, it was confirmed that a blue light with a luminance of 782 cd/m$^2$ (peak wavelength of light emission: 468 nm) and current efficiency of 7.8 cd/A was emitted at a voltage of 6.5 V and a current density of 10 mA/cm$^2$. Further, as a result of subjecting the device to a continuous test by passing DC electric current starting at an initial luminance of 500 cd/m$^2$, it was confirmed that the half lifetime thereof was 20000 hours or longer.

Comparative Example 1

An organic EL device was fabricated in accordance with the same procedures as those conducted in Example 1 except that Compound (9) was replaced with 6,12-bis(4-isopropylphenyl-p-tolylamino)chrysene.

As a result of subjecting the thus obtained organic EL device to a test by passing electric current, it was confirmed that a blue light with a luminance of 594 cd/m$^2$ (peak wavelength of light emission: 462 nm) and current efficiency of 5.9 cd/A was emitted at a voltage of 6.3 V and a current density of 10 mA/cm$^2$. Further, as a result of subjecting the device to a continuous test by passing DC electric current starting at an initial luminance of 500 cd/m$^2$, it was confirmed that the half lifetime thereof was 4590 hours.

From the above-mentioned result, it is apparent that when any substituent does not bond to diaminochrysene backbone structure, half lifetime shortens because of an association between compounds each other.

INDUSTRIAL APPLICABILITY

The organic EL device using the aromatic amine derivative according to the present invention can exhibit a practically sufficient luminance of light emission even upon applying a low voltage thereto, and has an enhanced efficiency of light emission and the device is free from deterioration in properties even after being used for a long period of time and, therefore, has a long lifetime. Resultantly, the EL device is useful as a flat panel light emitting member for a wall-hanging type television or as a light source of backlight and the like for display devices.

What is claimed is:

1. An aromatic amine derivative represented by the following general formula (1):

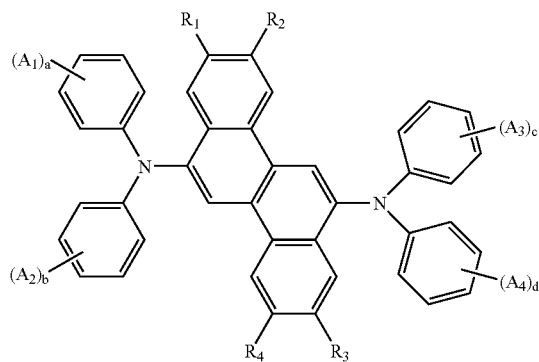

wherein $A_1$ to $A_4$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 ring carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 3 to 50 ring carbon atoms, a substituted or unsubstituted silyl group having 3 to 50 carbon atoms or a halogen atom;

a, b, c and d each independently represents an integer of 0 to 5, when a, b, c or d each is 2 or greater, $A_1$ to $A_4$ may be the same with or different from each other, and may bond each other to form a saturated or unsaturated ring; and further, a couple of $A_1$ and $A_2$, and a couple of $A_3$ and $A_4$ may bond each other to form a saturated or unsaturated ring;

$R_1$ to $R_4$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted arylamino group having 5 to 20 ring carbon atoms, a substituted or unsubstituted alkylamino group having 1 to 20 carbon atoms, a substituted or unsubstituted heterocyclic group having 3 to 50 ring carbon atoms or a substituted or unsubstituted silyl group having 3 to 50 carbon atoms; a couple of $R_1$ and $R_2$, and a couple of $R_3$ and $R_4$ may bond each other to form a saturated or unsaturated ring;

however, a case where all of $R_1$ to $R_4$ in the general formula (1) are hydrogen atoms is excluded.

2. The aromatic amine derivative according to claim 1, wherein at least one of $R_1$ or $R_3$ in the general formula (1) independently represents a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms or a substituted or unsubstituted cycloalkyl group having 3 to 50 ring carbon atoms.

3. The aromatic amine derivative according to claim 1, wherein $R_1$ and $R_3$ in the general formula (1) each independently represents a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms or a substituted or unsubstituted cycloalkyl group having 3 to 50 ring carbon atoms.

4. The aromatic amine derivative according to claim 1, wherein at least one of $R_2$ or $R_4$ in the general formula (1) independently represents a substituted or unsubstituted primary alkyl group having 1 to 50 carbon atoms, a substituted or unsubstituted secondary alkyl group having 1 to 50 carbon atoms, a substituted or unsubstituted aryl group having 5 to 50 ring carbon atoms, a substituted or unsubstituted aralkyl group having 1 to 50 ring carbon atoms or a substituted or unsubstituted cycloalkyl group having 3 to 50 ring carbon atoms.

5. The aromatic amine derivative according to claim 1, wherein $R_1$ to $R_4$ in the general formula (1) each independently represents a hydrogen atom, a substituted or unsubstituted arylamino group having 5 to 20 ring carbon atoms, a substituted or unsubstituted alkylamino group having 1 to 20 carbon atoms, a substituted or unsubstituted heterocyclic group having 3 to 50 ring carbon atoms or a substituted or unsubstituted silyl group having 3 to 50 carbon atoms.

6. The aromatic amine derivative according to claim 1, wherein $A_1$ to $A_4$ each independently represents a hydrogen atom, a substituted or unsubstituted alkyl group having 1 to 20 carbon atoms, a substituted or unsubstituted aryl group having 5 to 20 ring carbon atoms, a substituted or unsubstituted aralkyl group having 6 to 20 ring carbon atoms, a substituted or unsubstituted cycloalkyl group having 5 to 12 ring carbon atoms, a substituted or unsubstituted alkoxyl group having 1 to 6 ring carbon atoms, a substituted or unsubstituted aryloxy group having 5 to 18 ring carbon atoms, a substituted or unsubstituted arylamino group having 5 to 18 ring carbon atoms, a substituted or unsubstituted alkylamino group having 1 to 6 carbon atoms, a substituted or unsubstituted heterocyclic group having 3 to 20 ring carbon atoms, a substituted or unsubstituted silyl group having 3 to 20 carbon atoms or a halogen atom;

a, b, c and d each independently represents an integer of 0 to 2, when a, b, c or d each is 2 or greater, $A_1$ to $A_4$ may be the same with or different from each other, and may bond each other to form a saturated or unsaturated ring; and further, a couple of $A_1$ and $A_2$, and a couple of $A_3$ and $A_4$ may bond each other to form a saturated or unsaturated ring;

$R_1$ to $R_4$ each independently represents a hydrogen atom, a substituted or unsubstituted alkyl group having 1 to 20 carbon atoms, a substituted or unsubstituted aryl group having 5 to 20 ring carbon atoms, a substituted or unsubstituted aralkyl group having 6 to 20 ring carbon atoms, a substituted or unsubstituted cycloalkyl group having 5 to 12 ring carbon atoms, a substituted or unsubstituted arylamino group having 5 to 18 ring carbon atoms, a substituted or unsubstituted alkylamino group having 1 to 10 carbon atoms, a substituted or unsubstituted heterocyclic group having 3 to 20 ring carbon atoms or a substituted or unsubstituted silyl group having 3 to 20 carbon atoms; a couple of $R_1$ and $R_2$, and a couple of $R_3$ and $R_4$ may bond each other to form a saturated or unsaturated ring;

however, a case where all of $R_1$ to $R_4$ in the general formula (1) are hydrogen atoms is excluded.

7. The aromatic amine derivative according to claim 1, wherein the alkyl group represented by $R_2$ and $R_4$ in the general formula (1) are primary or secondary.

8. The aromatic amine derivative according to claim 1, wherein at least one of $R_1$ or $R_3$ in the general formula (1) represents a methyl group, an ethyl group, a propyl group, an isopropyl group, a butyl group, a s-butyl group, a t-butyl group or a cyclohexyl group.

9. The aromatic amine derivative according to claim 1, wherein at least one of $R_2$ or $R_4$ in the general formula (1) represents a methyl group, an ethyl group, a propyl group, an isopropyl group, a butyl group, a s-butyl group, a t-butyl group or a cyclohexyl group.

10. The aromatic amine derivative according to claim 1, which is represented by the following formula:

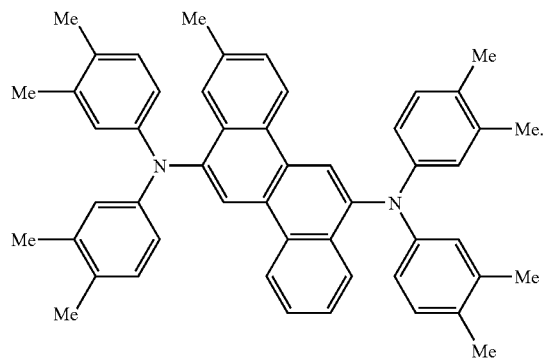

11. The aromatic amine derivative according to claim 1, which is represented by the following formula:

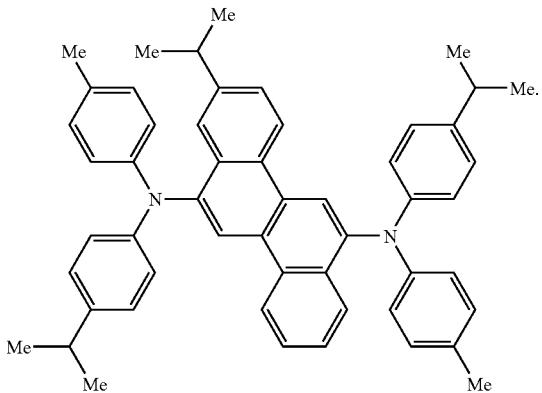

12. The aromatic amine derivative according to claim 1, which is represented by the following formula:

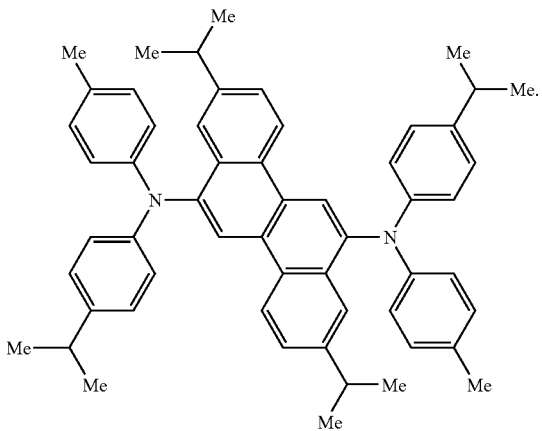

13. The aromatic amine derivative according to claim 1, which is represented by the following formula:

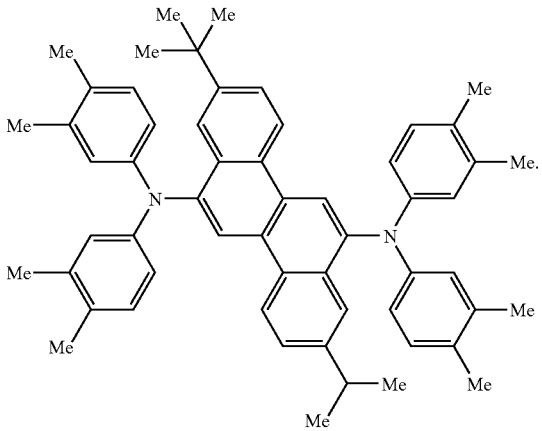

14. The aromatic amine derivative according to claim 1, which is represented by the following formula:

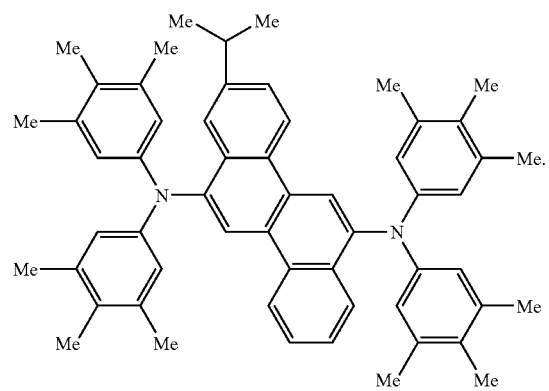

15. The aromatic amine derivative according to claim 1, which is represented by the following formula:

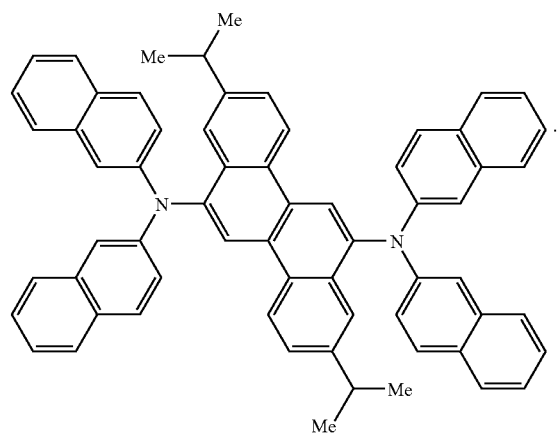

16. The aromatic amine derivative according to claim 1, which is represented by the following formula:

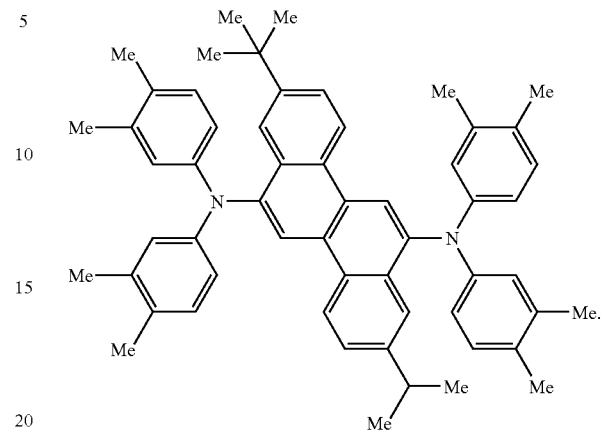

17. The aromatic amine derivative according to claim 1, which is represented by the following formula:

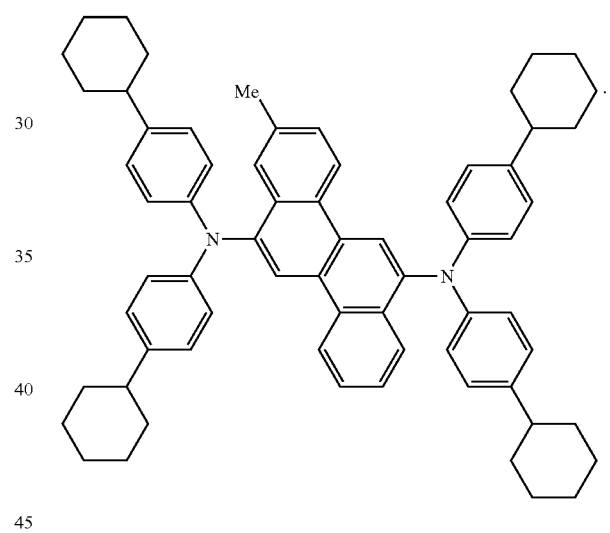

* * * * *